United States Patent
Han et al.

(10) Patent No.: US 9,288,869 B2
(45) Date of Patent: *Mar. 15, 2016

(54) STYRYL-BASED COMPOUND, COMPOSITION CONTAINING STYRYL-BASED COMPOUND, AND ORGANIC LIGHT EMITTING DIODE INCLUDING STYRYL-BASED COMPOUND

(75) Inventors: Sang-Hyun Han, Yongin (KR); Seok-Hwan Hwang, Yongin (KR); Young-Kook Kim, Yongin (KR); Hye-Jin Jung, Yongin (KR); Jin-O Lim, Yongin (KR); Soo-Yon Kim, Yongin (KR); Dae-Yup Shin, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

(*) Notice: Subject to any disclaimer, the term of this patent is extended or adjusted under 35 U.S.C. 154(b) by 714 days.

This patent is subject to a terminal disclaimer.

(21) Appl. No.: 13/609,633

(22) Filed: Sep. 11, 2012

(65) Prior Publication Data
US 2013/0119355 A1    May 16, 2013

(30) Foreign Application Priority Data
Nov. 10, 2011 (KR) .................. 10-2011-0117161

(51) Int. Cl.
*H01L 51/54* (2006.01)
*C07C 211/58* (2006.01)
(Continued)

(52) U.S. Cl.
CPC ............... *H05B 33/14* (2013.01); *C07B 59/00* (2013.01); *C07C 211/54* (2013.01);
(Continued)

(58) Field of Classification Search
CPC ............ C07C 2103/18; C07C 2103/24; C07C 2103/26; C07C 2103/42; C07C 2103/48; C07C 2103/50; C07C 2103/94; C07C 211/54; C07C 211/56; C07C 211/58; C07C 211/60; C07C 211/61; C07C 255/58; C07D 209/86; C07D 209/88; C07D 213/38; C07D 213/74; C07D 307/91; C07D 333/76; C07D 401/10; C07D 409/12; C09K 2211/1011; C09K 2211/1014; C09K 2211/1029; C09K 2211/1088; C09K 2211/1092; C09K 11/06; H01L 51/0058; H01L 51/0059; H01L 51/0061; H01L 51/0074; H01L 51/54; H05B 33/14

See application file for complete search history.

(56) References Cited

U.S. PATENT DOCUMENTS 5,635,308 A     6/1997 Inoue et al.
5,972,247 A    10/1999 Shi et al.
(Continued)

FOREIGN PATENT DOCUMENTS

CN    1854119 A    11/2006
JP    8-12600 A     1/1996
(Continued)

OTHER PUBLICATIONS

Chinese OA issued by the Chinese Patent Office on Jun. 26, 2015 in the examination of the Chinese Patent Application No. 201210443012.2, which corresponds to KR 10-2011-0117161. Request for Entry of the Accompanying Office Action is attached herewith.

*Primary Examiner* — Dawn L. Garrett
(74) *Attorney, Agent, or Firm* — Robert E. Bushnell, Esq.

(57) ABSTRACT

A styryl-based compound represented by Formula 1, a composition containing the styryl-based compound, and an organic light-emitting diode (OLED) including the styryl-based compound:

[Formula 1]

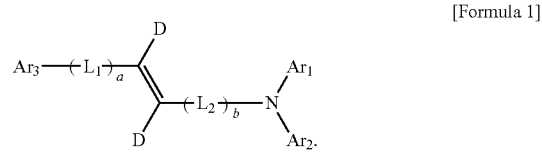

The styryl-based compound may exhibit high heat resistance and thus an OLED including the same may have low driving voltage, high brightness, high efficiency, and long lifetime.

17 Claims, 1 Drawing Sheet

(51) Int. Cl.
C07C 211/61 (2006.01)
C07D 213/38 (2006.01)
C07D 213/74 (2006.01)
C09K 11/06 (2006.01)
C07D 209/88 (2006.01)
H05B 33/14 (2006.01)
C07C 255/58 (2006.01)
C07B 59/00 (2006.01)
C07C 211/54 (2006.01)
C07C 211/56 (2006.01)
C07C 211/60 (2006.01)
C07D 307/91 (2006.01)
C07D 333/76 (2006.01)
C07D 401/10 (2006.01)
C07D 409/12 (2006.01)
C07D 209/86 (2006.01)
H01L 51/00 (2006.01)

(52) U.S. Cl.
CPC ............ *C07C 211/56* (2013.01); *C07C 211/58* (2013.01); *C07C 211/60* (2013.01); *C07C 211/61* (2013.01); *C07C 255/58* (2013.01); *C07D 209/86* (2013.01); *C07D 209/88* (2013.01); *C07D 213/38* (2013.01); *C07D 213/74* (2013.01); *C07D 307/91* (2013.01); *C07D 333/76* (2013.01); *C07D 401/10* (2013.01); *C07D 409/12* (2013.01); *C09K 11/06* (2013.01); *H01L 51/0059* (2013.01); *C07B 2200/05* (2013.01); *C07C 2103/18* (2013.01); *C07C 2103/24* (2013.01); *C07C 2103/26* (2013.01); *C07C 2103/42* (2013.01); *C07C 2103/48* (2013.01); *C07C 2103/50* (2013.01); *C07C 2103/94* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/0058* (2013.01); *H01L 51/0061* (2013.01); *H01L 51/0074* (2013.01)

(56) References Cited

U.S. PATENT DOCUMENTS

| 6,465,115 | B2 | 10/2002 | Shi et al. | |
|---|---|---|---|---|
| 6,596,415 | B2 | 7/2003 | Shi et al. | |
| 8,679,648 | B2 * | 3/2014 | Han et al. | 428/690 |
| 8,828,559 | B2 * | 9/2014 | Jung et al. | 428/690 |
| 2006/0246317 | A1 | 11/2006 | Lyu et al. | |
| 2010/0081846 | A1 | 4/2010 | Kim et al. | |
| 2013/0112948 | A1 * | 5/2013 | Jung et al. | 257/40 |
| 2014/0014916 | A1 * | 1/2014 | Han et al. | 257/40 |
| 2014/0027721 | A1 * | 1/2014 | Kim et al. | 257/40 |
| 2014/0239260 | A1 * | 8/2014 | Lee et al. | 257/40 |
| 2014/0332772 | A1 * | 11/2014 | Han et al. | 257/40 |

FOREIGN PATENT DOCUMENTS

| JP | 2000-3782 A | 1/2000 |
|---|---|---|
| JP | 2006-273737 A | 10/2006 |
| KR | 10-2006-0111048 A | 10/2006 |
| KR | 10-0835601 B1 | 5/2008 |
| KR | 10-2010-0069216 A | 6/2010 |
| KR | 10-2010-0118258 A | 11/2010 |
| WO | WO 2010/126233 * | 11/2010 |

* cited by examiner

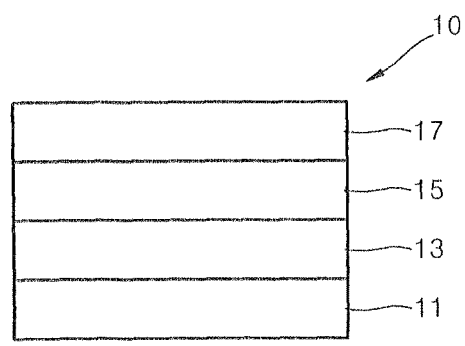

STYRYL-BASED COMPOUND, COMPOSITION CONTAINING STYRYL-BASED COMPOUND, AND ORGANIC LIGHT EMITTING DIODE INCLUDING STYRYL-BASED COMPOUND

CROSS-REFERENCE TO RELATED PATENT APPLICATION

This application claims the benefit of Korean Patent Application No. 10-2011-0117161, filed on Nov. 10, 2011, in the Korean Intellectual Property Office, the disclosure of which is incorporated herein in its entirety by reference.

BACKGROUND OF THE INVENTION

1. Field of the Invention

The present invention relates to a styryl-based compound and an organic light-emitting diode (OLED) including the same.

2. Description of the Related Art

Organic light-emitting diodes (OLEDs) are self-emitting devices, have advantages such as a wide viewing angle, excellent contrast, quick response, high brightness, and excellent driving voltage, and can provide multicolored images.

A general OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic layers formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

The present invention provides a styryl-based compound having a novel structure, a composition containing the styryl-based compound, and an organic light-emitting diode (OLED) including the styryl-based compound or the composition.

According to an aspect of the present invention, there is provided a styryl-based compound represented by Formula 1 below:

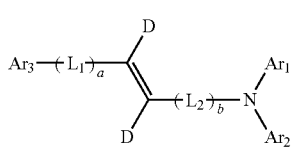

Formula 1 wherein $Ar_3$ is a substituted or unsubstituted $C_8$-$C_{20}$ aryl group having two ore more rings fused with each other, or a substituted or unsubstituted $C_2$-$C_{20}$ heteroaryl group having two ore more rings fused with each other;

$Ar_1$ and $Ar_2$ are each independently a substituted or unsubstituted $C_5$-$C_{60}$ aryl group or a substituted or unsubstituted $C_2$-$C_{60}$ heteroaryl group;

$L_1$ and $L_2$ are each independently a substituted or unsubstituted $C_5$-$C_{60}$ arylene group or a substituted or unsubstituted $C_2$-$C_{60}$ heteroarylene group; and a and b are each independently an integer of 0 to 5.

According to another aspect of the present invention, there is provided a composition containing a styryl-based compound, including a styryl-based compound represented by Formula 1 below; and at least one of a styryl-based compound represented by Formula 1-1H-1 below, a styryl-based compound represented by Formula 1-1H-2 below, and a styryl-based compound represented by Formula 1-2H below:

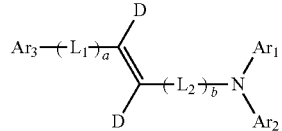

Formula 1

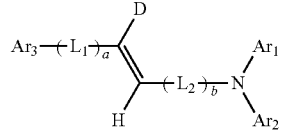

Formula 1-1H-1

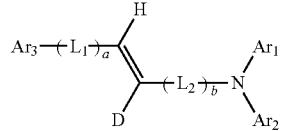

Formula 1-1H-2

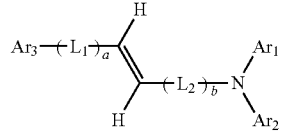

Formula 1-2H wherein substituents of Formulae 1-1H-1, 1-1H-2, and 1-2H are defined in a detailed description of Formula 1.

According to another aspect of the present invention, there is provided an organic light-emitting diode (OLED) including a first electrode; a second electrode facing the first electrode; and an organic layer interposed between the first electrode and the second electrode, wherein the organic layer includes at least one of the styryl-based compound, or at least one of the composition containing a styryl-based compound.

BRIEF DESCRIPTION OF THE DRAWINGS

The above and other features and advantages of the present invention will become more apparent by describing in detail exemplary embodiments thereof with reference to the attached drawings in which:

FIG. 1 is a schematic diagram illustrating an organic light-emitting diode (OLED) according to an embodiment of the present invention.

DETAILED DESCRIPTION OF THE INVENTION

Hereinafter, the present embodiments will be described more fully with reference to the accompanying drawing, in which exemplary embodiments are shown. As used herein, the term "and/or" includes any and all combinations of one or more of the associated listed items. Expressions such as "at least one of," when preceding a list of elements, modify the entire list of elements and do not modify the individual elements of the list.

A styryl-based compound according to an embodiment of the present invention is represented by Formula 1 below:

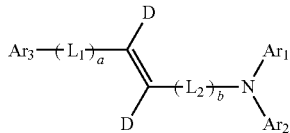

Formula 1 wherein $Ar_3$ may be a substituted or unsubstituted $C_8$-$C_{20}$ aryl group having two ore more rings fused with each other, or a substituted or unsubstituted $C_2$-$C_{20}$ heteroaryl group having two ore more rings fused with each other.

For example, in Formula 1, $Ar_3$ may be a substituted or unsubstituted naphthyl group, a substituted or unsubstituted phenanthrenyl group, a substituted or unsubstituted anthryl group, a substituted or unsubstituted pyrenyl group, a substituted or unsubstituted chrysenyl group, a substituted or unsubstituted fluorenyl group, a substituted or unsubstituted carbazolyl group, a substituted or unsubstituted dibenzofuranyl group, or a substituted or unsubstituted dibenzothiophenyl group. In this case, at least one substituent of the substituted naphthyl group, phenanthrenyl group, anthryl group, pyrenyl group, chrysenyl group, fluorenyl group, carbazolyl group, dibenzofuranyl group, and dibenzothiophenyl group may be selected from deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolinyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, a hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group.

According to $Ar_3$ in Formula 1, the styryl-based compound represented by Formula 1 may be represented by any one of Formulae 1A through 1I below:

Formula 1A

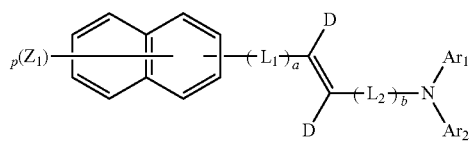

Formula 1B

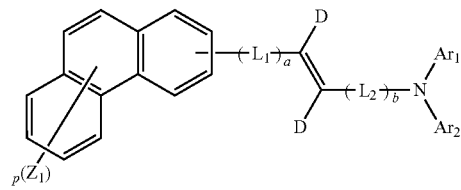

Formula 1C

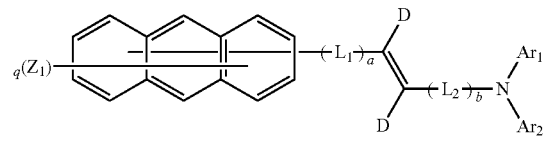

Formula 1D

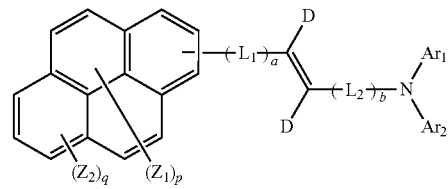

Formula 1E

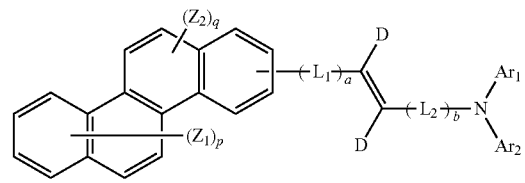

Formula 1F

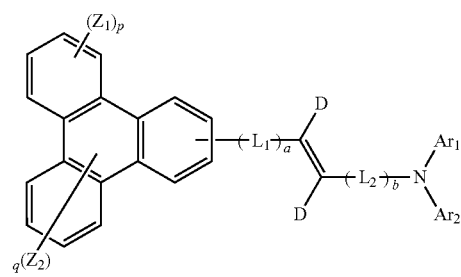

Formula 1G

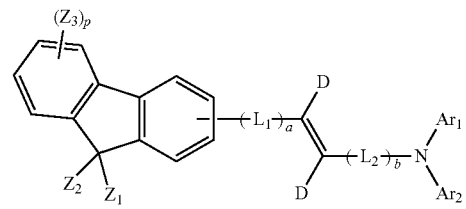

Formula 1H

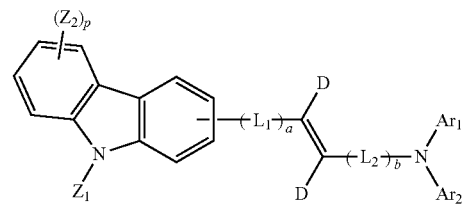

Formula 1I

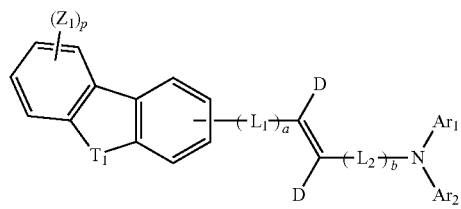

In Formulae 1A through 1I, $Z_1$ through $Z_3$ may be each independently hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$alkyl group; a $C_1$-$C_{10}$alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolinyl group; an imidazopyridinyl group; an imidazopyrimidinyl group; a pyridinyl group; a pyrazinyl group; a pyrimidinyl group; an indolyl group; an and phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted by at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$alkyl group, and a $C_1$-$C_{10}$alkoxy group. In this case, two or more neighboring substituents from among $Z_1$ through $Z_3$ may be optionally fused with each other or may be optionally connected by a single bond.

For example, $Z_1$ through $Z_3$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a methyl group, an ethyl group, a propyl group, a butyl group, a pentyl group, a hexyl group, a heptyl group, an octyl group, a phenyl group, a naphthyl group, a fluorenyl group, a deuterated phenyl group, or a dimethylfluorenyl group. In this case, when $Z_1$ and $Z_2$ of Formula 1G are each a phenyl group, $Z_1$ and $Z_2$ may be connected by a single bond.

In Formulae 1A through 1I, $T_1$ may be O or S.

In Formulae 1A through 1I, p may be an integer of 1 to 7, and q may be an integer of 1 to 4. When p is 2 or more, at least two $Z_1$ may be identical to or different from each other and at least two $Z_3$ may be identical to or different from each other. When q is 2 or more, at least two $Z_2$ may be identical to or different from each other.

In Formula 1, $Ar_1$ and $Ar_2$ may be each independently a substituted or unsubstituted $C_5$-$C_{60}$aryl group or a substituted or unsubstituted $C_2$-$C_{60}$heteroaryl group. In this case, at least one substituent of the substituted $C_5$-$C_{60}$ aryl group and the substituted $C_2$-$C_{60}$ heteroaryl group may be selected from deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$alkyl group; a $C_1$-$C_{10}$alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolinyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted by at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$alkyl group, and a $C_1$-$C_{10}$alkoxy group.

For example, in Formula 1, $Ar_1$ and $Ar_2$ may be each independently, but are not limited to, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzoxazolyl group, a substituted or unsubstituted dibenzofuranyl group, a substituted or unsubstituted dibenzothiophenyl group, or a substituted or unsubstituted benzocarbazolyl group.

For example, in Formula 1 above, $Ar_1$ and $Ar_2$ may be each independently, but are not limited to, a substituted or unsubstituted phenyl group, a substituted or unsubstituted naphthyl group, a substituted or unsubstituted phenanthrenyl group, a substituted or unsubstituted pyrenyl group, a substituted or unsubstituted carbazolyl group, a substituted or unsubstituted fluorenyl group, a substituted or unsubstituted dibenzofuranyl group, a substituted or unsubstituted dibenzothiophenyl group, or a substituted or unsubstituted benzocarbazolyl group.

$Ar_1$ and $Ar_2$ may be each independently represented by any one of Formulae 2A through 2J below:

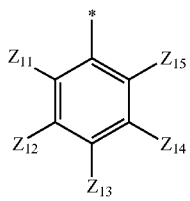

Formula 2A

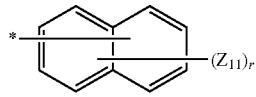

Formula 2B

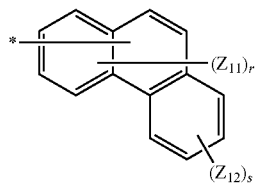

Formula 2C

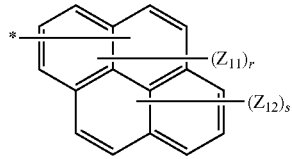

Formula 2D

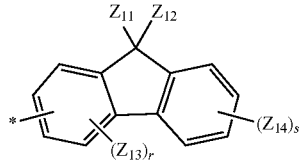

Formula 2E

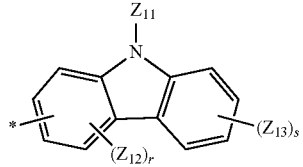

Formula 2F

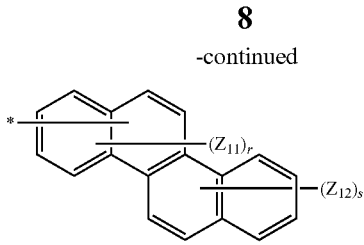

Formula 2G

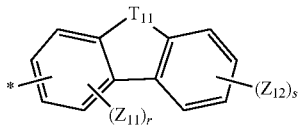

Formula 2H

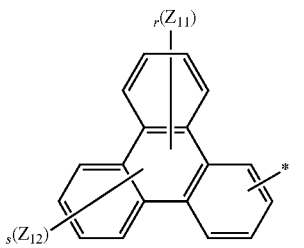

Formula 2I

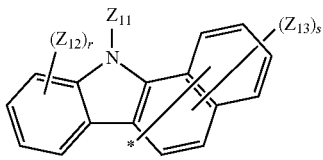

Formula 2J

In Formulae 2A through 2J above, $Z_{11}$ through $Z_{15}$ may be each independently selected from hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$alkyl group; a $C_1$-$C_{10}$alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolinyl group; an imidazopyridinyl group; an imidazopyrimidinyl group; a pyridinyl group; a pyrimidinyl group; a pyrazinyl group; an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, hydrazine, hydrazone, a carboxyl group or a salt thereof, sulfonic acid group or a salt thereof, a phosphoric acid or a salt thereof, a $C_1$-$C_{10}$alkyl group, and a $C_1$-$C_{10}$alkoxy group. In this case, two or more neighboring substituents from among $Z_{11}$ through $Z_{15}$ may be optionally fused with each other or may be optionally connected by a single bond.

In Formulae 2A through 2J above, $T_{11}$ may be O or S.

In Formulae 2A and 2J above, r may be an integer of 1 to 7 and s may be an integer of 1 to 5. When r is 2 or more, at least two $Z_{11}$ may be identical to or different from each other and at least two $Z_{13}$ may be identical to or different from each other. When s is 2 or more, at least two $Z_{12}$ may be identical to or different from each other.

For example, Ar₁ and Ar₂ may be each independently represented by any one of Formulae 3A through 3O below:

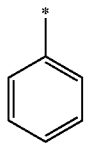
Formula 3A

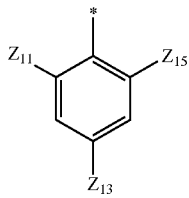
Formula 3B

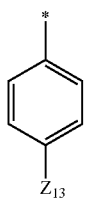
Formula 3C

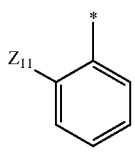
Formula 3D

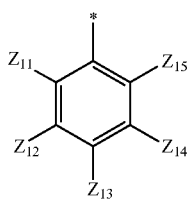
Formula 3E

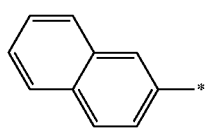
Formula 3F

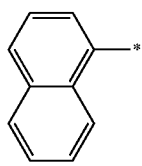
Formula 3G

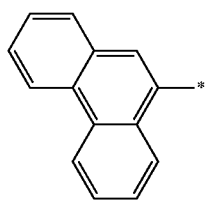
Formula 3H

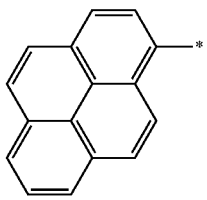
Formula 3I

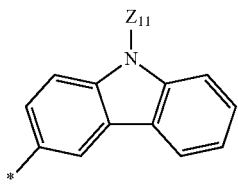
Formula 3J

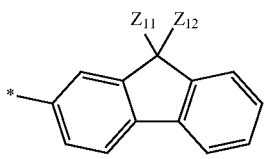
Formula 3K

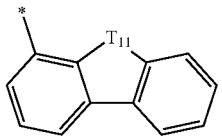
Formula 3L

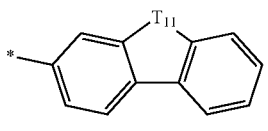
Formula 3M

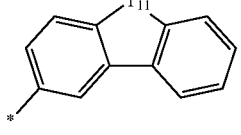
Formula 3N

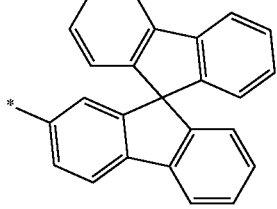
Formula 3O wherein a detailed description of $Z_{11}$ through $Z_{15}$ is already provided above (however, Formulae 3A through 3O above, $Z_{11}$ through $Z_{15}$ are not hydrogen). For example, in Formulae 3A through 3O above, $Z_{11}$ through $Z_{15}$ may be each independently, but are not limited to, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a methyl group, an ethyl group, a propyl group, a butyl group, a pentyl group, a hexyl group, a heptyl group, an octyl group, a phenyl group, a naphthyl group, or a fluorenyl group. In Formulae 3A through 3O above, $T_{11}$ may be O or S.

In Formula 1 above, $L_1$ and $L_2$ may be each independently a substituted or unsubstituted $C_5$-$C_{60}$ arylene group or a substituted or unsubstituted $C_2$-$C_{60}$ heteroarylene group. At least one substituent of the substituted $C_5$-$C_{60}$ arylene group and the substituted $C_2$-$C_{60}$ heteroarylene group may be selected from deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group.

For example, $L_1$ and $L_2$ may be each independently a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanyl group, a substituted or unsubstituted benzofuranylene group, a substituted or unsubstituted thiophenylene group, a substituted or unsubstituted benzothiophenyl group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzofuranylene group, a substituted or unsubstituted triazinylene group, or a substituted or unsubstituted oxadiazolylene group.

For example, in Formula 1 above, $L_1$ and $L_2$ may be each independently, but are not limited to, a substituted or unsubstituted phenylenyl group, a substituted or unsubstituted naphthylene group, a substituted or unsubstituted fluorenylene group, a substituted or unsubstituted phenanthrenylene group, a substituted or unsubstituted pyridinylene group, or a substituted or unsubstituted pyrazinylene group.

In Formula 1 above, $L_1$ and $L_2$ may be each independently represented by any one of Formulae 5A through 5K below:

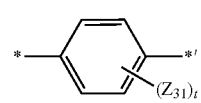

Formula 5A

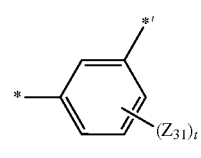

Formula 5B

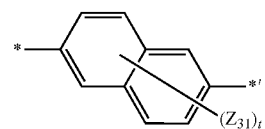

Formula 5C

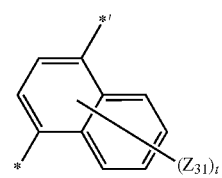

Formula 5D

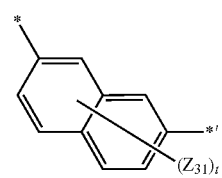

Formula 5E

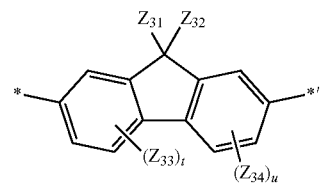

Formula 5F

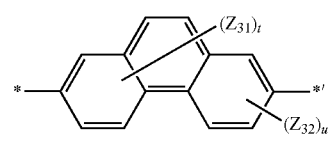

Formula 5G

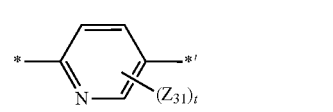

Formula 5H

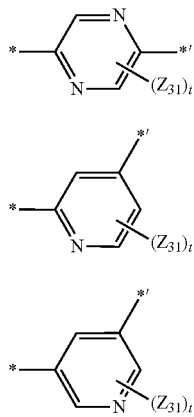

Formula 5I

Formula 5J

Formula 5K

In Formulae 5A through 5K above, $Z_{31}$ through $Z_{34}$ may be each independently selected from hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolinyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group. In this case, two or more neighboring substituents from among $Z_{31}$ through $Z_{34}$ may be optionally fused with each other or may be optionally connected by a single bond.

For example, $Z_{31}$ through $Z_{34}$ may be each independently, but are not limited to, hydrogen, deuterium, a halogen atom, a hydroxyl group, a cyano group, a methyl group, an ethyl group, a propyl group, a butyl group, a pentyl group, a hexyl group, or a heptyl group.

In Formulae 5A through 5K above, t may be an integer of 1 to 6 and u may be an integer of 1 to 3. When t is 2 or more, at least two $Z_{31}$ may be identical to or different from each other. When u is 2 or more, at least two $Z_{32}$ may be identical to or different from each other.

In Formula 1 above, a and b may be each independently an integer of 0 to 5.

For example, in Formula 1 above, a may be, but is not limited to, 0 or 1, and b may be, but is limited to, 1 or 2.

According to an embodiment of the present invention, the styryl-based compound of Formula 1 above may be represented by any one of Formula 1A-1 through 1I-3 below:

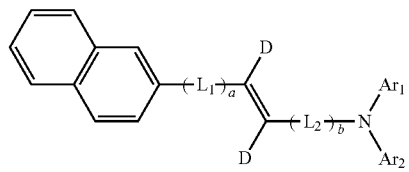

Formula 1A-1

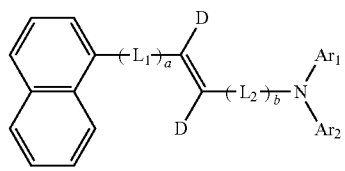

Formula 1A-2

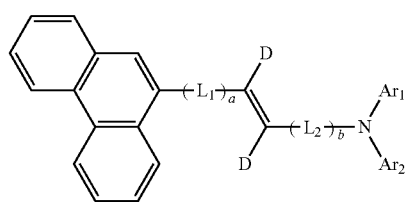

Formula 1B-1

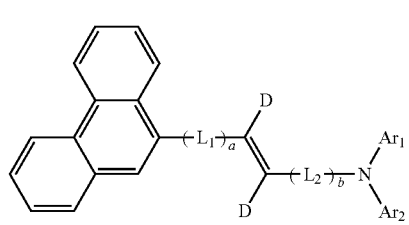

Formula 1B-2

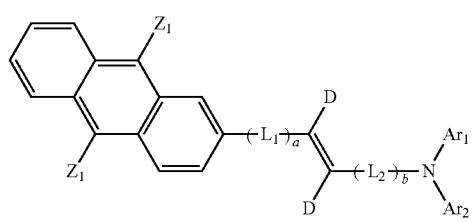

Formula 1C-1

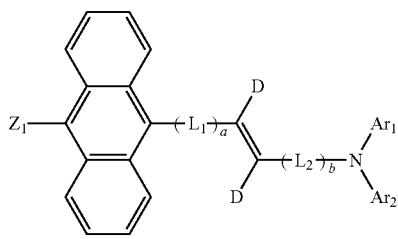

Formula 1C-2

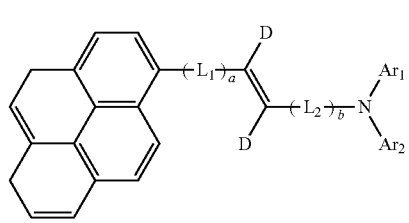

Formula 1D-1

-continued

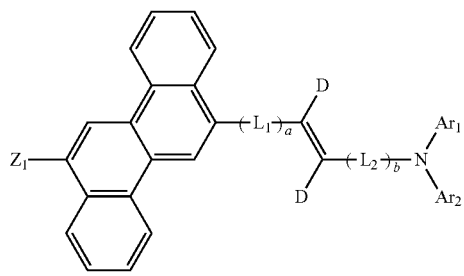
Formula 1E-1

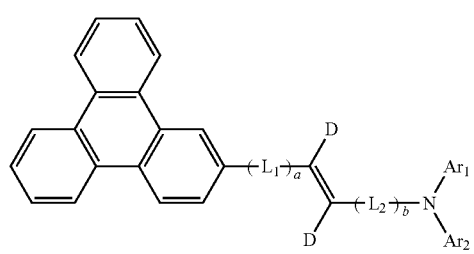
Formula 1F-1

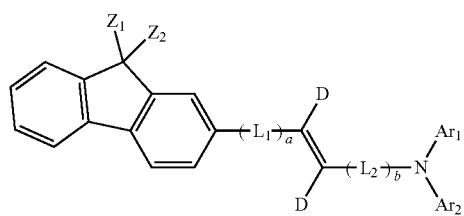
Formula 1G-1

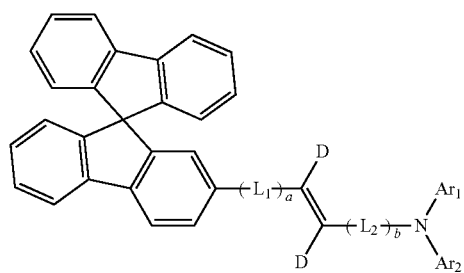
Formula 1G-2

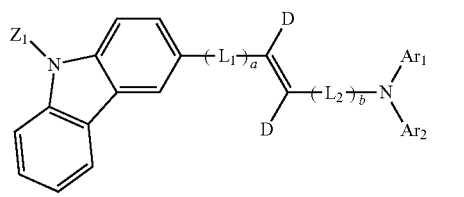
Formula 1H-1

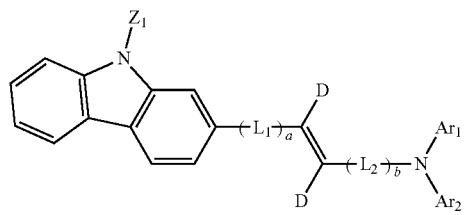
Formula 1H-2

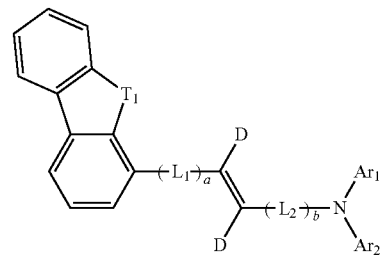
Formula 1I-1

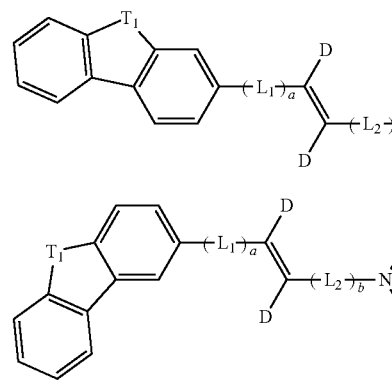
Formula 1I-2

Formula I-3

In Formula 1A-1 through 1I-3 above, detailed descriptions for $Z_1$, $Z_2$, $T_1$, $Ar_1$, $Ar_2$, $L_1$, $L_2$, a, and b are already provided above.

For example, in Formula 1A-1 through 1I-3 above, $Z_1$ and $Z_2$ may be each indecently selected from hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolinyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group; $T_1$ may be O or S; $Ar_1$ and $Ar_2$ may be each independently a substituted or unsubstituted phenyl group, a substituted or unsubstituted naphthyl group, a substituted or unsubstituted phenanthrenyl group, a substituted or unsubstituted pyrenyl group, a substituted or unsubstituted carbazolyl group, a substituted or unsubstituted fluorenyl group, a substituted or unsubstituted dibenzofuranyl group, a substituted or unsubstituted dibenzothiophenyl group, or a substituted or unsubstituted benzocarbazolyl group; $L_1$ and $L_2$ may be each independently a substituted or unsubstituted phenylenyl group, a substituted or unsubstituted naphthylene group, a substituted or unsubstituted fluorenylene group, a substituted or unsubstituted phenanthrenylene group, a substituted or unsubstituted pyridinylene group, or a substituted or unsubstituted pyrazinylene group; a is 0 or 1; and b is 1 or 2, but the present embodiment is not limited thereto.

For example, in Formulae 1A-1 through 1I-3 above, $Z_1$ and $Z_2$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a methyl group, an ethyl group, a propyl group, a butyl group, a pentyl group, a hexyl group, a heptyl group, an octyl group, a phenyl group, a naphthyl group, a fluorenyl group, a deuterated phenyl group, or a dimethylfluorenyl group; $T_1$ may be O or S; $Ar_t$ and $Ar_2$ may be each independently represented by any one of Formulae 2A through 2J above; $L_1$ and $L_2$ may be each independently represented by any one of Formulae 5A through 5K above; a may be 0 or 1; and b may be 1 or 2, but the present embodiment is not limited thereto.

The styryl-based compound represented by Formula 1 above may be, but is not limited to, any one of Compounds 1 through 95 and 101 through 182 below:

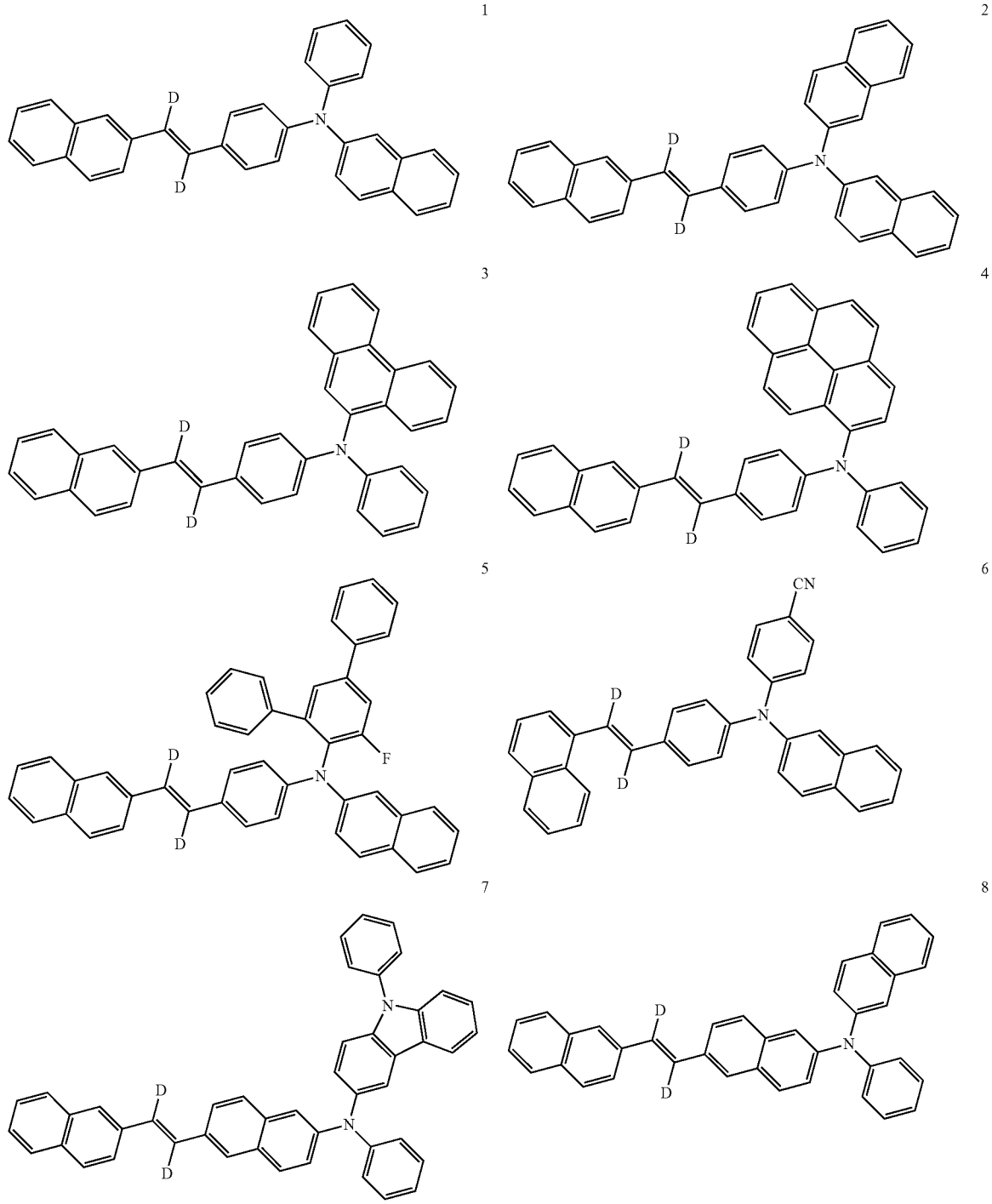

-continued
9
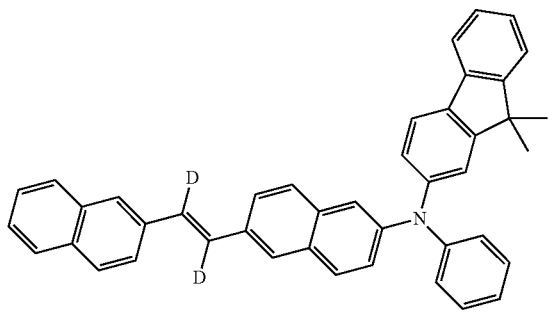
10
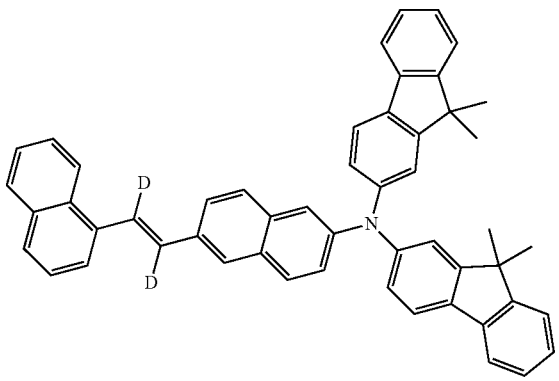
11
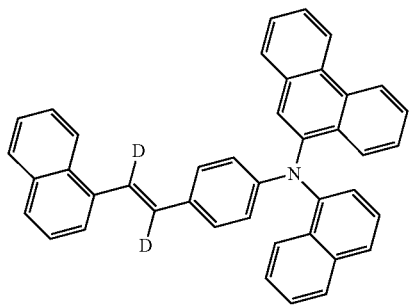
12
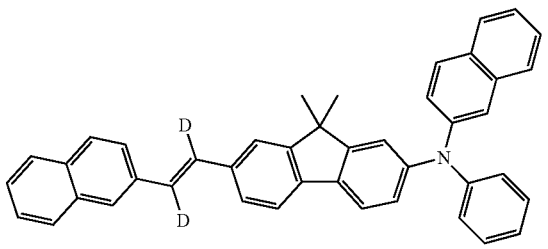
13
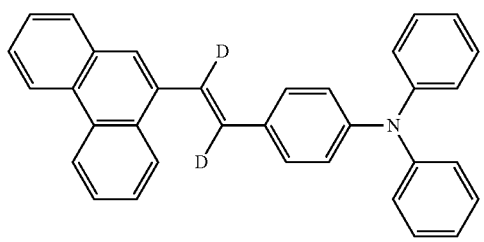
14
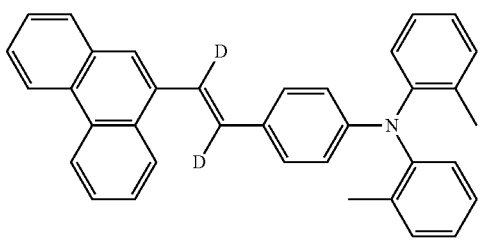
15
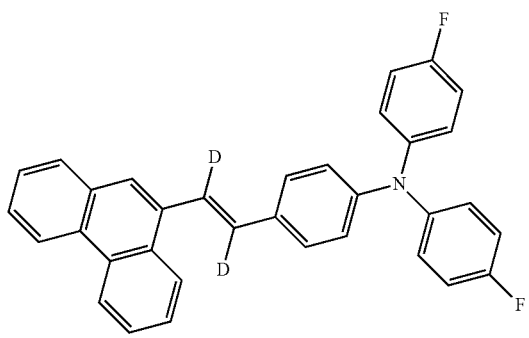
16
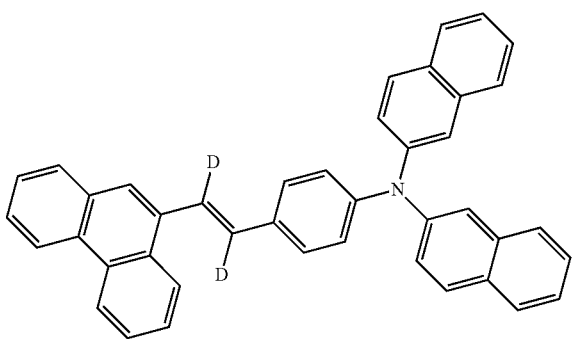

-continued
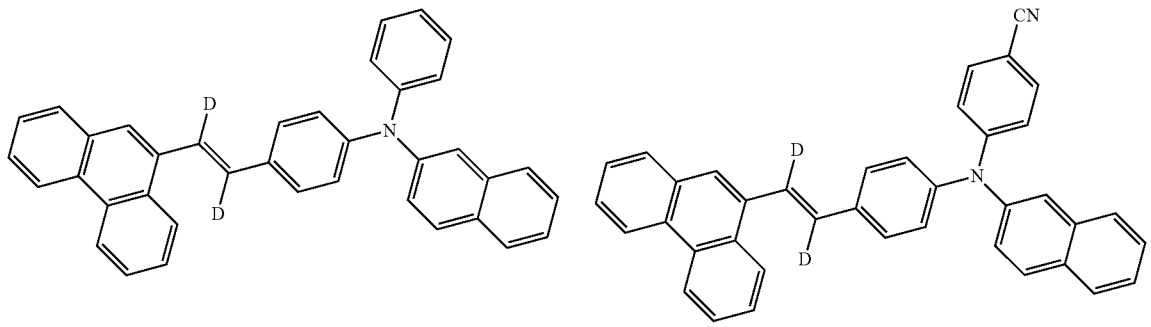
17
18
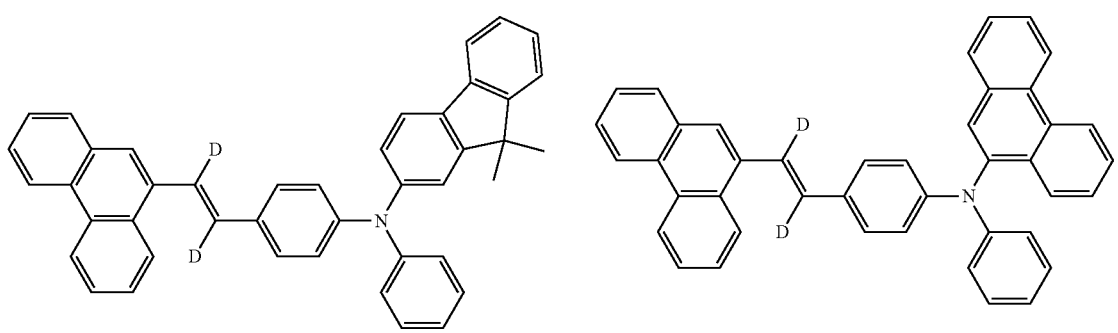
19
20
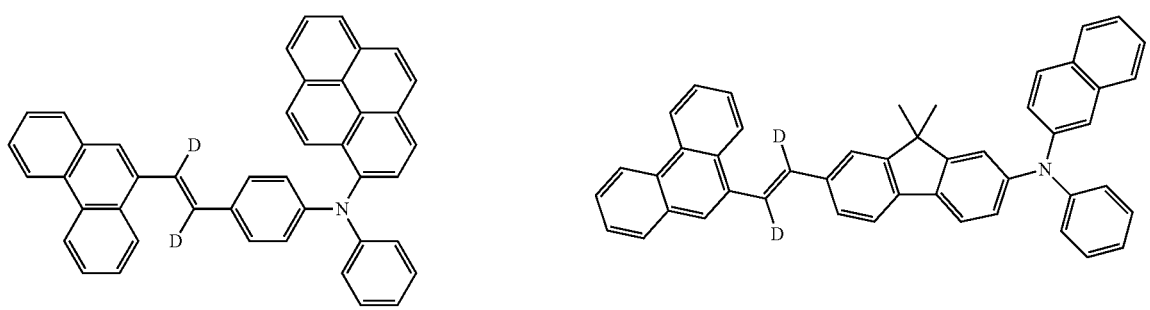
21
22
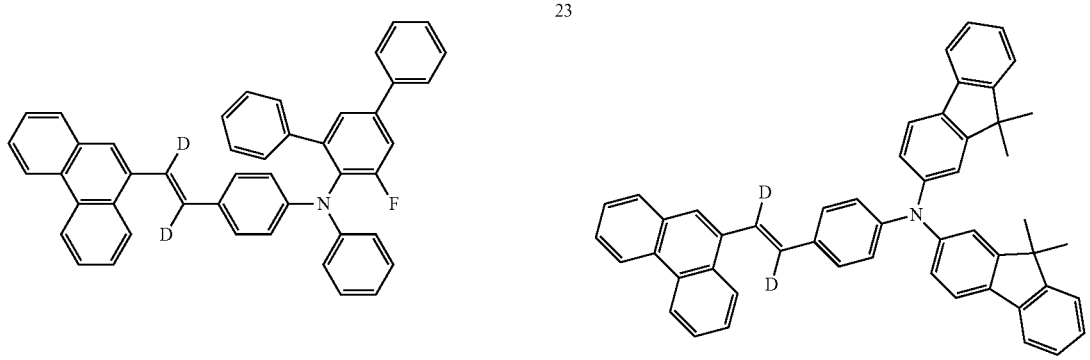
23
24

-continued
25
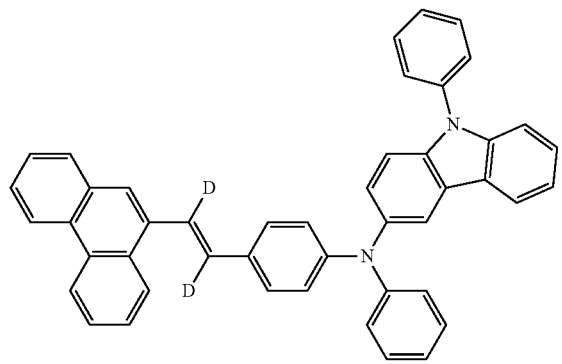
26
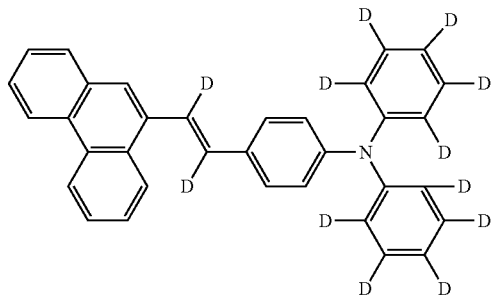
27
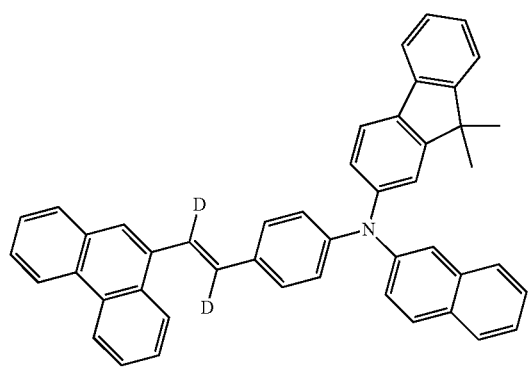
28
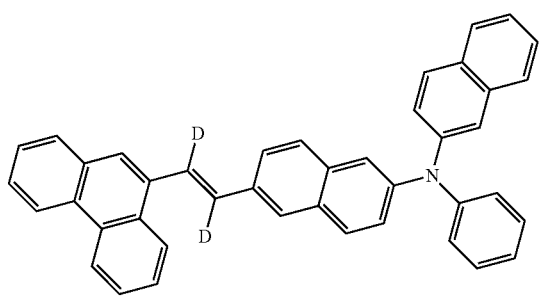
29
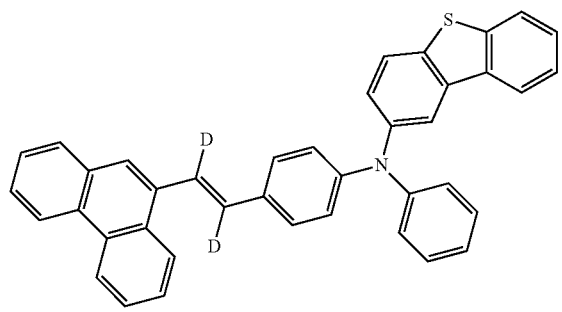
30
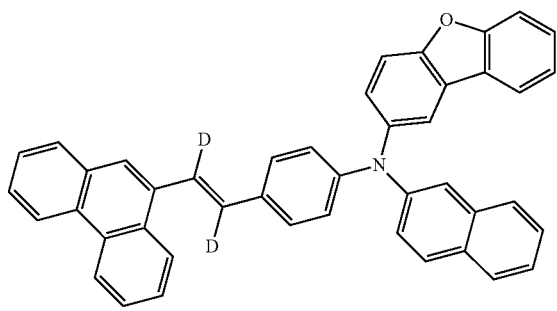
31
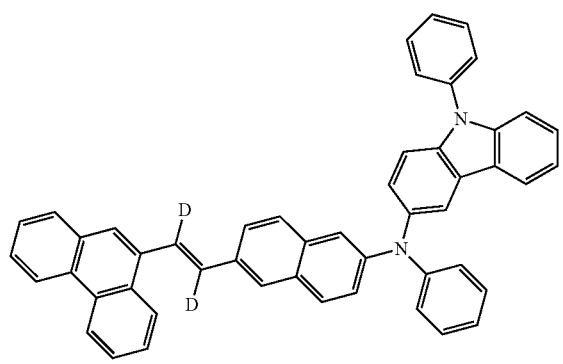
32
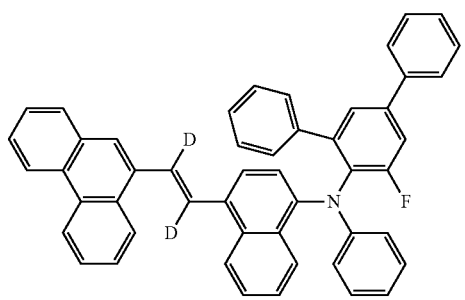

-continued
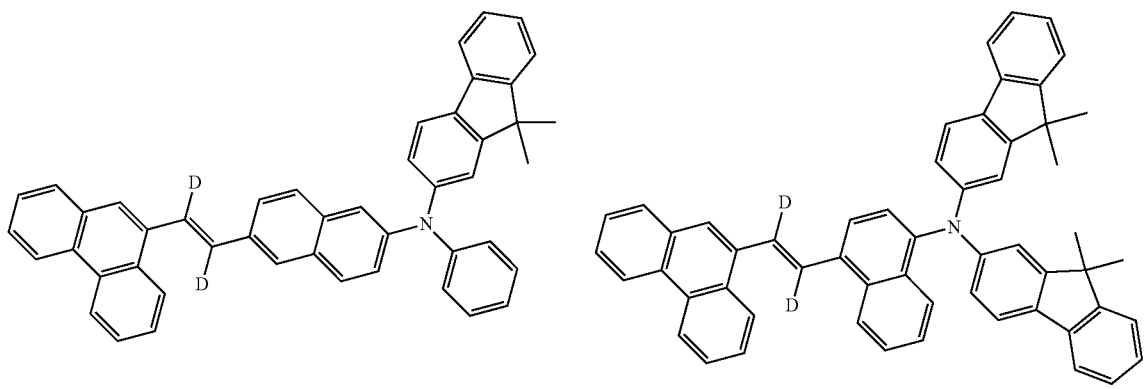
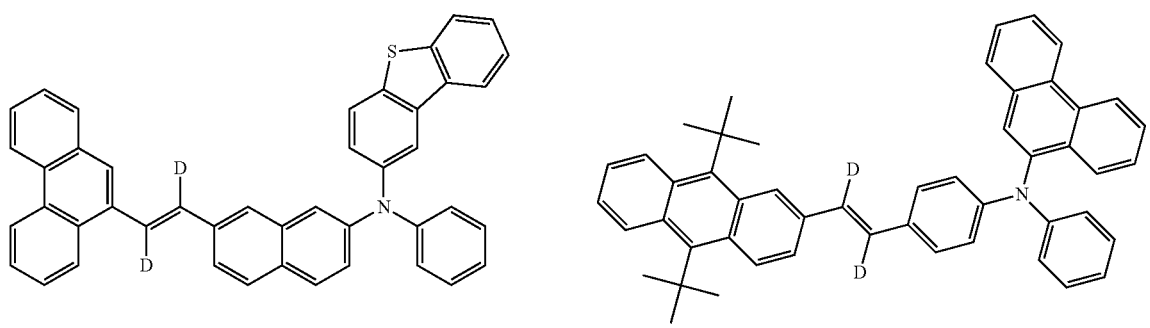
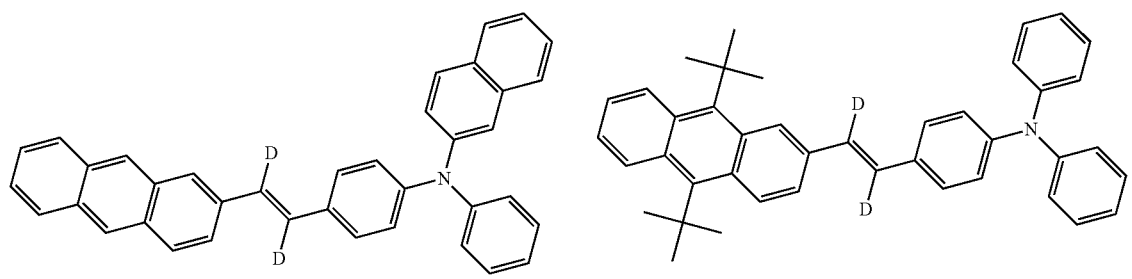
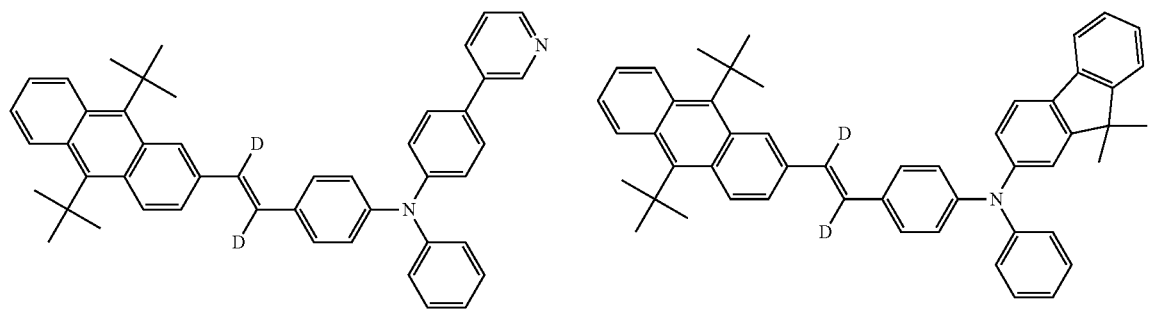

-continued
41
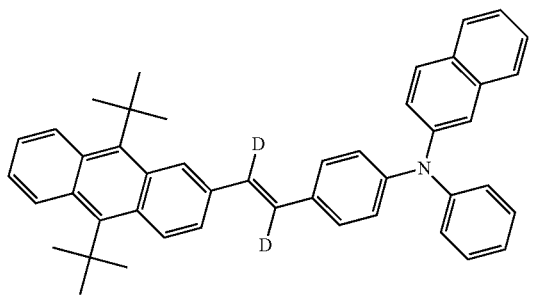
42
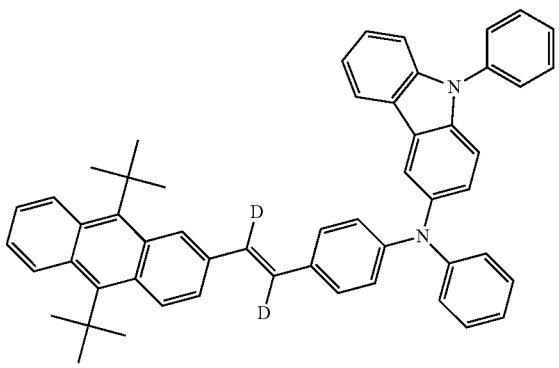
43
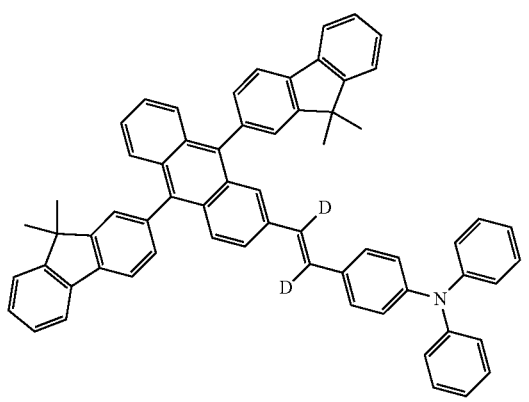
44
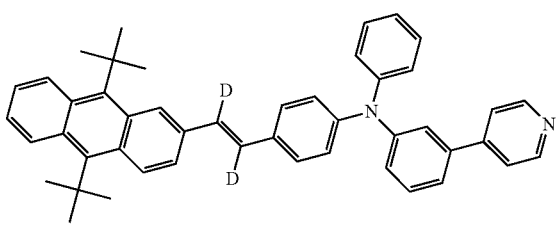
45
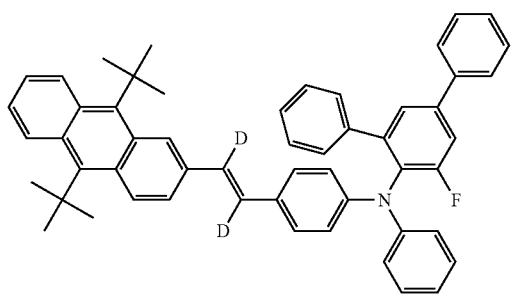
46
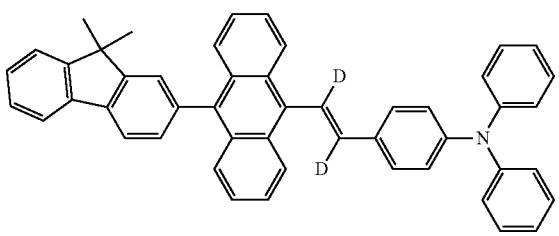
47
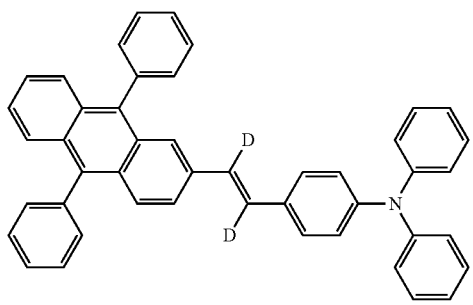
48
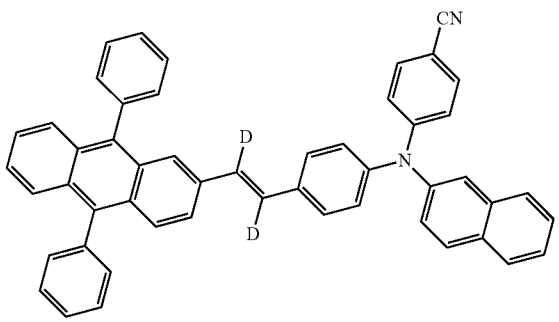

-continued
49
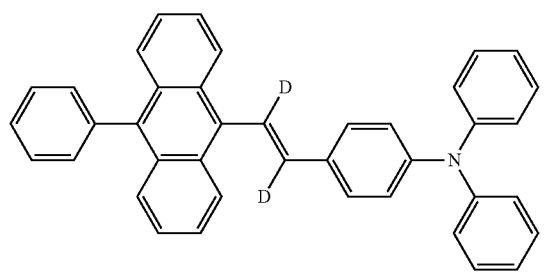
50
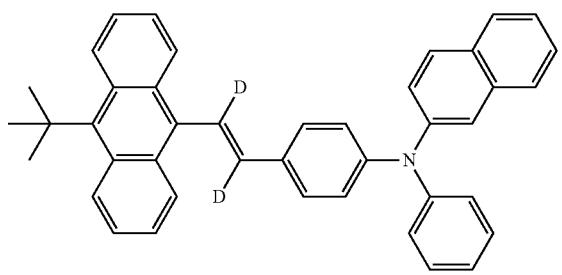
51
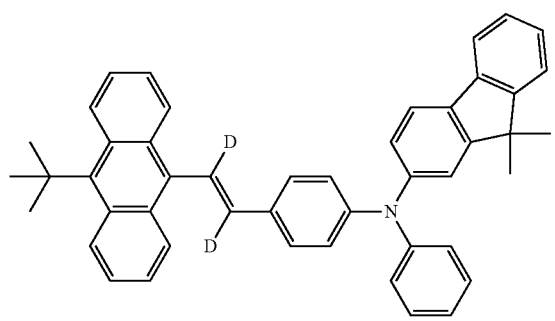
52
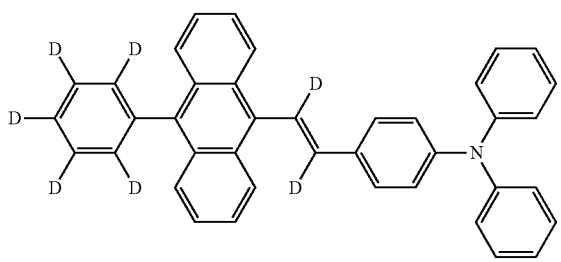
53
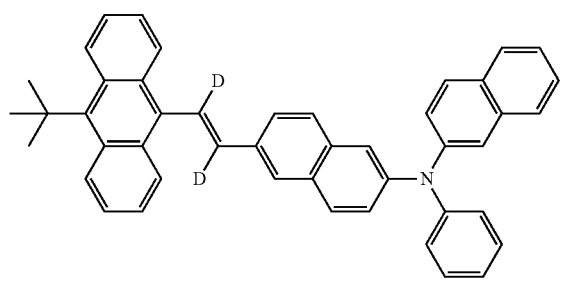
54
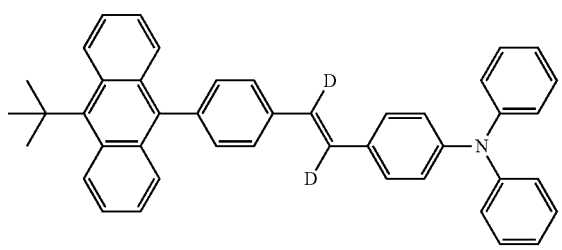
55
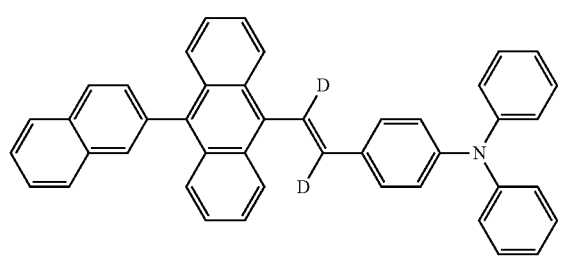
56
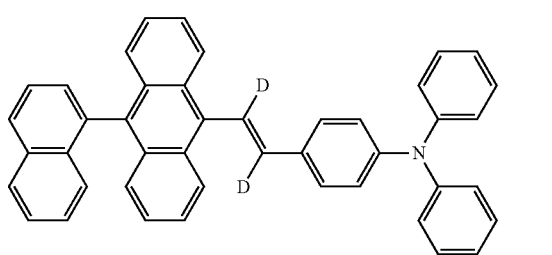
57
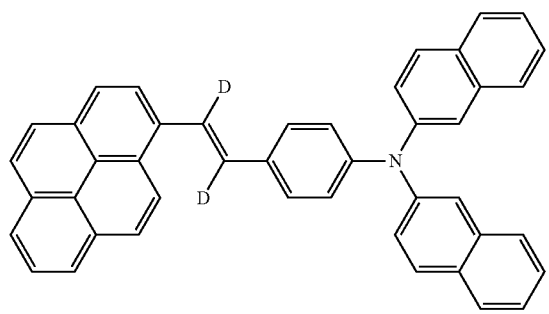
58
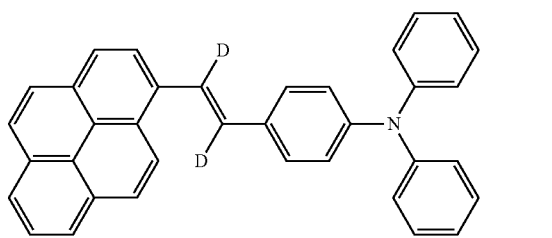

-continued
59
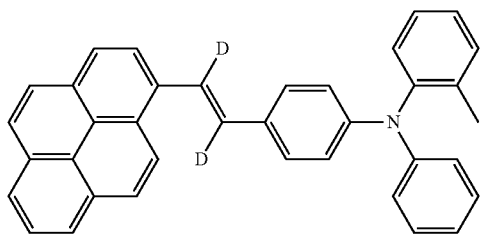
60
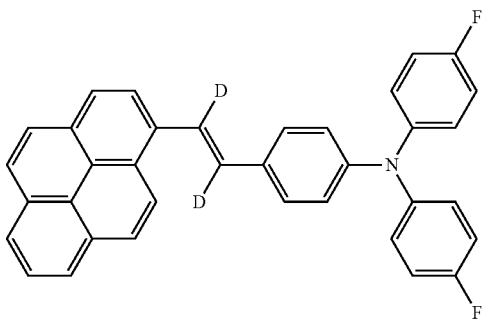
61
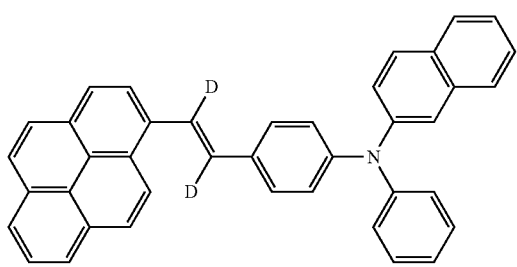
62
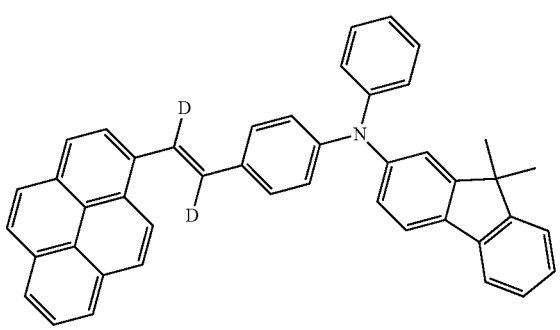
63
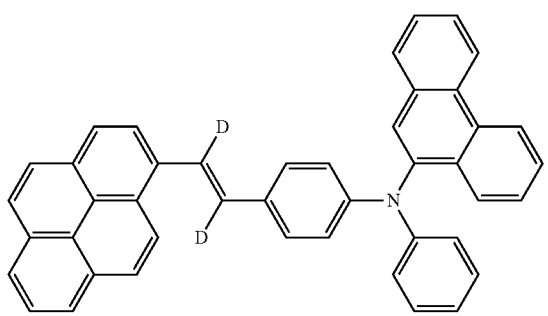
64
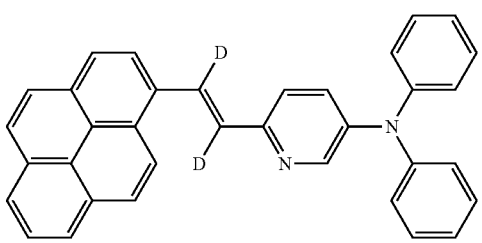
65
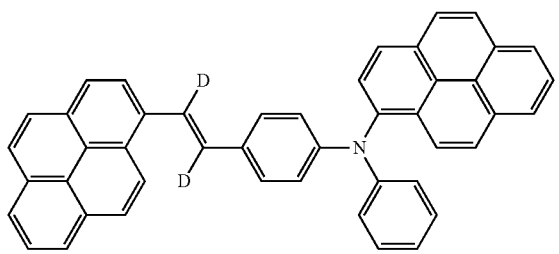
66
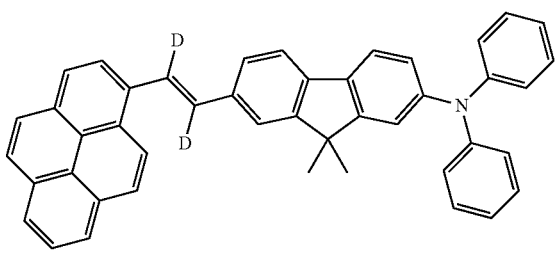
67
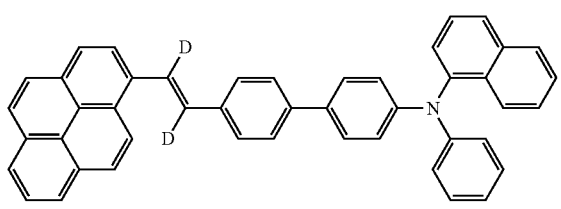
68
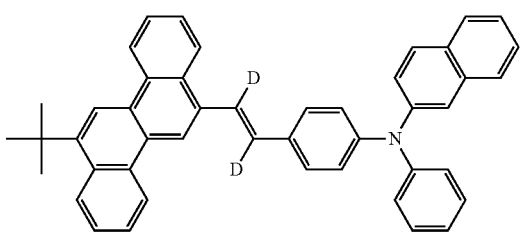

-continued
69
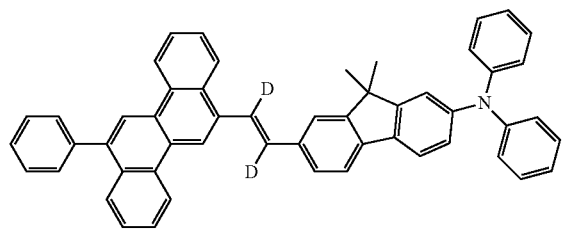
70
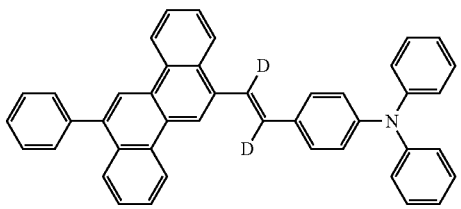
71
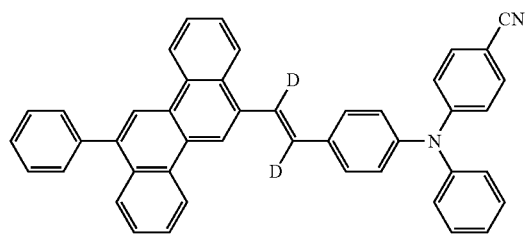
72
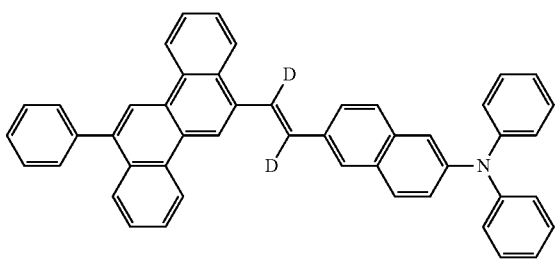
73
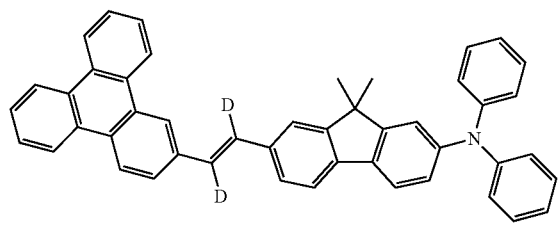
74
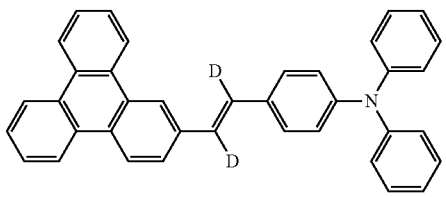
75
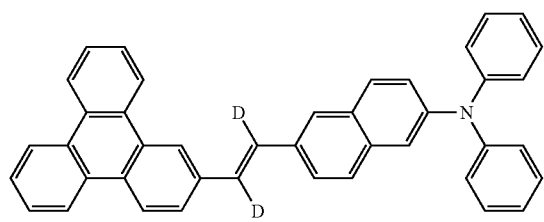
76
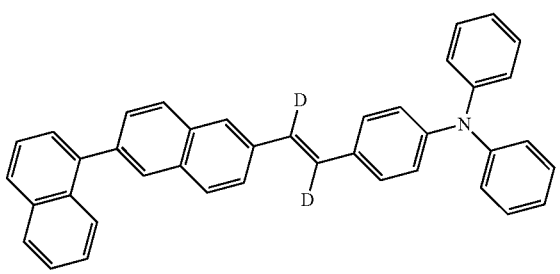
77
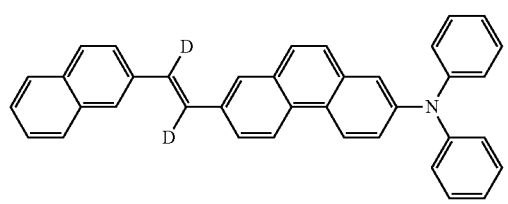
78
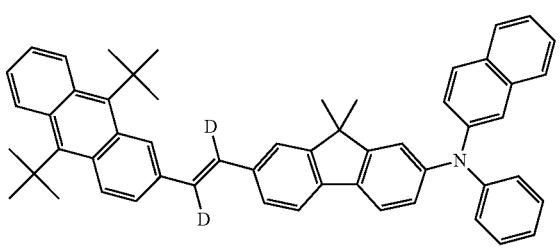
79
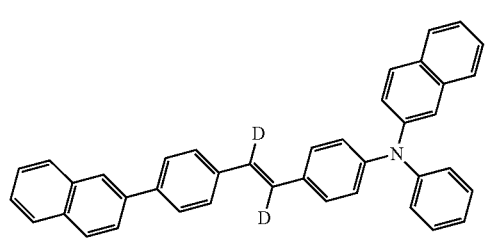
80
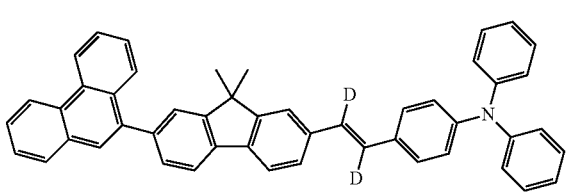

-continued
81
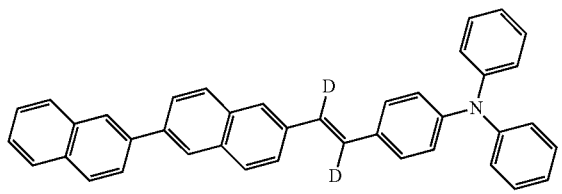
82
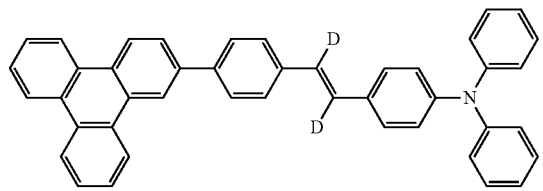
83
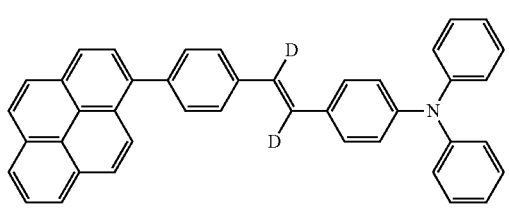
84
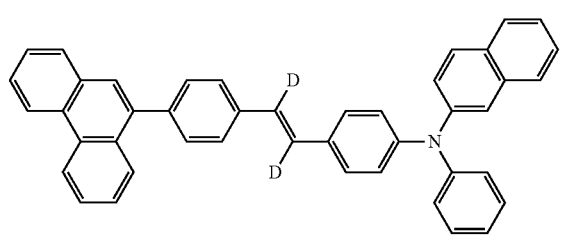
85
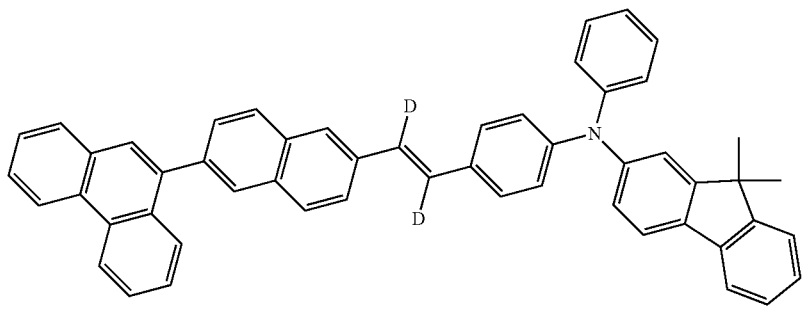
86
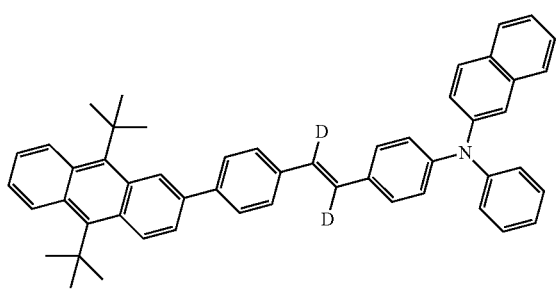
87
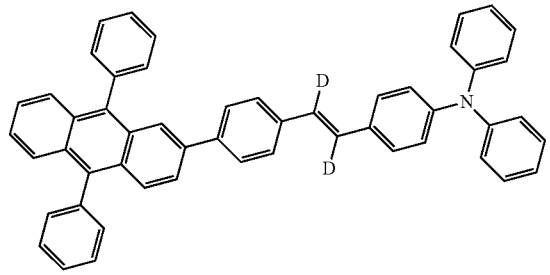
88
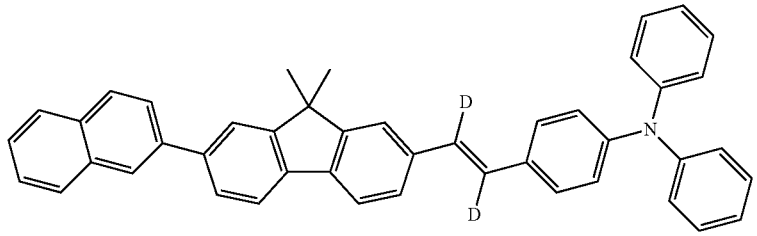
89
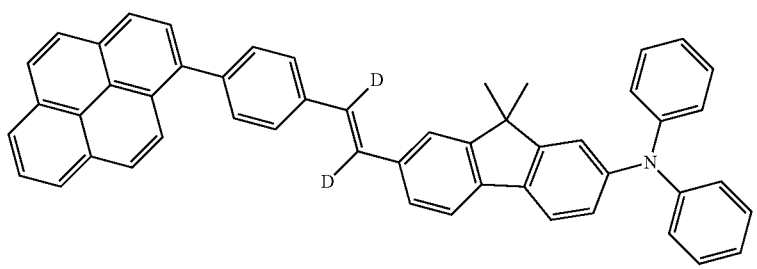

-continued
90
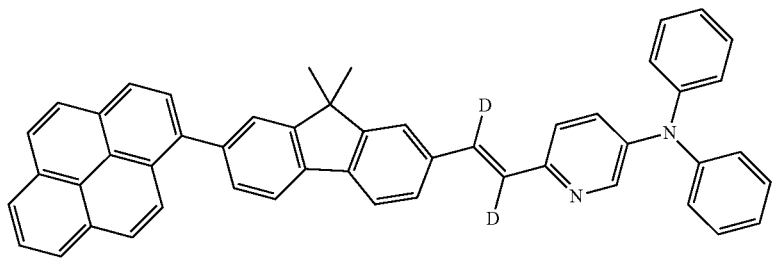
91
92
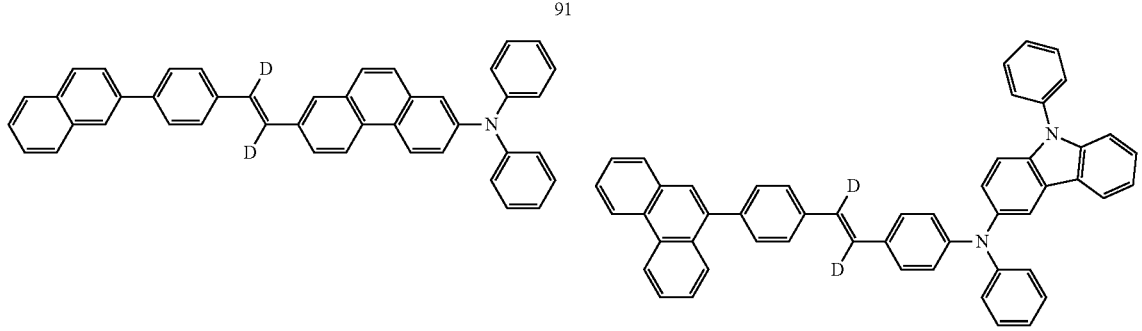
93
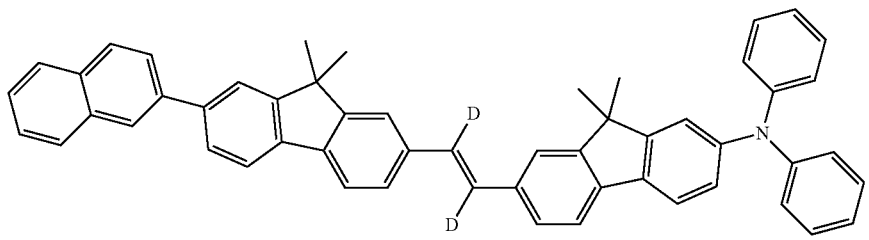
94
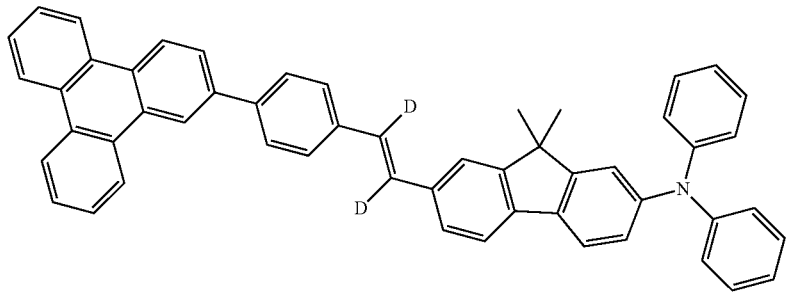
95
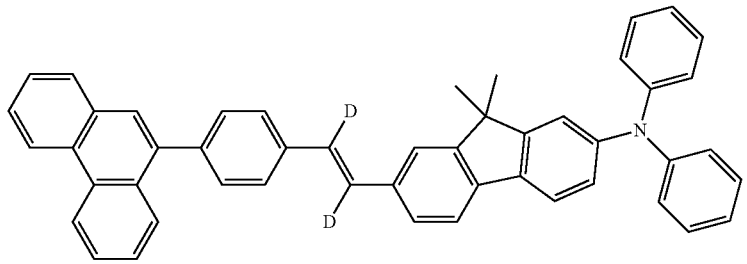

-continued
101
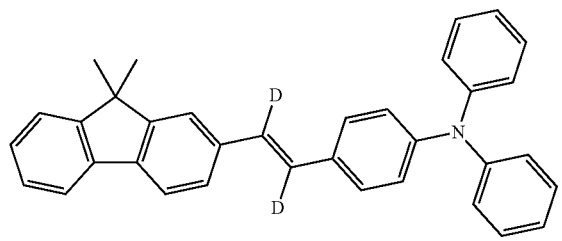
102
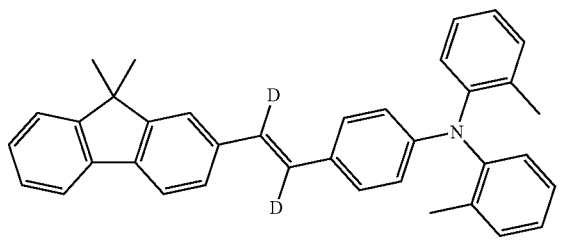
103
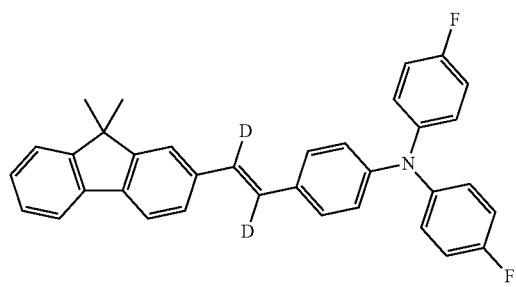
104
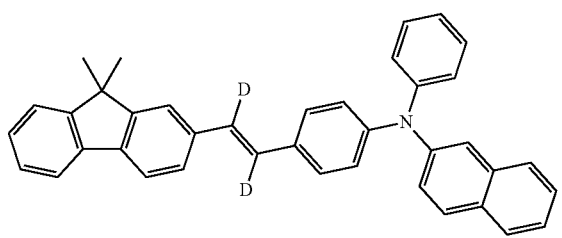
105
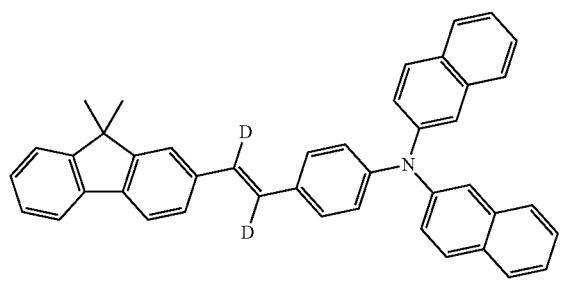
106
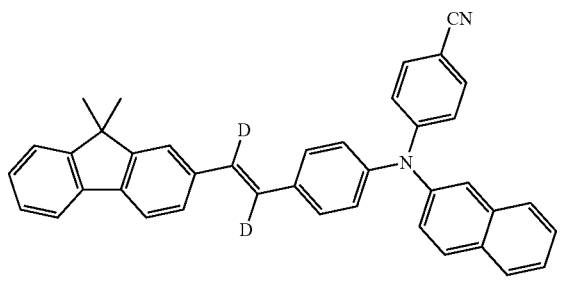
107
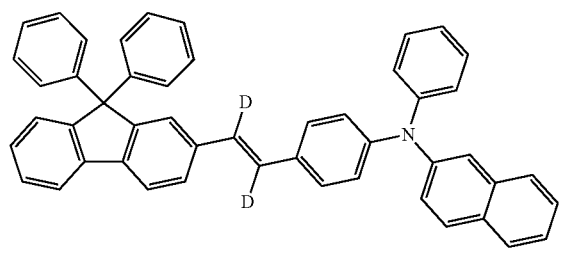
108
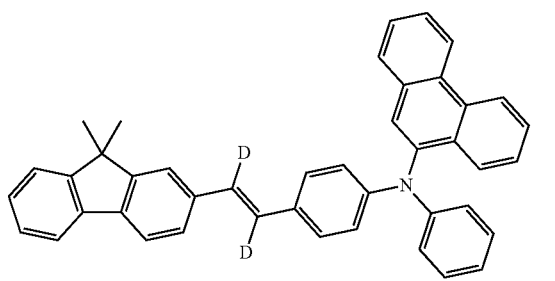
109
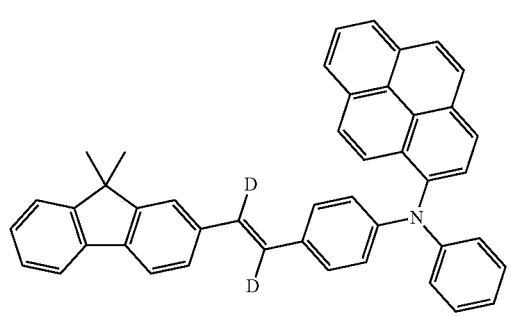
110
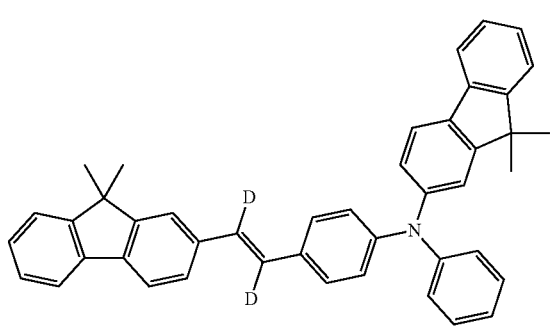

-continued
111
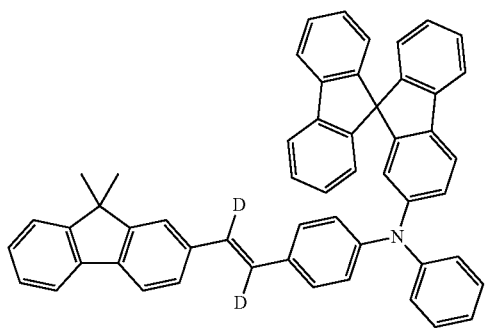
112
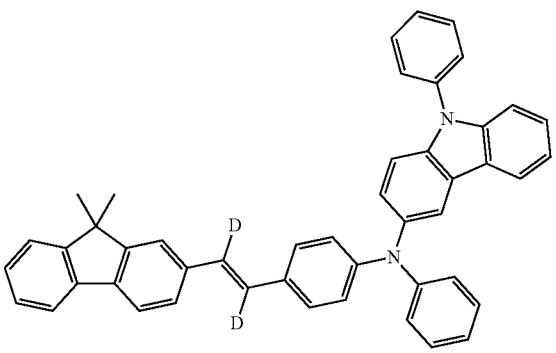
113
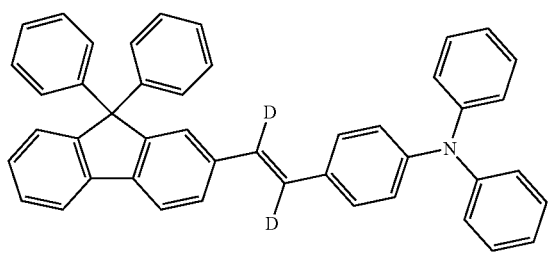
114
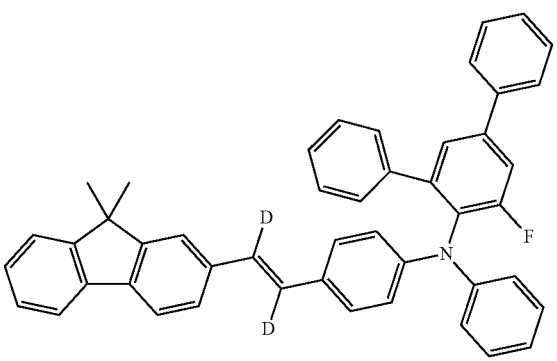
115
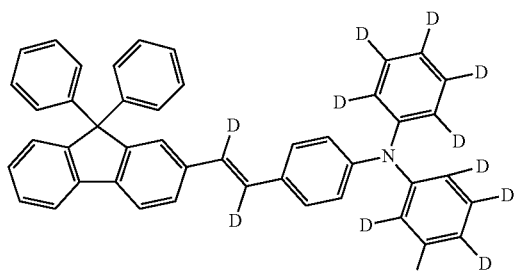
116
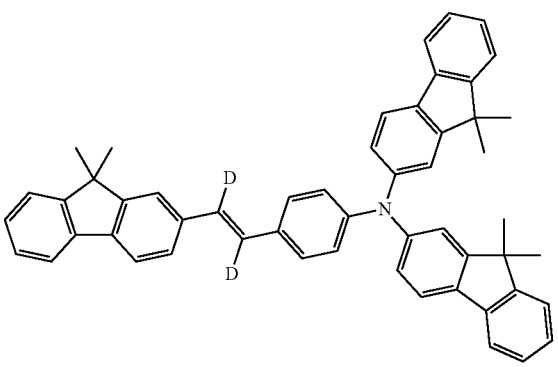
117
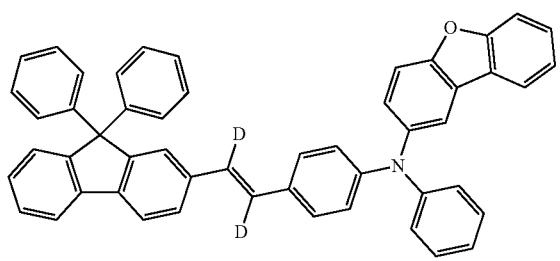
118
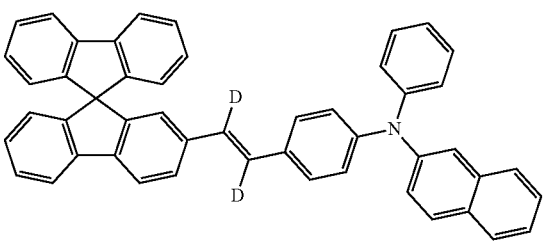

-continued
119
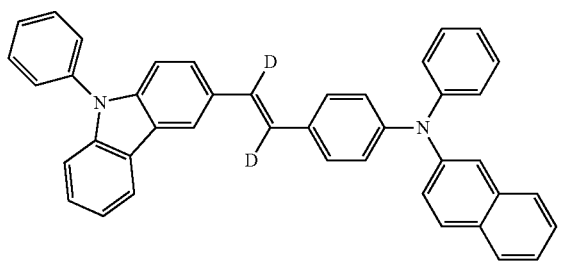
120
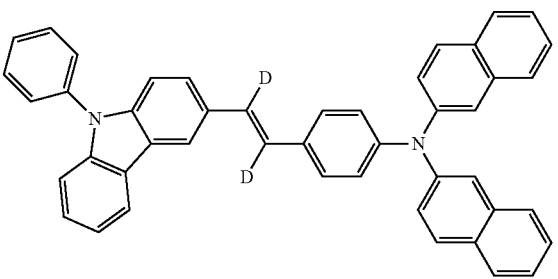
121
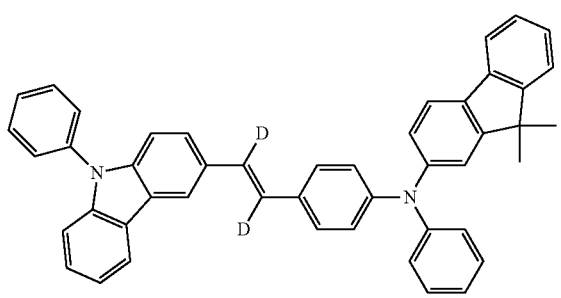
122
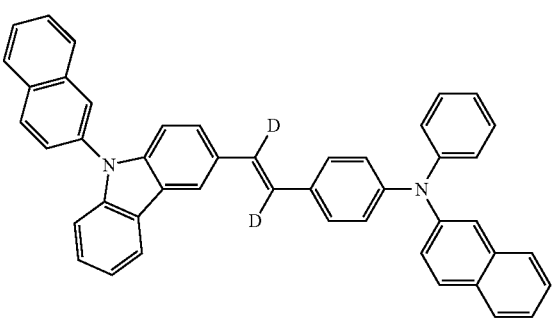
123
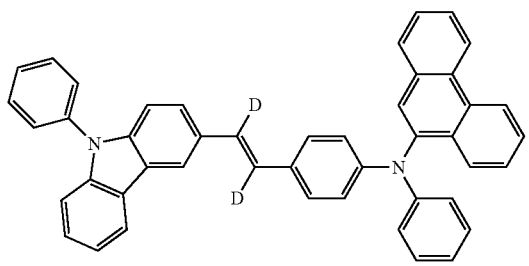
124
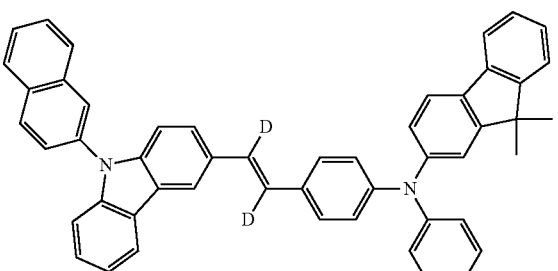
125
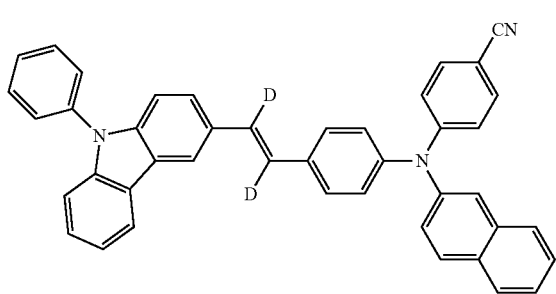
126
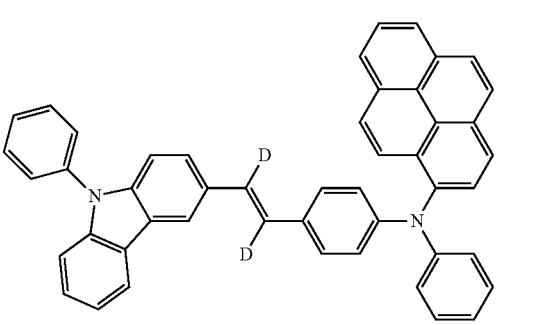
127
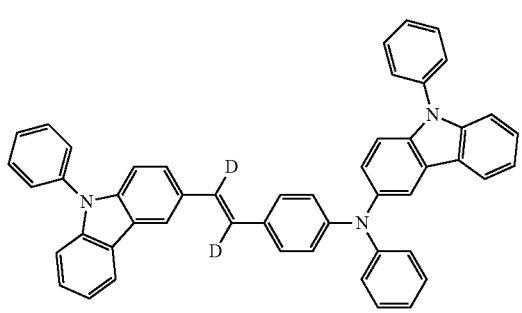
128
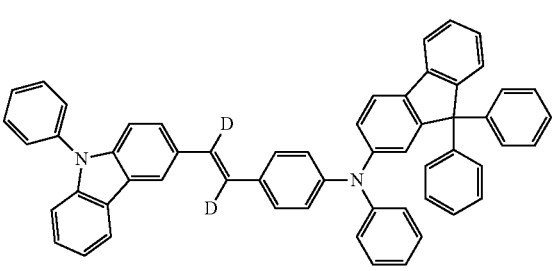

-continued
129
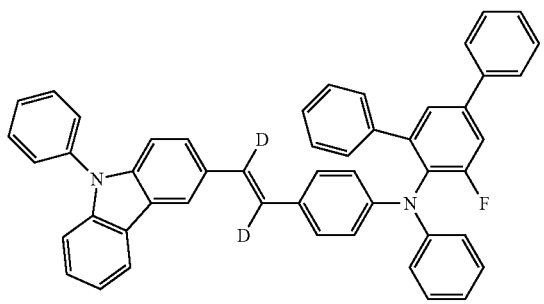
130
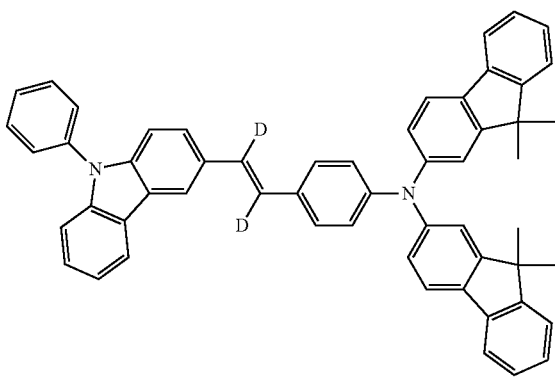
131
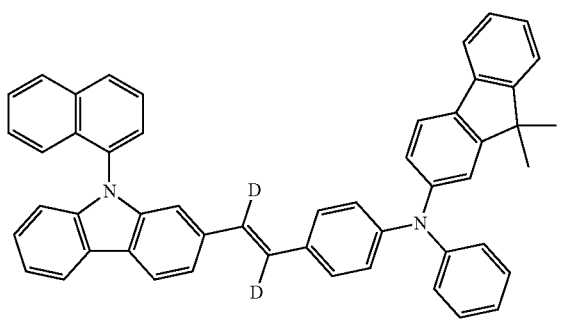
132
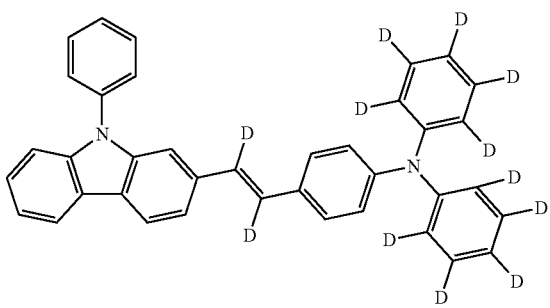
133
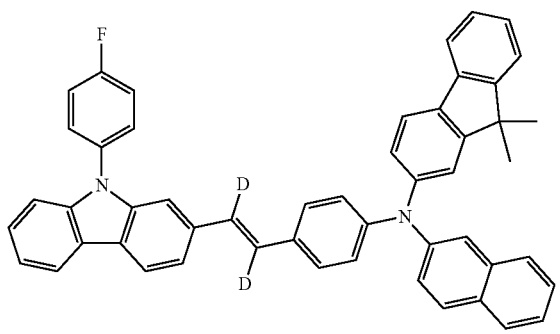
134
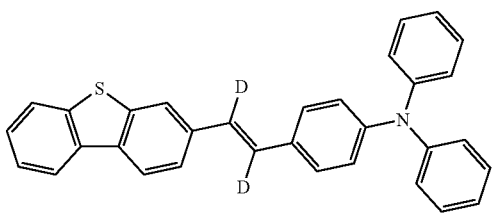
135
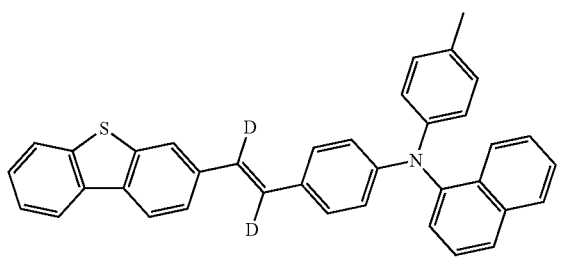
136
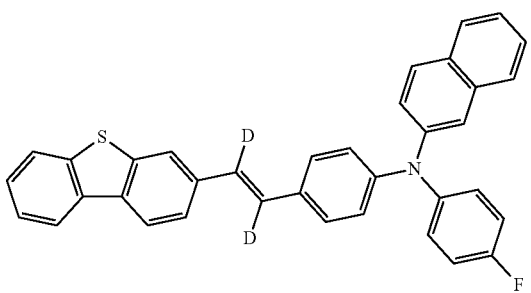

-continued
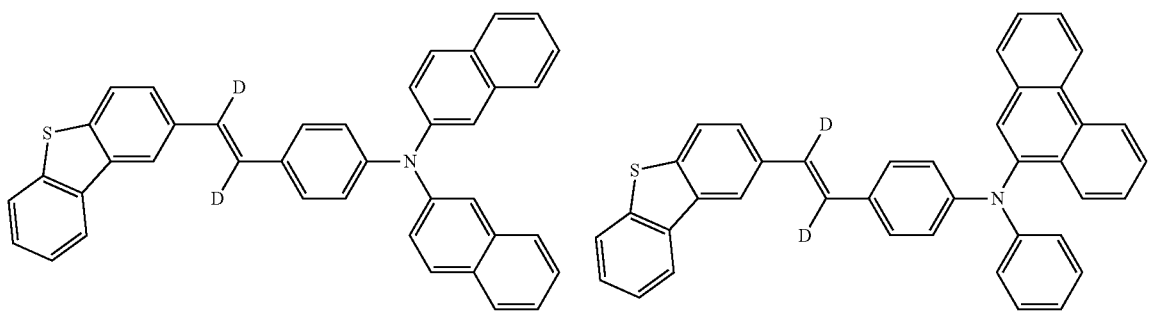
137  138
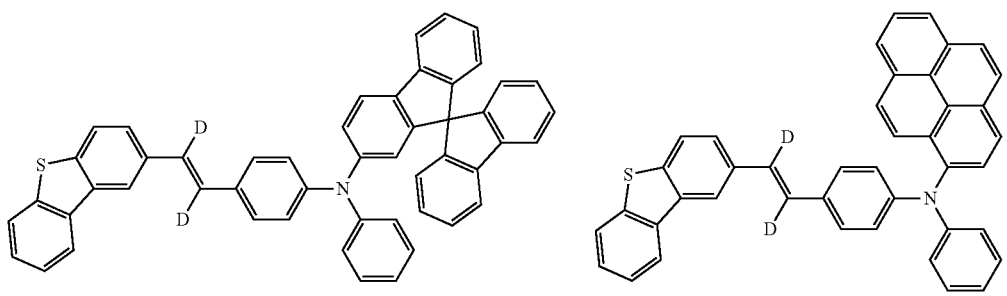
139  140
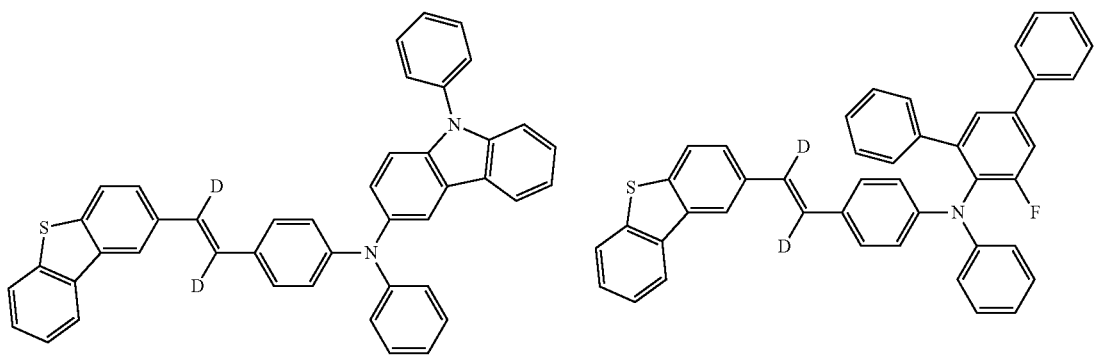
141  142
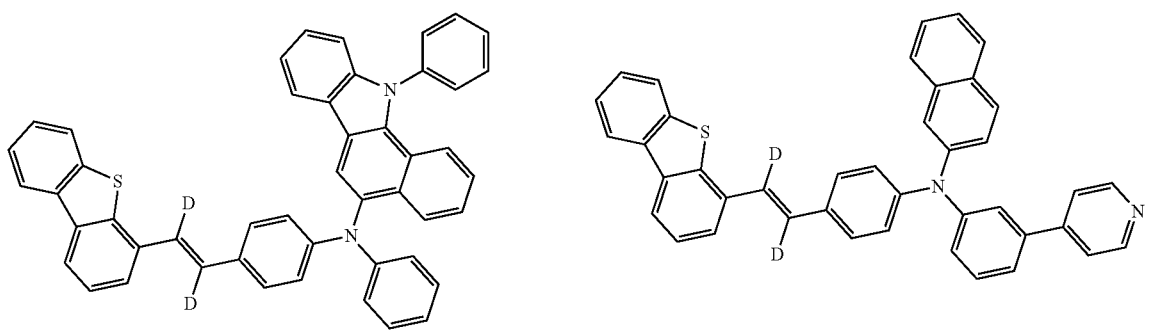
143  144

-continued
145
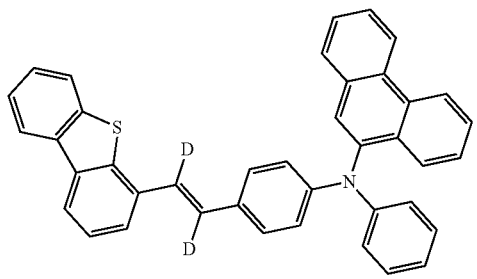
146
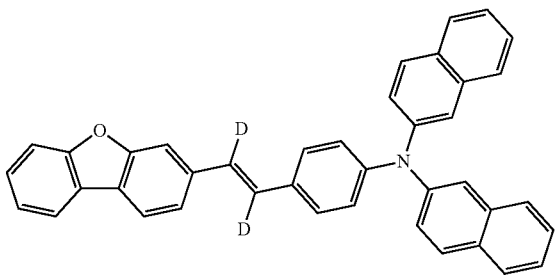
147
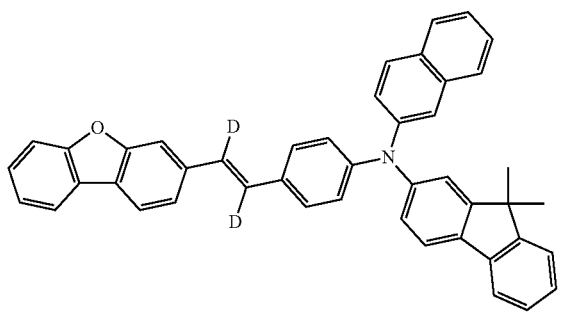
148
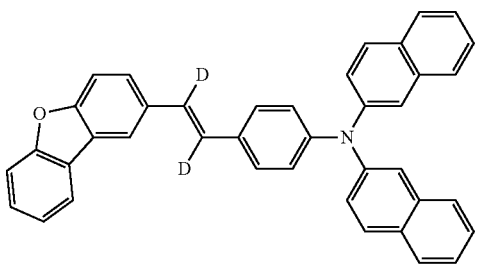
149
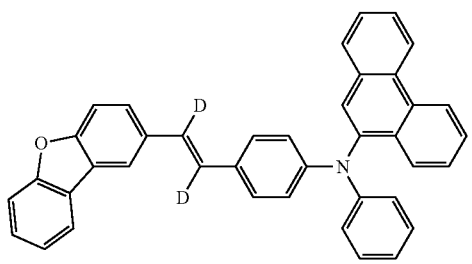
150
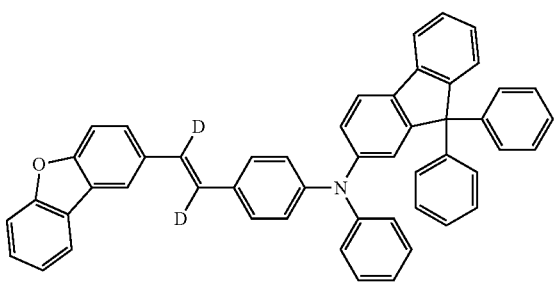
151
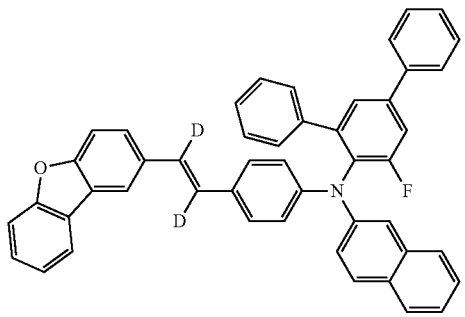
152
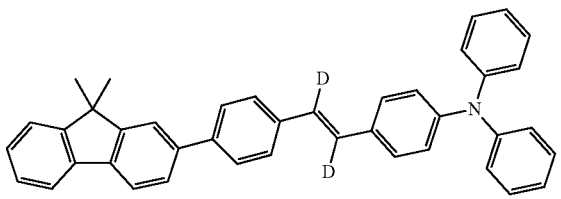
153
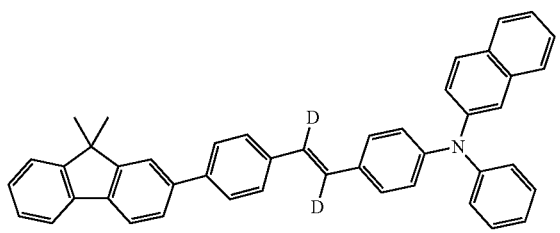
154
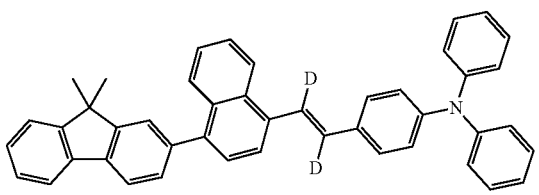

-continued
155
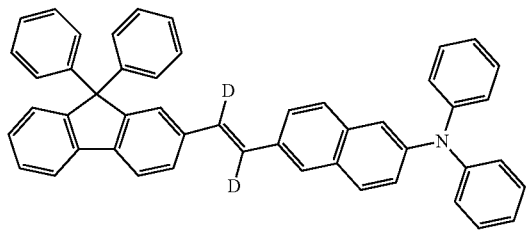
156
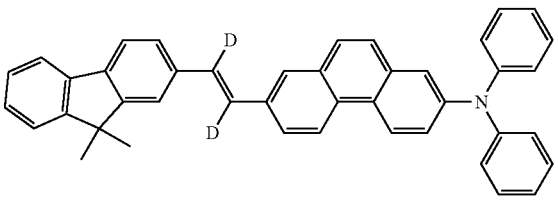
157
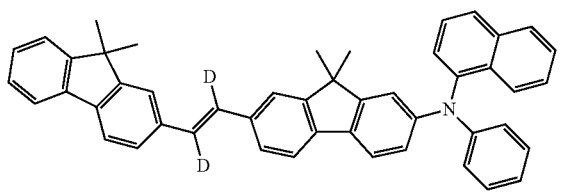
158
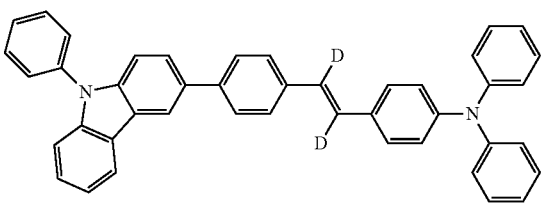
159
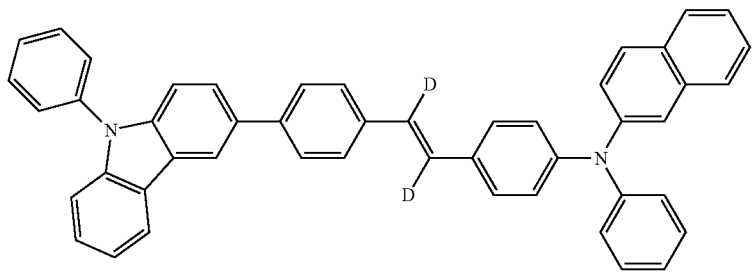
160
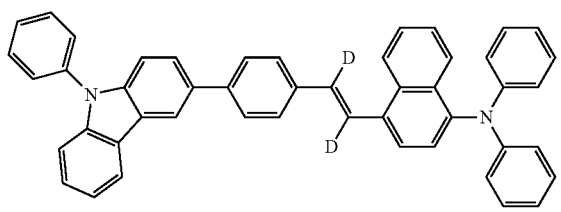
161
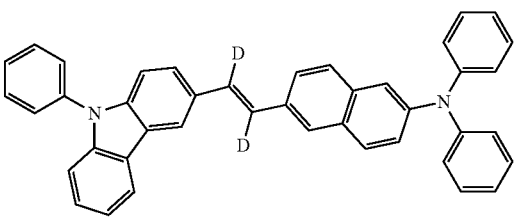
162
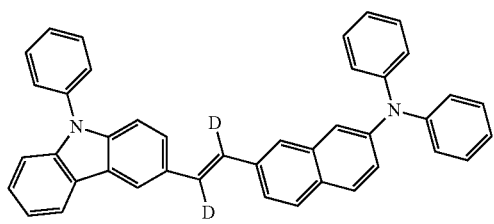
163
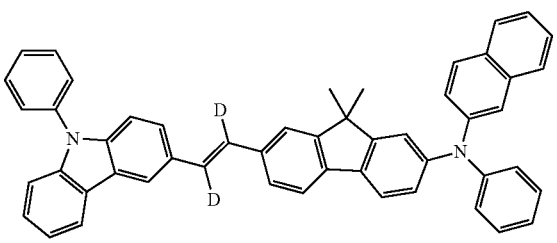
164
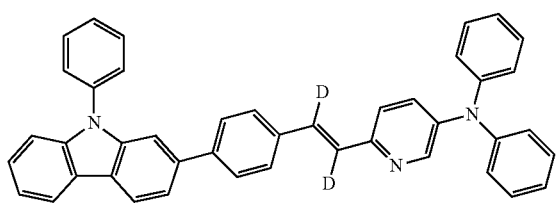
165
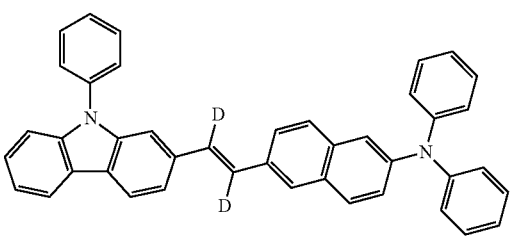

-continued
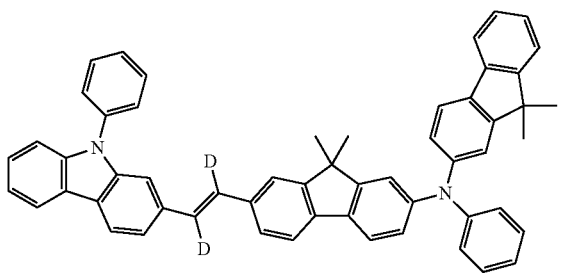
166
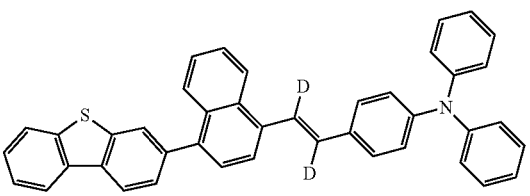
167
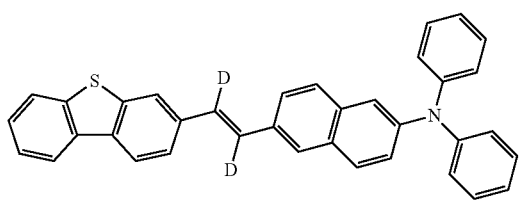
168
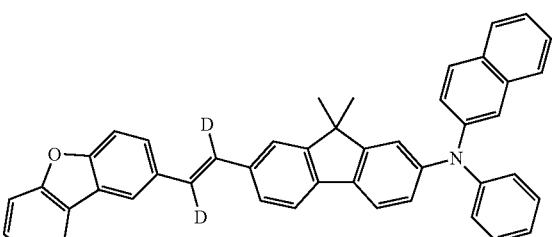
169
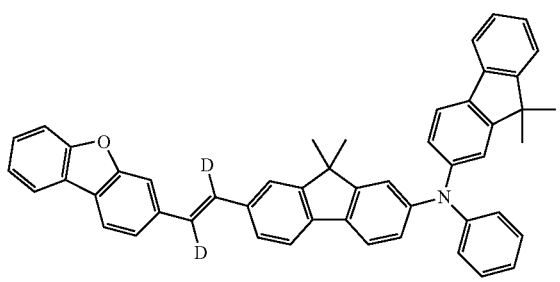
170
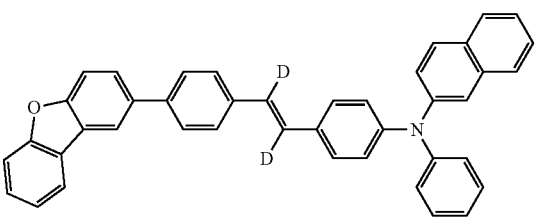
171
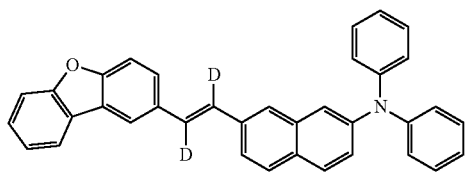
172
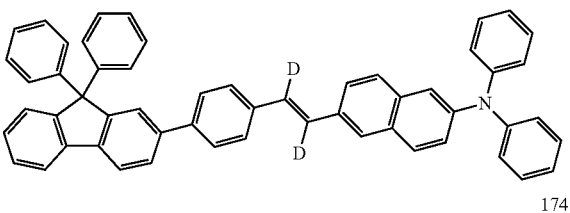
173
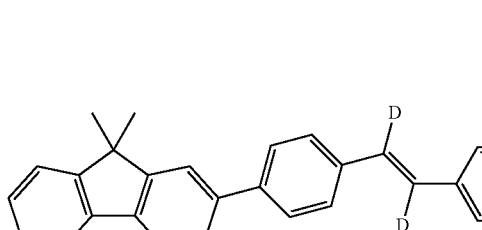
174
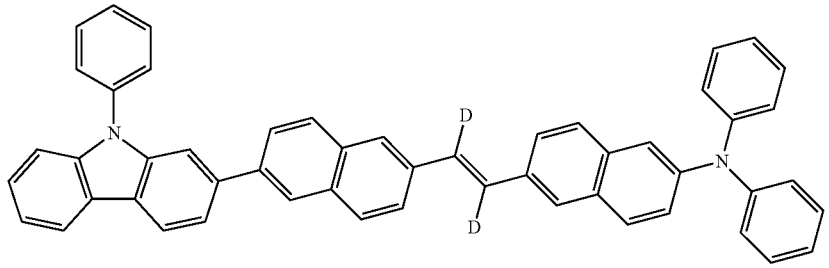
175

-continued
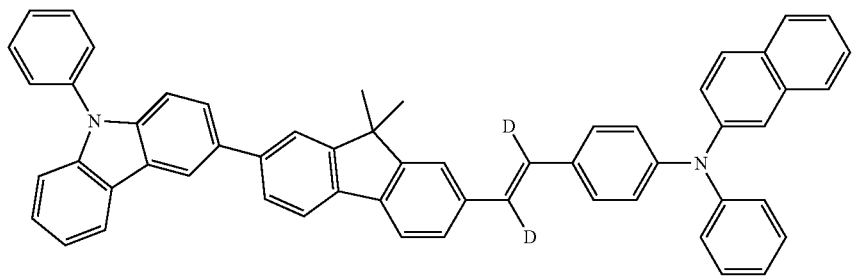
176
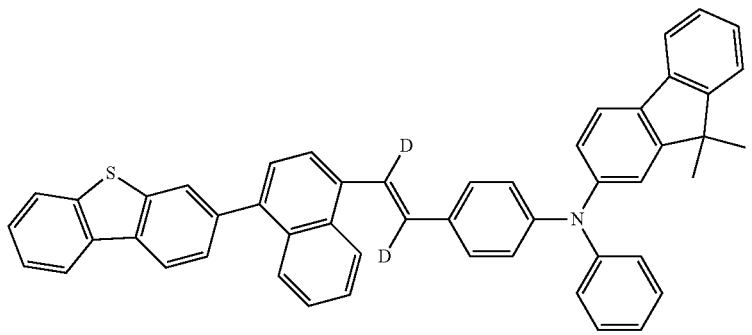
177
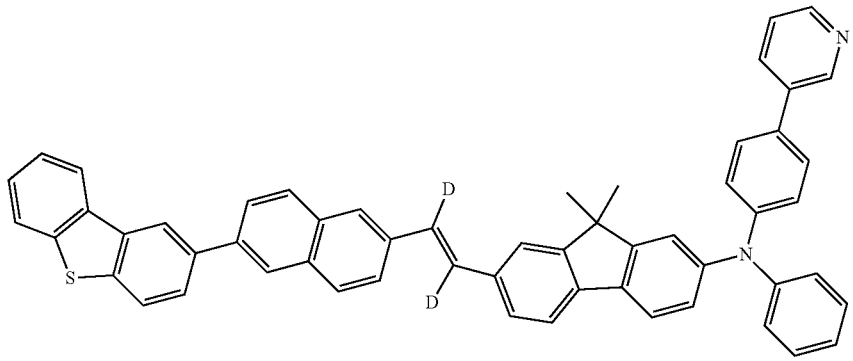
178
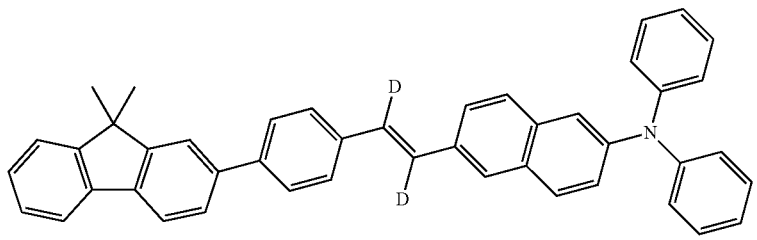
179
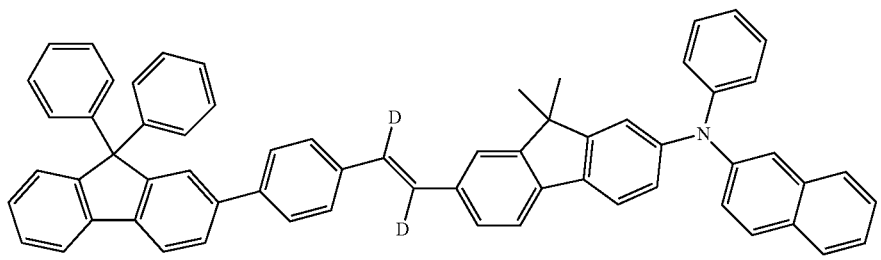
180

181

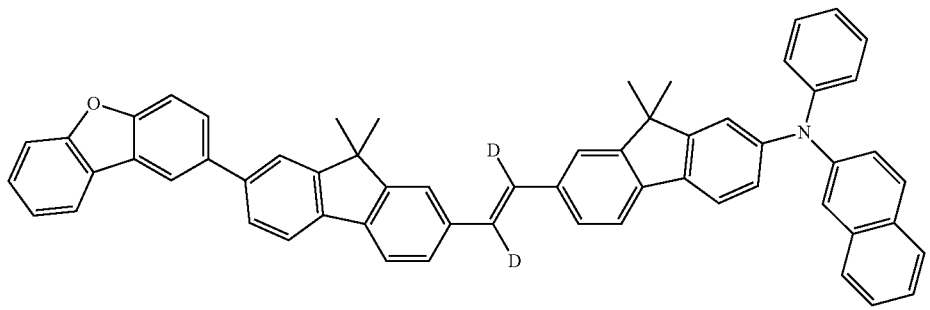

182

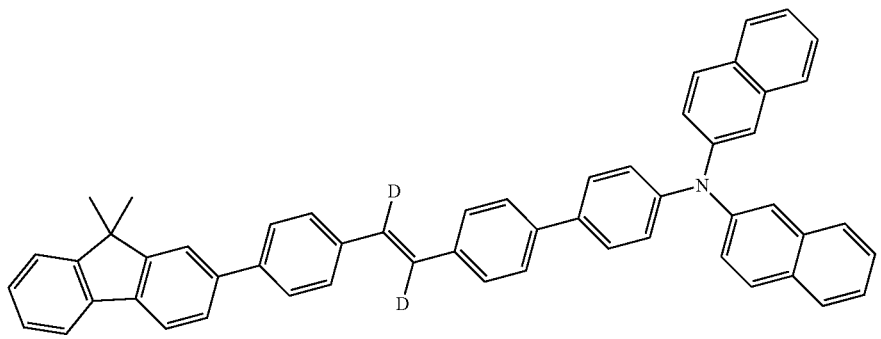

When the styryl-based compound represented by Formula 1 above is synthesized, 100% deuteration of a styryl group may not be performed and thus a compound in which one of two carbon atoms of the styryl group is not substituted with deuterium and/or a compound in which both two carbon atoms of the styryl group are not substituted with deuterium may be simultaneously synthesized. Thus, a composition containing a styryl-based compound according to an embodiment of the present invention may include the styryl-based compound represented by Formula 1 above and may also include at least one of a styryl-based compound represented by Formula 1-1H-1 below, a styryl-based compound represented by Formula 1-1H-2 below, and a styryl-based compound represented by Formula 1-2H below:

Formula 1-1H-1
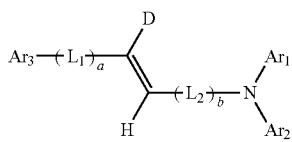

Formula 1-H-2
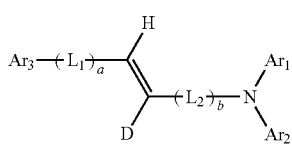

Formula 1-2H
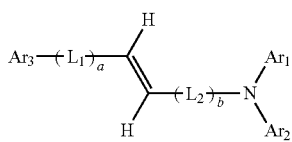

A detailed description of substituents of Formula 1-1H-1, 1-1H-2, and 1-2H above is already provided above.

For example, when Compound 3 is synthesized, i) only Compound 3 may be obtained, or ii) a composition including Compound 3 and at least one of Compounds 3-1H-1, 3-1H-2, and 3-2H may be obtained:

Compound 3
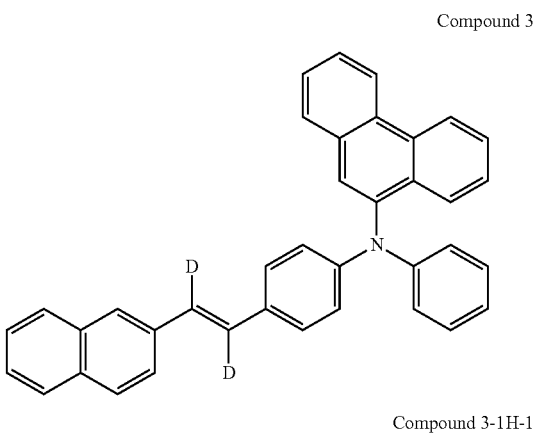

Compound 3-1H-1
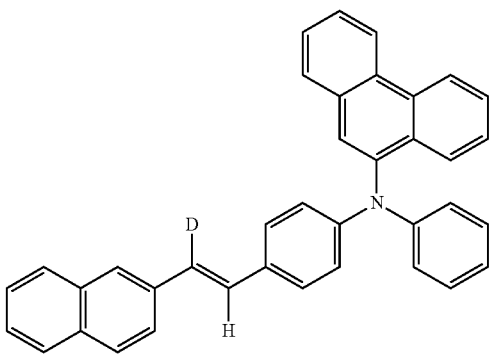

Compound 3-1H-2

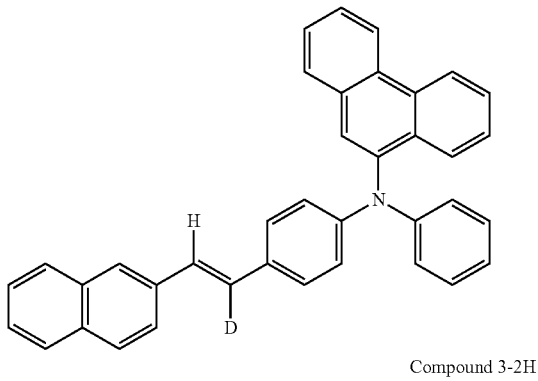

Compound 3-2H

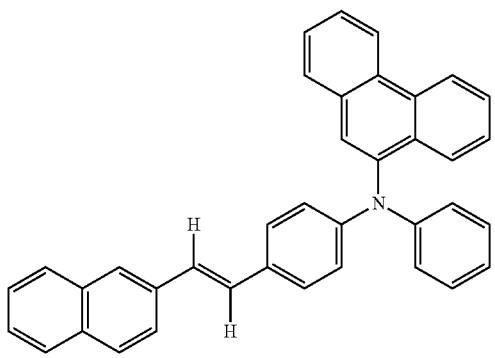

A deuterium substitution rate of the composition may be defined according to Equation 1 below and may be 70% or more:

Deuterium substitution rate(%)=$N_D/N_{D+H}\times100$ (1)

In Equation 1 above, $N_D$ is the number of deuterium atoms bonded to carbon atoms of the styryl group in Formulae 1, 1-1H-1, and 1-1H-2 above; and $N_{D+H}$ is the total number of deuterium atoms and hydrogen atoms that are bonded to carbon atoms of the styryl group in Formulae 1, 1-1H-1, 1-1H-2, and 1-2H above.

When the deuterium substitution rate of the composition is 70% or more, an organic light-emitting diode (OLED) including an organic layer including the composition may exhibit low driving voltage, high efficiency, high brightness, long lifetime, and the like due to the styryl-based compound of Formula 1 above, which will be described later.

For example, the deuterium substitution rate of the composition may be, but is not limited to, 75% or more, 80% or more, 85% or more, 90% or more, or 95% or more.

For example, the deuterium substitution rate of the composition may be, but is not limited to, 96% or more, 97% or more, 98% or more, or 99% or more.

When an OLED including a compound having a styryl group (that is, —CH═CH—) having a carbon-carbon double bond is stored and/or operated, the styryl group may have low resistance to Joule's heat or an electric field that is generated between organic layers, inside the organic layers, and/or between one of the organic layers and one of the electrodes and may have low resistance to heat provided during sublimation refinement or vapor deposition of a compound. Thus, a single bond of carbon-hydrogen, which is connected to a double bond in a styryl group exposed to heat and/or an electric field, may be weakened and may be disconnected in the form of radical. However, since a single bond of carbon-deuterium is about 7 times greater than a single bond of carbon-hydrogen, a styryl group having a single bond of carbon-deuterium may have a stable structure. Since carbon is connected to deuterium by a single bond (refer to an ellipse indicated by dotted lines of Formula 1' below) in the styryl group of the styryl-based compound represented by Formula 1 above, although the styryl group is exposed to heat and/or an electric field, a single bond of carbon-deuterium may be effectively maintained according to a kinetic isotope effect:

Formula 1'

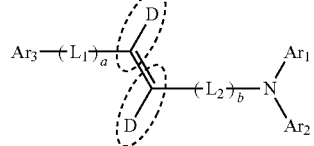

Thus, although the styryl-based compound represented by Formula 1 above is exposed to heat and/or an electric field when an OLED including the same, since radicalization of a fully deuterated styryl group (i.e., -DC═CD-) of Formula 1 above is remarkably delayed compared to radicalization of a styryl group without deuterium (i.e., —CH═CH—), a structure of the styryl-based compound represented by Formula 1 may be maintained. Thus, an OLED including the styryl-based compound represented by Formula 1 may have low driving voltage, high efficiency high brightness, and long lifetime.

The styryl-based compound of Formula 1 and a composition including the same may be synthesized using a known organic synthesis method. The synthesis method of the styryl-based compound of Formula 1 may be easily understood by one of ordinary skill in the art with reference to Examples, which will be described later. The composition including the styryl-based compound represented by Formula 1 and at least one of the compounds represented by Formula 1-1H-1, Formula 1-1H-2, and Formula 1-2H may be obtained when a styryl group is imperfectly deuterated in the synthesis of the compound represented by Formula 1 above rather than being obtained by adding at least one of the compound represented by Formula 1-1H-1 above, the compound represented by Formula 1-1H-2 above, and the compound represented by Formula 1-2H above.

The styryl-based compound of Formula 1 or the composition containing the same may be used between a pair of electrodes of an OLED. For example, the styryl-based compound of Formula 1 or the composition containing the same may be used in an emission layer (EML) and/or between an anode and the EML (e.g., a hole injection layer (HIL), a hole transport layer (HTL), or a functional layer having hole injection and transport abilities).

According to another embodiment of the present invention, there is provided an OLED including a first electrode, a second electrode facing the first electrode, and an organic layer interposed between the first electrode and the second electrode, wherein the organic layer includes at least one of the styryl-based compound of Formula 1 or at least of the composition containing the same as described above.

The expression "the organic layer may include at least one of the styryl-based compound of Formula 1" as used herein means that the organic layer includes one of the styryl-based compounds represented by Formula 1 above or at least two different compounds selected from the styryl-based compounds represented by Formula 1 above.

For example, the organic layer may include only Compound 3 as the styryl-based compound. In this regard, Compound 3 may be included in an EML of the OLED. Also, the organic layer may include Compound 3 and Compound 19 as the styryl-based compound. In this regard, Compounds 3 and 19 may be included in the same layer (e.g., in an EML) or in different layers (e.g., Compound 3 may be included in an EML and Compound 19 may be included in a HTL).

Throughout this specification, the expression "the organic layer may include at least one of the composition" means that "the organic layer includes one of the composition or at least two different compounds selected from the compositions.

For example, the organic layer may include, as the composition, a composition containing Compound 3 above and at least one of Compound 3-1H-1, Compound 3-1H-2, and Compound 3-2H. In this case, the composition may be included in an EML of the OLED.

In addition, the organic layer may include, as the composition, a first composition including Compound 3 above and at least one of Compound 3-1H-1, Compound 3-1H-2, and Compound 3-2H, and a second composition including Compound 19 above and at least one of Compound 19-1H-1, Compound 19-1I-1-2, and Compound 19-2H. In this case, the first composition and the second composition may be included in the same layer (e.g., the first composition and the second composition may be included in an EML) or in different layers (e.g, the first composition is included in an EML, and the second composition is included in a HTL).

Compound 19

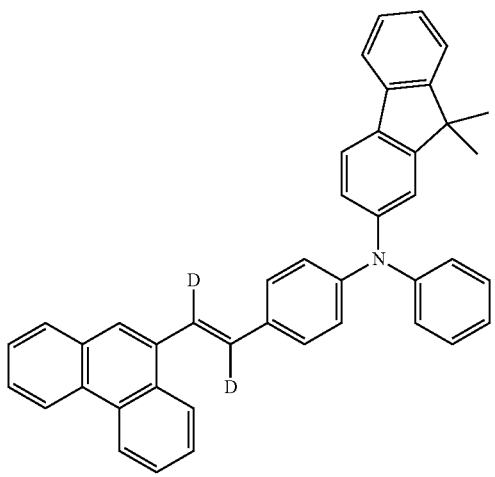

Compound 19-1H-1

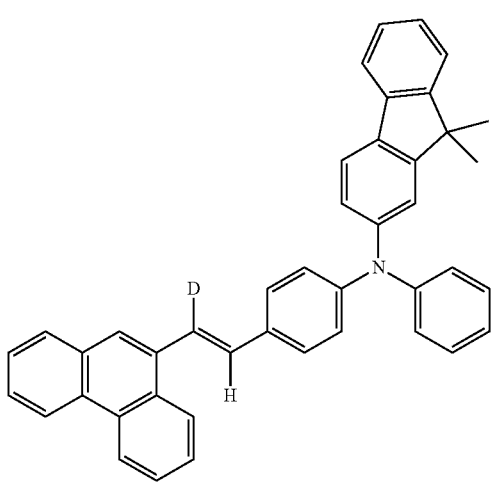

Compound 19-1H-2

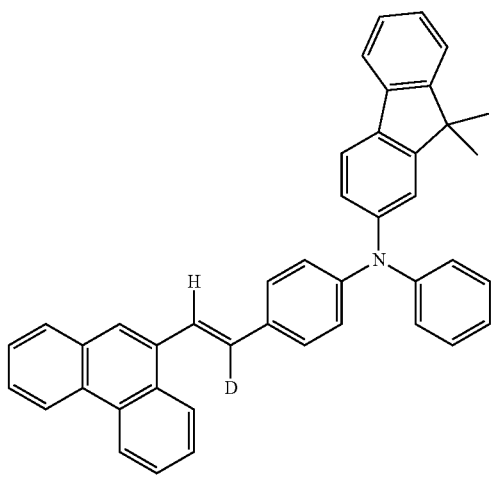

Compound 19-2H

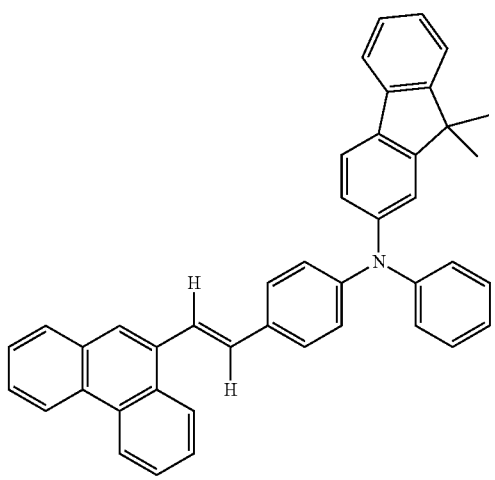

The organic layer may include at least one of a HIL, a HTL, a functional layer having hole injection and transport abilities (hereinafter, referred to as "H-functional layer"), a buffer layer, an electron blocking layer (EBL), a hole blocking layer (HBL), an electron transport layer (ETL), an electron injection layer (EIL), and a functional layer having electron transport and injection abilities (hereinafter, referred to as "E-functional layer").

The term "organic layer" used herein refers to a single layer or multiple layers interposed between the first electrode and the second electrode.

The organic layer may include an EML and the EML may include the styryl-based compound or the composition containing the styryl-based compound.

The styryl-based compound included in the EML may act as a fluorescent dopant. For example, the styryl-based compound may act as a blue fluorescent dopant that emits blue light.

FIG. 1 is a schematic cross-sectional view of an OLED 10 according to an embodiment of the present invention. Hereinafter, a structure and a manufacturing method of an OLED will be described in more detail with reference to FIG. 1.

A substrate 11 may be a substrate used in a general OLED, and may be a glass substrate or a transparent plastic substrate having excellent mechanical strength, thermal stability, transparency, surface smoothness, ease of handling, and waterproofness.

A first electrode 13 may be formed by applying a first electrode material on the substrate 11 by deposition or sputtering. When the first electrode 13 is an anode, the first electrode material may be selected from materials having a high work function so as to facilitate hole injection. The first electrode 13 may be a reflective electrode or a transparent electrode. Examples of the first electrode material may include indium-tin oxide (ITO), Indium-zinc-oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode 13 may be formed as a reflective electrode.

The first electrode 13 may be formed as a single layer or have a multi-layered structure having at least two layers. For example, the first electrode 13 may have a three-layered structure, e.g., ITO/Ag/ITO, but is not limited thereto.

An organic layer 15 is formed on the first electrode 13.

The organic layer 15 may include at least one of a HIL, a HTL, and a H-functional layer; an EML; an ETL; and an EIL.

The HIL may be formed on the first electrode 13 by using various methods such as vacuum deposition, spin coating, casting, or Langmuir-Blodgett (LB) deposition.

When the HIL is formed by vacuum deposition, the deposition conditions may vary according to a compound used as a material for forming the HIL, a structure of a desired HIL, and thermal characteristics. For example, the deposition condition may be, but is not limited to, a deposition temperature of about 100 to about 500° C., a degree of vacuum of about $10^{-8}$ to about $10^{-3}$ torr, and a deposition speed of about 0.01 to about 100 Å/sec.

When the HIL is formed by spin coating, the coating condition may vary according to a compound used as a material for forming the HIL, a structure of a desired HIL, and thermal characteristics. For example, the coating condition may be, but is not limited to, a coating speed of about 2,000 to about 5,000 rpm and a heat treatment temperature for removing a solvent after coating of about 80 to about 200° C.

The material for forming the HIL may be a known hole injection material. Examples of the known hole injection material include, but are limited to, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), and polyaniline/poly(4-styrenesulfonate) (PANI/PSS):

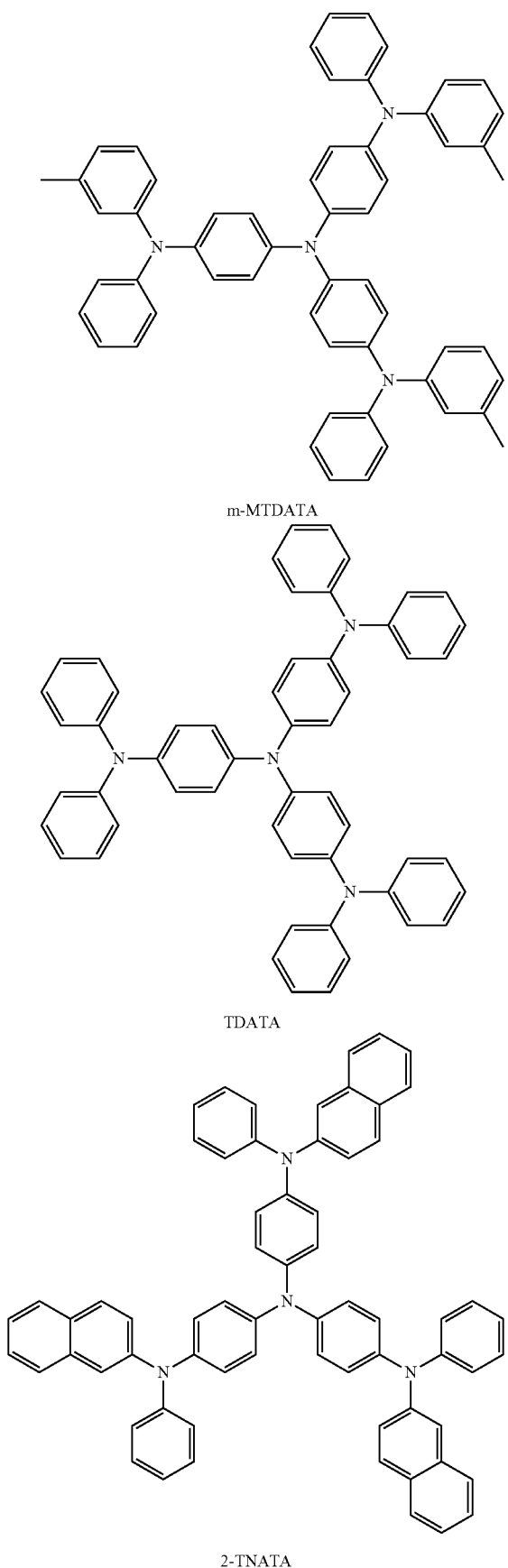

m-MTDATA

TDATA

2-TNATA

The thickness of the HIL may be in the range of about 100 Å to about 10,000 Å, for example, in the range of about 100 Å to about 1,000 Å. When the thickness of the HIL is within this range, satisfactory hole injection properties may be obtained without a substantial increase in driving voltage.

Next, an HTL may be formed on the HIL by using various methods such as vacuum deposition, spin coating, casting, or LB deposition. When the HTL is formed by vacuum deposition or spin coating, the deposition and coating conditions vary according to a used compound. However, in general, the condition may be almost the same as the condition for forming the HIL.

As a material for forming the HTL, at least one of a styryl-based compound, a composition containing a styryl-based compound, and a known hole transporting material. Examples of the known hole transporting material include, but are not limited to, carbazole derivatives such as N-phenylcarbazole and polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine (NPB).

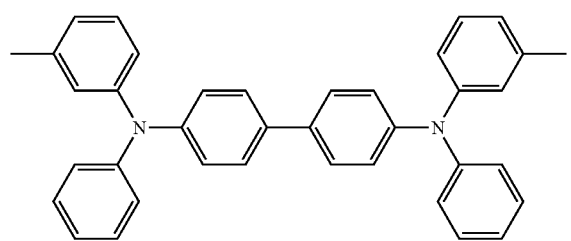

TPD

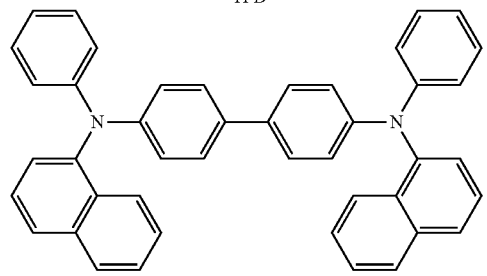

NPB

The thickness of the HTL may be in the range of about 50 Å to about 2,000 Å, for example, in the range of about 100 Å to about 1,500 Å. When the thickness of the HTL is within this range, satisfactory hole transport properties may be obtained without a substantial increase in driving voltage.

At least one of the hole injection material and the hole transporting material as described above may be included in the H-functional layer. The thickness of the H-functional layer may be in the range of about 500 Å to about 10,000 Å, for example, in the range of about 100 Å to about 1,000 Å. When the thickness of the H-functional layer is within this range, satisfactory hole injection and transport properties may be obtained without a substantial increase in driving voltage.

At least one of the HIL, the HTL, and the H-functional layer may include at least one of a compound represented by Formula 300 below and a compound represented by Formula 350 below:

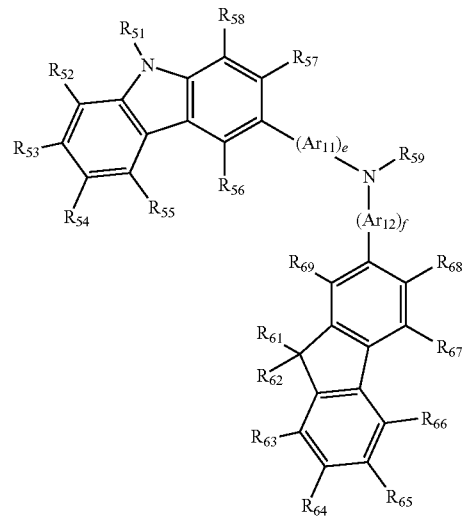

Formula 300

Formula 350 wherein $Ar_{11}$, $Ar_{12}$, $Ar_{21}$, and $Ar_{22}$ may be each independently a substituted or unsubstituted $C_5$-$C_{60}$ arylene group. Detailed descriptions for $Ar_{11}$, $Ar_{12}$, $Ar_{21}$, and $Ar_{22}$ refer to the detailed description for $L_1$ above.

In Formula 300 above, e and f may be each independently an integer of 0 to 5, for example, 0, 1, or 2. For example, e may be 1, and f may be 0, but e and f are not limited to the above example.

In Formulae 300 and 350 above, $R_{51}$ through $R_{58}$, $R_{61}$ through $R_{69}$, and $R_{71}$ and $R_{72}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ through $R_{58}$, $R_{61}$ through $R_{69}$, and $R_{71}$ and $R_{72}$ may be each independently one of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group (e.g., methyl, ethyl, propyl, butyl, pentyl, hexyl, and the like), a $C_1$-$C_{10}$ alkoxy group (e.g., methoxy, ethoxy, propoxy, butoxy, pentoxy, and the like); a $C_1$-$C_{10}$ alkyl group and a $C_1$-$C_{10}$ alkoxy group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group, but are not limited thereto.

In Formula 300 above, $R_{59}$ may be one of a phenyl group; a naphthyl group; an anthryl group; a biphenyl group; a pyridinyl group; and a phenyl group, a naphthyl group, an anthryl group, a biphenyl group, and a pyridinyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{20}$ alkyl group, and a substituted or unsubstituted $C_1$-$C_{20}$ alkoxy group.

The compound of Formula 300 may be represented by Formula 300A below, but is not limited thereto:

Formula 300A

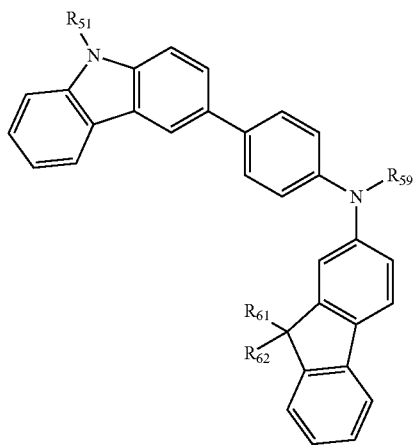

wherein a detailed description of $R_{51}$, $R_{60}$, $R_{61}$, and $R_{59}$ is already provided above.

For example, at least one of the HIL, the HTL, and the H-functional layer may be include at least one of Compounds 301 through 320 below, but is not limited thereto:

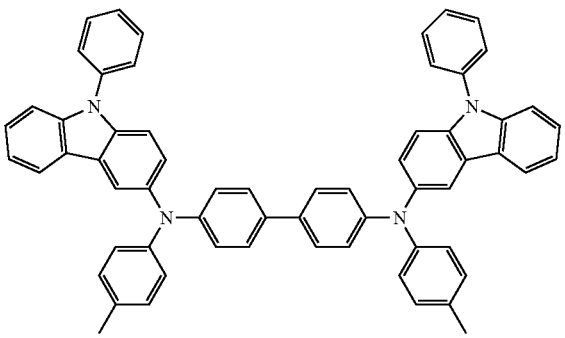

302

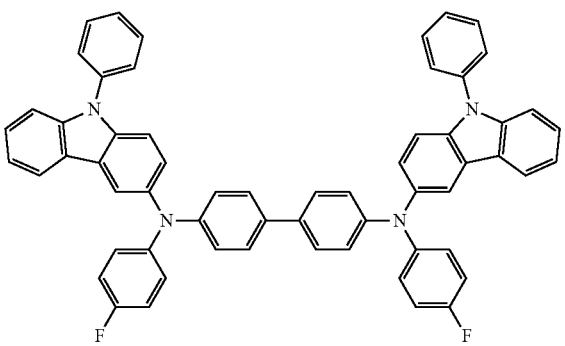

303

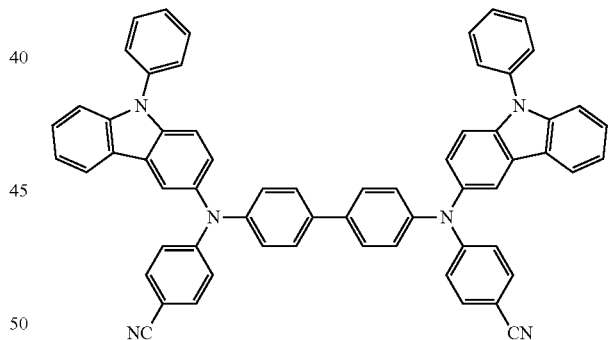

304

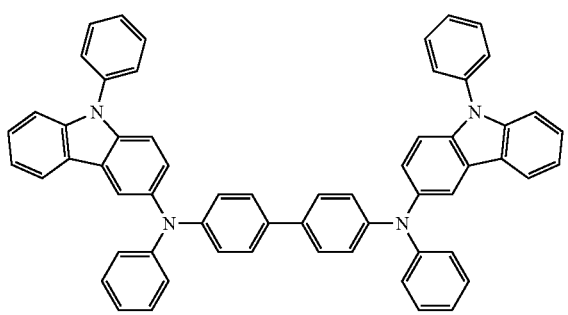

301

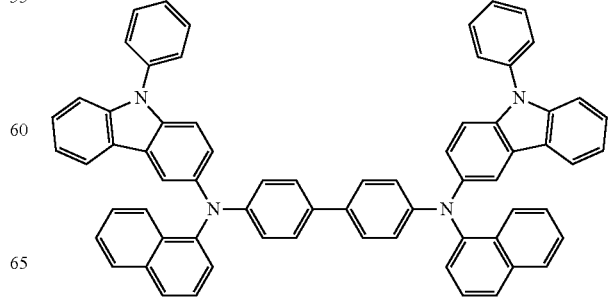

305

-continued
306
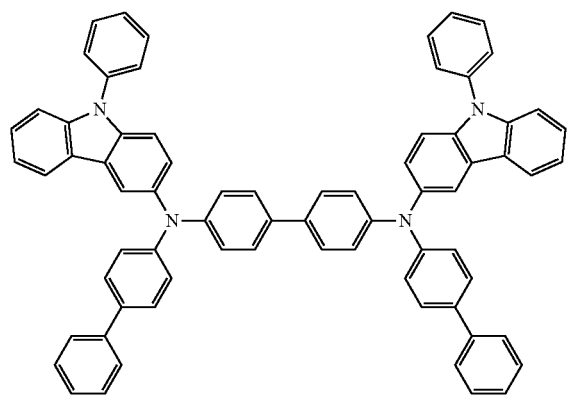
307
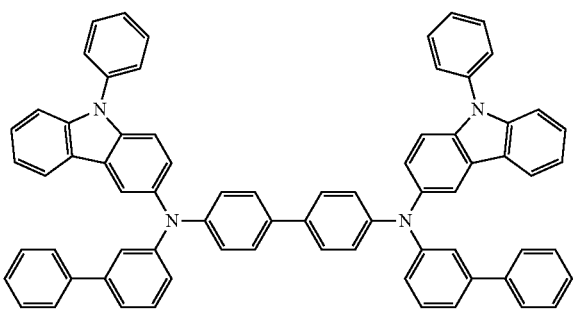
308
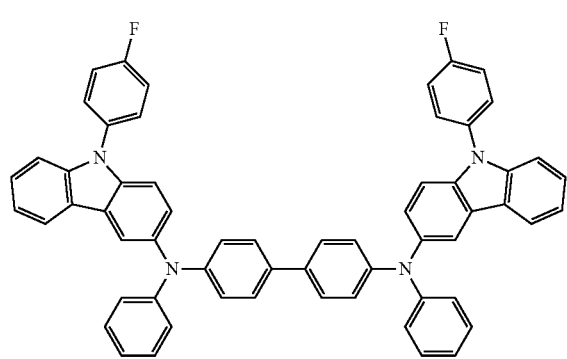
-continued
309
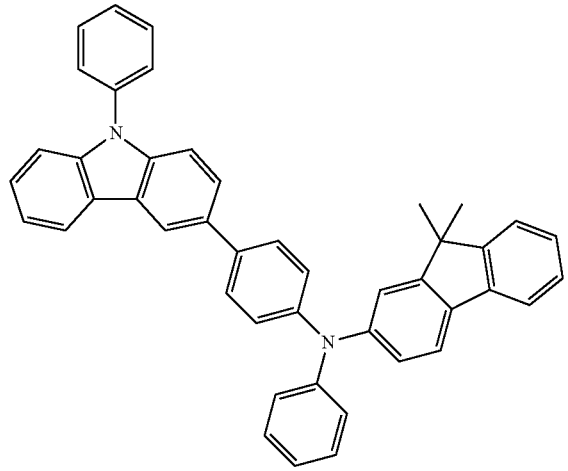
310
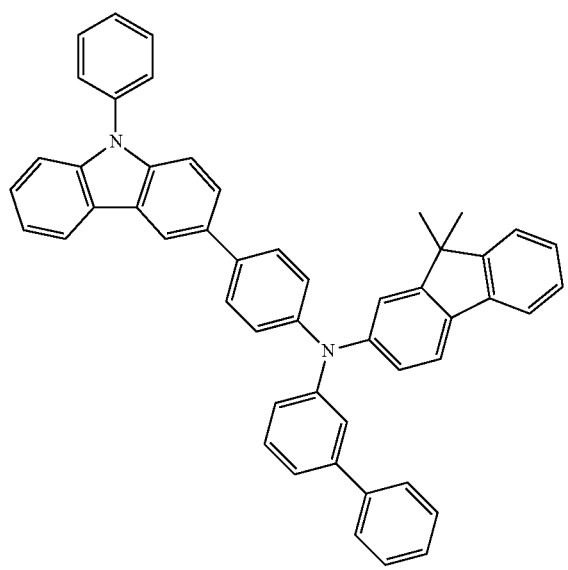
311
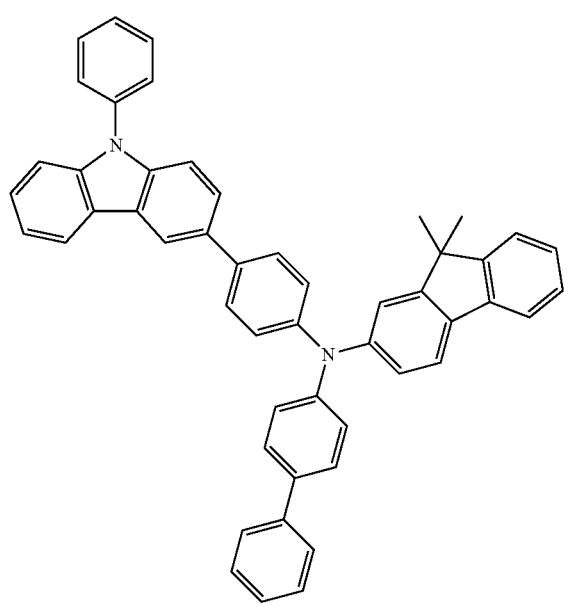

-continued
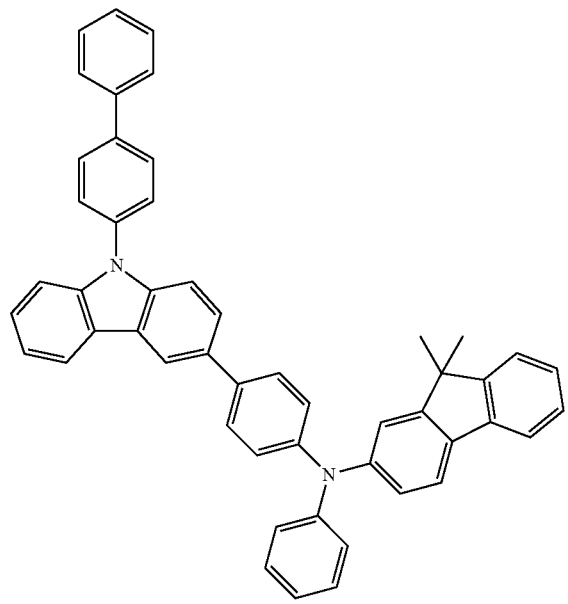
312
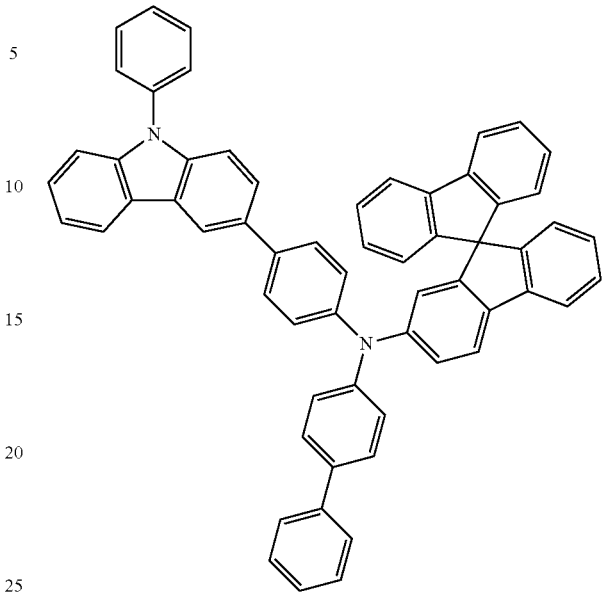
314
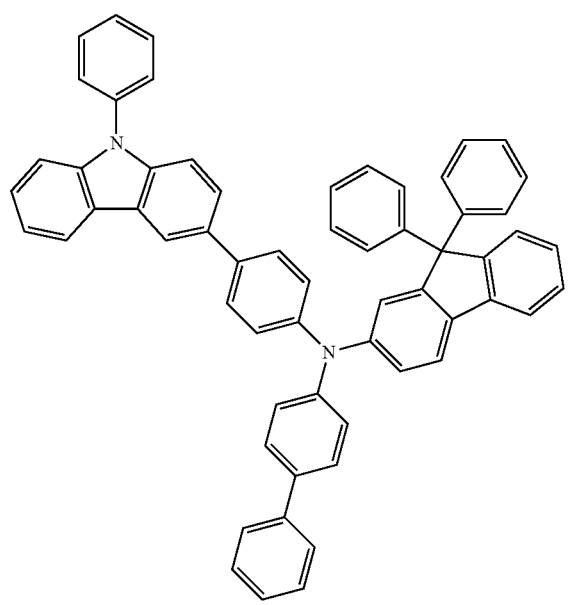
313
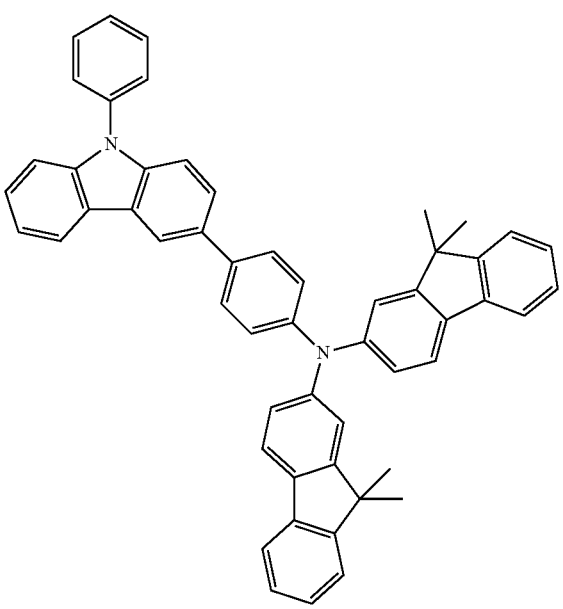
315

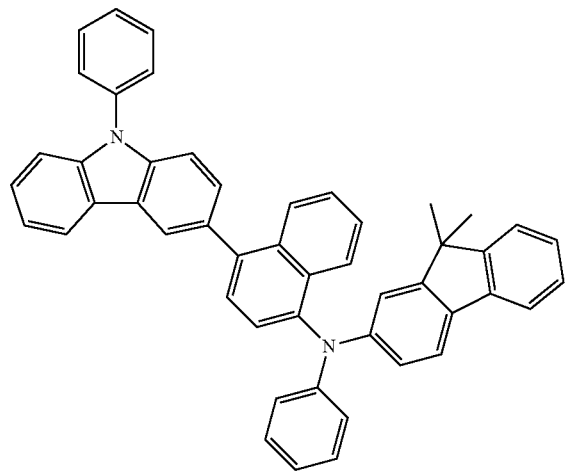
316
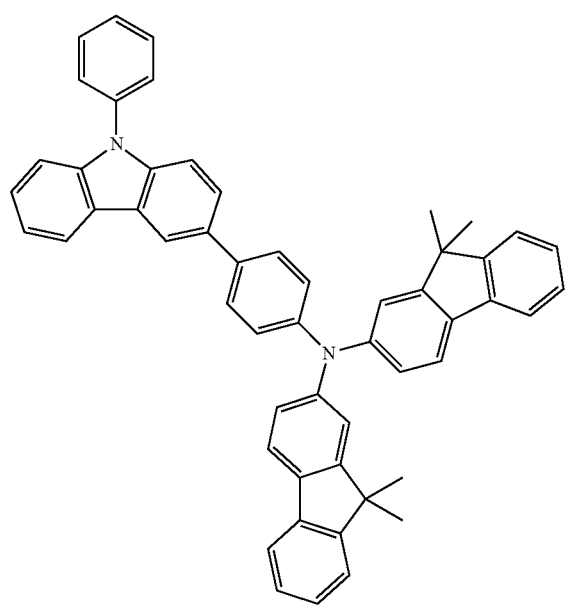
317
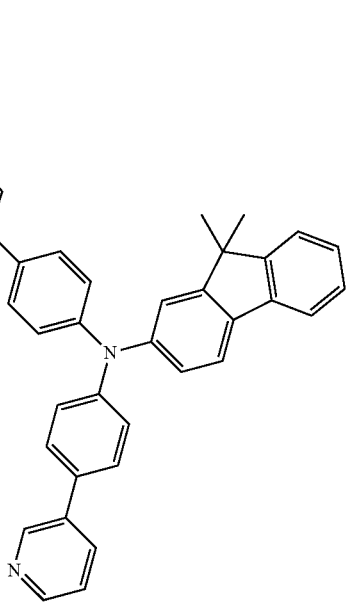
318
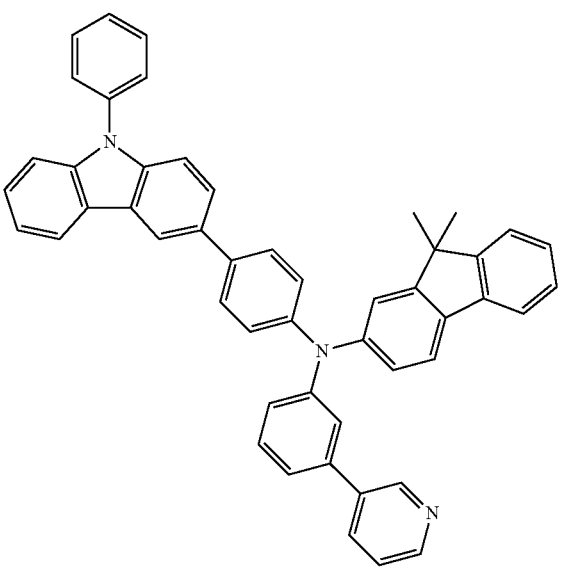
319

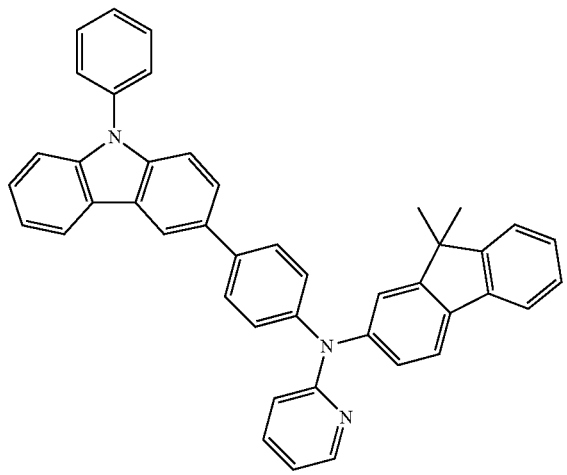

320

At least one of the HIL, the HTL, and the H-functional layer may further include a charge-generating material so as to increase the conductive of the layers, in addition to the known hole injection material, the known hole transporting material, the material for forming the H-functional layer having hole injection and transport abilities, the styryl-based compound and/or the composition containing the styryl-based compound.

The charge-generating material may be, for example, a p-dopant. The p-dopant may be one of a quinine derivative, a metal oxide, and a cyano-containing compound, but is not limited thereto. Examples of the p-dopant may include, but are not limited to, quinone derivatives such as tetra-cyano-quinodimethane (TCNQ) and 2,3,5,6-tetrafluoro-tetracyano-1,4-benzoquinodimethane (F4-CTNQ); metal oxides such as an tungsten oxide and a molybdenum oxide; and cyano-containing compounds such as Compound 200 below and the like.

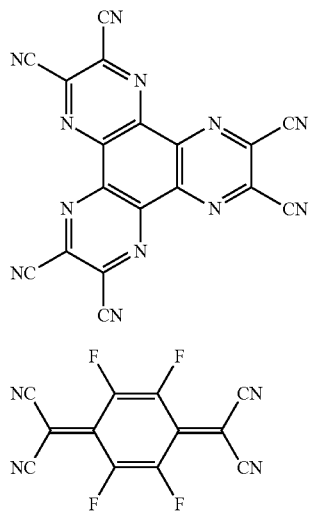

<Compound 200>

<F4-CTNQ>

When the HIL, the HTL, or the H-functional layer further includes the charge-generating material, the charge-generating material may be homogeneously or inhomogeneously dispersed in the HIL, the HTL, or the H-functional layer.

A buffer layer may be interposed between the EML and at least one of the HIL, the HTL, and the H-functional layer. The buffer layer increases efficiency by compensating for an optical resonance distance according to the wavelength of light emitted from the EML. The buffer layer may include a known hole injection material and a known hole transporting material. Also, the buffer layer may include the same material as one of the materials included in the HIL, the HTL, and the H-functional layer.

An EML may be formed on the HTL, the H-functional layer, or the buffer layer by vacuum deposition, spin coating, casting, or LB deposition. When the EML is formed by vacuum deposition or spin coating, the deposition and coating conditions vary according to a used compound. However, in general, the condition may be almost the same as the condition for forming the HIL.

The EML may include at least one of the styryl-based compound or at least one of the composition containing the styryl-based compound.

The EML may further include a host.

Examples of the host may include, but are not limited to, Alq$_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, and distyrylarylene (DSA), dmCBP (refer to Formula below), and Compounds 501 through 509 below.

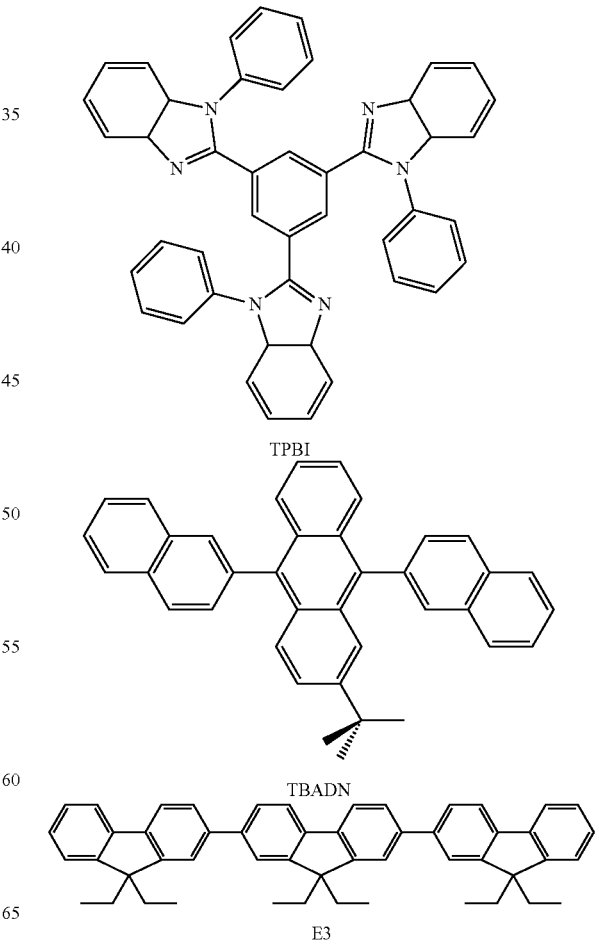

TPBI

TBADN

E3

-continued
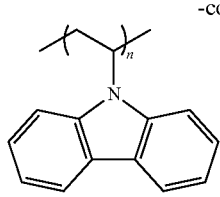
PVK
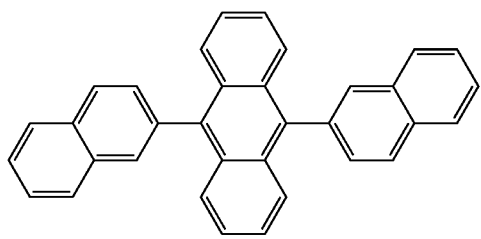
AND
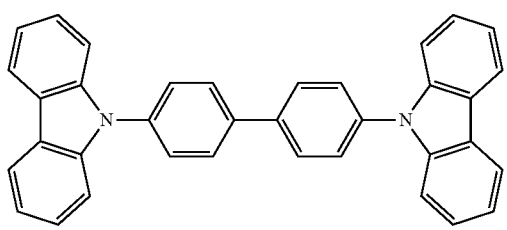
CBP
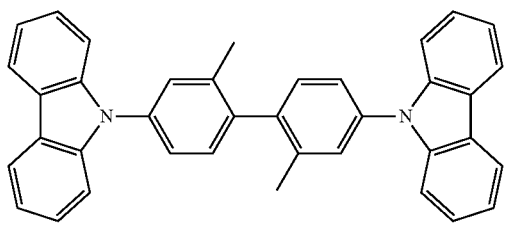
dmCBP
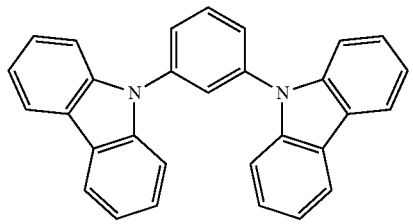
501
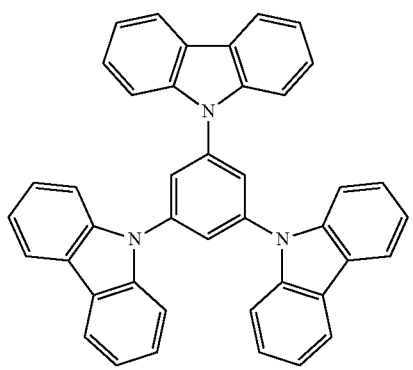
502
-continued
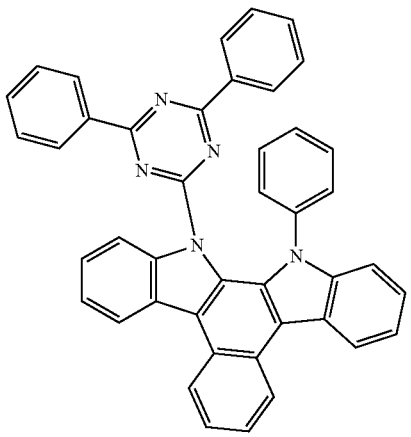
503
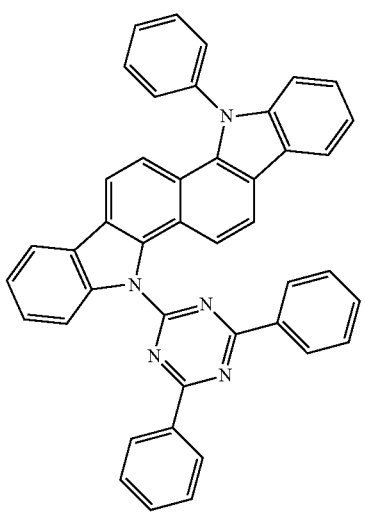
504
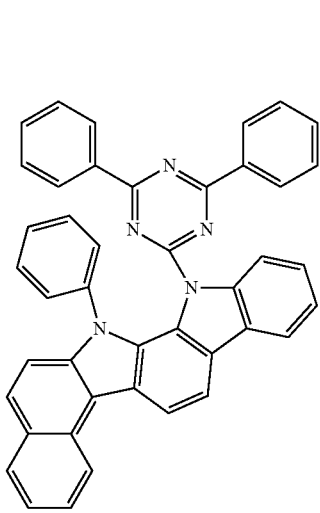
505

-continued

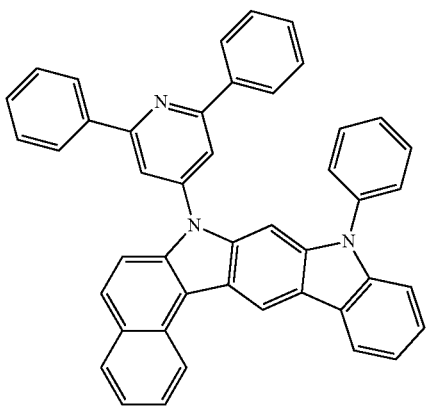
506

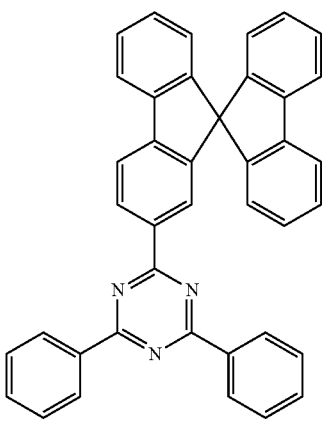
507

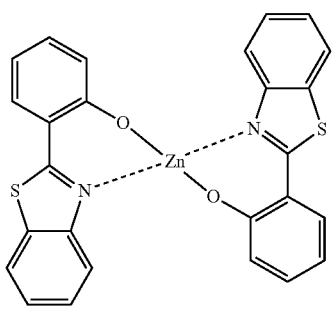
508

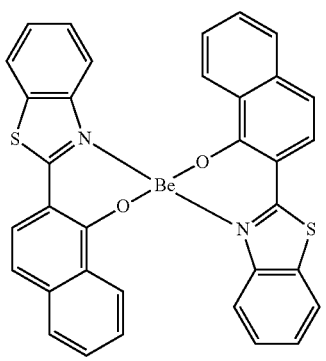
509

Also, the host may be an anthracene-based compound represented by Formula 400 below:

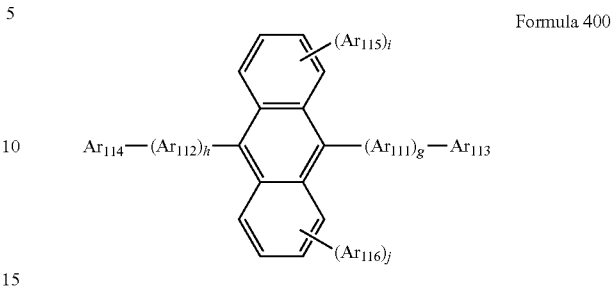

Formula 400 wherein $Ar_{111}$ and $Ar_{112}$ may be each independently a substituted or unsubstituted $C_5$-$C_{60}$ arylene group; $Ar_{113}$ through $Ar_{116}$ may be each independently a substituted or unsubstituted $C_1$-$C_{10}$ alkyl group or a substituted or unsubstituted $C_5$-$C_{60}$ aryl group; and g, h, i, and j may be each independently an integer of 0 to 4.

For example, in Formula 400 above, $Ar_{111}$ and $Ar_{112}$ may be each independently one of a phenylene group; a naphthylene group; a phenanthrenylene group; a pyrenylene group; and a phenylene group, a naphthylene group, a phenanthrenylene group, a fluorenyl group, and a pyrenylene group that are substituted with at least one of a phenyl group, a naphthyl group, and an anthryl group.

In Formula 400 above, g, h, i, and j may be each independently 0, 1, or 2.

In Formula 400 above, $Ar_{113}$ through $Ar_{116}$ may be each independently, but are not limited to, a $C_1$-$C_{10}$ alkyl group that is substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

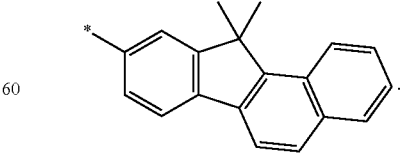

For example, the anthracene-based compound of Formula 400 may be, but is not limited to, one of the compounds below:

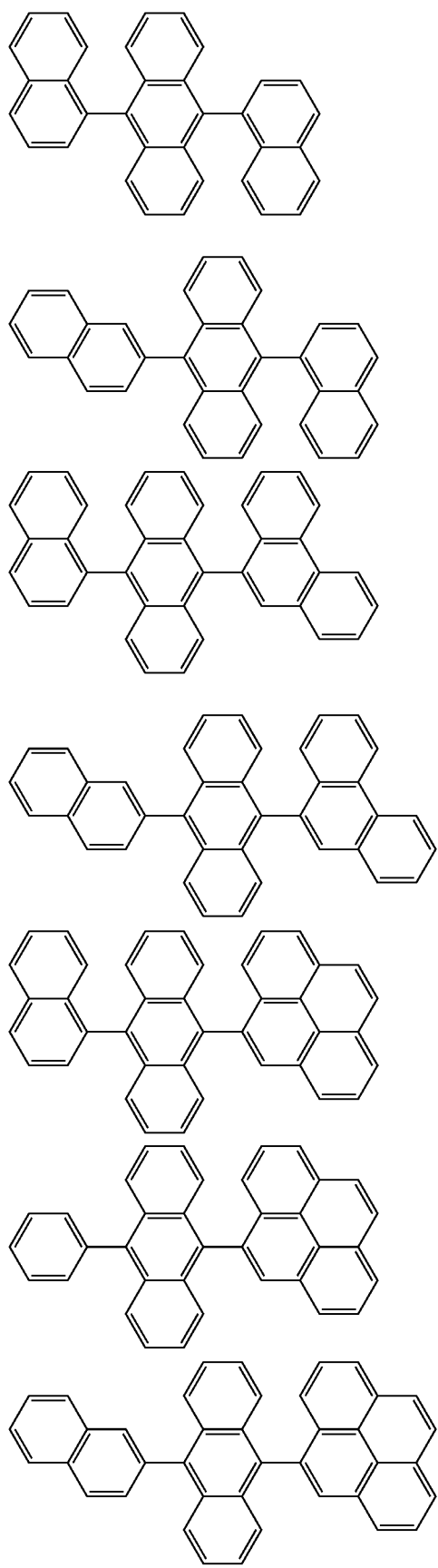
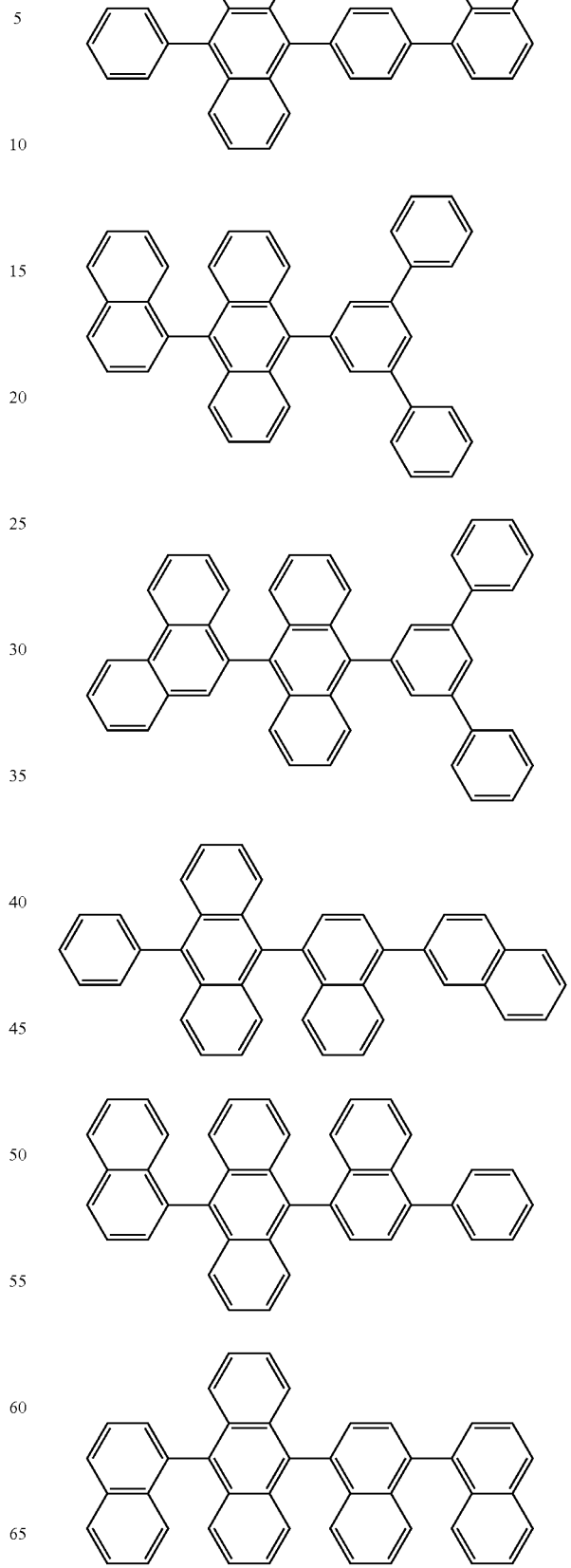

83
-continued
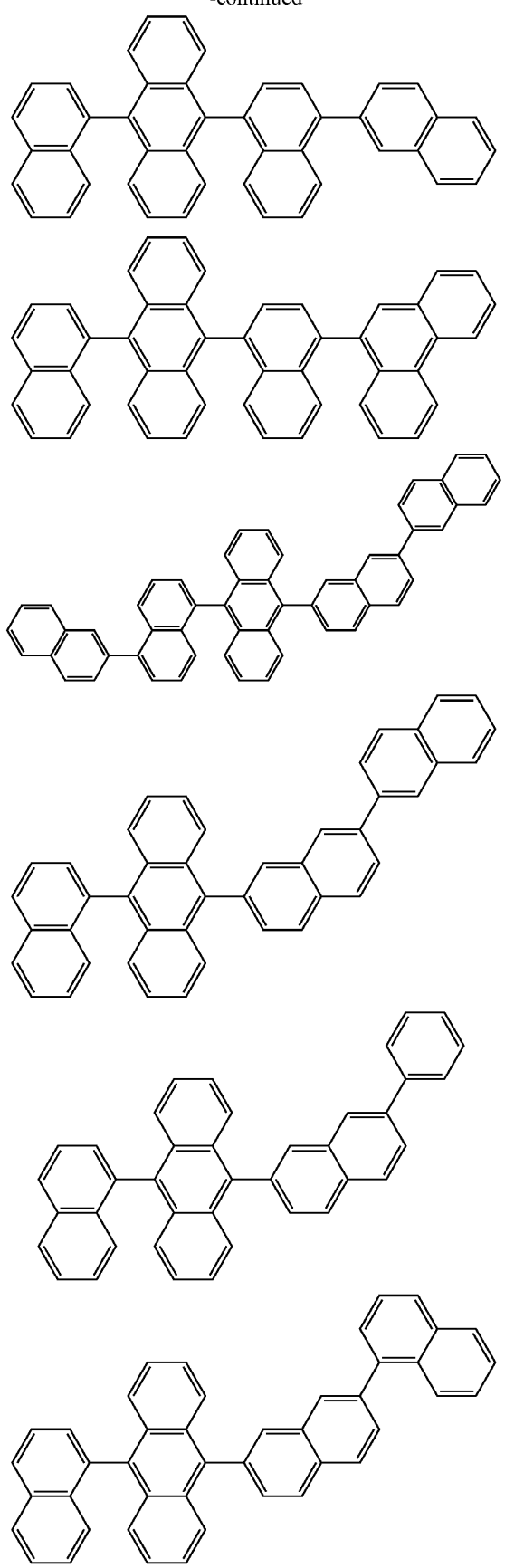
84
-continued
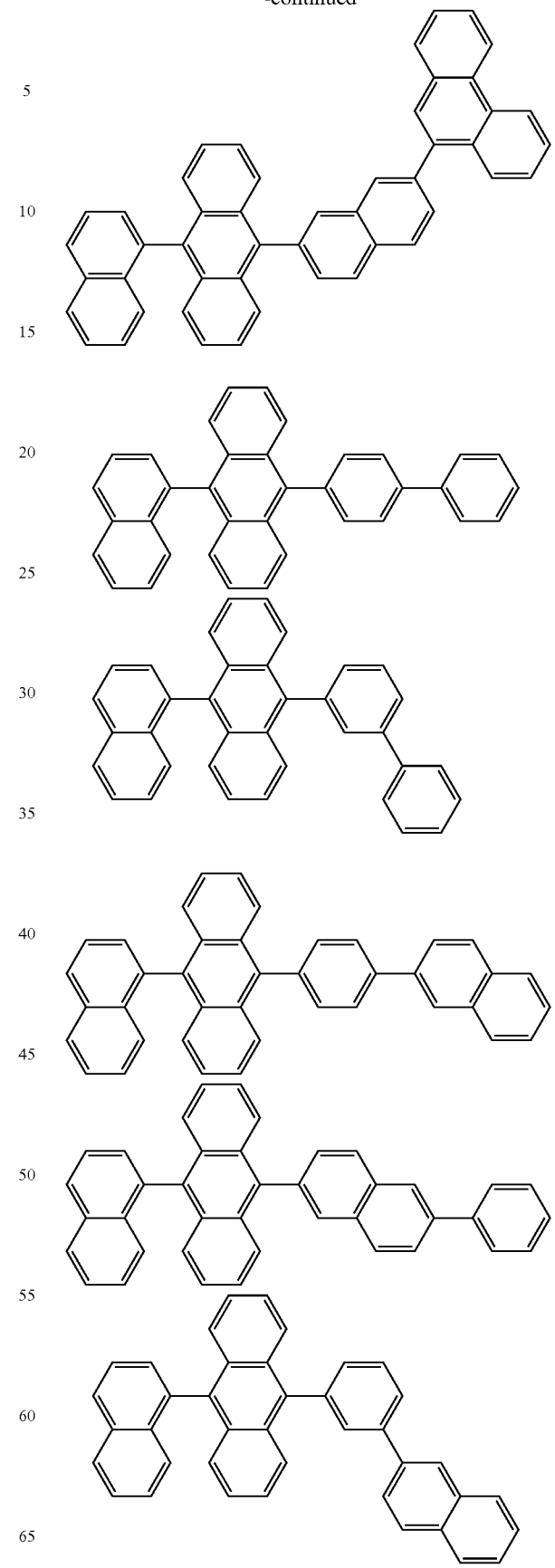

85
-continued
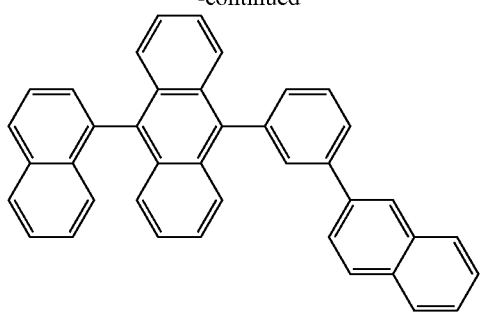
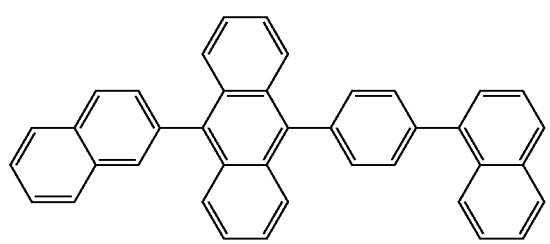
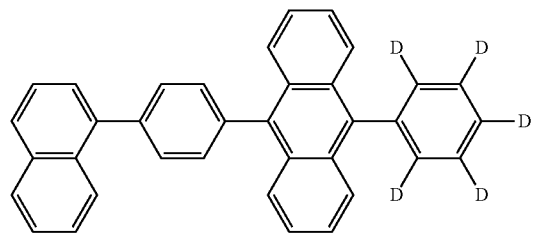
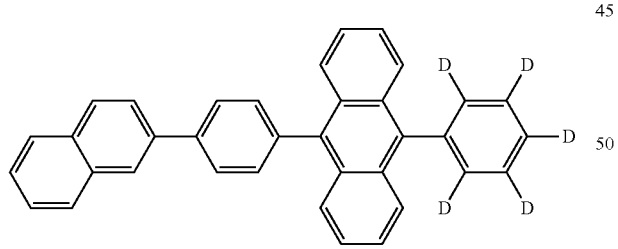
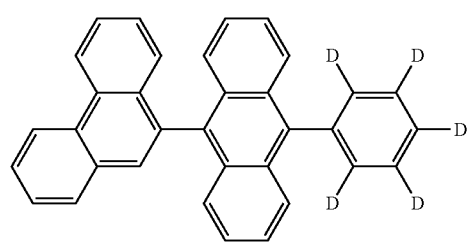
86
-continued
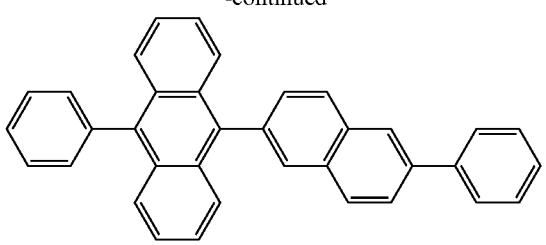
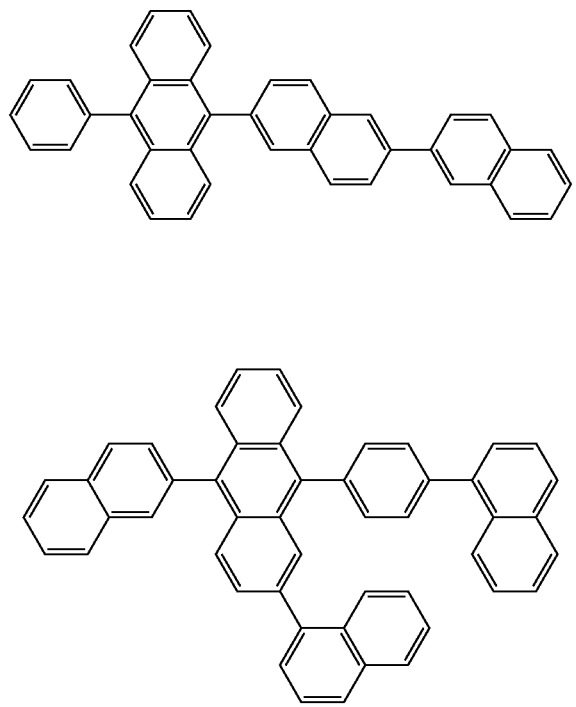
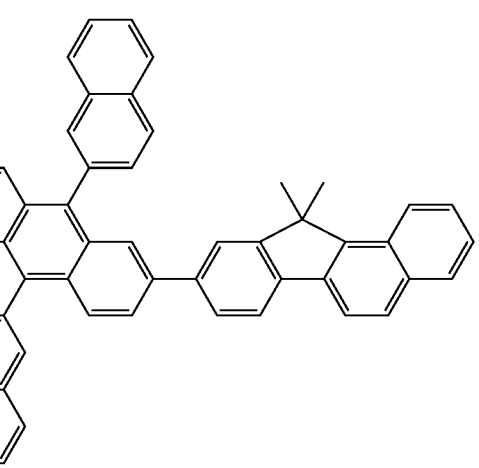

-continued

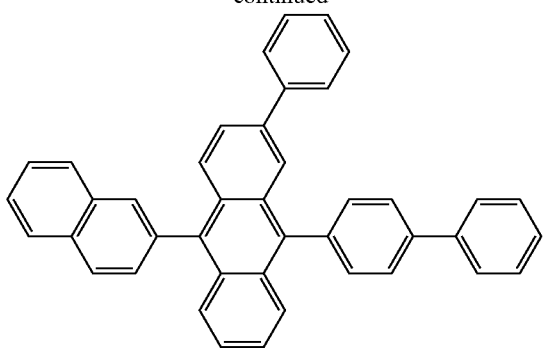

-continued

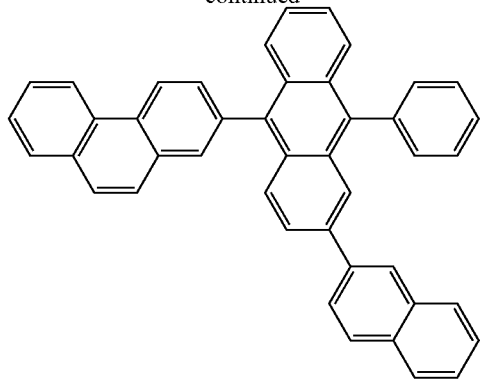

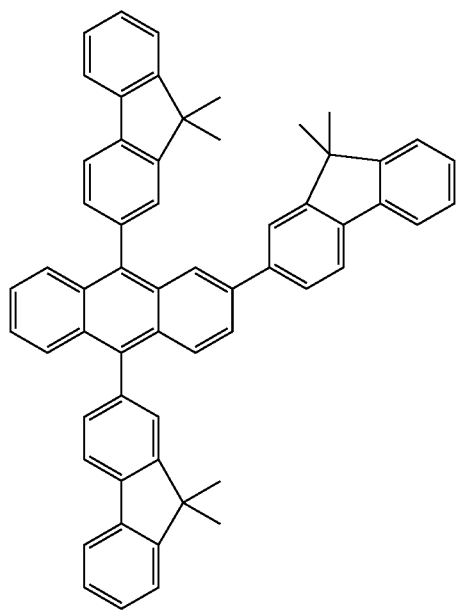

Also, an anthracene-based compound represented by Formula 401 below may be used as the host:

<Formula 401>

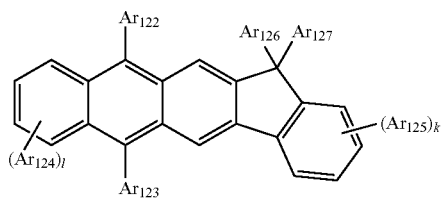

wherein a detailed description of $Ar_{122}$ through $Ar_{125}$ is the same as the description of $Ar_{113}$ of Formula 400 above.

In Formula 401 above, $Ar_{126}$ and $Ar_{127}$ may be each independently a $C_1$-$C_{10}$ alkyl group (e.g., a methyl group, an ethyl group, or a propyl group).

In Formula 401 above, k and l may be each independently an integer of 0 to 4. For example, k and l may be each independently 0, 1, or 2.

For example, the anthracene-based compound of Formula 401 may be, but is not limited to, one of the following compounds:

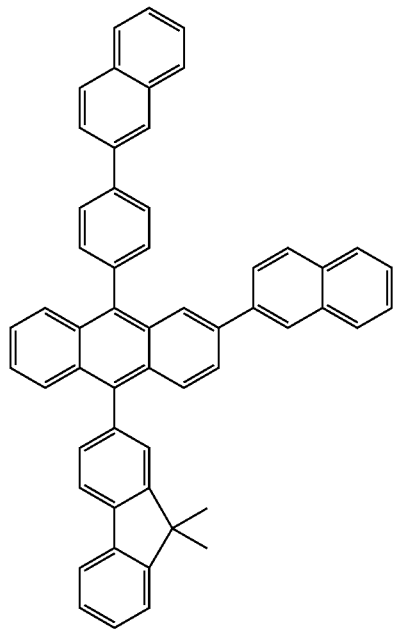

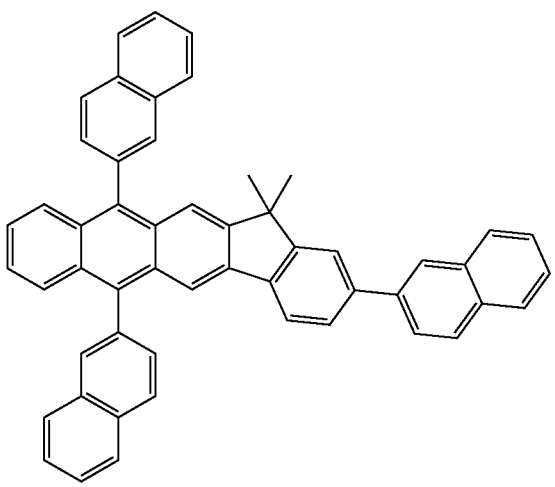

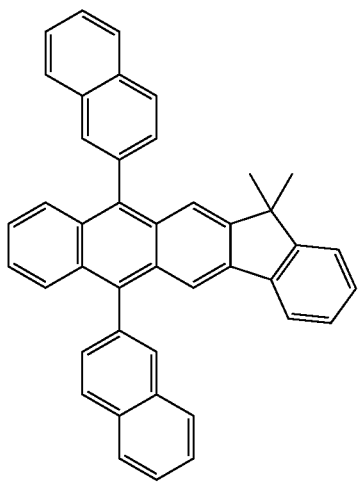

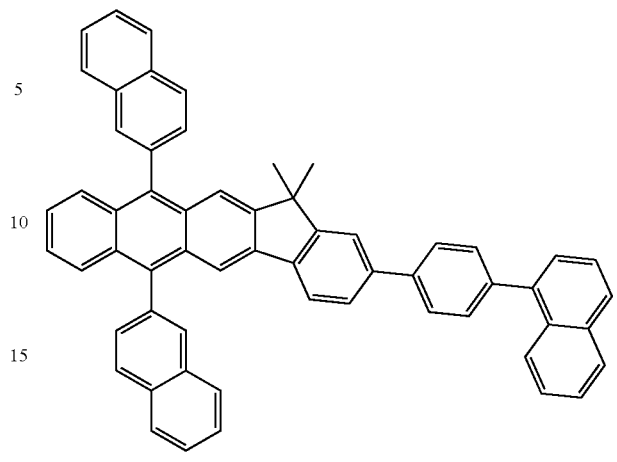

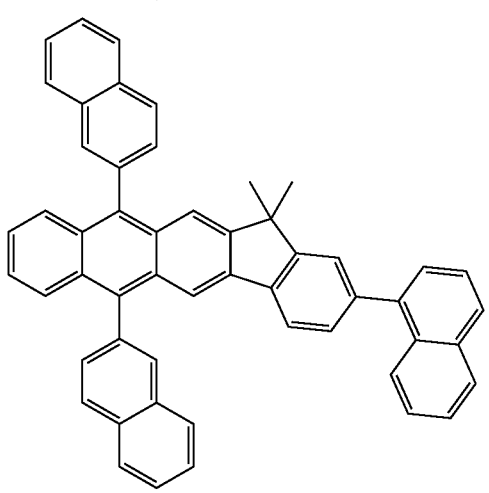

If the OLED is a full-color OLED, the EML may be patterned as a red EML, a green EML, and a blue EML. In this regard, the above-described styryl-based compound or the composition containing the styryl-based compound may be included in the blue EML as a blue fluorescent dopant.

At least one of the red EML, the green EML, and the blue EML may include the following dopants (ppy=phenylpyridine).

For example, compounds described below may be used as a blue dopant, but are not limited thereto.

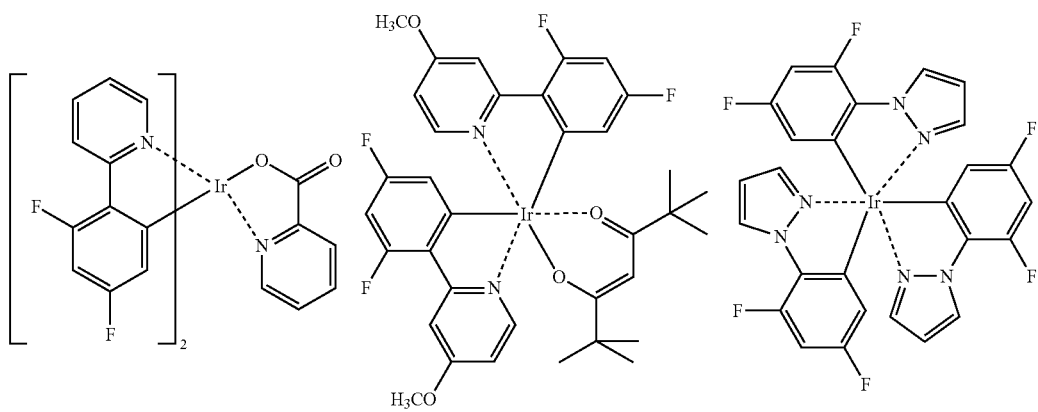

F$_2$Irpic     (F$_2$ppy)$_2$Ir(tmd)     Ir(dfpp)$_3$

-continued
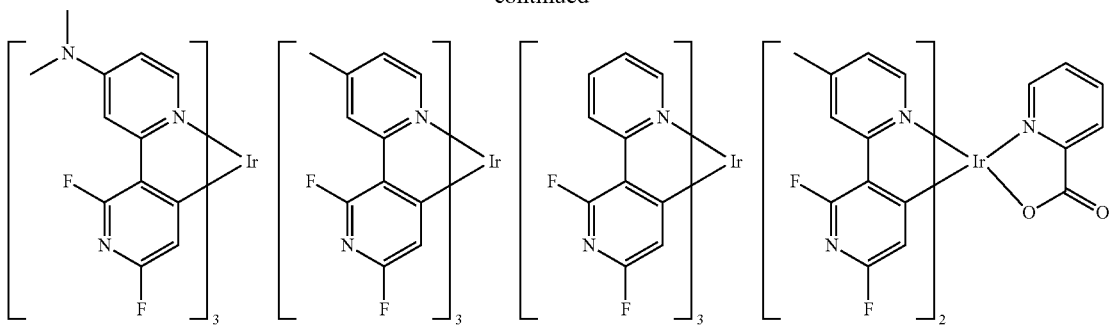
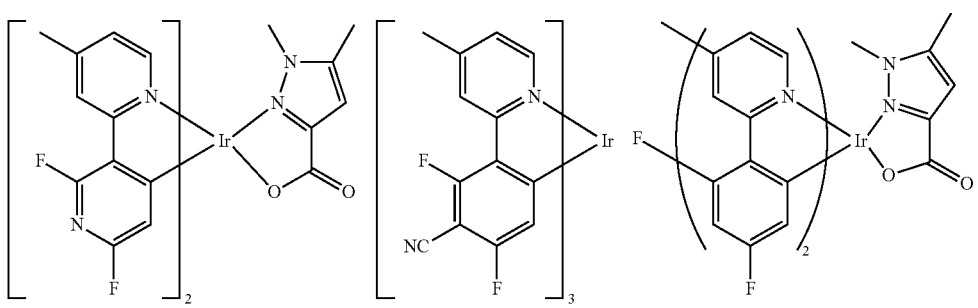
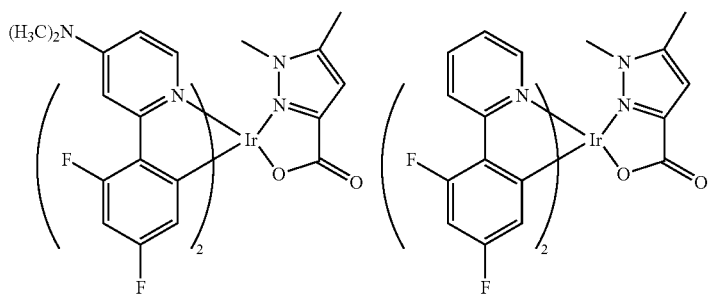
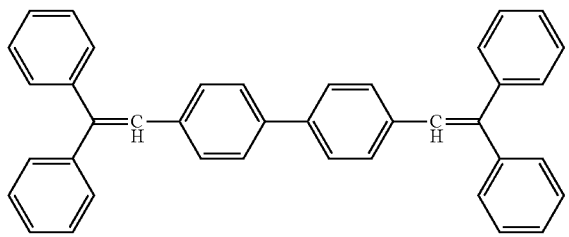
DPVBi
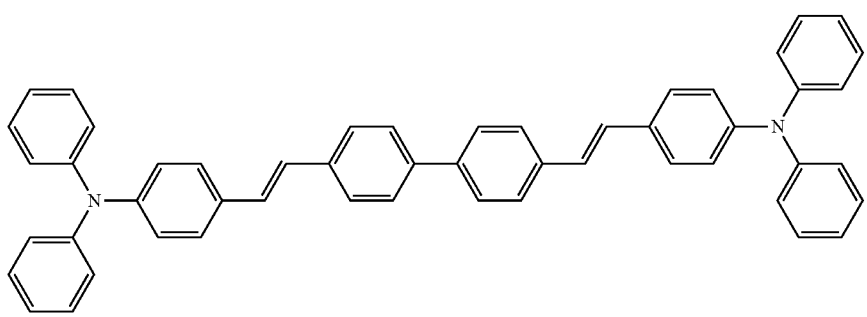
DPAVBi

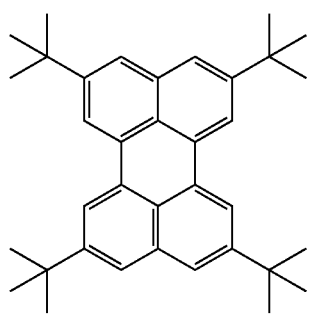
TBPe
For example, compounds described below may be used as a red dopant, but are not limited thereto. In addition, DCM or DCJTB below may be used as the red dopant.
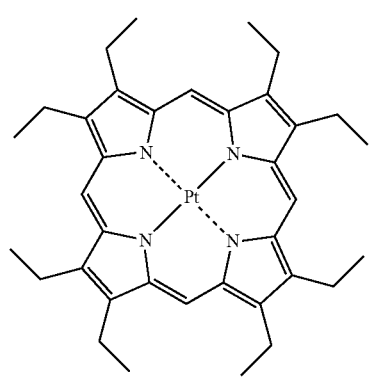
PtOEP
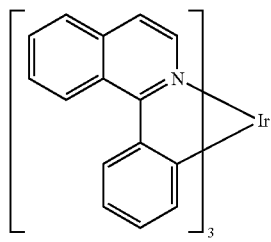
Ir(piq)₃
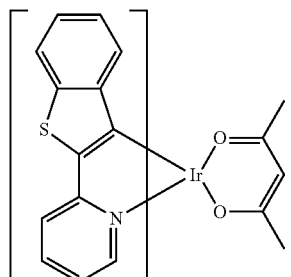
Btp₂Ir(acac)
-continued
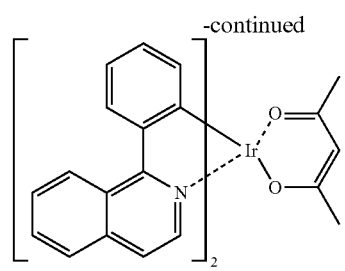
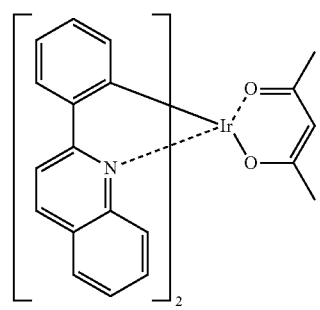
Ir(pq)₂(acac)
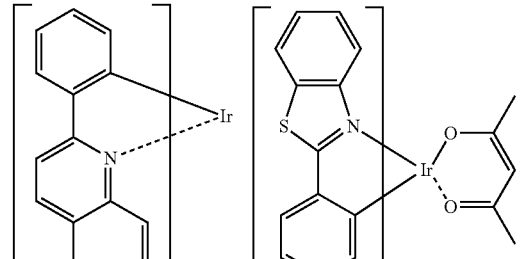
Ir(2-phq)₃     Ir(BT)₂(acac)

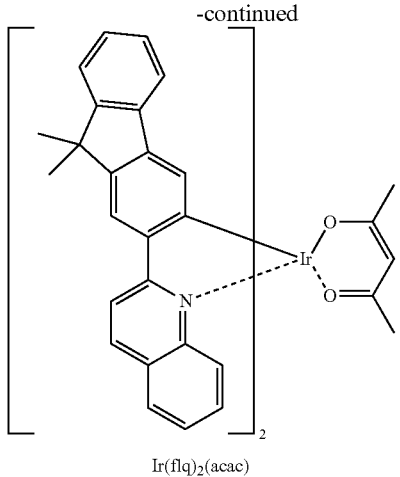
Ir(flq)₂(acac)
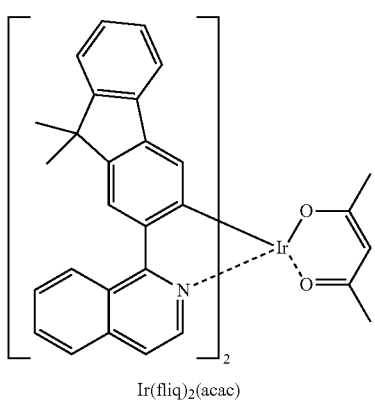
Ir(fliq)₂(acac)
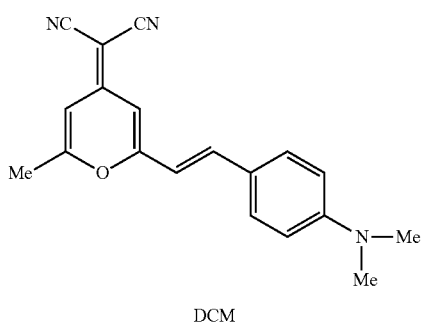
DCM
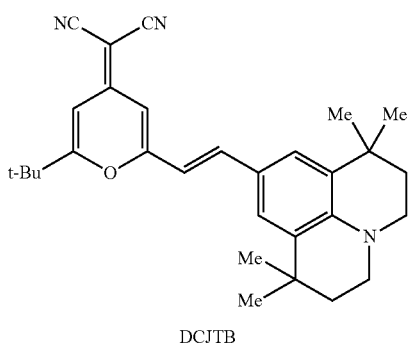
DCJTB
For example, compounds described below may be used as a green dopant, but are not limited thereto. C545T below may be used as the green dopant.
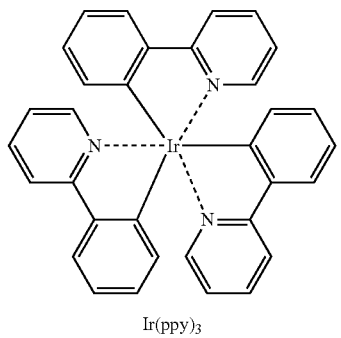
Ir(ppy)₃
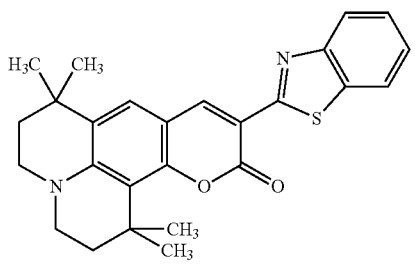
Ir(ppy)₂(acac)   Ir(mpyp)₃
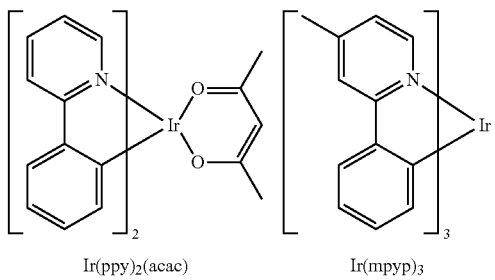
C545T
Examples of the dopant included in the EML include Pt-complexes below, but are not limited thereto:
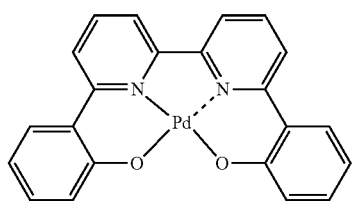
D1
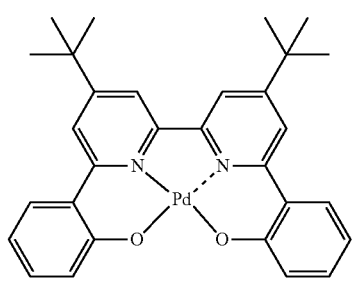
D2

-continued
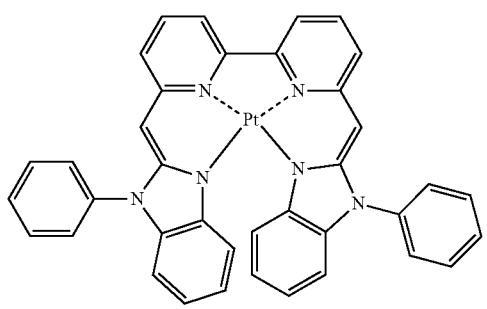
D3
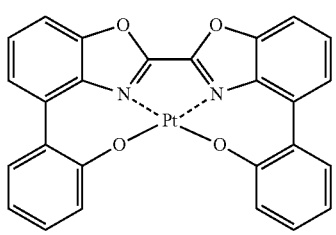
D4
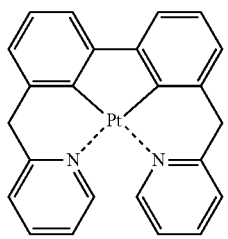
D5
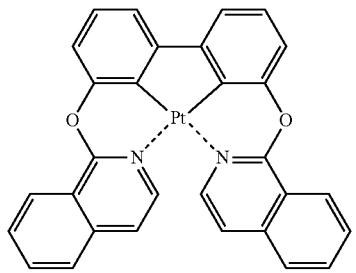
D6
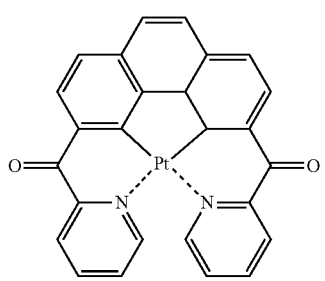
D7
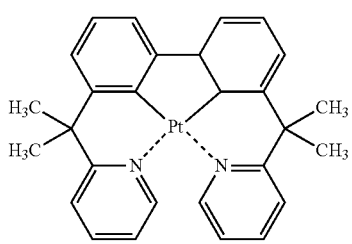
D8
-continued
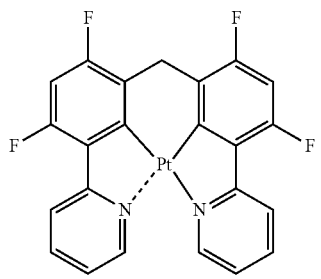
D9
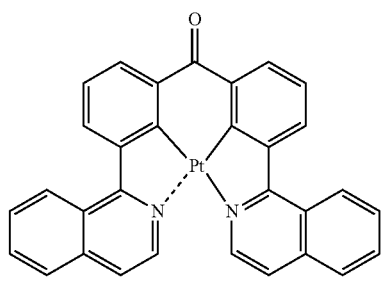
D10
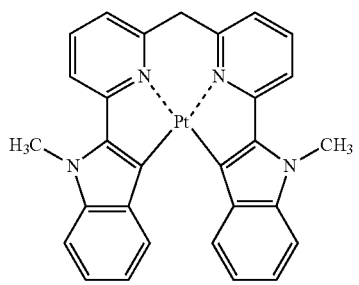
D11
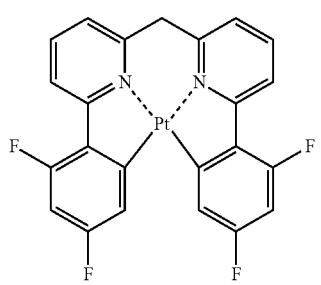
D12
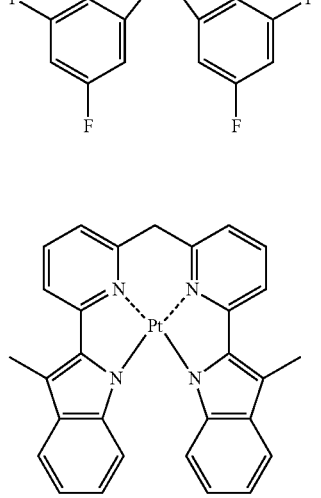
D13

-continued
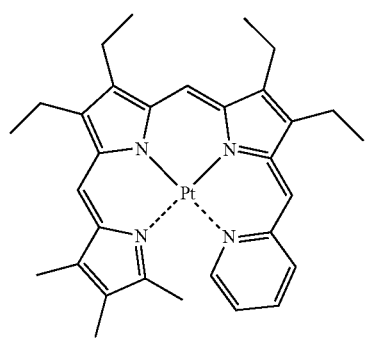
D14
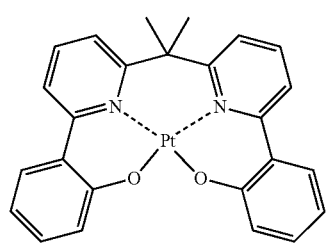
D15
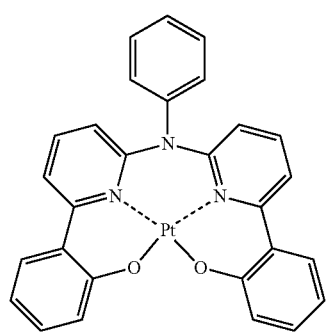
D16
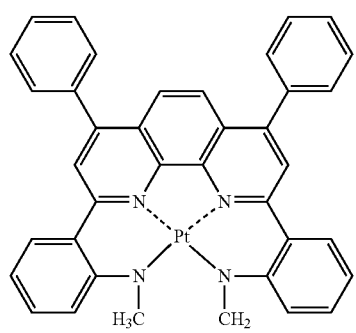
D17
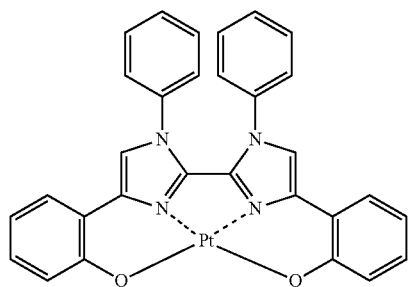
D18
-continued
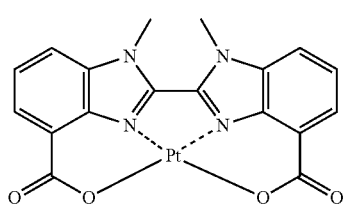
D19
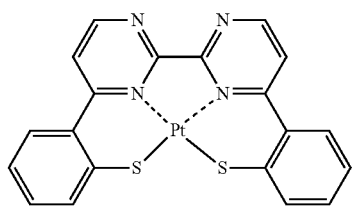
D20
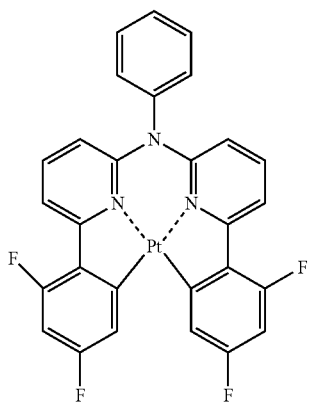
D21
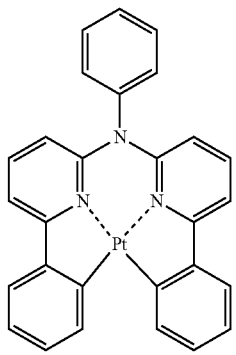
D22
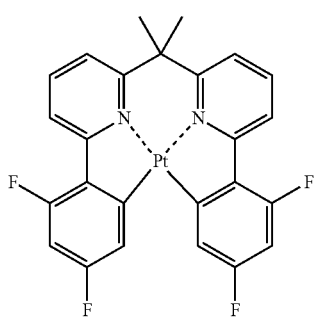
D23

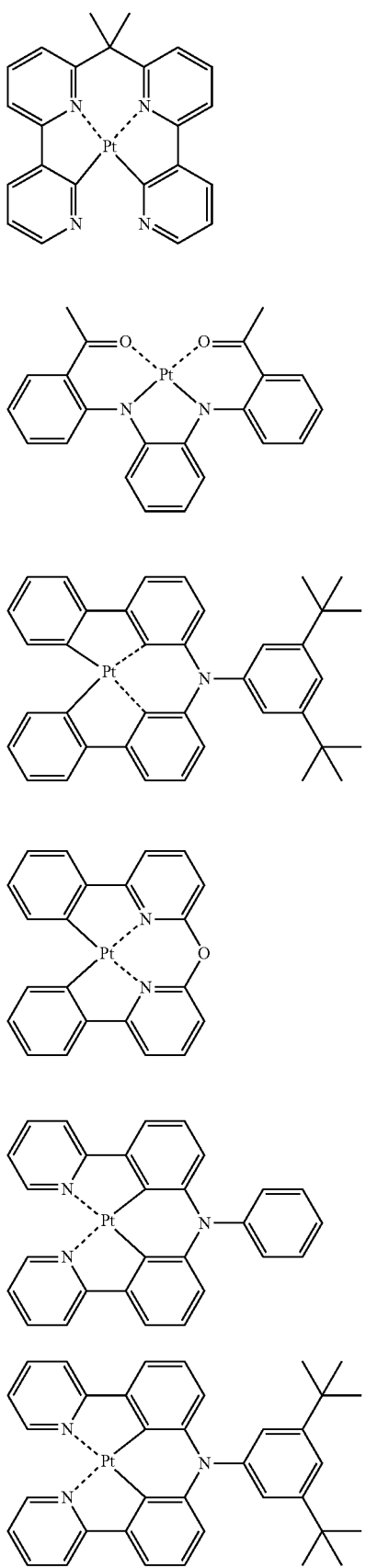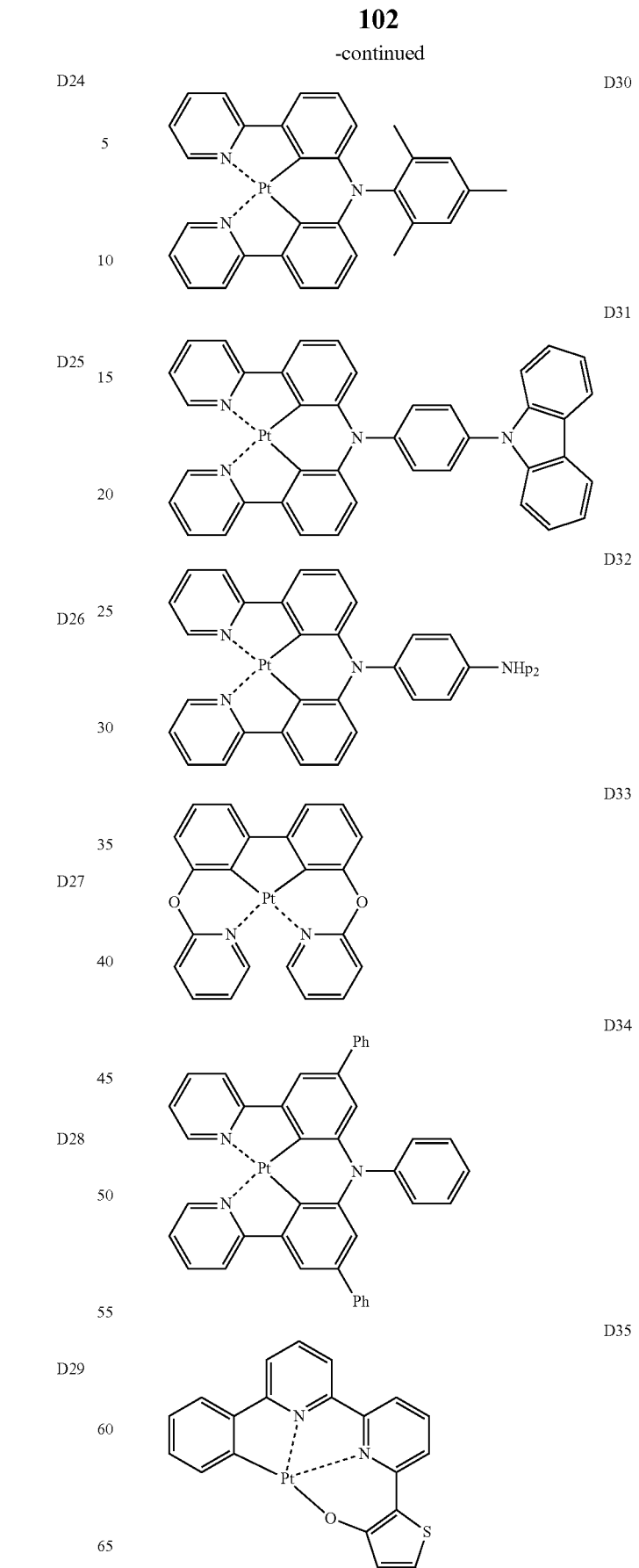

D36
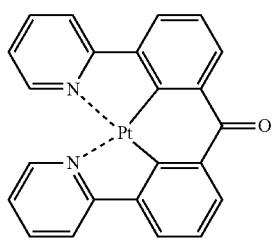
D37
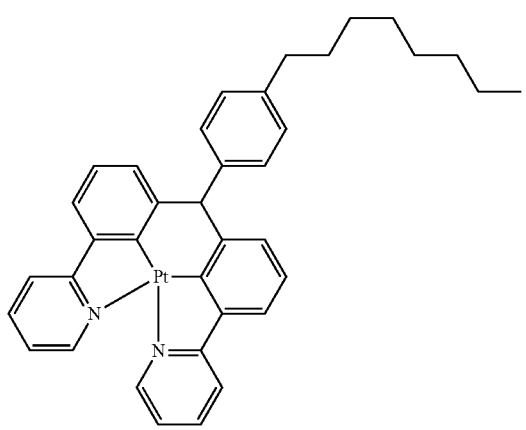
D38
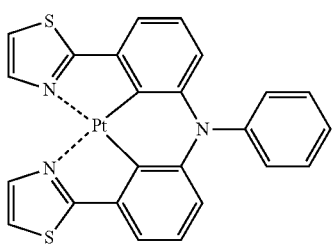
D39
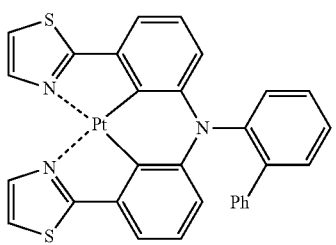
D40
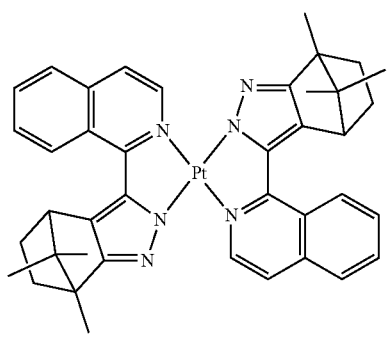
D41
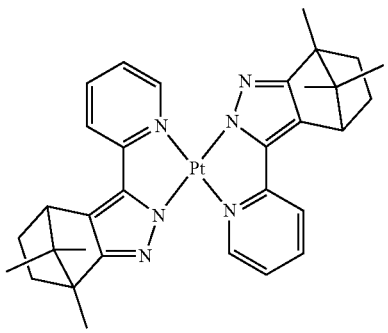
D42
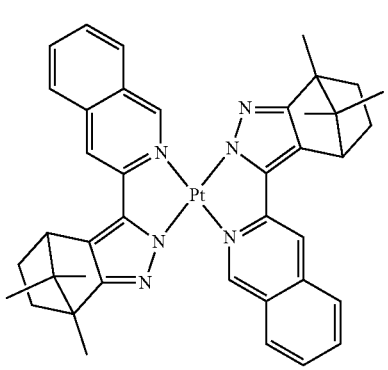
D43
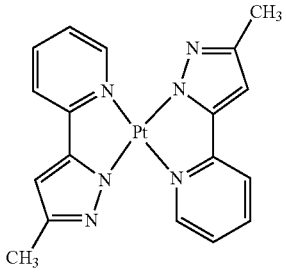
D44
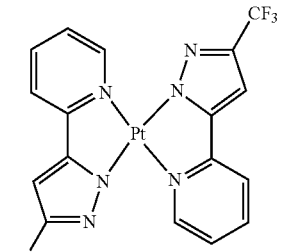
D45
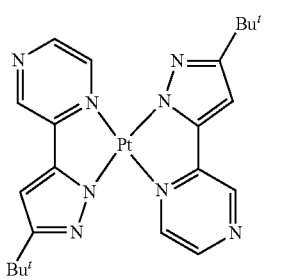

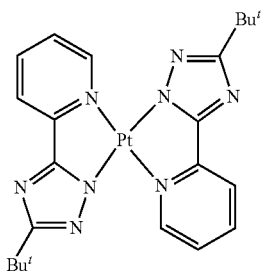

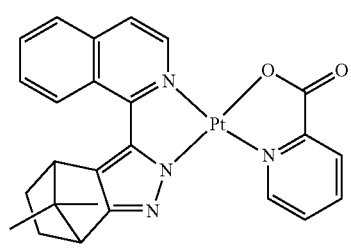

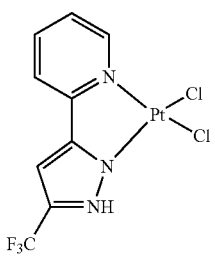

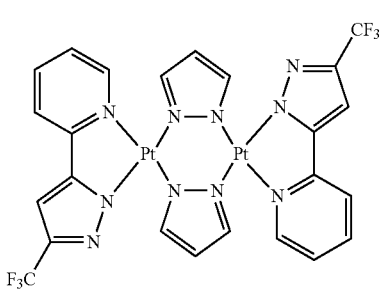

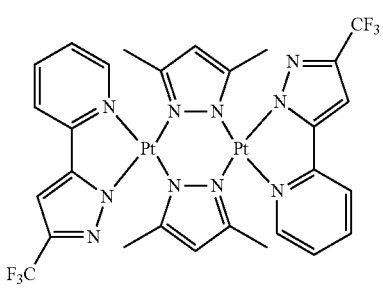

Also, examples of the dopant included in the EML include, but are not limited to, Os-complexes:

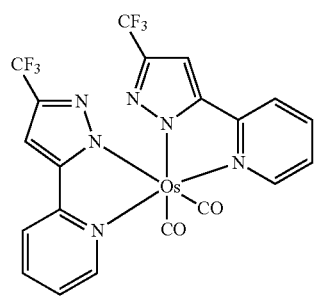

Os(fppz)$_2$(CO)$_2$

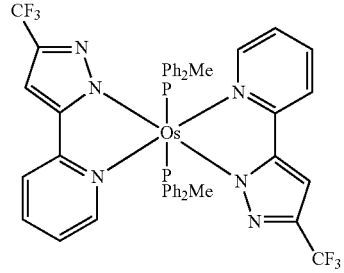

Os(fppz)$_2$(PPh$_2$Me)$_2$

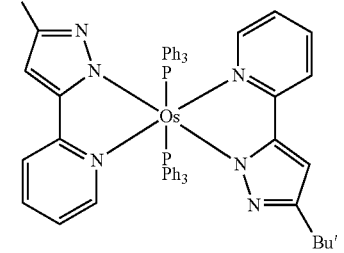

Os(bppz)$_2$(PPh$_3$)$_2$

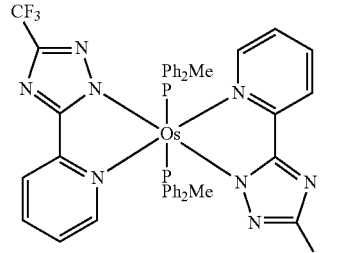

Os(fptz)$_2$(PPh$_2$Me)$_2$

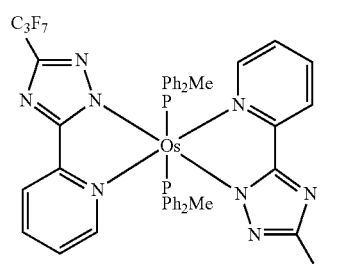

Os(hptz)$_2$(PPhMe$_2$)$_2$

When the EML includes a host and a dopant, the amount of the dopant in the EML may be generally in the range of about 0.01 to about 15 parts by weight based on 100 parts by weight of the host, but is not limited thereto.

The thickness of the EML may be in the range of about 100 Å to about 1,000 Å, for example, in the range of about 200 Å to about 600 Å. When the thickness of the EML is within this range, excellent luminescent properties may be obtained without a substantial increase in driving voltage.

Next, an ETL may be formed using various methods such as vacuum deposition, spin coating, or casting. When the ETL is formed by vacuum deposition or spin coating, the deposition and coating conditions vary according to a used compound. However, in general, the condition may be almost the same as the condition for forming the HIL. A material for forming the ETL may be a known electron transporting material that stably transports electrons injected from a cathode. Examples of the known electron transporting material may include, but are not limited to, a quinoline derivative such as tris(8-quinolinolate)aluminum ($Alq_3$), TAZ, Balq, beryllium bis(benzoquinoline-10-olate ($Bebq_2$), ADN, and known materials such as Compound 201 and Compound 202 below.

TAZ

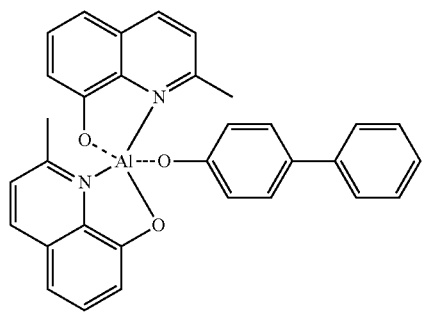

BAlq

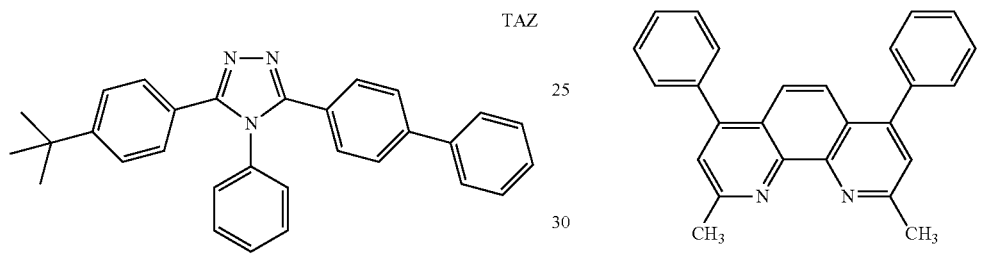

Compound 201

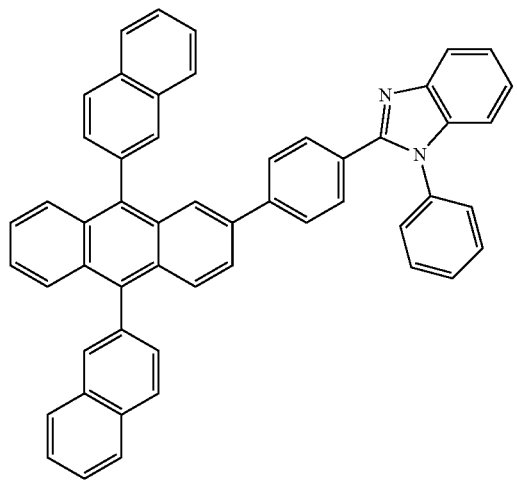

Compound 202

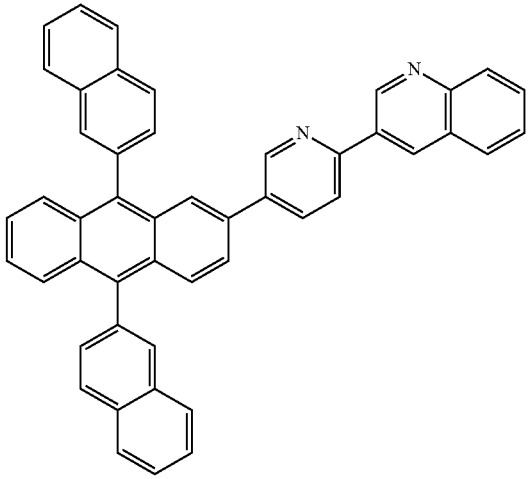

BCP

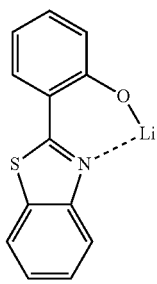

The thickness of the ETL may be in the range of about 100 Å to about 1,000 Å, for example, in the range of about 150 Å to about 500 Å. When the thickness of the ETL is within this range, satisfactory electron transport properties may be obtained without a substantial increase in driving voltage.

In addition, the ETL may further include a metal-containing material, in addition to a known electron transporting organic compound.

The metal-containing material may include a Li-complex. Examples of the Li-complex may include lithium quinolate (LiQ) and Compound 203 below:

Compound 203

Also, an EIL, which facilitates electron injection from a cathode, may be formed on the ETL, and a material for forming the EIL is not particularly limited.

The material for forming the EIL may include a known material for forming an EIL, such as LiF, NaCl, CsF, $Li_2O$, or BaO. The deposition condition of the EIL may vary according a used compound. However, in general, the condition may be almost the same as the condition for forming the HIL.

The thickness of the EIL may be in the range of about 1 Å to about 100 Å, for example, in the range of about 3 Å to about 90 Å. When the thickness of the EIL is within this range, satisfactory electron injection properties may be obtained without a substantial increase in driving voltage.

A second electrode 17 is formed on the organic layer 15. The second electrode 17 may be a cathode, which is an electron injection electrode. In this regard, a metal for forming the second electrode 17 may include a metal having low work function, such as metal, an alloy, an electric conducting compound, and mixtures thereof. In particular, the second electrode 17 may be formed as a thin film by using lithium (Li), magnesium (Mg), aluminum (Al), aluminum-lithium (Al—Li), calcium (Ca), magnesium-indium (Mg—In), or magnesium-silver (Mg—Ag), thus being transparent. In order to obtain a top-emission type OLED, the second electrode 17 may be formed as a transparent electrode by using ITO or IZO.

The OLED has been described with reference to FIG. 1, but is not limited thereto.

Also, when a phosphorescent dopant is included in the EML, a HBL may be formed between the ETL and the EML or between the H-functional layer and the EML by vacuum deposition, spin coating, casting or LB deposition so as to prevent triplet excitons or holes from being diffused to the ETL. When the HBL is formed by vacuum deposition or spin coating, the conditions thereof may vary according to a used compound. However, in general, the conditions may be almost the same as the condition for forming the HIL. The HBL may include a known hole blocking material. Examples of the known hole blocking material may include an oxadiazole derivative, a triazole derivative, and a phenanthroline derivative. For example, BCP may be used as a hole blocking material.

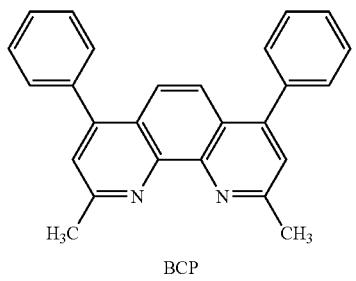 [SMILES: Cc1cc(-c2ccccc2)c2ccc3c(-c4ccccc4)cc(C)nc3c2n1 ; "BCP"]

BCP

The thickness of the HBL may be in the range of about 20 Å to about 1,000 Å, for example, in the range of about 30 Å to about 300 Å. When the thickness of the HBL is within this range, excellent hole blocking properties may be obtained without a substantial increase in driving voltage.

Examples of the unsubstituted $C_1$-$C_{60}$ alkyl group (or $C_1$-$C_{60}$ alkyl group) include $C_1$-$C_{60}$ linear or branched alkyl groups such as methyl, ethyl, propyl, isobutyl, sec-butyl, pentyl, iso-amyl, hexyl, and the like. The substituted $C_1$-$C_{60}$ alkyl group may be a group in which at least one hydrogen of the unsubstituted $C_1$-$C_{60}$ alkyl group is substituted with deuterium, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —N($Q_{11}$)($Q_{12}$), and —Si($Q_{13}$)($Q_{14}$)($Q_{15}$) (wherein $Q_{11}$ through $Q_{15}$ may be each independently selected from hydrogen, a $C_1$-$C_{60}$ alkyl group, a $C_2$-$C_{60}$ alkenyl group, a $C_2$-$C_{60}$ alkynyl group, a $C_5$-$C_{60}$ aryl group, and a $C_2$-$C_{60}$ heteroaryl group).

The unsubstituted $C_1$-$C_{60}$ alkoxy group (or $C_1$-$C_{60}$ alkoxy group) has a formula of —OA (in this regard, A is the unsubstituted $C_1$-$C_{60}$ alkyl group as described above) and examples thereof include methoxy, ethoxy, isopropyloxy, and the like. At least one hydrogen atom of the unsubstituted $C_1$-$C_{60}$ alkoxy group may be substituted with the same substituent as in the substituted $C_1$-$C_{60}$ alkyl group described above.

The unsubstituted $C_2$-$C_{60}$ alkenyl group (or $C_2$-$C_{60}$ alkenyl group) is interpreted to contain at least one carbon-carbon double bond in the middle or at a terminal of the unsubstituted $C_2$-$C_{60}$ alkyl group. Examples of the unsubstituted $C_2$-$C_{60}$ alkenyl group include ethenyl, propenyl, butenyl, and the like. At least one hydrogen atom of the unsubstituted $C_2$-$C_{60}$ alkenyl group may be substituted with the same substituent as in the substituted $C_1$-$C_{60}$ alkyl group described above.

The unsubstituted $C_2$-$C_{60}$ alkynyl group (or $C_2$-$C_{60}$ alkynyl group) is interpreted to contain at least one carbon-carbon triple bond in the middle or at a terminal of the $C_2$-$C_{60}$ alkyl group defined above. Examples of the unsubstituted $C_2$-$C_{60}$ alkynyl group include ethynyl, propynyl, and the like. At least one hydrogen atom of the unsubstituted $C_2$-$C_{60}$ alkynyl group may be substituted with the same substituent as in the substituted $C_1$-$C_{60}$ alkyl group described above.

The unsubstituted $C_5$-$C_{60}$ aryl group indicates a monovalent group having an aromatic carbocyclic system that has 5 to 60 carbon atoms and at least one aromatic ring and the unsubstituted $C_5$-$C_{60}$ arylene group indicates a divalent group having an aromatic carbocyclic system that has 5 to 60 carbon atoms and at least one aromatic ring. If the $C_5$-$C_{60}$ aryl group and the $C_5$-$C_{60}$ arylene group each independently have two or more aromatic rings, the rings may be fused with each other. At least one hydrogen atom of each of the unsubstituted $C_5$-$C_{60}$ aryl group and the unsubstituted $C_5$-$C_{60}$ arylene group may be substituted with the same substituent as in the substituted $C_1$-$C_{60}$ alkyl group described above.

Examples of the substituted or unsubstituted $C_5$-$C_{60}$ aryl group include, but are not limited to, a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- and p-fluorophenyl group, and a dichlorophenyl group), a dicyanophenyl group, a trifluoromethoxyphenyl group, an o-, m-, and p-tolyl group, an o-, m- and p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentalenyl group, a tetraphenylenyl group, a hexaphenyl group, a hexacenyl group, a rubicenyl group, a coroneryl group, a trinaphthylenyl group, a heptaphenyl group, a heptacenyl, a pyranthrenyl group, and an ovalenyl group. Examples of the substituted $C_5$-$C_{60}$ aryl group may be easily understood with reference to the examples of the unsubstituted $C_5$-$C_{60}$ aryl group described above and the substituents of the substituted $C_1$-$C_{60}$ alkyl group. Examples of the substituted or unsubstituted $C_5$-$C_{60}$ arylene group may be easily understood with reference to the substituted or unsubstituted $C_5$-$C_{60}$ aryl group described above.

The unsubstituted $C_2$-$C_{60}$ heteroaryl group indicates a monovalent group having at least one aromatic ring system including carbon rings and at least one hetero atom selected from the group consisting of N, O, P, and S, and the unsubstituted $C_2$-$C_{60}$ heteroarylene group indicates a divalent group having at least one aromatic ring system including carbon rings and at least one hetero atom selected from the group consisting of N, O, P, and S. In this regard, if the $C_2$-$C_{60}$ heteroaryl group and the $C_2$-$C_{60}$ heteroarylene group each independently have two or more aromatic rings, the rings may be fused with each other. At least one hydrogen atom of each of the unsubstituted $C_2$-$C_{60}$ heteroaryl group and the unsubstituted $C_2$-$C_{60}$ heteroarylene group may be substituted with the same substituents as in the $C_1$-$C_{60}$ alkyl group described above.

Examples of the unsubstituted $C_2$-$C_{60}$ heteroaryl group include, but are not limited to, a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ heteroarylene group may be easily understood with reference to the examples of the substituted or unsubstituted $C_2$-$C_{60}$ arylene group.

The substituted or unsubstituted $C_5$-$C_{60}$ aryloxy group has a formula of $-OA_2$ wherein $A_2$ is the substituted or unsubstituted $C_5$-$C_{60}$ aryl group as described above, and the substituted or unsubstituted $C_5$-$C_{60}$ arylthio group has a formula of $-SA_3$ wherein $A_3$ is the substituted or unsubstituted $C_5$-$C_{60}$ aryl group described above.

An OLED according to an embodiment of the present invention will now be described in detail with reference to the following Examples. These Examples are for illustrative purposes only and are not intended to limit the scope of the invention.

EXAMPLE

Synthesis Example 1

Synthesis of Compound 3

Compound 3 was synthesized according to Reaction Scheme 1 below:

Reaction scheme 1

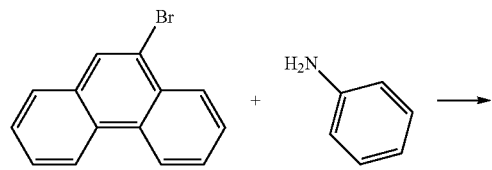

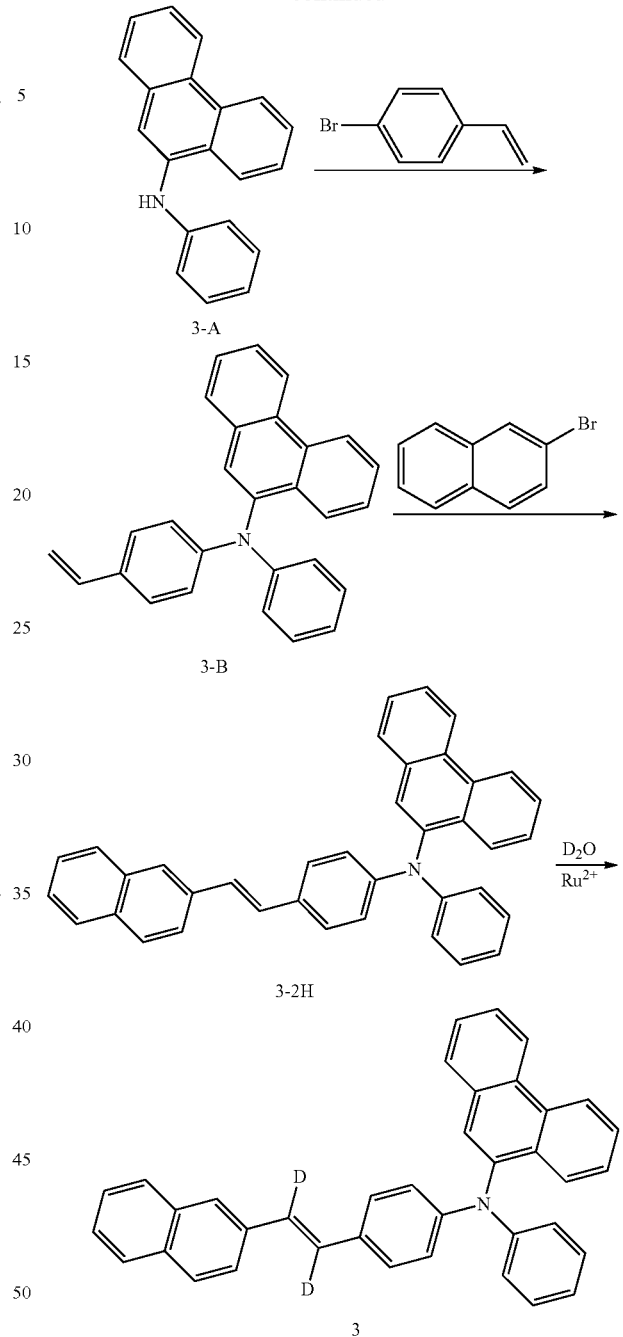

Synthesis of Intermediate 3-A 5.14 g (20.0 mmol) of 9-bromophenathrene, 2.8 g (30.0 mmol) of aniline, 0.366 g (0.4 mmol) of tris(dibenzylideneacetone)dipalladium(0):$Pd_2(dba)_3$), 0.081 g (0.4 mmol) of tri-tert-butylphosphine:P(t-Bu)$_3$), and 2.88 g (30.0 mmol) of KOtBu were dissolved in 60 mL of toluene and stirred at 85° C. for 4 hours. The obtained reaction solution was cooled down to room temperature and then extracted three times with 50 ml of water and 50 ml of diethylether. The obtained organic layer was dried with magnesium sulfate and a solvent was evaporated therefrom to obtain a crude product. The crude product was purified with silica gel column chromatography to obtain 4.63 g of Intermediate 3-A (yield 86%). The obtained compound was confirmed by MS/FAB.

C$_{20}$H$_{15}$N: cal. 269.12. found 270.13.

Synthesis of Intermediate 3-B 2.69 g (10.0 mmol) of Intermediate 3-A, 2.75 g (15.0 mmol) of 2-bromo-4-vinylbenzene, 0.183 g (0.2 mmol) of Pd$_2$(dba)$_3$, 0.041 g (0.2 mmol) of P(t-Bu)$_3$, and 1.44 g (15.0 mmol) of KOtBu were dissolved in 30 mL of toluene and stirred at 85° C. for 4 hours. The obtained reaction solution was cooled down to room temperature and then extracted three times with 30 ml of water and 30 ml of diethylether. The obtained organic layer was dried with magnesium sulfate and a solvent was evaporated therefrom to obtain a crude product. The crude product was purified with silica gel column chromatography to obtain 2.30 g of Intermediate 3-B (yield 62%). The obtained compound was confirmed by MS/FAB.

C$_{28}$H$_{21}$N: cal. 371.17. found 372.16.

Synthesis of Compound 3-2H 1.86 g (5.0 mmol) of Intermediate 3-B, 1.04 g (5.0 mmol) of 2-bromonaphthalene, 0.056 g (0.25 mmol) of palladium (II) acetate:Pd(OAc)$_2$, 0.76 g (0.25 mmol) of tri(o-tolyl)phosphine ((p-tolyl)$_3$P), and 1.019 g (10.0 mmol) of Et$_3$N were dissolved in 30 ml of dimethylacetamide (DMAc) and stirred at 100° C. for 4 hours. The obtained reaction solution was cooled down to room temperature and then extracted three times with 30 ml of water and 30 ml of diethylether. The obtained organic layer was dried with magnesium sulfate and a solvent was evaporated therefrom to obtain a crude product. The crude product was purified with silica gel column chromatography to obtain 1.82 g of Compound 3-2H (yield 73%). The obtained compound was confirmed by MS/FAB and $^1$H nuclear magnetic resonance (NMR).

C$_{38}$H$_{27}$N: cal. 497.21. found 498.22.

$^1$H NMR (CDCl$_3$, 400 MHz) δ (ppm) 8.59 (d, 1H), 8.20-8.17 (m, 1H), 8.00-7.92 (m, 3H), 7.85-7.82 (m, 3H), 7.71-7.67 (m, 2H), 7.60-7.39 (m, 7H), 7.22-7.12 (m, 2H), 7.08-7.02 (m, 3H), 6.97-6.91 (m, 3H), 6.85-6.83 (m, 2H)

Synthesis of Compound 3

1.49 g (3.0 mmol) of Compound 3-2H, 0.086 g (0.09 mmol) of carbonylchlorohydridotris(triphenylphosphine)ruthenium(II) ([(Ph$_3$)P]$_3$Ru(CO)(Cl)H), and 0.54 mL (30.0 mmol) of D$_2$O were dissolved in 30 ml of 1,4-dioxane and stirred at 80° C. for 12 hours. The obtained reaction solution was cooled down to room temperature to remove a solvent and then extracted three times with 30 ml of water and 30 ml of dichloromethane. The obtained organic layer was dried with magnesium sulfate and a solvent was evaporated therefrom to obtain a crude product. The crude product was purified with silica gel column chromatography to obtain 1.33 g of Compound 3 (yield 89%). The obtained compound was confirmed by MS/FAB and $^1$H NMR.

C$_{38}$H$_{25}$D$_2$N: cal. 499.23. found 450.25.

$^1$H NMR (CDCl$_3$, 400 MHz) δ (ppm) 8.59 (d, 1H), 8.20-8.17 (m, 1H), 7.95-7.93 (m, 1H), 7.85-7.83 (m, 4H), 7.71-7.63 (m, 3H), 7.59-7.50 (m, 3H), 7.47-7.39 (m, 4H), 7.12-7.06 (m, 3H), 6.98-6.93 (m, 3H), 6.83-6.80 (m, 2H), deuterium substitution rate: 92.5%

Synthesis Example 2

Synthesis of Compound 33

Compound 33 was synthesized according to Reaction Scheme 2 below:

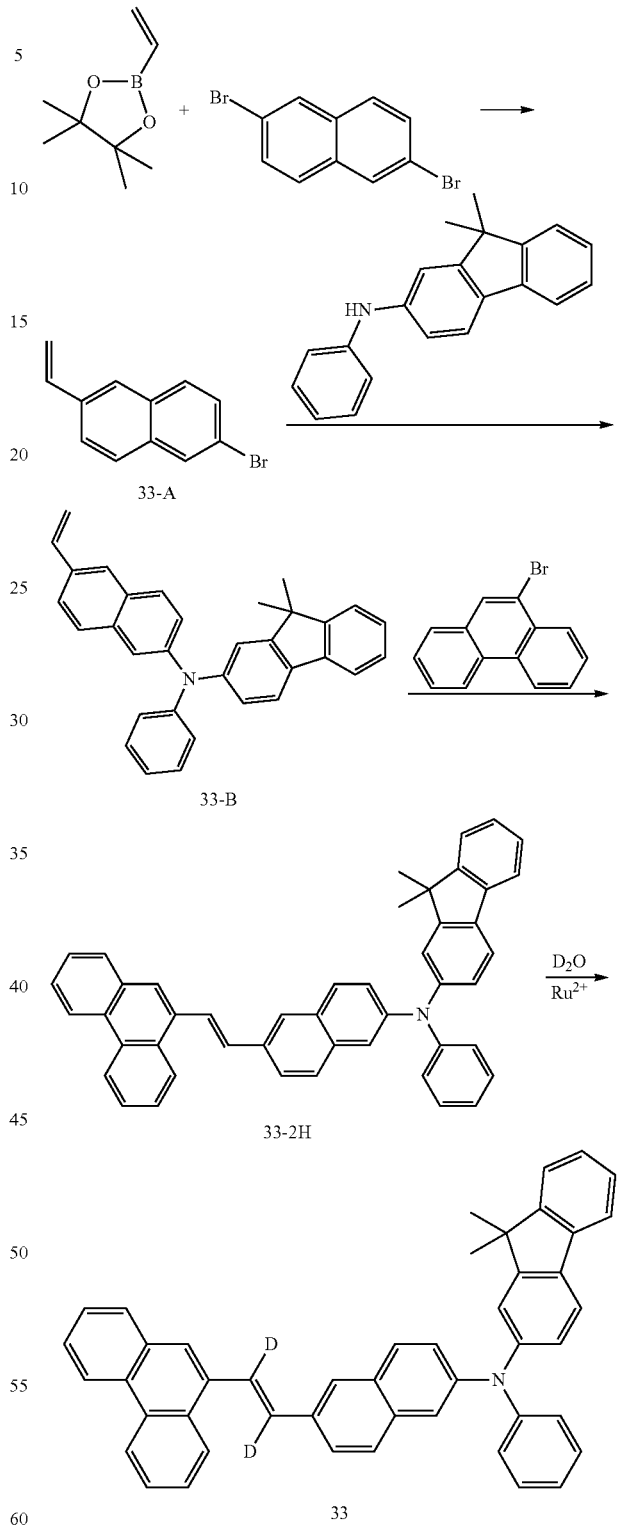

Reaction scheme 2

Intermediate 33-A 3.14 mL (20.0 mmol) of vinylboronic acid pinacol ester, 8.58 g (30.0 mmol) of 2,6-dibromonaphthalene, 1.15 g (1.0 mmol) of Pd(PPh₃)₄, and 8.29 g (60.0 mmol) of K₂CO₃ were dissolved in 60 mL of a mixture solution of THF/H₂O (volume ratio of 2/1) and stirred at 75° C. for 5 hours. The obtained reaction solution was cooled down to room temperature and then extracted three times with 30 ml of water and 50 ml of diethylether. The obtained organic layer was dried with magnesium sulfate and a solvent was evaporated therefrom to obtain a crude product. The crude product was purified with silica gel column chromatography to obtain 2.98 g of Intermediate 33-A (yield 64%). The obtained compound was confirmed by MS/FAB.

$C_{12}H_9Br$: cal. 231.99. found 233.01.

Synthesis of Intermediate 33-B 2.84 g of Intermediate 33-B (yield 65%) was prepared in the same manner as in the synthesis of Intermediate 3-B of Synthesis Example 1, except that 9,9'-dimethylfluoren-2-ylphenylamine was used instead of Intermediate 3-A and Intermediate 33-A was used instead of 1-bromo-4-vinylbenzene. The obtained compound was confirmed by MS/FAB.

$C_{33}H_{27}N$: cal. 437.21. found 438.24.

Synthesis of Compound 33-2H 2.27 g of Compound 33-2H (yield 74%) was prepared in the same manner as in the synthesis of Compound 3-2H of Synthesis Example 1, except that Intermediate 33-B was used instead of Intermediate 3-B and 9-bromophenathrene was used instead of 2-bromonaphthalene. The obtained compound was confirmed by MS/FAB and ¹H NMR.

$C_{47}H_{35}N$: cal. 613.28. found 614.29.

¹H NMR (CDCl₃, 400 MHz) δ (ppm) 8.66 (d, 1H), 8.46 (d, 1H), 8.15-8.06 (m, 3H), 7.92 (s, 1H), 7.83-7.58 (m, 9H), 7.47 (dt, 1H), 7.36-7.27 (m, 3H), 7.14-7.02 (m, 5H), 6.95-6.92 (m, 2H), 6.87 (s, 1H), 6.82-6.80 (m, 2H), 1.67 (s, 6H)

Synthesis of Compound 33

Compound 33 (yield 85%) was prepared in the same manner as in the synthesis of Compound 3 of Synthesis Example 1, except that Compound 33-2H was used instead of Compound 3-2H. The obtained compound was confirmed by MS/FAB and ¹H NMR.

$C_{47}H_{33}D_2N$: cal. 615.29. found 616.30.

¹H NMR (CDCl₃, 400 MHz) δ (ppm) 8.66 (d, 1H), 8.46 (d, 1H), 8.11 (d, 1H), 7.93-7.91 (m, 2H), 7.83-7.62 (m, 8H), 7.58 (d, 1H), 7.48 (dt, 1H), 7.36-7.30 (m, 2H), 7.14-7.05 (m, 4H), 6.98 (dt, 1H), 6.93-6.90 (m, 2H), 6.87 (s, 1H), 6.81-6.79 (m, 2H), 1.67 (s, 6H), deuterium substitution rate: 84%

Synthesis Example 3

Synthesis of Compound 1

Compound 1 was prepared in the same manner as in Synthesis Example 1, except that N-phenylnaphthalen-2-amine was used instead of Intermediate 3-A. The obtained compound was confirmed by MS/FAB and ¹H NMR.

$C_{34}H_{23}D_2N$: cal. 449.21. found 450.22.

¹H NMR (CDCl₃, 400 MHz) δ (ppm) 7.86-7.82 (m, 4H), 7.79-7.76 (m, 1H), 7.68-7.64 (m, 2H), 7.57-7.38 (m, 9H), 7.13-7.06 (m, 3H), 6.99-6.96 (m, 2H), 6.86-6.83 (m, 1H), 6.45-6.42 (m, 2H), deuterium substitution rate: 91.8%

Synthesis Example 4

Synthesis of Compound 5

Compound 5 was prepared in the same manner as in Synthesis Example 1, except that 2-bromonaphthalene was used instead of 9-bromophenathrene, and Intermediate 5-A-(1) was used instead of aniline in the synthesis of Intermediate 3-A. The obtained compound was confirmed by MS/FAB and ¹H NMR.

$C_{46}H_{30}D_2FN$: cal. 619.26. found 620.24.

¹H NMR (CDCl₃, 400 MHz) δ (ppm) 7.87-7.83 (m, 4H), 7.78-7.76 (m, 1H), 7.74-7.69 (m, 2H), 7.67-7.60 (m, 5H), 7.56-7.38 (m, 14H), 7.14-7.09 (m, 2H), 6.93-6.89 (m, 2H)

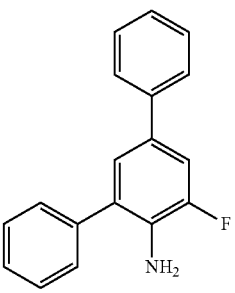

5-A-(1)

Synthesis Example 5

Synthesis of Compound 6

Compound 6 was prepared in the same manner as in Synthesis Example 1, except that 4-bromobenzonitrile was used instead of 9-bromophenathrene and naphtalene-2-amine was used instead of aniline in the synthesis of Intermediate 3-A. The obtained compound was confirmed by MS/FAB and ¹H NMR.

$C_{35}H_{22}D_2N_2$: cal. 474.21. found 445.22.

¹H NMR (CDCl₃, 400 MHz) δ (ppm) 7.81-7.76 (m, 4H), 7.71-7.64 (m, 2H), 7.59-7.53 (m, 4H), 7.48-7.44 (m, 2H), 7.42-7.31 (m, 4H), 7.13-7.09 (m, 1H), 7.02-6.99 (m, 1H), 6.94-6.88 (m, 4H), deuterium substitution rate: 93.4%

Synthesis Example 6

Synthesis of Compound 9

Compound 9 was prepared in the same manner as in Synthesis Example 2, except that 2-bromonaphthalene was used instead of 9-bromophenathrene in the synthesis of Compound 33-2H. The obtained compound was confirmed by MS/FAB and ¹H NMR.

$C_{43}H_{31}D_2N$: cal. 565.27. found 566.29.

¹H NMR (CDCl₃, 400 MHz) δ (ppm) 7.90-7.82 (m, 5H), 7.78-7.62 (m, 6H), 7.58-7.43 (m, 3H), 7.35-7.30 (m, 2H), 7.13-7.06 (m, 4H), 6.90-6.83 (m, 2H), 6.65-6.63 (m, 1H), 6.42-6.40 (m, 2H), 1.68 (s, 6H) deuterium substitution rate: 86.4%

Synthesis Example 7

Synthesis of Compound 12

Compound 12 was prepared in the same manner as in Synthesis Example 2, except that 2,7-dibromo-9,9-dimethyl-9H-fluorene was used instead of 2,6-dibromonaphthalene in the synthesis of Intermediate 33-A, N-phenylnaphthalen-2-amine was used instead of 9,9-dimethyl-N-phenyl-9H-fluoren-2-amine in the synthesis of Intermediate 33-B, and 2-bromonaphthalene was used instead of 9-bromophenathrene in the synthesis of Compound 33-2H. The obtained compound was confirmed by MS/FAB and $^1$H NMR.

$C_{43}H_{31}D_2N$: cal. 565.27. found 566.28.
$^1$H NMR (CDCl$_3$, 400 MHz) δ (ppm) 7.89-7.83 (m, 4H), 7.78-7.64 (m, 6H), 7.58-7.51 (m, 4H), 7.46-7.33 (m, 3H), 7.20-7.15 (m, 3H), 6.91-6.83 (m, 2H), 6.73-6.71 (m, 1H), 6.42-6.40 (m, 2H), 1.67 (s, 6H) deuterium substitution rate: 84.4%

Synthesis Example 8

Synthesis of Compound 18

Compound 18 was prepared in the same manner as in Synthesis Example 1, except that 4-bromobenzonitrile was used instead of 9-bromophenathrene and naphtalene-2-amine was used instead of aniline in the synthesis of Intermediate 3-A, and 9-bromophenathrene was used instead of 2-bromonaphthalene in the synthesis of Compound 3-2H. The obtained compound was confirmed by MS/FAB and $^1$H NMR $C_{39}H_{24}D_2N_2$: cal. 524.22. found 525.24.
$^1$H NMR (CDCl$_3$, 400 MHz) δ (ppm) 8.67-8.64 (m, 1H), 8.46-8.44 (m, 1H), 8.10-8.08 (m, 1H), 7.85-7.76 (m, 3H), 7.69-7.63 (m, 4H), 7.57-7.36 (m, 8H), 7.18-6.98 (m, 6H), deuterium substitution rate: 91.3%

Synthesis Example 9

Synthesis of Compound 19

Compound 19 was prepared in the same manner as in Synthesis Example 1, except that 9,9-dimethyl-N-phenyl-9H-fluoren-2-amine was used instead of Intermediate 3-A, and 9-bromophenathrene was used instead of 2-bromonaphthalene in the synthesis of Compound 3-2H. The obtained compound was confirmed by MS/FAB and $^1$H NMR.

$C_{43}H_{31}D_2N$: cal. 565.27. found 566.26.
$^1$H NMR (CDCl$_3$, 400 MHz) δ (ppm) 8.67-8.64 (m, 1H), 8.46-8.44 (m, 1H), 8.10-8.08 (m, 1H), 7.85-7.81 (m, 2H), 7.78-7.76 (m, 1H), 7.69-7.64 (m, 2H), 7.56-7.46 (m, 4H), 7.36-7.30 (m, 1H), 7.14-7.04 (m, 5H), 6.96-6.83 (m, 4H), 6.59-6.58 (m, 1H), 6.43-6.40 (m, 2H), 1.67 (s, 6H), deuterium substitution rate: 85.8%

Synthesis Example 10

Synthesis of Compound 25

Compound 25 was prepared in the same manner as in Synthesis Example 1, except that 3-iodo-9-phenyl-9H-carbazole was used instead of 9-bromophenathrene in the synthesis of Intermediate 3-A, and 9-bromophenathrene was used instead of 2-bromonaphthalene in the synthesis of Compound 3-2H. The obtained compound was confirmed by MS/FAB and $^1$H NMR.

$C_{46}H_{30}D_2N_2$: cal. 614.27. found 615.28.
$^1$H NMR (CDCl$_3$, 400 MHz) δ (ppm) 8.67-8.64 (m, 1H), 8.46-8.44 (m, 1H), 8.22-8.19 (m, 1H), 8.11-8.09 (m, 1H), 7.85-7.81 (m, 2H), 7.69-7.64 (m, 2H), 7.52-7.22 (m, 13H), 7.18-7.14 (m, 2H), 7.06-7.04 (m, 1H), 6.97-6.94 (m, 3H), 6.86-6.83 (m, 1H), 6.52-6.50 (m, 2H), deuterium substitution rate: 89.4%

Synthesis Example 11

Synthesis of Compound 29

Compound 29 was prepared in the same manner as in Synthesis Example 1, except that Intermediate A-29-(1) below was used instead of 9-bromophenathrene in the synthesis of Intermediate 3-A, and 9-bromophenathrene was used instead of 2-bromonaphthalene in the synthesis of Compound 3-2H. The obtained compound was confirmed by MS/FAB and $^1$H NMR.

$C_{40}H_{25}D_2NS$: cal. 555.20. found 556.23.
$^1$H NMR (CDCl$_3$, 400 MHz) δ (ppm) 8.67-8.64 (m, 1H), 8.46-8.44 (m, 1H), 8.12-8.04 (m, 2H), 7.85-7.81 (m, 3H), 7.72-7.58 (m, 5H), 7.50-7.42 (m, 4H), 7.18-7.14 (m, 2H), 7.06-7.04 (m, 1H), 6.97-6.94 (m, 3H), 6.86-6.83 (m, 1H), 6.51-6.49 (m, 2H), deuterium substitution rate: 86.9%

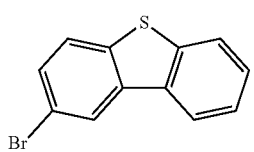

29-A-(1)

Synthesis Example 12

Synthesis of Compound 30

Compound 30 was prepared in the same manner as in Synthesis Example 1, except that Intermediate 30-A-(1) below was used instead of 9-bromophenathrene and naphtalene-2-amine was used instead of aniline in the synthesis of Intermediate 3-A, and 9-bromophenathrene was used instead of 2-bromonaphthalene in the synthesis of Compound 3-2H. The obtained compound was confirmed by MS/FAB and $^1$H NMR.

$C_{44}H_{27}D_2NO$: cal. 589.24. found 590.27.
$^1$H NMR (CDCl$_3$, 400 MHz) δ (ppm) 8.67-8.64 (m, 1H), 8.46-8.44 (m, 1H), 8.12-8.09 (m, 1H), 7.85-7.36 (m, 19H), 7.28-7.08 (m, 5H)

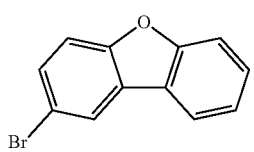

30-A-(1)

Synthesis Example 13

Synthesis of Compound 34

Compound 34 was prepared in the same manner as in Synthesis Example 2, except that 1,4-dibromonaphthalene was used instead of 2,6-dibromonaphthalene in the synthesis of Intermediate 33-A, and bis(9,9-dimethyl-9H-fluoren-2-yl)amine was used instead of 9,9-dimethyl-N-phenyl-9H-fluoren-2-amine in the synthesis of Intermediate 33-B. The obtained compound was confirmed by MS/FAB and $^1$H NMR.

$C_{56}H_{41}D_2N$: cal. 731.35. found 732.36.

$^1$H NMR (CDCl$_3$, 400 MHz) δ (ppm) 8.66 (d, 1H), 8.46 (d, 1H), 8.11 (d, 1H), 7.93-7.76 (m, 5H), 7.69-7.63 (m, 3H), 7.55-7.46 (m, 4H), 7.36-7.24 (m, 3H), 7.14-7.08 (m, 5H), 6.98-6.92 (m, 2H), 6.86-6.84 (m, 2H), 6.61-6.59 (m, 2H), 1.67 (s, 12H), deuterium substitution rate: 82%

Synthesis Example 14

Synthesis of Compound 36

Compound 36 was prepared in the same manner as in Synthesis Example 1, except that 9,10-di-tert-butyl-2-bromoanthracene was used instead of 2-bromonaphthalene in the synthesis of Compound 3-2H. The obtained compound was confirmed by MS/FAB and $^1$H NMR.

$C_{50}H_{43}D_2N$: cal. 661.37. found 662.35.

$^1$H NMR (CDCl$_3$, 400 MHz) δ (ppm) 8.58 (d, 1H), 8.43 (d, 1H), 8.20-8.07 (d, 4H), 7.95-7.93 (m, 1H), 7.71-7.68 (m, 2H), 7.61-7.56 (m, 3H), 7.48-7.39 (m, 5H), 7.07-7.03 (m, 3H), 6.97-6.91 (m, 3H), 6.52-6.49 (m, 2H), 1.72 (s, 9H), 1.71 (s, 9H), deuterium substitution rate: 84.6%

Synthesis Example 15

Synthesis of Compound 44

Compound 44 was prepared in the same manner as in Synthesis Example 1, except that Intermediate 44-A-(1) below was used instead of 9-bromophenathrene in the synthesis of Intermediate 3-A, and 9,10-di-tert-butyl-2-bromoanthracene was used instead of 2-bromonaphthalene in the synthesis of Compound 3-2H. The obtained compound was confirmed by MS/FAB and $^1$H NMR.

$C_{47}H_{42}D_2N_2$: cal. 638.36. found 639.37.

$^1$H NMR (CDCl$_3$, 400 MHz) δ (ppm) 8.68 (d, 1H), 8.43 (d, 1H), 8.20-8.07 (d, 4H), 7.60 (dd, 1H), 7.50-7.41 (m, 7H), 7.17 (t, 1H), 7.10-7.04 (m, 3H), 6.99-6.96 (m, 2H), 6.86-6.83 (m, 1H), 6.54-6.48 (m, 3H), 1.72 (s, 9H), 1.71 (s, 9H), deuterium substitution rate: 82.6%

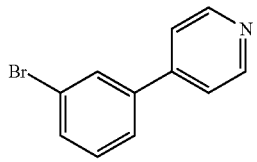

44-A-(1)

Synthesis Example 16

Synthesis of Compound 45

Compound 45 was prepared in the same manner as in Synthesis Example 1, except that bromobenzene was used instead of 9-bromophenathrene, and Intermediate 5-A-(1) was used instead of aniline in the synthesis of Intermediate 3-A, and 9,10-di-tert-butyl-2-bromoanthracene was used instead of 2-bromonaphthalene in the synthesis of Compound 3-2H. The obtained compound was confirmed by MS/FAB and $^1$H NMR.

$C_{54}H_{46}D_2FN$: cal. 731.38. found 732.37.

$^1$H NMR (CDCl$_3$, 400 MHz) δ (ppm) 8.43 (t, 1H), 8.19 (d, 1H), 8.14-8.06 (d, 2H), 7.72-7.39 (m, 16H), 7.14-7.04 (m, 3H), 6.97-6.90 (m, 3H), 6.64-6.62 (m, 2H), 1.71 (s, 9H), 1.70 (s, 9H)

Synthesis Example 17

Synthesis of Compound 47

Compound 47 was prepared in the same manner as in Synthesis Example 1, except that diphenylamine was used instead of Intermediate 3-A, and Intermediate 47-2H-(1) below was used instead of 2-bromonaphthalene in the synthesis of Compound 3-2H. The obtained compound was confirmed by MS/FAB and $^1$H NMR.

$C_{46}H_{31}D_2N$: cal. 601.27. found 602.24.

$^1$H NMR (CDCl$_3$, 400 MHz) δ (ppm) 8.22 (d, 1H), 8.01 (d, 1H), 7.82-7.65 (m, 6H), 7.57-7.28 (m, 11H), 7.08-7.04 (m, 4H), 6.99-6.93 (m, 4H), 6.56-6.53 (m, 4H)

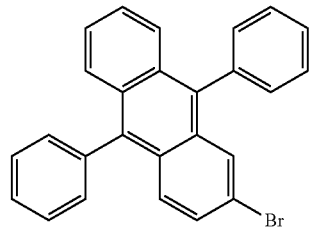

47-2H-(1)

Synthesis Example 18

Synthesis of Compound 52

Compound 52 was prepared in the same manner as in Synthesis Example 1, except that diphenylamine was used instead of Intermediate 3-A, and Intermediate 52-2H-(1) below was used instead of 2-bromonaphthalene in the synthesis of Compound 3-2H. The obtained compound was confirmed by MS/FAB and $^1$H NMR.

$C_{40}H_{22}D_7N$: cal. 530.27. found 531.24.

$^1$H NMR (CDCl$_3$, 400 MHz) δ (ppm) 8.03 (dd, 2H), 7.93 (dd, 2H), 7.46-7.44 (m, 2H), 7.35-7.31 (m, 2H), 7.08-7.03 (m, 4H), 6.95-6.91 (m, 2H), 6.89-6.86 (m, 2H), 6.76-6.73 (m, 2H), 6.56-6.53 (m, 4H), deuterium substitution rate: 90.7%

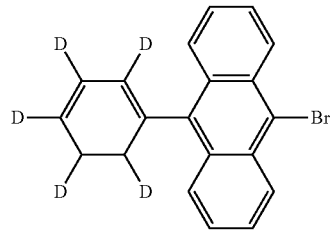

52-2H-(1)

Synthesis Example 19

Synthesis of Compound 54

Compound 54 was prepared in the same manner as in Synthesis Example 1, except that diphenylamine was used instead of Intermediate 3-A, and Intermediate 54-2H-(1) below was used instead of 2-bromonaphthalene in the synthesis of Compound 3-2H. The obtained compound was confirmed by MS/FAB and $^1$H NMR.

$C_{44}H_{35}D_2N$: cal. 581.30. found 582.31.

$^1$H NMR (CDCl$_3$, 400 MHz) δ (ppm) 8.18 (dd, 2H), 7.96 (dd, 2H), 7.70-7.63 (m, 4H), 7.52-7.49 (m, 2H), 7.44-7.40 (m, 2H), 7.06-7.02 (m, 6H), 6.89-6.83 (m, 4H), 6.56-6.52 (m, 4H), 1.68 (s, 9H), deuterium substitution rate: 83.2%

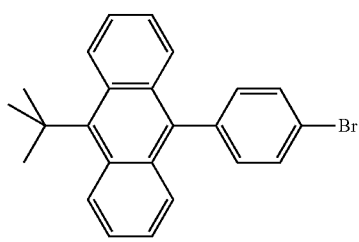

54-2H-(1)

Synthesis Example 20

Synthesis of Compound 56

Compound 56 was prepared in the same manner as in Synthesis Example 1, except that diphenylamine was used instead of Intermediate 3-A, and Intermediate 56-2H-(1) was used instead of 2-bromonaphthalene in the synthesis of Compound 3-2H. The obtained compound was confirmed by MS/FAB and $^1$H NMR.

$C_{44}H_{29}D_2N$: cal. 575.25. found 576.27.

$^1$H NMR (CDCl$_3$, 400 MHz) δ (ppm) 8.02 (dd, 2H), 7.83 (d, 1H), 7.75-7.64 (m, 5H), 7.46-7.26 (m, 6H), 7.08-6.94 (m, 7H), 6.89-6.86 (m, 2H), 6.76-6.73 (m, 2H), 6.56-6.52 (m, 4H), deuterium substitution rate: 94.6%

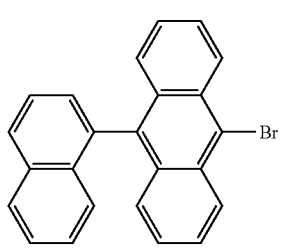

56-2H-(1)

Synthesis Example 21

Synthesis of Compound 60

Compound 60 was prepared in the same manner as in Synthesis Example 1, except that bis(4-fluorophenyl)amine was used instead of Intermediate 3-A, and 1-bromopyrene was used instead of 2-bromonaphthalene in the synthesis of Compound 3-2H. The obtained compound was confirmed by MS/FAB and $^1$H NMR.

$C_{36}H_{21}D_2F_2N$: cal. 509.19. found 510.21.

$^1$H NMR (CDCl$_3$, 400 MHz) δ (ppm) 8.37 (d, 1H), 8.17 (d, 2H), 8.11-8.10 (m, 2H), 8.04-7.95 (m, 3H), 7.86 (d, 1H), 7.45-7.41 (m, 2H), 7.22-7.03 (m, 6H), 6.86-6.80 (m, 4H), deuterium substitution rate: 90.1%

Synthesis Example 22

Synthesis of Compound 61

Compound 61 was prepared in the same manner as in Synthesis Example 1, except that N-phenylnaphthalen-2-amine was used instead of Intermediate 3-A, and 1-bromopyrene was used instead of 2-bromonaphthalene in the synthesis of Compound 3-2H. The obtained compound was confirmed by MS/FAB and $^1$H NMR.

$C_{40}H_{25}D_2N$: cal. 523.22. found 524.21.

$^1$H NMR (CDCl$_3$, 400 MHz) δ (ppm) 8.37 (d, 1H), 8.17 (d, 2H), 8.04-7.95 (m, 3H), 7.86 (d, 1H), 7.79-7.77 (m, 1H), 7.65 (d, 1H), 7.58-7.38 (m, 6H), 7.13-7.04 (m, 3H), 6.86-6.83 (m, 1H), 6.54-6.52 (m, 2H)

Synthesis Example 23

Synthesis of Compound 64

Compound 64 was prepared in the same manner as in Synthesis Example 2, except that 5-bromo-2-fluoropyridine was used instead of 2,6-dibromonaphthalene in the synthesis of Intermediate 33-A, diphenylamine was used instead of 9,9-dimethyl-N-phenyl-9H-fluoren-2-amine in the synthesis of Intermediate 33-B, and 1-bromopyrene was used instead of 9-bromophenathrene in the synthesis of Compound 33-2H. The obtained compound was confirmed by MS/FAB and $^1$H NMR.

$C_{35}H_{22}D_2N_2$: cal. 474.20. found 475.21.

$^1$H NMR (CDCl$_3$, 400 MHz) δ (ppm) 8.45 (d, 1H), 8.29 (d, 1H), 8.17 (d, 2H), 8.10-7.88 (m, 6H), 7.35-7.33 (m, 1H), 7.18-7.08 (m, 5H), 7.06-7.03 (m, 2H), 6.73-6.71 (m, 4H), deuterium substitution rate: 91.5%

Synthesis Example 24

Synthesis of Compound 69

Compound 69 was prepared in the same manner as in Synthesis Example 1, except that 2,7-dibromo-9,9-dimethyl-9H-fluorene was used instead of 2,6-dibromonaphthalene in the synthesis of Intermediate 33-A, diphenylamine was used instead of 9,9-dimethyl-N-phenyl-9H-fluoren-2-amine in the synthesis of Intermediate 33-B, and Intermediate 69-2H-(1) below was used instead of 9-bromophenathrene in the synthesis of Compound 33-2H. The obtained compound was confirmed by MS/FAB and $^1$H NMR.

$C_{53}H_{37}D_2N$: cal. 691.32. found 692.29.

$^1$H NMR (CDCl$_3$, 400 MHz) δ (ppm) 8.99 (s, 1H), 8.69 (s, 1H), 8.33-8.31 (m, 2H), 8.13-8.05 (m, 4H), 7.75-7.61 (m, 6H), 7.50-7.35 (m, 4H), 7.18-7.03 (m, 5H), 6.85-6.83 (m, 3H), 6.77-6.75 (m, 1H), 6.55-6.52 (m, 4H), 1.68 (s, 6H)

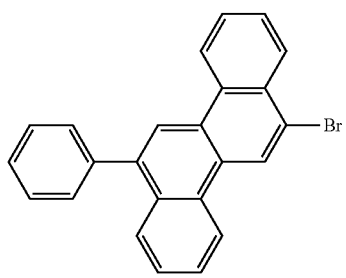

62-2H-(1)

Synthesis Example 25

Synthesis of Compound 71

Compound 71 was prepared in the same manner as in Synthesis Example 1, except that 4-bromobenzonitrile was used instead of 9-bromophenathrene in the synthesis of Intermediate 3-A and Intermediate 69-2H-(1) was used instead of 2-bromonaphthalene in the synthesis of Compound 3-2H. The obtained compound was confirmed by MS/FAB and $^1$H NMR.

$C_{45}H_{28}D_2N_2$: cal. 600.25. found 601.24.

$^1$H NMR (CDCl$_3$, 400 MHz) δ (ppm) 8.80 (s, 1H), 8.69 (s, 1H), 8.33-8.31 (m, 2H), 8.13-8.05 (m, 3H), 7.71-7.63 (m, 3H), 7.50-7.35 (m, 7H), 7.18-7.03 (m, 4H), 6.92-6.73 (m, 5H), 6.52-6.50 (m, 2H), deuterium substitution rate: 90.6%

Synthesis Example 26

Compound 74

Compound 74 was prepared in the same manner as in Synthesis Example 1, except that diphenylamine was used instead of Intermediate 3-A, and 2-bromotriphenylene was used instead of 2-bromonaphthalene in the synthesis of Compound 3-2H. The obtained compound was confirmed by MS/FAB and $^1$H NMR.

$C_{38}H_{25}D_2N$: cal. 499.22. found 450.21.

$^1$H NMR (CDCl$_3$, 400 MHz) δ (ppm) 8.86-8.81 (m, 5H), 8.50-8.49 (m, 1H), 7.70-7.60 (m, 5H), 7.47-7.44 (m, 2H), 7.08-7.04 (m, 4H), 6.89-6.83 (m, 4H), 6.56-6.52 (m, 4H), deuterium substitution rate: 91%

Synthesis Example 27

Synthesis of Compound 80

Compound 80 was prepared in the same manner as in Synthesis Example 1, except that diphenylamine was used instead of Intermediate 3-A, and Intermediate 80-2H-(1) was used instead of 2-bromonaphthalene in the synthesis of Compound 3-2H. The obtained compound was confirmed by MS/FAB and $^1$H NMR.

$C_{49}H_{35}D_2N$: cal. 641.30. found 642.31.

$^1$H NMR (CDCl$_3$, 400 MHz) δ (ppm) 8.64 (d, 1H), 8.42 (d, 1H), 7.89-7.86 (m, 2H), 7.79-7.77 (m, 1H), 7.68-7.63 (m, 6H), 7.54-7.34 (m, 5H), 7.15-7.03 (m, 5H), 6.89-6.83 (m, 4H), 6.56-6.54 (m, 4H), 1.69 (s, 6H)

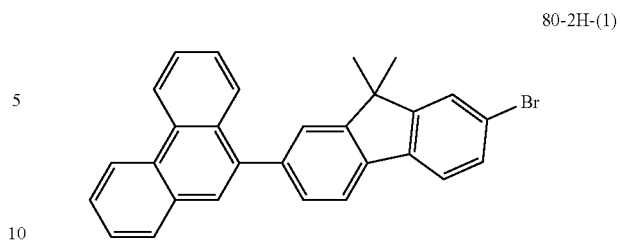

80-2H-(1)

Synthesis Example 28

Synthesis of Compound 83

Compound 83 was prepared in the same manner as in Synthesis Example 1, except that diphenylamine was used instead of Intermediate 3-A, and Intermediate 83-2H-(1) below was used instead of 2-bromonaphthalene in the synthesis of Compound 3-2H. The obtained compound was confirmed by MS/FAB and $^1$H NMR.

$C_{42}H_{27}D_2N$: cal. 549.24. found 550.21.

$^1$H NMR (CDCl$_3$, 400 MHz) δ (ppm) 8.16-7.98 (m, 7H), 7.85 (d, 1H), 7.73-7.70 (m, 2H), 7.63-7.54 (m, 3H), 7.44-7.40 (m, 2H), 7.08-7.04 (m, 4H), 6.99-6.93 (m, 4H), 6.56-6.54 (m, 4H), deuterium substitution rate: 90.8%

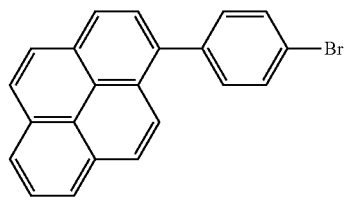

83-2H-(1)

Synthesis Example 29

Synthesis of Compound 86

Compound 86 was prepared in the same manner as in Synthesis Example 1, except that N-phenylnaphthalen-2-amine was used instead of Intermediate 3-A, and Intermediate 86-2H-(1) below was used instead of 2-bromonaphthalene in the synthesis of Compound 3-2H. The obtained compound was confirmed by MS/FAB and $^1$H NMR.

$C_{52}H_{45}D_2N$: cal. 687.38. found 688.37.

$^1$H NMR (CDCl$_3$, 400 MHz) δ (ppm) 8.22-8.21 (m, 1H), 8.13-8.07 (m, 2H), 7.78-7.73 (m, 3H), 7.66-7.39 (m, 13H), 7.13-7.05 (m, 3H), 6.99-6.95 (m, 2H), 6.86-6.83 (m, 1H), 6.64-6.62 (m, 2H), 1.74 (s, 9H), 1.71 (s. 9H)

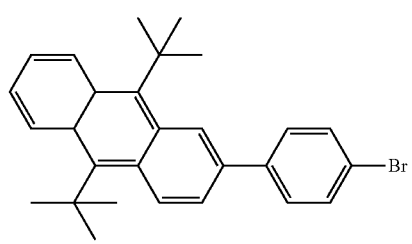

86-2H-(1)

Synthesis Example 30

Synthesis of Compound 88

Compound 88 was prepared in the same manner as in Synthesis Example 1, except that diphenylamine was used instead of Intermediate 3-A, and Intermediate 88-2H-(1) below was used instead of 2-bromonaphthalene in the synthesis of Compound 3-2H. The obtained compound was confirmed by MS/FAB and $^1$H NMR.

$C_{45}H_{33}D_2N$: cal. 591.28. found 592.31.
$^1$H NMR (CDCl$_3$, 400 MHz) δ (ppm) 8.06-8.04 (m, 1H), 7.93-7.86 (m, 3H), 7.79-7.75 (m, 2H), 7.65-7.43 (m, 8H), 7.36-7.34 (m, 1H), 7.08-7.03 (m, 4H), 6.99-6.93 (m, 4H), 6.66-6.64 (m, 4H), 1.69 (s. 6H), deuterium substitution rate: 82%

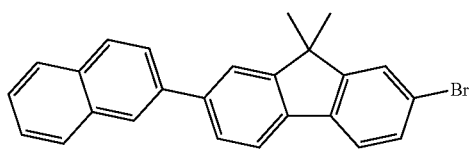

88-2H-(1)

Synthesis Example 31

Synthesis of Compound 91

Compound 91 was prepared in the same manner as in Synthesis Example 2, except that 2,7-dibromophenathrene was used instead of 2,6-dibromonaphthalene in the synthesis of Intermediate 33-A, diphenylamine was used instead of 9,9-dimethyl-N-phenyl-9H-fluoren-2-amine in the synthesis of Intermediate 33-B, and Intermediate 91-2H-(1) below was used instead of 9-bromophenathrene in the synthesis of Compound 33-2H. The obtained compound was confirmed by MS/FAB and $^1$H NMR.

$C_{44}H_{29}D_2N$: cal. 575.25. found 576.24.
$^1$H NMR (CDCl$_3$, 400 MHz) δ (ppm) 8.48-8.44 (m, 2H), 8.15-8.14 (m, 1H), 7.97-7.96 (m, 1H), 7.91-7.81 (m, 5H), 7.75-7.49 (m, 9H), 7.08-7.03 (m, 4H), 6.99-6.97 (m, 1H), 6.86-6.83 (m, 2H), 6.68-6.66 (m. 4H), deuterium substitution rate: 92.5%

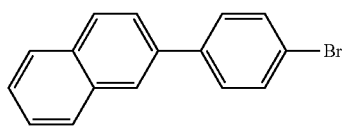

91-2H-(1)

Synthesis Example 32

Synthesis of Compound 93

Compound 93 was prepared in the same manner as in Synthesis Example 2, except that 2,7-dibromo-9,9-dimethyl-9H-fluorene was used instead of 2,6-dibromonaphthalene in the synthesis of Intermediate 33-A, diphenylamine was used instead of 9,9-dimethyl-N-phenyl-9H-fluoren-2-amine in the synthesis of Intermediate 33-B, and Intermediate 88-2H-(1) was used instead of 9-bromophenathrene in the synthesis of Compound 33-2H. The obtained compound was confirmed by MS/FAB and $^1$H NMR.

$C_{54}H_{41}D_2N$: cal. 707.35. found 708.36.
$^1$H NMR (CDCl$_3$, 400 MHz) δ (ppm) 8.05-8.04 (m, 1H), 7.96-7.93 (m, 3H), 7.79-7.73 (m, 3H), 7.68-7.49 (m, 8H), 7.36-7.33 (m, 2H), 7.08-7.03 (m, 4H), 6.97-6.93 (m, 3H), 6.86-6.83 (m, 1H), 6.45-6.43 (m. 4H), 1.69 (s. 6H), 1.67 (s. 6H)

Synthesis Example 33

Synthesis of Compound 101

Compound 101 was prepared in the same manner as in Synthesis Example 1, except that diphenylamine was used instead of Intermediate 3-A, and 2-bromo-9,9-dimethyl-9H-fluorene was used instead of 2-bromonaphthalene in the synthesis of Compound 3-2H. The obtained compound was confirmed by MS/FAB and $^1$H NMR.

$C_{35}H_{27}D_2N$: cal. 465.24. found 466.25.
$^1$H NMR (CDCl$_3$, 400 MHz) δ (ppm) 7.85 (dd, 1H), 7.74 (dd, 1H), 7.46-7.44 (m, 2H), 7.38-7.33 (m, 2H), 7.28-7.27 (m, 1H), 7.20-7.04 (m, 6H), 6.99-6.93 (m, 4H), 6.66-6.63 (m, 4H), 1.67 (s. 6H), deuterium substitution rate: 85.6%

Synthesis Example 34

Synthesis of Compound 106

Compound 106 was prepared in the same manner as in Synthesis Example 1, except that 4-bromobenzonitrile was used instead of 9-bromophenathrene and naphtalene-2-amine was used instead of aniline in the synthesis of Intermediate 3-A, and 2-bromo-9,9-dimethyl-9H-fluorene was used instead of 2-bromonaphthalene in the synthesis of Compound 3-2H. The obtained compound was confirmed by MS/FAB and $^1$H NMR.

$C_{43}H_{28}D_2N_2$: cal. 540.25. found 541.26.
$^1$H NMR (CDCl$_3$, 400 MHz) δ (ppm) 7.87-7.83 (m, 1H), 7.78-7.76 (m, 1H), 7.72 (d, 1H), 7.65 (d, 1H), 7.58-7.53 (m, 3H), 7.48-7.45 (m, 2H), 7.41-7.27 (m, 6H), 7.20-7.18 (m, 1H), 7.13-7.09 (m. 1H), 7.02-6.99 (m. 1H), 6.93-6.88 (m. 4H), 1.68 (s. 6H), deuterium substitution rate: 87.4%

Synthesis Example 35

Synthesis of Compound 110

Compound 110 was prepared in the same manner as in Synthesis Example 1, except that 9,9-dimethyl-N-phenyl-9H-fluoren-2-amine was used instead of Intermediate, and 2-bromo-9,9-dimethyl-9H-fluorene was used instead of 2-bromonaphthalene in the synthesis of Compound 3-2H. The obtained compound was confirmed by MS/FAB and $^1$H NMR.

$C_{44}H_{35}D_2N$: cal. 581.30. found 582.31.
$^1$H NMR (CDCl$_3$, 400 MHz) δ (ppm) 7.86-7.84 (m, 1H), 7.78-7.76 (m, 1H), 7.72 (d, 1H), 7.72 (d, 1H), 7.55 (d, 1H), 7.48-7.45 (m, 2H), 7.36-7.31 (m, 3H), 7.28-7.27 (m, 1H), 7.14-7.04 (m. 5H), 6.93-6.83 (m. 4H), 6.69-6.67 (m. 1H), 6.53-6.51 (m. 2H), 1.68 (s. 6H), 1.65 (s. 6H), deuterium substitution rate: 82.1%

Synthesis Example 36

Synthesis of Compound 112

Compound 112 was prepared in the same manner as in Synthesis Example 1, except that 3-iodo-9-phenyl-9H-carbazole was used instead of 9-bromophenathrene in the synthesis of Intermediate 3-A, and 2-bromo-9,9-dimethyl-9H-fluorene was used instead of 2-bromonaphthalene in the synthesis of Compound 3-2H. The obtained compound was confirmed by MS/FAB and $^1$H NMR.

$C_{47}H_{34}D_2N_2$: cal. 630.30. found 631.32.

$^1$H NMR (CDCl$_3$, 400 MHz) δ (ppm) 8.22-8.20 (m, 1H), 7.86-7.84 (m, 1H), 7.73-7.71 (m, 1H), 7.54-7.04 (m, 19H), 6.87-6.82 (m, 3H), 6.76-6.73 (m, 1H), 6.61-6.59 (m, 2H), 1.68 (s. 6H)

Synthesis Example 37

Synthesis of Compound 118

Compound 118 was prepared in the same manner as in Synthesis Example 1, except that N-phenylnaphthalen-2-amine was used instead of Intermediate 3-A, and Intermediate 118-2H-(1) below was used instead of 2-bromonaphthalene in the synthesis of Compound 3-2H. The obtained compound was confirmed by MS/FAB and $^1$H NMR.

$C_{49}H_{31}D_2N$: cal. 637.27. found 638.24.

$^1$H NMR (CDCl$_3$, 400 MHz) δ (ppm) 8.11-8.10 (m, 1H), 7.96 (d, 1H), 7.92-7.90 (m, 1H), 7.78-7.76 (m, 1H), 7.73-7.71 (m, 1H), 7.65 (d, 1H), 7.58-7.34 (m, 10H), 7.24-7.04 (m, 6H), 6.93-6.86 (m. 6H), 6.80-6.78 (m. 1H), 6.54-6.52 (m. 2H)

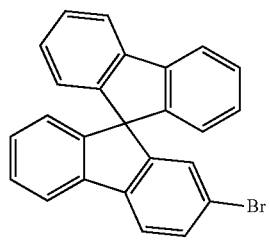

118-2H-(1)

Synthesis Example 38

Synthesis of Compound 121

Compound 121 was prepared in the same manner as in Synthesis Example 1, except that 9,9-dimethyl-N-phenyl-9H-fluoren-2-amine was used instead of Intermediate 3-A, and 3-Iodo-9-phenyl-9H-carbazole was used instead of 2-bromonaphthalene in the synthesis of Compound 3-2H. The obtained compound was confirmed by MS/FAB and $^1$H NMR.

$C_{47}H_{34}D_2N_2$: cal. 449.21. found 450.22.

$^1$H NMR (CDCl$_3$, 400 MHz) δ (ppm) 8.28-8.24 (m, 1H), 8.02-8.00 (m, 1H), 7.77 (dd, 1H), 7.55 (d, 1H), 7.51-7.26 (m, 13H), 7.14-7.05 (m, 4H), 6.93-6.83 (m, 4H), 6.79-6.77 (m, 1H), 6.63-6.61 (m. 2H), 1.68 (s. 6H)

Synthesis Example 39

Synthesis of Compound 125

Compound 125 was prepared in the same manner as in Synthesis Example 1, except that 4-bromobenzonitrile was used instead of 9-bromophenathrene and naphtalene-2-amine was used instead of aniline in the synthesis of Intermediate 3-A, and 3-iodo-9-phenyl-9H-carbazole was used instead of 2-bromonaphthalene during synthesis of Compound 3-2H. The obtained compound was confirmed by MS/FAB and H NMR.

$C_{43}H_{27}D_2N_3$: cal. 589.24. found 590.24.

$^1$H NMR (CDCl$_3$, 400 MHz) δ (ppm) 8.26-8.24 (m, 1H), 8.02-8.00 (m, 1H), 7.78-7.76 (m, 1H), 7.65 (d, 1H), 7.57-7.52 (m, 3H), 7.50-7.25 (m, 15H), 7.12-7.10 (m, 1H), 6.93-6.88 (m, 4H), deuterium substitution rate: 88.1%

Synthesis Example 40

Synthesis of Compound 127

Compound 127 was prepared in the same manner as in Synthesis Example 1, except that 3-iodo-9-phenyl-9H-carbazole was used instead of 9-bromophenathrene in the synthesis of Intermediate 3-A, and 3-iodo-9-phenyl-9H-carbazole was used instead of 2-bromonaphthalene in the synthesis of Compound 3-2H. The obtained compound was confirmed by MS/FAB and $^1$H NMR.

$C_{50}H_{33}D_2N_3$: cal. 679.29. found 680.28.

$^1$H NMR (CDCl$_3$, 400 MHz) δ (ppm) 8.26-8.20 (m, 2H), 8.02-8.01 (m, 1H), 7.54-7.23 (m, 22H), 7.08-7.04 (m, 2H), 6.97-6.91 (m, 3H), 6.86-6.83 (m, 1H), 6.61-6.59 (m, 2H), deuterium substitution rate: 90.5%

Synthesis Example 41

Synthesis of Compound 128

Compound 128 was prepared in the same manner as in Synthesis Example 1, except that N,9,9-triphenyl-9H-fluoren-2-amine was used instead of Intermediate 3-A, and 3-iodo-9-phenyl-9H-carbazole was used instead of 2-bromonaphthalene in the synthesis of Compound 3-2H. The obtained compound was confirmed by MS/FAB and $^1$H NMR.

$C_{57}H_{38}D_2N_2$: cal. 754.33. found 755.34.

$^1$H NMR (CDCl$_3$, 400 MHz) δ (ppm) 8.26-8.24 (m, 1H), 8.02-8.00 (m, 1H), 7.85 (dd, 1H), 7.57 (d, 1H), 7.51-7.26 (m, 13H), 7.19-7.04 (m, 13H), 6.91-6.89 (m, 1H), 6.83-6.73 (m, 4H), 6.68-6.67 (m, 1H), 6.53-6.51 (m, 2H)

Synthesis Example 42

Synthesis of Compound 133

Compound 133 was prepared in the same manner as in Synthesis Example 1, except that 9,9-dimethyl-N-(naphthalen-3-yl)-9H-fluoren-2-amine was used instead of Intermediate 3-A, and Intermediate 133-2H-(1) below was used instead of 2-bromonaphthalene in the synthesis of Compound 3-2H. The obtained compound was confirmed by MS/FAB and $^1$H NMR.

$C_{51}H_{35}D_2FN_2$: cal. 698.30. found 699.31.

$^1$H NMR (CDCl$_3$, 400 MHz) δ (ppm) 8.14-8.12 (m, 1H), 7.93-7.91 (m, 1H), 7.79-7.76 (m, 2H), 7.69 (d, 1H), 7.58-7.54 (m, 4H), 7.49-7.23 (m, 1H), 7.16-7.05 (m, 5H), 6.99-6.91 (m, 3H), 6.79-6.78 (m, 1H), 1.67 (s, 6H)

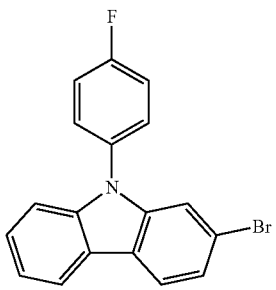

133-2H-(1)

Synthesis Example 43

Synthesis of Compound 136

Compound 136 was prepared in the same manner as in Synthesis Example 1, except that 1-bromo-4-fluorobenzene was used instead of 9-bromophenathrene and naphtalene-2-amine was used instead of aniline in the synthesis of Intermediate 3-A, and Intermediate 136-2H-(1) below was used instead of 2-bromonaphthalene in the synthesis of Compound 3-2H. The obtained compound was confirmed by MS/FAB and $^1$H NMR.

$C_{36}H_{22}D_2FNS$: cal. 523.17. found 524.27.

$^1$H NMR (CDCl$_3$, 400 MHz) δ (ppm) 8.29 (d, 1H), 8.10-8.04 (m, 2H), 7.80-7.76 (m, 2H), 7.65 (d, 1H), 7.58-7.54 (m, 4H), 7.48-7.35 (m, 5H), 7.25-7.20 (m, 3H), 7.04-7.01 (m, 2H), 6.84-6.81 (m, 2H), deuterium substitution rate: 91.3%

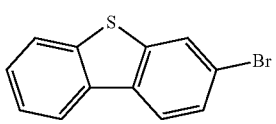

136-2H-(1)

Synthesis Example 44

Synthesis of Compound 138

Compound 138 was prepared in the same manner as in Synthesis Example 1, except that Intermediate 29-A-(1) above was used instead of 2-bromonaphthalene in the synthesis of Compound 3-2H. The obtained compound was confirmed by MS/FAB and $^1$H NMR.

$C_{40}H_{25}D_2NS$: cal. 555.19. found 556.17.

$^1$H NMR (CDCl$_3$, 400 MHz) δ (ppm) 8.58 (d, 1H), 8.27-8.26 (m, 1H), 8.21-8.11 (m, 2H), 7.95-7.92 (m, 1H), 7.86 (d, 1H), 7.79 (d, 1H), 7.72-7.54 (m, 6H), 7.46-7.39 (m, 4H), 7.07-7.03 (m, 3H), 6.97-6.91 (m, 3H), 6.52-6.49 (m, 2H), deuterium substitution rate: 90%

Synthesis Example 45

Synthesis of Compound 139

Compound 139 was prepared in the same manner as in Synthesis Example 1, except that Intermediate 118-2H-(1) above was used instead of 9-bromophenathrene and naphtalene-2-amine was used instead of aniline in the synthesis of Intermediate 3-A, and Intermediate 29-A-(1) above was used instead of 2-bromonaphthalene in the synthesis of Compound 3-2H. The obtained compound was confirmed by MS/FAB and $^1$H NMR.

$C_{51}H_{31}D_2NS$: cal. 693.24. found 694.21.

$^1$H NMR (CDCl$_3$, 400 MHz) δ (ppm) 8.27-8.26 (m, 1H), 8.12 (d, 1H), 7.93-7.85 (m, 4H), 7.79 (d, 1H), 7.64-7.41 (m, 9H), 7.21-7.15 (m, 3H), 7.09-7.04 (m, 2H), 6.93-6.73 (m, 7H), 6.67-6.66 (m, 1H), 6.53-6.51 (m, 2H)

Synthesis Example 46

Synthesis of Compound 142

Compound 142 was prepared in the same manner as in Synthesis Example 1, except that bromobenzene was used instead of 9-bromophenathrene, and Intermediate 5-A-(1) above was used instead of aniline in the synthesis of Intermediate 3-A, and Intermediate 29-A-(1) above was used instead of 2-bromonaphthalene in the synthesis of Compound 3-2H. The obtained compound was confirmed by MS/FAB and $^1$H NMR.

$C_{44}H_{28}D_2FNS$: cal. 625.22. found 626.23.

$^1$H NMR (CDCl$_3$, 400 MHz) δ (ppm) 8.27-8.26 (m, 1H), 8.12 (d, 1H), 7.86 (d, 1H), 7.79 (d, 1H), 7.72-7.70 (m, 2H), 7.66-7.40 (m, 14H), 7.13-7.03 (m, 3H), 6.98-6.90 (m, 3H), 6.54-6.52 (m, 2H), deuterium substitution rate: 92.8%

Synthesis Example 47

Synthesis of Compound 147

Compound 147 was prepared in the same manner as in Synthesis Example 1, except that 9,9-dimethyl-N-(naphthalen-3-yl)-9H-fluoren-2-amine was used instead of Intermediate 3-A, and Intermediate 147-2H-(1) below was used instead of 2-bromonaphthalene in the synthesis of Compound 3-2H. The obtained compound was confirmed by MS/FAB and $^1$H NMR.

$C_{45}H_{31}D_2NO$: cal. 605.26. found 606.24.

$^1$H NMR (CDCl$_3$, 400 MHz) δ (ppm) 7.96-7.94 (m, 1H), 7.78-7.68 (m, 5H), 7.57-7.30 (m, 12H), 7.16-7.10 (m, 4H), 6.99-6.97 (m, 2H), 6.93-6.91 (m, 1H), 6.69-6.68 (m, 1H). 1.67 (s, 6H), deuterium substitution rate: 93%

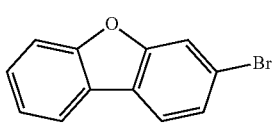

147-2H-(1)

Synthesis Example 48

Synthesis of Compound 150

Compound 150 was prepared in the same manner as in Synthesis Example 1, except that N,9,9-triphenyl-9H-fluoren-2-amine was used instead of Intermediate 3-A, and Intermediate 30-A-(1) above was used instead of 2-bromonaphthalene in the synthesis of Compound 3-2H. The obtained compound was confirmed by MS/FAB and $^1$H NMR.

$C_{51}H_{33}D_2NO$: cal. 679.28. found 680.29.

$^1$H NMR (CDCl$_3$, 400 MHz) δ (ppm) 7.99-7.97 (m, 1H), 7.93-7.92 (m, 1H), 7.86-7.84 (m, 1H), 7.72 (d, 1H), 7.58-7.35

(m, 8H), 7.19-7.04 (m, 13H), 6.90 (dd, 1H), 6.83-6.73 (m, 4H), 6.67-6.66 (m, 1H), 6.53-6.51 (m, 2H)

Synthesis Example 49

Synthesis of Compound 157

Compound 157 was prepared in the same manner as in Synthesis Example 2, except that 2,7-dibromo-9,9-dimethyl-9H-fluorene was used instead of 2,6-dibromonaphthalene in the synthesis of Intermediate 33-A, N-phenylnaphthalen-1-amine was used instead of 9,9-dimethyl-N-phenyl-9H-fluoren-2-amine in the synthesis of Intermediate 33-B, and 2-bromo-9,9-dimethyl-9H-fluorene was used instead of 9-bromophenathrene in the synthesis of Compound 33-2H. The obtained compound was confirmed by MS/FAB and $^1$H NMR.

$C_{48}H_{37}D_2N$: cal. 631.32. found 632.33.
$^1$H NMR (CDCl$_3$, 400 MHz) δ (ppm) 8.13-8.10 (m, 1H), 7.87-7.84 (m, 2H), 7.73-7.64 (m, 5H), 7.49-7.43 (m, 3H), 7.36-7.02 (m, 8H), 6.93 (d, 1H), 6.85-6.78 (m, 2H), 6.55-6.54 (m, 1H), 6.46-6.44 (m, 2H), 1.69 (s, 6H), 1.67 (s, 6H)

Synthesis Example 50

Synthesis of Compound 161

Compound 161 was prepared in the same manner as in Synthesis Example 2, except that diphenylamine was used instead of 9,9-dimethyl-N-phenyl-9H-fluoren-2-amine in the synthesis of Intermediate 33-B and 3-iodo-9-phenyl-9H-carbazole was used instead of 9-bromophenathrene in the synthesis of Compound 33-2H. The obtained compound was confirmed by MS/FAB and $^1$H NMR.

$C_{42}H_{28}D_2N_2$: cal. 564.25. found 565.24.
$^1$H NMR (CDCl$_3$, 400 MHz) δ (ppm) 8.26-8.24 (m, 1H), 8.01-8.00 (m, 1H), 7.88-7.87 (m, 1H), 7.76-7.67 (m, 3H), 7.63-7.62 (m, 1H), 7.52-7.26 (m, 10H), 7.09-7.04 (m, 4H), 6.97-6.95 (m, 1H), 6.86-6.83 (m, 2H), 6.58-6.56 (m, 4H), deuterium substitution rate: 90%

Synthesis Example 51

Synthesis of Compound 163

Compound 163 was prepared in the same manner as in Synthesis Example 2, except that 2,7-dibromo-9,9-dimethyl-9H-fluorene was used instead of 2,6-dibromonaphthalene in the synthesis of Intermediate 33-A, N-phenylnaphthalen-2-amine was used instead of 9,9-dimethyl-N-phenyl-9H-fluoren-2-amine in the synthesis of Intermediate 33-B, and 3-iodo-9-phenyl-9H-carbazole was used instead of 9-bromophenathrene in the synthesis of Compound 33-2H. The obtained compound was confirmed by MS/FAB and $^1$H NMR.

$C_{51}H_{36}D_2N_2$: cal. 680.31. found 681.34.
$^1$H NMR (CDCl$_3$, 400 MHz) δ (ppm) 8.26-8.24 (m, 1H), 8.01-8.00 (m, 1H), 7.78-7.64 (m, 5H), 7.58-7.26 (m, 15H), 7.10-7.05 (m, 3H), 6.91-6.83 (m, 2H), 6.74-6.73 (m, 1H), 6.52-6.50 (m, 2H), 1.68 (s, 6H)

Synthesis Example 52

Synthesis of Compound 164

Compound 164 was prepared in the same manner as in Synthesis Example 2, except that 5-bromo-2-iodopyridine was used instead of 2,6-dibromonaphthalene in the synthesis of Intermediate 33-A, diphenylamine was used instead of 9,9-dimethyl-N-phenyl-9H-fluoren-2-amine in the synthesis of Intermediate 33-B, and Intermediate 164-2H-(1) below was used instead of 9-bromophenathrene in the synthesis of Compound 33-2H. The obtained compound was confirmed by MS/FAB and $^1$H NMR.

$C_{49}H_{29}D_2N_3$: cal. 591.26. found 592.27.
$^1$H NMR (CDCl$_3$, 400 MHz) δ (ppm) 8.14-8.12 (m, 1H), 8.08-8.07 (m, 1H), 7.92-7.89 (m, 2H), 7.82-7.80 (m, 2H), 7.70-7.67 (m, 2H), 7.54-7.48 (m, 4H), 7.39-7.26 (m, 4H), 7.21-7.19 (m, 2H), 7.14-7.08 (m, 5H), 6.96-6.93 (m, 2H), 6.73-6.71 (m, 4H), deuterium substitution rate: 93.5%

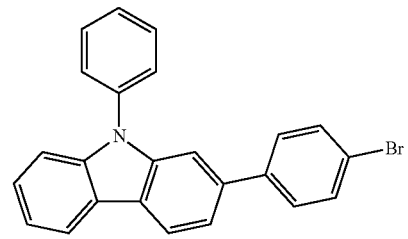

164-2H-(1)

Synthesis Example 53

Synthesis of Compound 167

Compound 167 was prepared in the same manner as in Synthesis Example 1, except that diphenylamine was used instead of Intermediate 3-A, and Intermediate 167-2H-(1) below was used instead of 2-bromonaphthalene in the synthesis of Compound 3-2H. The obtained compound was confirmed by MS/FAB and $^1$H NMR.

$C_{42}H_{27}D_2NS$: cal. 581.21. found 582.24.
$^1$H NMR (CDCl$_3$, 400 MHz) δ (ppm) 8.36 (d, 1H), 8.16-8.06 (m, 2H), 7.98-7.97 (m, 1H), 7.89-7.78 (m, 3H), 7.63-7.58 (m, 2H), 7.46-7.35 (m, 4H), 7.12-6.94 (m, 6H), 6.85-6.73 (m, 4H), 6.66-6.63 (m, 4H)

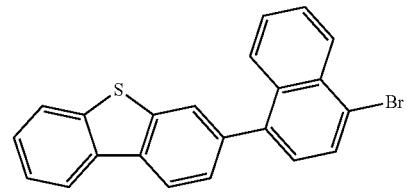

167-2H-(1)

Synthesis Example 54

Synthesis of Compound 169

Compound 169 was prepared in the same manner as in Synthesis Example 2, except that 2,7-dibromo-9,9-dimethyl-9H-fluorene was used instead of 2,6-dibromonaphthalene in the synthesis of Intermediate 33-A, N-phenylnaphthalen-2-amine was used instead of 9,9-dimethyl-N-phenyl-9H-fluoren-2-amine in the synthesis of Intermediate 33-B, and Intermediate 30-A-(1) was used instead of 9-bromophenathrene in the synthesis of Compound 33-2H. The obtained compound was confirmed by MS/FAB and $^1$H NMR.

$C_{45}H_{31}D_2NO$: cal. 605.26. found 606.27.

$^1$H NMR (CDCl$_3$, 400 MHz) δ (ppm) 7.99-7.97 (m, 1H), 7.93-7.92 (m, 1H), 7.78-7.64 (m, 6H), 7.58-7.51 (m, 6H), 7.42-7.34 (m, 3H), 7.10-7.06 (m, 3H), 6.91-6.87 (m, 2H), 6.74-6.73 (m, 1H), 6.52-6.50 (m, 2H), 1.68 (s, 6H)

Synthesis Example 55

Synthesis of Compound 176

Compound 176 was prepared in the same manner as in Synthesis Example 1, except that N-phenylnaphthalen-2-amine was used instead of Intermediate 3-A, and Intermediate 176-2H-(1) below was used instead of 2-bromonaphthalene in the synthesis of Compound 3-2H. The obtained compound was confirmed by MS/FAB and $^1$H NMR.

$C_{57}H_{40}D_2N_2$: cal. 756.34. found 757.34.

$^1$H NMR (CDCl$_3$, 400 MHz) δ (ppm) 8.24-8.22 (m, 1H), 8.00-7.99 (m, 1H), 7.90-7.85 (m, 2H), 7.80-7.76 (m, 2H), 7.66-7.64 (m, 3H), 7.59-7.04 (m, 20H), 6.99-6.96 (m, 2H), 6.86-6.83 (m, 1H), 6.54-6.52 (m, 2H), 1.67 (s, 6H)

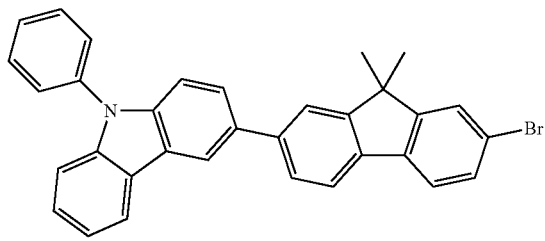

176-2H-(1)

Synthesis Example 56

Synthesis of Compound 179

Compound 179 was prepared in the same manner as in Synthesis Example 2, except that diphenylamine was used instead of 9,9-dimethyl-N-phenyl-9H-fluoren-2-amine during synthesis of Intermediate 33-B, and Intermediate 179-2H-(1) below was used instead of 9-bromophenathrene in the synthesis of Compound 33-2H. The obtained compound was confirmed by MS/FAB and $^1$H NMR.

$C_{45}H_{33}D_2N$: cal. 591.28. found 592.29.

$^1$H NMR (CDCl$_3$, 400 MHz) δ (ppm) 7.83-7.79 (m, 2H), 7.75-7.67 (m, 6H), 7.63-7.62 (m, 1H), 7.57-7.55 (m, 1H), 7.50-7.46 (m, 2H), 7.35-7.31 (m, 1H), 7.28-7.27 (m, 1H), 7.15-7.04 (m, 6H), 6.96 (dd, 1H), 6.86-6.83 (m, 2H), 6.68-6.66 (m, 4H), 1.64 (s, 6H), deuterium substitution rate: 82%

179-2H-(1)

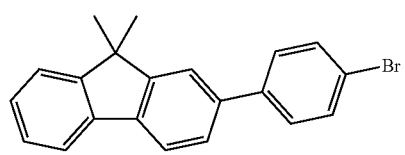

Synthesis Example 57

Synthesis of Compound 180

Compound 180 was prepared in the same manner as in Synthesis Example 2, except that 2,7-dibromo-9,9-dimethyl-9H-fluorene was used instead of 2,6-dibromonaphthalene in the synthesis of Intermediate 33-A, N-phenylnaphthalen-2-amine was used instead of 9,9-dimethyl-N-phenyl-9H-fluoren-2-amine in the synthesis of Intermediate 33-B, Intermediate 180-2H-(1) below was used instead of 9-bromophenathrene in the synthesis of Compound 33-2H. The obtained compound was confirmed by MS/FAB and $^1$H NMR.

$C_{64}H_{45}D_2N$: cal. 831.38. found 832.40.

$^1$H NMR (CDCl$_3$, 400 MHz) δ (ppm) 7.90-7.88 (m, 1H), 7.85-7.64 (m, 8H), 7.58-7.33 (m, 10H), 7.22-7.05 (m, 14H), 6.94-6.92 (m, 1H), 6.81-6.73 (m, 2H), 6.73-6.72 (m, 1H), 6.53-6.50 (m, 2H), 1.67 (s, 6H)

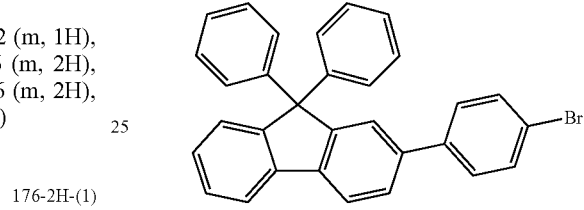

180-2H-(1)

Comparative Synthesis Example A

Compound A was synthesized according to Reaction Scheme A below:

Reaction Scheme A

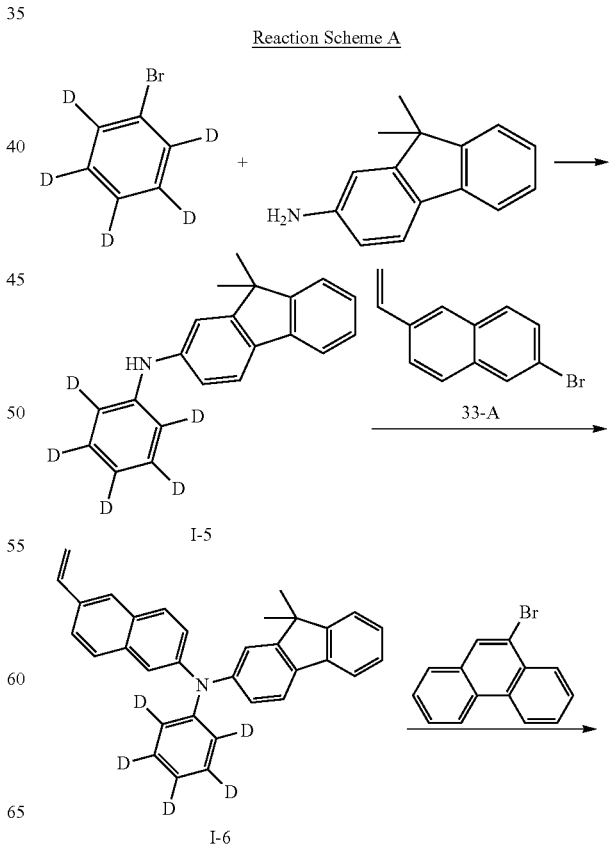

-continued

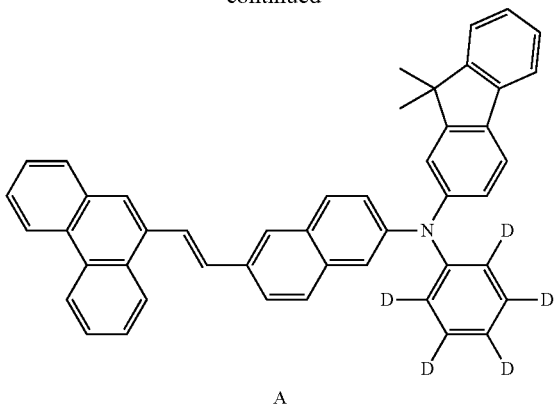

A

Synthesis of Intermediate I-5

Intermediate I-5 was prepared in the same manner as in the synthesis of Intermediate 3-A of Synthesis Example 1, except that bromobenzene-$d_5$ was used instead of 9-bromophenathrene, and 9,9-dimethyl-9H-fluoren-2-amine was used instead of aniline in the synthesis of Intermediate 3-A Synthesis of Intermediate I-6

Intermediate I-6 was prepared in the same manner as in the synthesis of Intermediate 33-B of Synthesis Example 2, except that Intermediate I-5 was used instead of 9,9-dimethyl-N-phenyl-9H-fluorene-2-amine.

Synthesis of Compound A

Compound A was prepared in the same manner as in the synthesis of Compound 33-2H of Synthesis Example 2, except that Intermediate I-6 was used instead of Intermediate 33-B. The obtained compound was confirmed by MS/FAB and $^1$H NMR.

$C_{47}H_{30}D_5N$: cal. 618.31. found 619.32.

$^1$H NMR (CDCl$_3$, 400 MHz) δ (ppm) 8.66 (d, 1H), 8.46 (d, 1H), 8.15-8.06 (m, 3H), 7.92 (s, 1H), 7.83-7.56 (m, 9H), 7.48 (dt, 1H), 7.36-7.27 (m, 3H), 7.14-7.08 (m, 2H), 7.02 (dt, 1H), 6.97-6.95 (m, 1H), 6.89 (s, 1H), 1.66 (s, 6H)

Example 1

As an anode, a 15 Ω/cm² (1200 Å) Corning ITO glass substrate was cut to a size of 50 mm×50 mm×0.7 mm, washed with ultrasonic waves in isopropyl alcohol and pure water for 5 minutes each, and then cleaned with UV and ozone for 30 minutes. The ITO glass substrate was mounted on a vacuum depositor.

2-TNATA was deposited on the ITO glass substrate to form a HIL having a thickness of 600 Å and 4,4'-bis[N-(1-naphthyl)-N-phenyl amino]biphenyl (NPB) was then deposited on the HIL to form a HTL having a thickness of 300 Å.

Then, 9,10-di(naphthalene-2-yl)anthracene (ADN) and Compound 3 were co-deposited on the HTL at a weight ratio of 98:2 to form an EML having a thickness of 300 Å.

Then, Alq$_3$ was deposited on the EML to form an ETL having a thickness of 300 Å, LiF was deposited on the ETL to form an EIL having a thickness of 10 Å, and Al was deposited on the EIL to form a second electrode (cathode) having a thickness of 3,000 Å, thereby completing the manufacture of an OLED.

Example 2

An OLED was manufactured in the same manner as in Example 1, except that Compound 19 was used instead of Compound 3 in the formation of the EML.

Example 3

An OLED was manufactured in the same manner as in Example 1, except that Compound 33 was used instead of Compound 3 in the formation of the EML.

Example 4

An OLED was manufactured in the same manner as in Example 1, except that Compound 45 was used instead of Compound 3 in the formation of the EML.

Example 5

An OLED was manufactured in the same manner as in Example 1, except that Compound 47 was used instead of Compound 3 in the formation of the EML.

Example 6

An OLED was manufactured in the same manner as in Example 1, except that Compound 54 was used instead of Compound 3 in the formation of the EML Example 7

An OLED was manufactured in the same manner as in Example 1, except that Compound 69 was used instead of Compound 3 in the formation of the EML.

Example 8

An OLED was manufactured in the same manner as in Example 1, except that Compound 74 was used instead of Compound 3 in the formation of the EML.

Example 9

An OLED was manufactured in the same manner as in Example 1, except that Compound 80 was used instead of Compound 3 in the formation of the EML.

Example 10

An OLED was manufactured in the same manner as in Example 1, except that Compound 92 was used instead of Compound 3 in the formation of the EML.

Example 11

An OLED was manufactured in the same manner as in Example 1, except that Compound 106 was used instead of Compound 3 in the formation of the EML.

Example 12

An OLED was manufactured in the same manner as in Example 1, except that Compound 118 was used instead of Compound 3 in the formation of the EML.

Example 13

An OLED was manufactured in the same manner as in Example 1, except that Compound 128 was used instead of Compound 3 in the formation of the EML.

Example 14

An OLED was manufactured in the same manner as in Example 1, except that Compound 136 was used instead of Compound 3 in the formation of the EML.

Example 15

An OLED was manufactured in the same manner as in Example 1, except that Compound 161 was used instead of Compound 3 in the formation of the EML.

Example 16

An OLED was manufactured in the same manner as in Example 1, except that Compound 169 was used instead of Compound 3 in the formation of the EML.

Example 17

An OLED was manufactured in the same manner as in Example 1, except that Compound 180 was used instead of Compound 3 in the formation of the EML.

Example 18

An OLED was manufactured in the same manner as in Example 1, except that Compound 3 was used instead of NPB in the formation of the HTL and Compound DPAVBi was used instead of Compound 3 in the formation of the EML.

Example 19

An OLED was manufactured in the same manner as in Example 1, except that Compound 136 was used instead of NPB in the formation of the HTL and Compound DPAVBi was used instead of Compound 3 in the formation of the EML.

Example 20

An OLED was manufactured in the same manner as in Example 1, except that Compound 161 was used instead of NPB in the formation of the HTL and Compound DPAVBi was used instead of Compound 3 in the formation of the EML.

Comparative Example 1

An OLED was manufactured in the same manner as in Example 1, except that 1,4-bis-2,2-diphenylvinyl)biphenyl (DPAVBi) was used instead of Compound 3 in the formation of the EML.

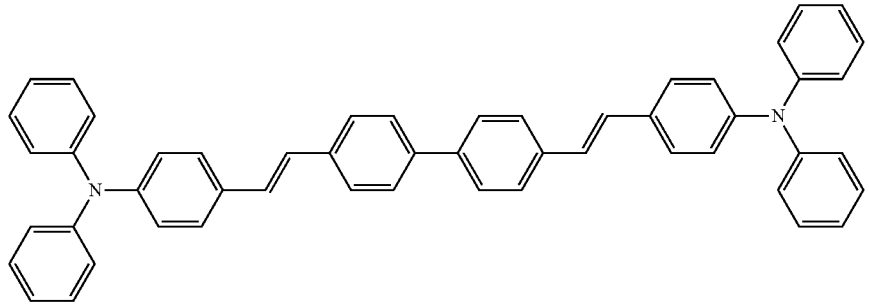

DPAVBi

Comparative Example 2

An OLED was manufactured in the same manner as in Example 1, except that Compound A was used instead of Compound 3 in the formation of the EML.

Evaluation Example 1

Driving voltage, current density, brightness, emission color, efficiency, and half lifetime (@100 mA/cm$^2$) of each of the OLEDs of Examples 1 through 20 and Comparative Examples 1 and 2 were evaluated using PR650 Spectroscan Source Measurement Unit (available from PhotoResearch), and the results are shown in Table 1 below.

TABLE 1

| | Hole transport layer | Dopant of Emission layer | Driving voltage (V) | Current density (mA/cm$^2$) | Brightness (cd/m$^2$) | efficiency (cd/A) | Emission color | Half lifetime (hr) |
|---|---|---|---|---|---|---|---|---|
| Example 1 | NPB | Compound 3 | 6.39 | 50 | 3,075 | 6.15 | Blue | 259 |
| Example 2 | NPB | Compound 19 | 6.41 | 50 | 3,045 | 6.09 | Blue | 263 |
| Example 3 | NPB | Compound 33 | 6.42 | 50 | 3,085 | 6.17 | Blue | 269 |
| Example 4 | NPB | Compound 45 | 6.36 | 50 | 3,205 | 6.41 | Blue | 287 |

TABLE 1-continued

| | Hole transport layer | Dopant of Emission layer | Driving voltage (V) | Current density (mA/cm$^2$) | Brightness (cd/m$^2$) | efficiency (cd/A) | Emission color | Half lifetime (hr) |
|---|---|---|---|---|---|---|---|---|
| Example 5 | NPB | Compound 47 | 6.38 | 50 | 3,260 | 6.52 | Blue | 322 |
| Example 6 | NPB | Compound 54 | 6.39 | 50 | 3,120 | 6.24 | Blue | 271 |
| Example 7 | NPB | Compound 69 | 6.37 | 50 | 3,055 | 6.11 | Blue | 254 |
| Example 8 | NPB | Compound 74 | 6.36 | 50 | 2,985 | 5.97 | Blue | 322 |
| Example 9 | NPB | Compound 80 | 6.40 | 50 | 3,235 | 6.47 | Blue | 307 |
| Example 10 | NPB | Compound 92 | 6.38 | 50 | 3,035 | 6.07 | Blue | 297 |
| Example 11 | NPB | Compound 106 | 6.37 | 50 | 3,105 | 6.21 | Blue | 264 |
| Example 12 | NPB | Compound 118 | 6.41 | 50 | 3,290 | 6.58 | Blue | 326 |
| Example 13 | NPB | Compound 128 | 6.28 | 50 | 3,160 | 6.32 | Blue | 302 |
| Example 14 | NPB | Compound 136 | 6.31 | 50 | 3,165 | 6.33 | Blue | 273 |
| Example 15 | NPB | Compound 161 | 6.29 | 50 | 3,140 | 6.28 | Blue | 267 |
| Example 16 | NPB | Compound 169 | 6.28 | 50 | 3,305 | 6.61 | Blue | 279 |
| Example 17 | NPB | Compound 180 | 6.39 | 50 | 3,330 | 6.66 | Blue | 286 |
| Example 18 | Compound 3 | DPVABi | 5.72 | 50 | 2,680 | 5.36 | Blue | 209 |
| Example 19 | Compound 136 | DPVABi | 5.53 | 50 | 2,710 | 5.42 | Blue | 219 |
| Example 20 | Compound 161 | DPVABi | 5.54 | 50 | 2,880 | 5.76 | Blue | 226 |
| Comparative Example 1 | NPB | DPVABi | 7.35 | 50 | 2,065 | 4.13 | Blue | 145 |
| Comparative Example 2 | NPB | Compound A | 6.43 | 50 | 3,050 | 6.10 | Blue | 152 |

From the results shown in Table 1, it is confirmed that the OLEDs of Examples 1 through 20 each generally have excellent driving voltage, higher luminance, higher efficiency, higher color purity, and longer lifetime, as compared to the OLEDs of Comparative Examples 1 and 2.

In detail, it may be confirmed that the OLED of Example 3 using Compound 33 as a dopant of an EML has long lifetime compared to the OLED of Example 2 using Compound A as a dopant of an EML. The Compound A is different from Compound 33 in that a phenyl group bonded to nitrogen instead of a styryl group is substituted with deuterium. Thus, it may be confirmed that the lifetime properties of an OLED is increased by substituting carbon of the styryl group with deuterium styryl group.

It may be confirmed that the OLEDs of Examples 18 through 20 including Compounds 3, 136, and 161 as a hole transport material each have low driving voltage while having long lifetime compared to the OLED of Comparative Example 1.

As described above, according to the one or more embodiments of the present invention, a styryl-based compound may exhibit high heat resistance and thus an OLED including the same may have low driving voltage, high brightness, high efficiency, and long lifetime.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A styryl-based compound represented by any one of Formulae 1A through 1I below:

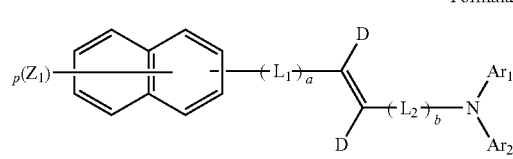

Formula 1A

-continued

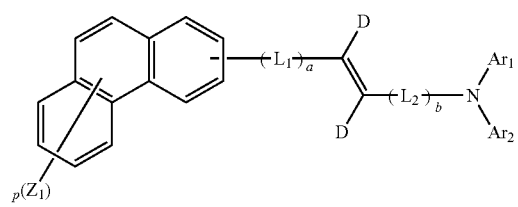

Formula 1B

Formula 1C

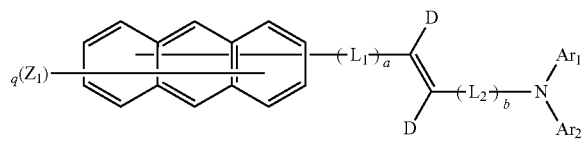

Formula 1D

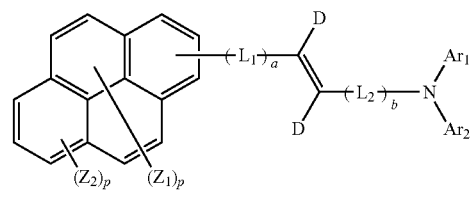

Formula 1E

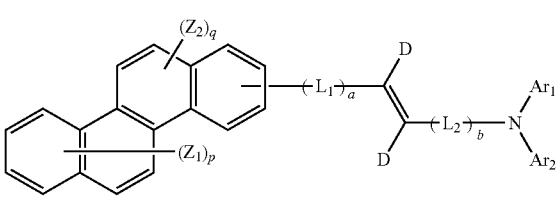

-continued

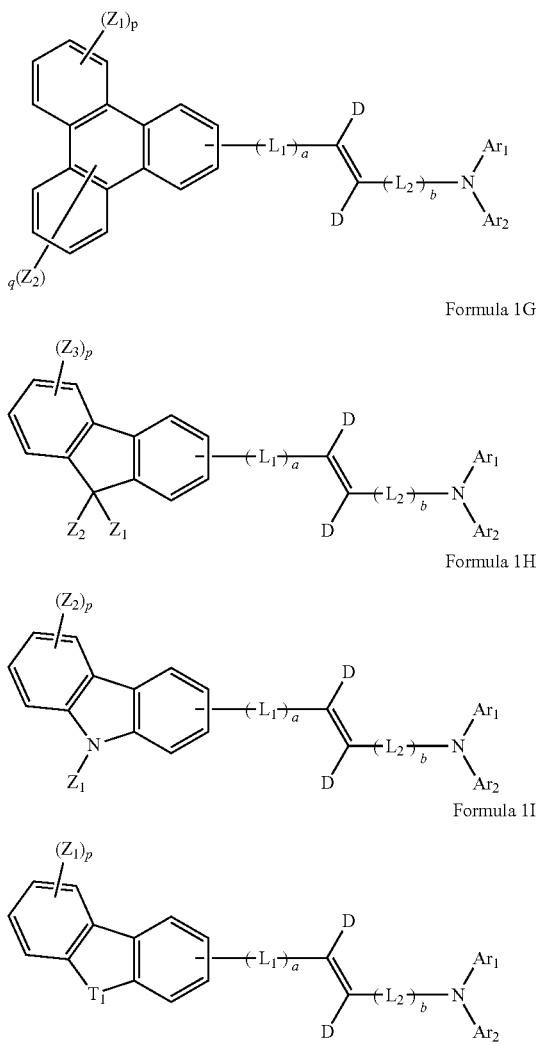

Formula 1F

Formula 1G

Formula 1H

Formula 1I wherein $Z_1$ through $Z_3$ are each independently selected from the group consisting of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group; a naphthyl group; a fluorenyl group; a phenanthrenyl group; an anthryl group; an triphenylenyl group; a pyrenyl group; a chrysenyl group; an imidazolyl group: an imidazolynyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, a phenanthrenyl group, an anthryl group, an triphenylenyl group, a pyrenyl group, a chrysenyl group, an imidazolyl group, an imidazolynyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group;

two or more neighboring substituents from among $Z_1$ through $Z_3$ are optionally fused with each other or are optionally connected by a single bond;

$T_1$ is O or S;

p is an integer of 1 to 7; and q is an integer of 1 to 4;

$Ar_1$ and $Ar_2$ are each independently a substituted or unsubstituted $C_6$-$C_{60}$ aryl group, or a substituted or unsubstituted $C_2$-$C_{60}$ heteroaryl group;

$L_1$ and $L_2$ are each independently a substituted or unsubstituted $C_6$-$C_{60}$ arylene group, or a substituted or unsubstituted $C_2$-$C_{60}$ heteroarylene group; and a and b are each independently an integer of 0 to 5.

2. The styryl-based compound of claim 1, wherein $Ar_1$ and $Ar_2$ are each independently a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted, or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, to substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzoxazolyl group, a substituted or unsubstituted dibenzofuranyl group, a substituted or unsubstituted dibenzothiophenyl group, or a substituted or unsubstituted benzocarbazolyl group.

3. The styryl-based compound of claim 1, wherein $Ar_1$ and $Ar_2$ are each independently a substituted or unsubstituted phenyl group, a substituted or unsubstituted naphthyl group, a substituted or unsubstituted phenanthrenyl group, a substituted or unsubstituted pyrenyl group, a substituted or unsubstituted carbazolyl group, a substituted or unsubstituted fluorenyl group, a substituted or unsubstituted dibenzofuranyl group, a substituted or unsubstituted dibenzothiophenyl group, or a substituted or unsubstituted benzocarbazolyl group.

4. The styryl-based compound of claim 1, wherein $Ar_1$ and $Ar_2$ are each independently represented by any one of Formulae 2A through 2J below:

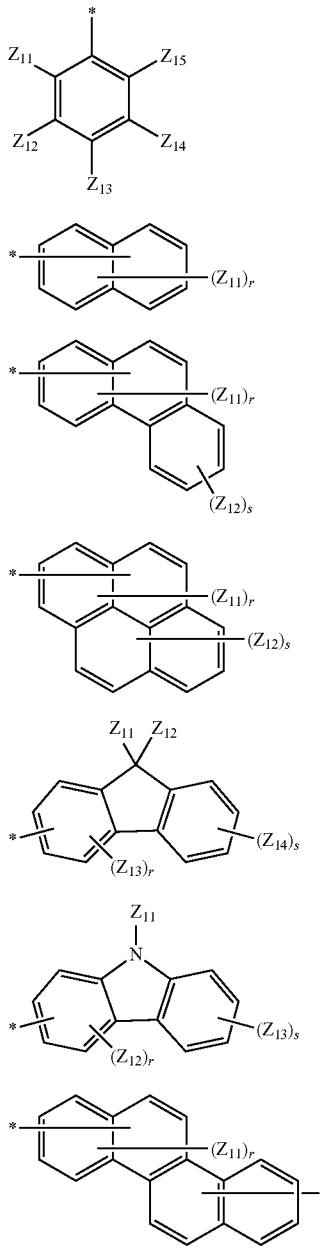

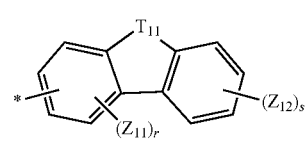

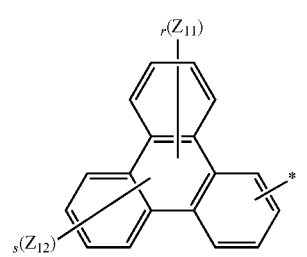

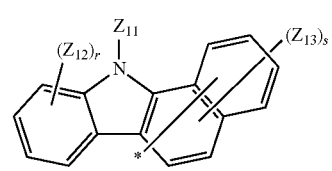

wherein $Z_{11}$ through $Z_{15}$ are each independently selected from the group consisting of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolynyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolynyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amid no group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group;

two or more neighboring substituents from among $Z_{11}$ through $Z_{15}$ are optionally fused with each other or are optionally connected by a single bond;

$T_{11}$ is O or S;

r is an integer of 1 to 7; and s is an integer of 1 to 5.

5. The styryl-based compound of claim 1, wherein $L_1$ and $L_2$ are each independently a substituted or unsubstituted phenylenyl group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted Or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanyl group, a substituted or unsubstituted benzofuranylene group, a substituted or unsubstituted thiophenylene group, a substituted or unsubstituted benzothiophenyl group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzofuranylene group, a substituted or unsubstituted triazinylene group, or a substituted or unsubstituted oxadiazolylene group.

6. The styryl-based compound of claim 1, wherein $L_1$ and $L_2$ are each independently a substituted or unsubstituted phenylenyl group, a substituted or unsubstituted naphthylene group, a substituted or unsubstituted fluorenylene group, a substituted or unsubstituted phenanthrenylene group, a substituted or unsubstituted pyridinylene group, or a substituted or unsubstituted pyrazinylene group.

7. The styryl-based compound of claim 1, wherein $L_1$ and $L_2$ are each independently represented by any one of Formulae 5A through 5K:

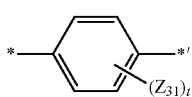

Formula 5A

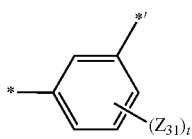

Formula 5B

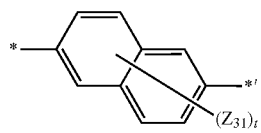

Formula 5C

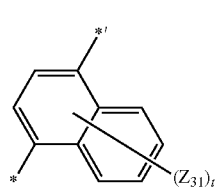

Formula 5D

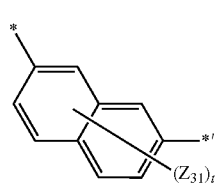

Formula 5E

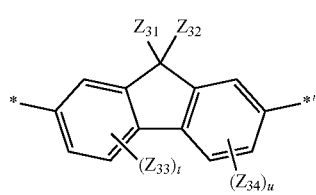

Formula 5F

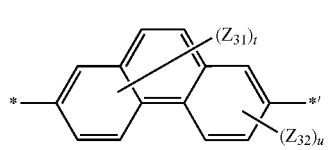

Formula 5G

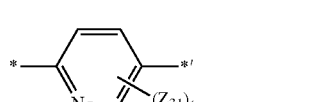

Formula 5H

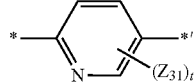

Formula 5I

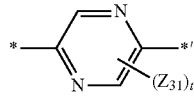

Formula 5J

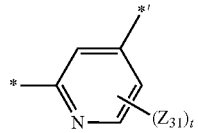

Formula 5K wherein $Z_{31}$ through $Z_{34}$ are each independently selected from the group consisting of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolinyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group;

two or more neighboring substituents from among $Z_{31}$ through $Z_{34}$ are optionally fused with each other or are optionally connected by a single bond;

t is an integer of 1 to 6; and u is an integer of 1 to 3.

8. The styryl-based compound of claim 1, wherein the styryl-based compound is represented by any one of Formulae 1A-1 through 1I-3 below:

Formula 1A-1

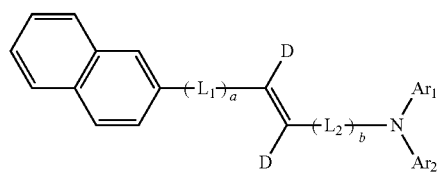

Formula 1A-2

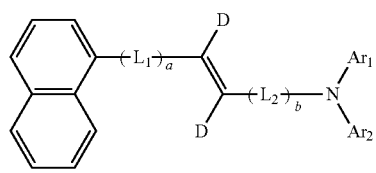

Formula 1B-1

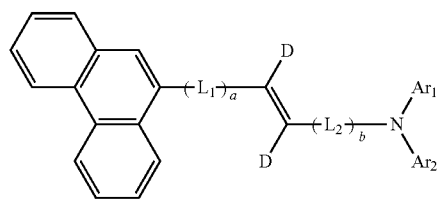

Formula 1B-2

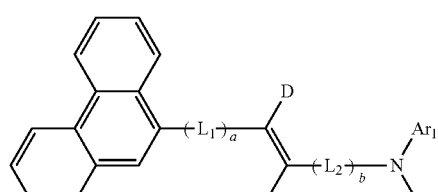

Formula 1C-1

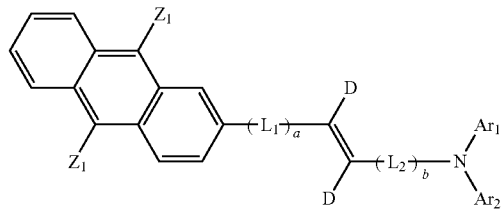

Formula 1C-2

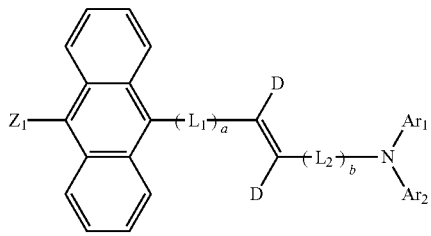

Formula 1D-1

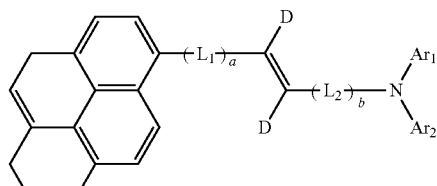

Formula 1E-1

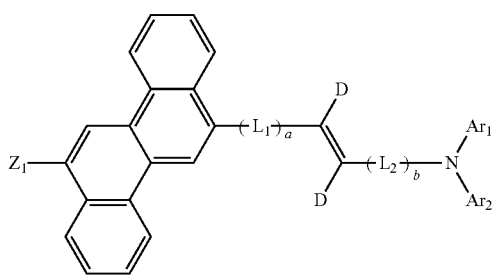

Formula 1F-1

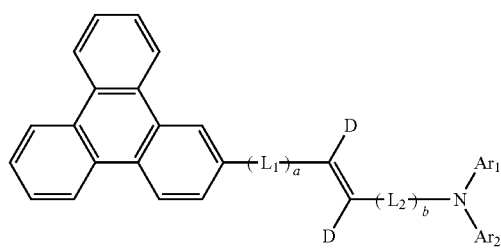

Formula 1G-1

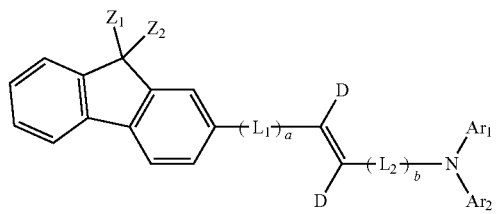

-continued

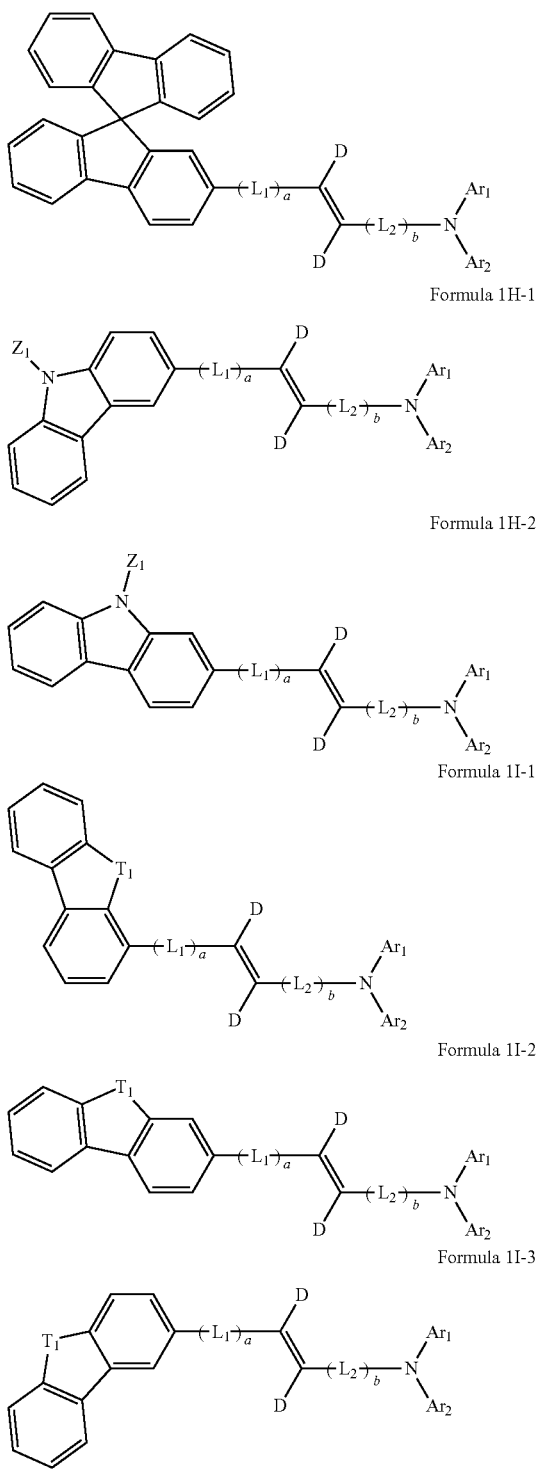

wherein $Z_1$ and $Z_2$ are each independently selected from the group consisting of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group; a naphthyl group; a fluorenyl group; a phenan- threnyl group; an anthryl group; a triphenylenyl group; a pyrenyl group; a chrysenyl group; an imidazolyl group; an imidazolynyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolynyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, hydrazine, hydrazone, a carboxyl group or a salt thereof, as sulfonic acid group or a salt thereof, a phosphoric acid or a salt thereof, a $C_1$-$C_{10}$ alkyl group, and a $C_1$-$C_{10}$ alkoxy group;

$T_1$ is O or S;

$Ar_1$ and $Ar_2$ are each independently a substituted or unsubstituted phenyl group, a substituted or unsubstituted naphthyl group, a substituted or unsubstituted phenanthrenyl group, a substituted or unsubstituted pyrenyl group, a substituted or unsubstituted carbazolyl group, a substituted or unsubstituted fluorenyl group, a substituted or unsubstituted dibenzofuranyl group, a substituted or unsubstituted dibenzothiophenyl group, or a substituted or unsubstituted benzocarbazolyl group;

$L_1$ and $L_2$ are each independently a substituted or unsubstituted phenylenyl group, as substituted or unsubstituted naphthylene group, a substituted or unsubstituted fluorenylene group, a substituted or unsubstituted phenanthrenylene group, a substituted or unsubstituted pyridinylene group, or a substituted or unsubstituted pyrazinylene group;

a is 0 or 1; and b is 1 or 2.

9. The styryl-based compound of claim 8, wherein $Ar_1$ and $Ar_2$ are each independently represented by any one of Formulae 2A through 2J below:

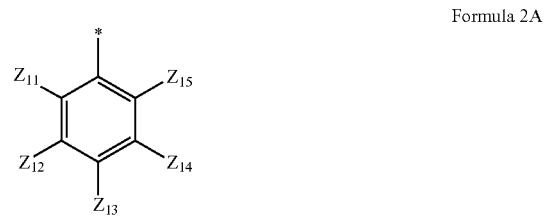

-continued

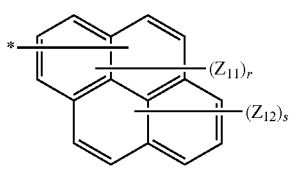
Formula 2D

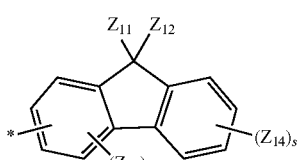
Formula 2E

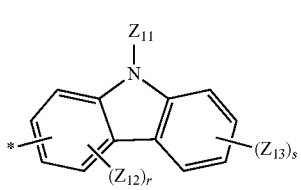
Formula 2F

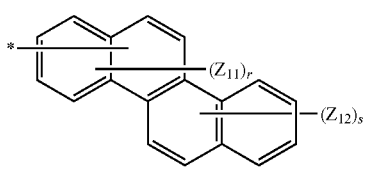
Formula 2G

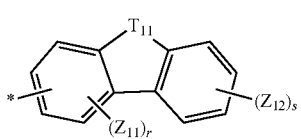
Formula 2H

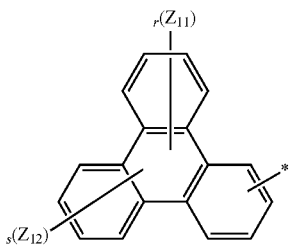
Formula 2I

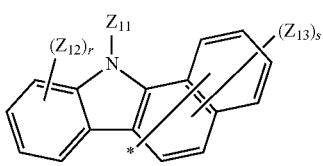
Formula 2J wherein $Z_{11}$ through $Z_{15}$ are each independently hydrogen; deuterium; a halogen atom; a hydroxyl group; a cyano group; a intro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolinyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, as phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group;

two or more neighboring substituents from among $Z_{11}$ through $Z_{15}$ are fused with each other or optionally are connected by a single bond;

$T_{11}$ is O or S;

r is an integer of 1 to 7; and s is an integer of 1 to 5.

10. The styryl-based compound of claim 8, wherein $L_1$ and $L_2$ are each independently represented by any one of Formulae 5A through 5K below:

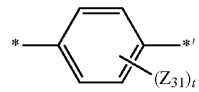
Formula 5A

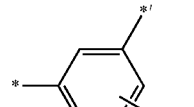
Formula 5B

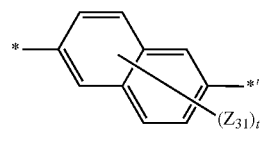
Formula 5C

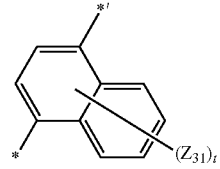
Formula 5D

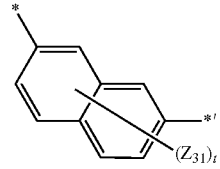
Formula 5E

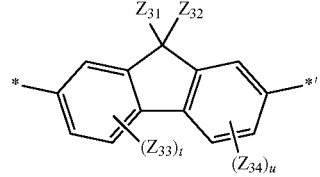
Formula 5F

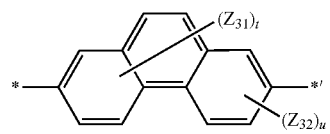
Formula 5G

-continued

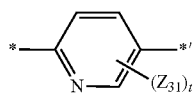
Formula 5H

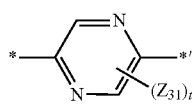
Formula 5I

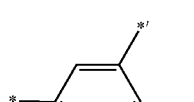
Formula 5J

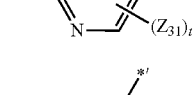
Formula 5K

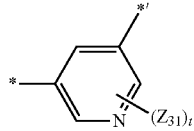

wherein $Z_{31}$ through $Z_{34}$ are each independently hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group; a naphthyl group; a fluorenyl group; a phenanthrenyl group; an anthryl group; a triphenylenyl group; a pyrenyl group; a chrysenyl group; an imidazolyl group; an imidazolinyl group; an imidazopyridinyl group; an imidazopyrimidinyl group; a pyridinyl group; a pyrazinyl group; a pyrimidinyl group; an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ ail group;

two or more neighboring substituents from among $Z_{31}$ through $Z_{34}$ are optionally fused with each other or are optionally connected by a single bond;

t is an integer of 1 to 6; and u is an integer of 1 to 3.

11. The styryl-based compound of claim 1, wherein the styryl-based compound is any one of Compounds 1 through 95 and 101 through 182 below:

1

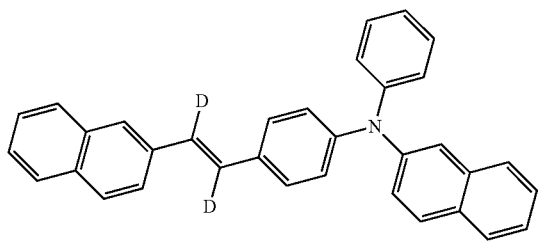

2

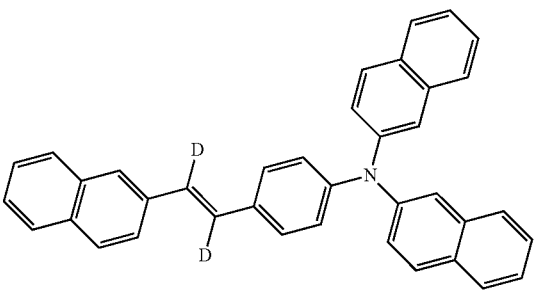

3

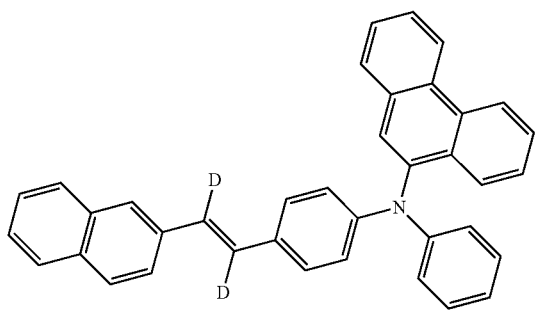

4

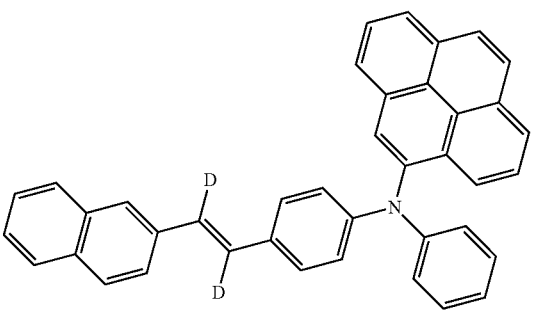

5

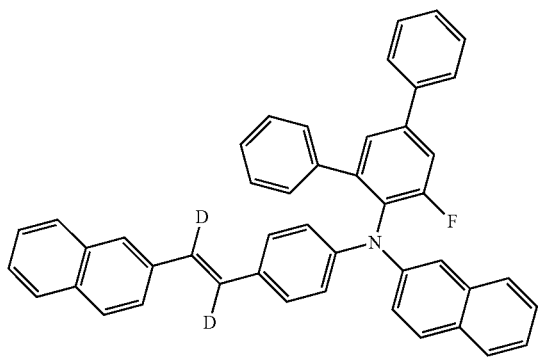

6

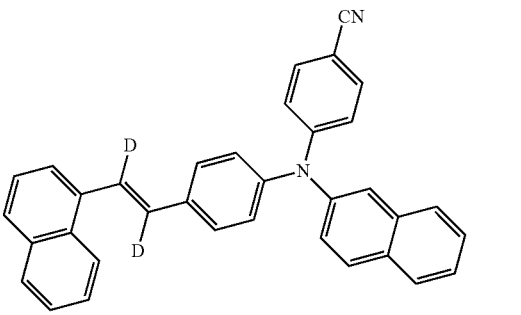

-continued
7
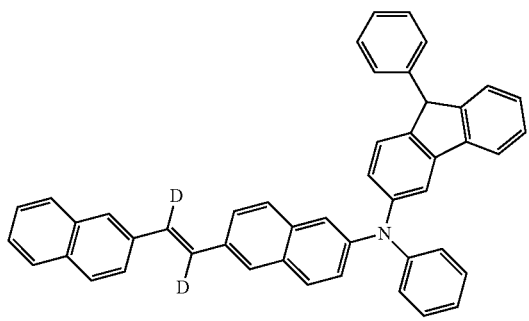
8
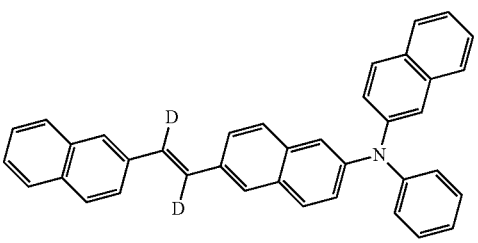
9
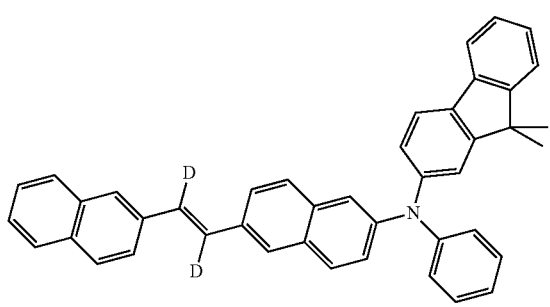
10
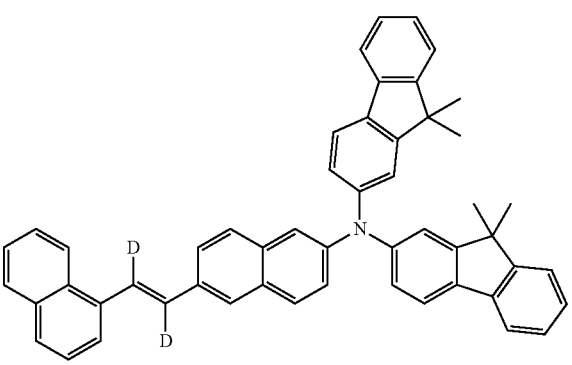
11
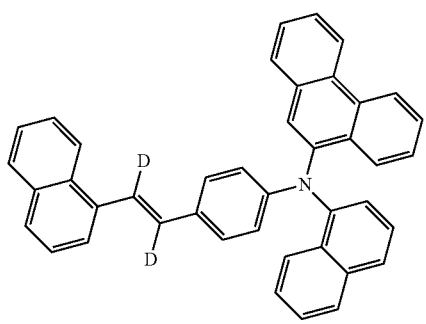
12
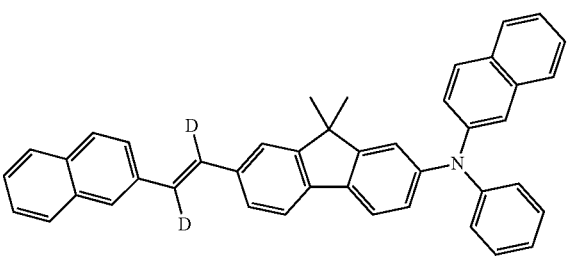
13
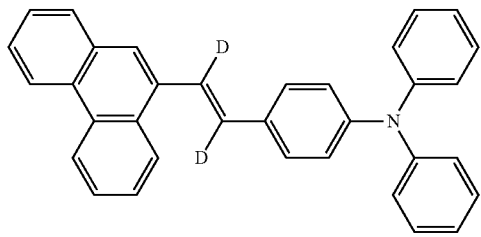
14
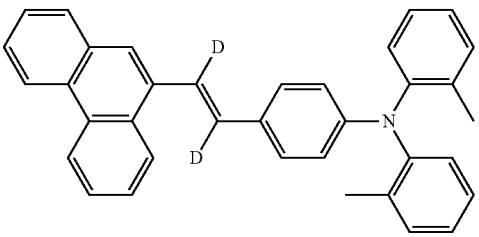
15
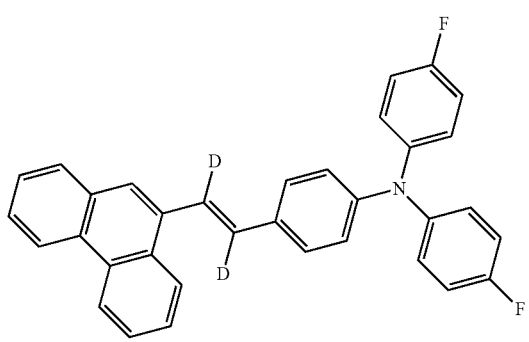
16
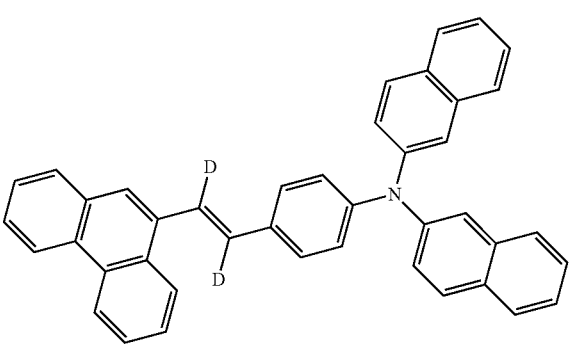

-continued
17
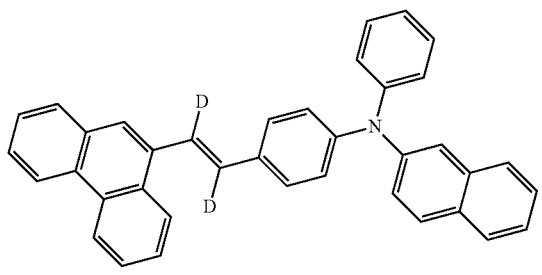
18
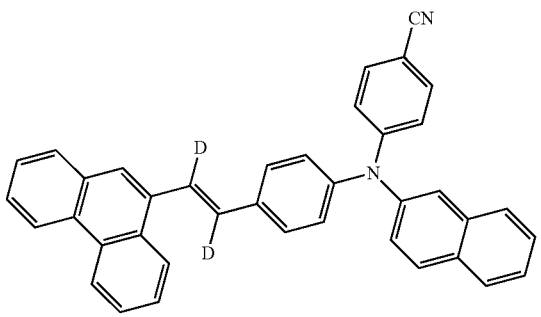
19
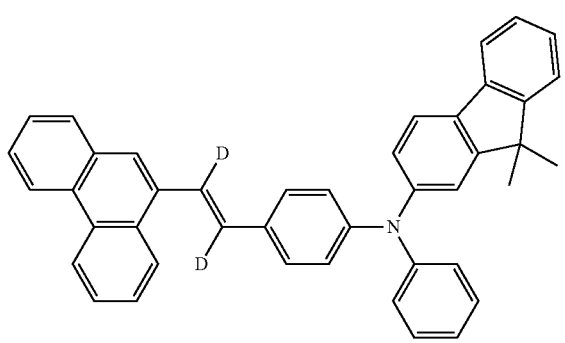
20
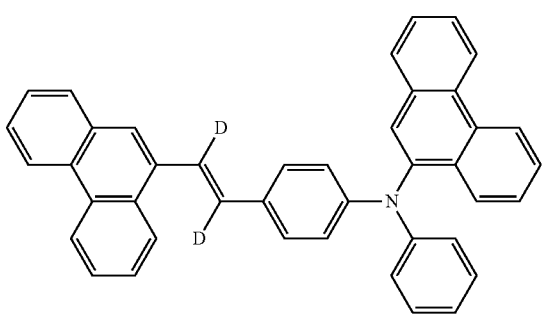
21
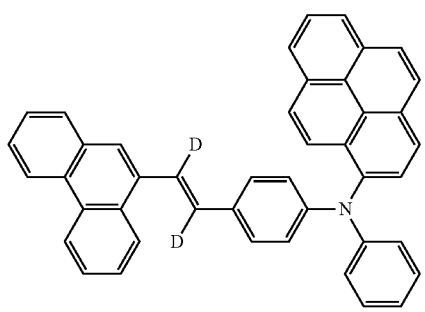
22
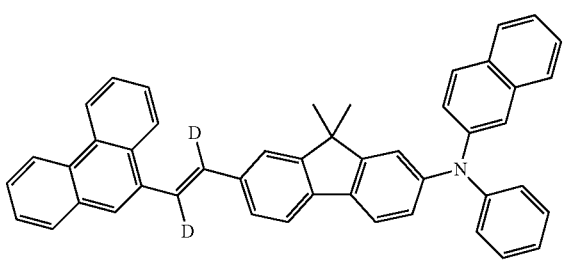
23
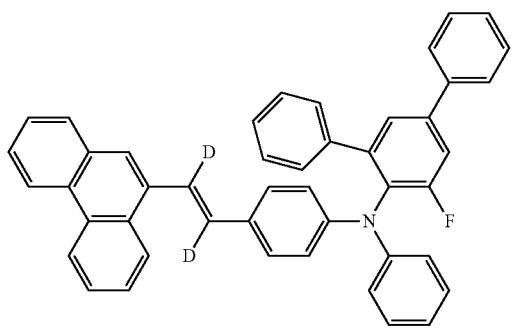
24
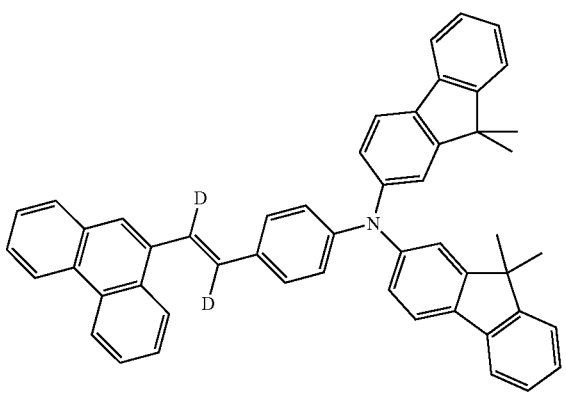

-continued
25
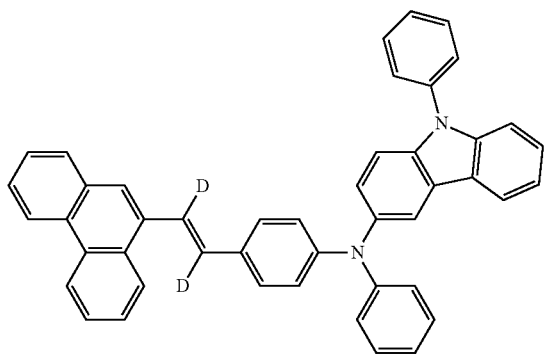
26
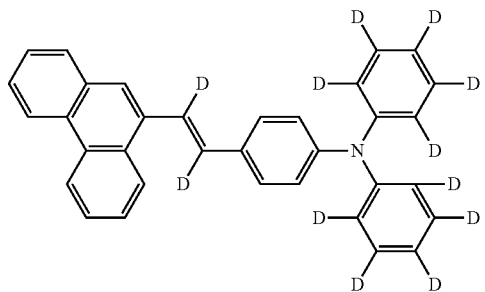
27
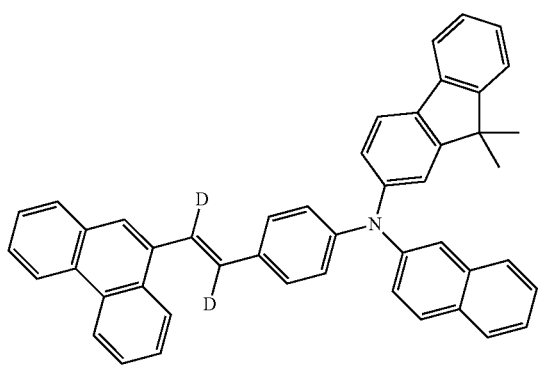
28
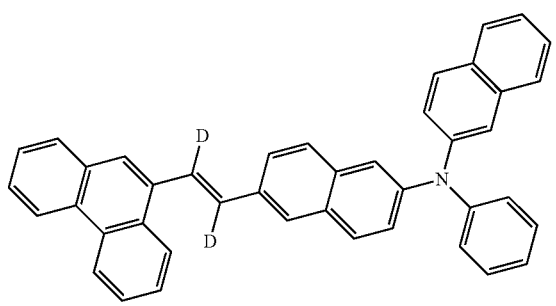
29
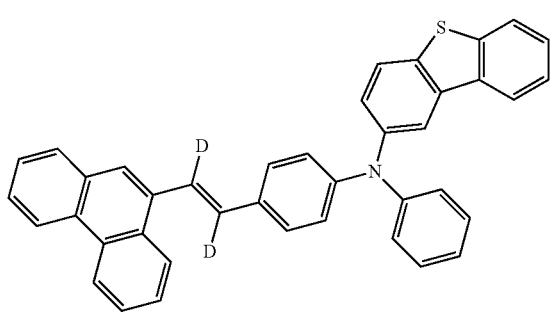
30
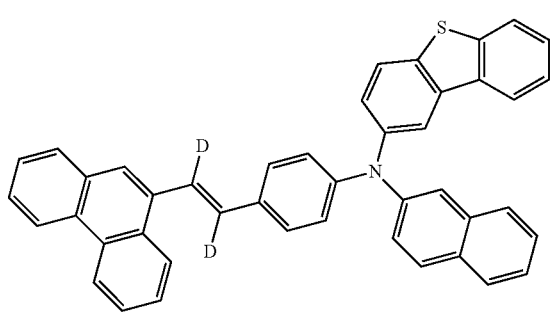
31
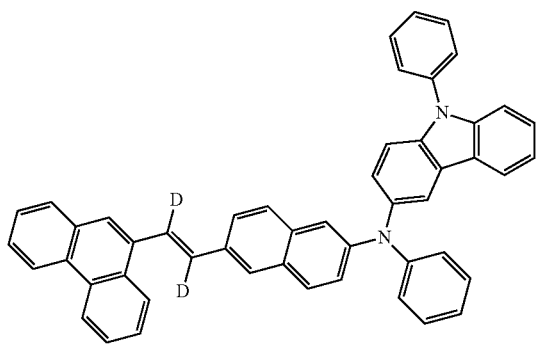
32
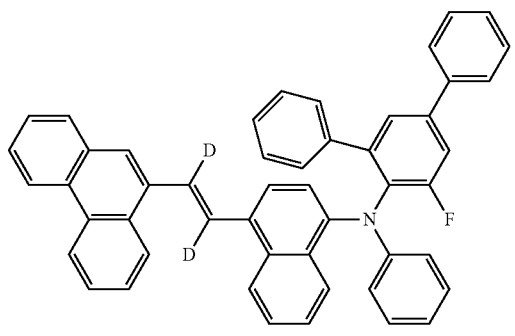

-continued
33
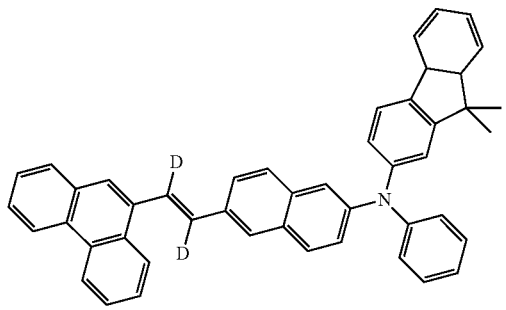
34
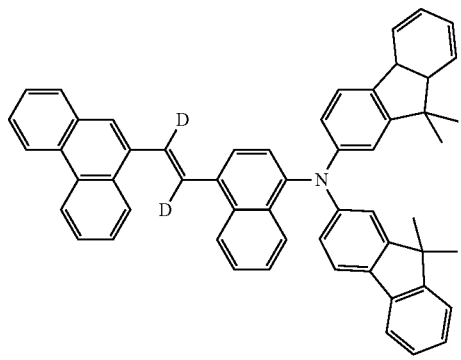
35
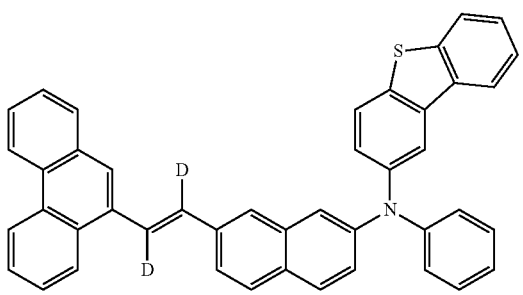
36
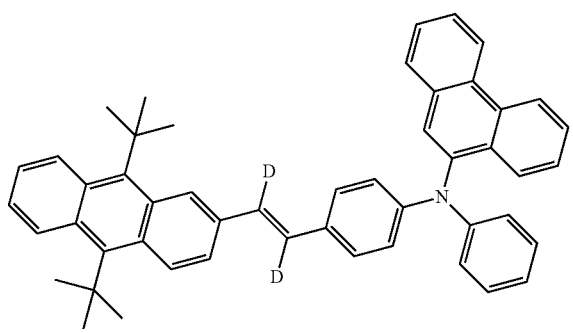
37
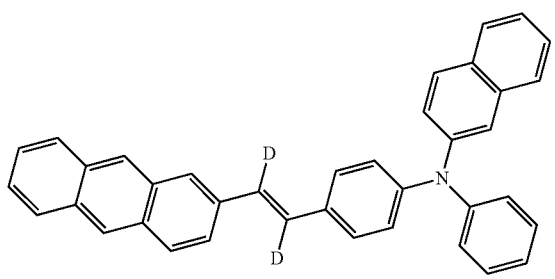
38
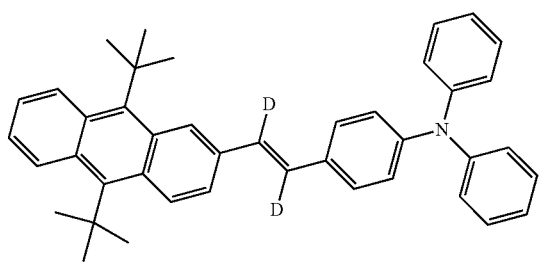
39
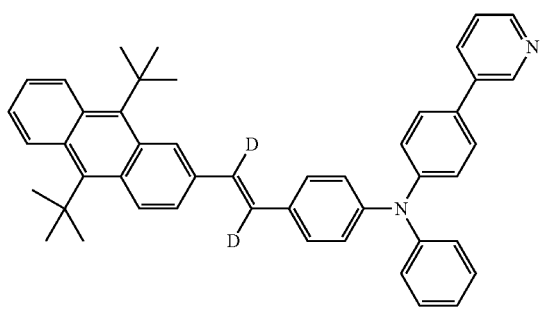
40
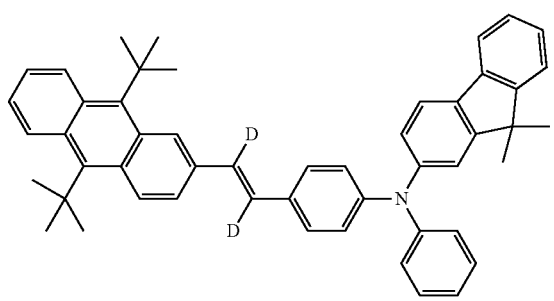

-continued
41
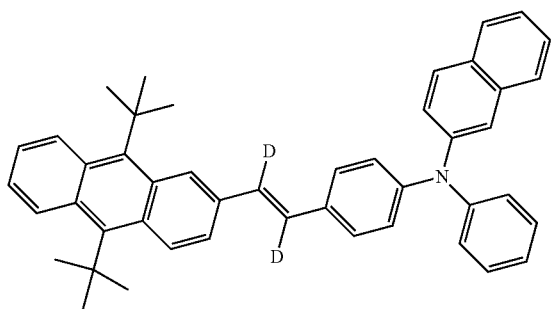
42
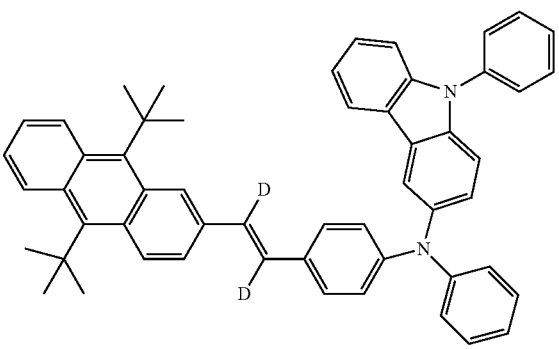
43
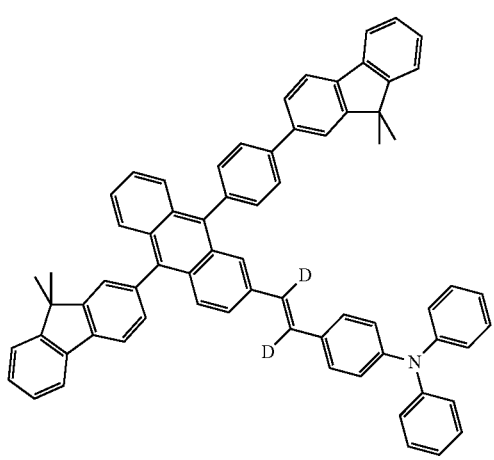
44
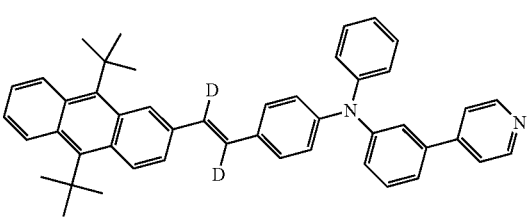
45
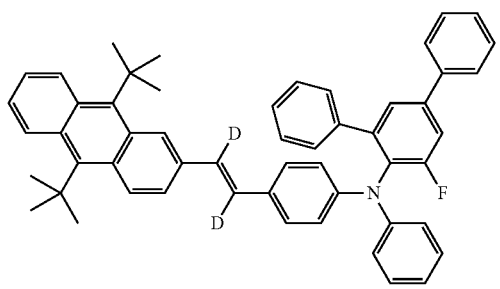
46
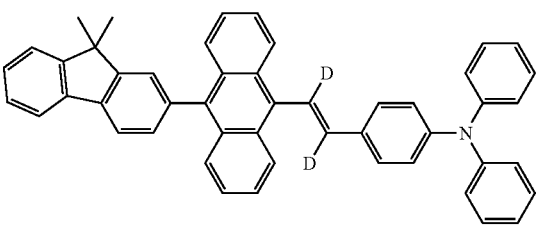
47
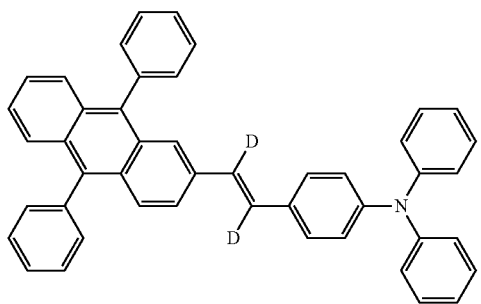
48
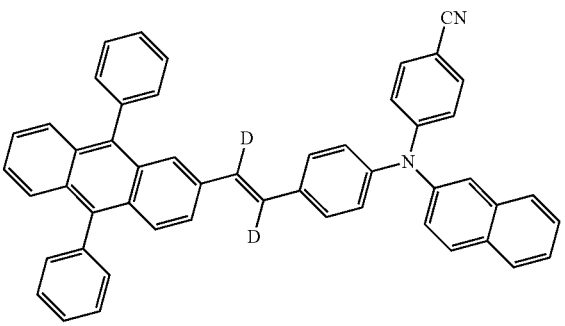

-continued
49
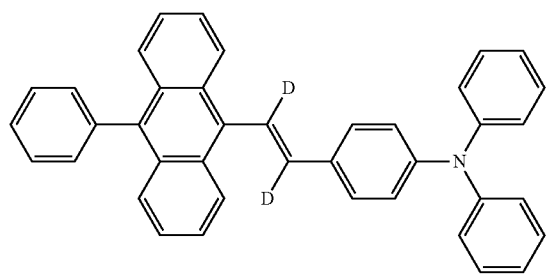
50
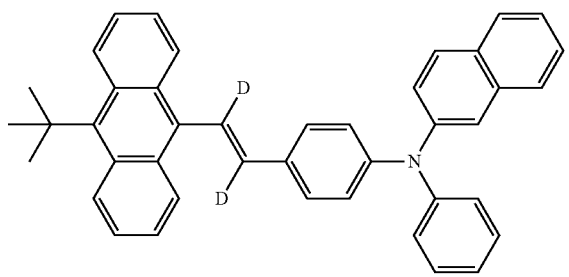
51
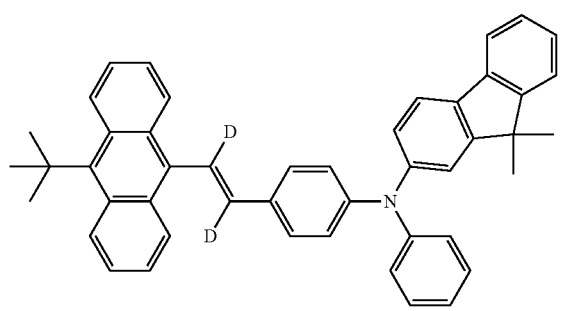
52
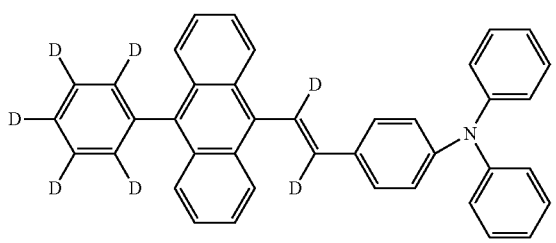
53
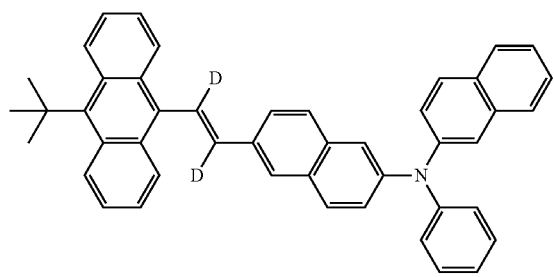
54
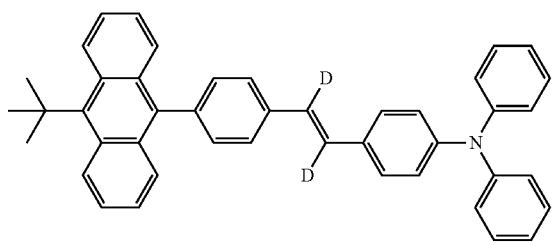
55
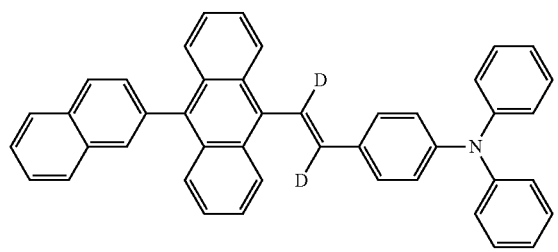
56
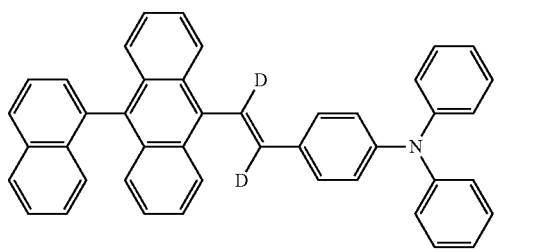
57
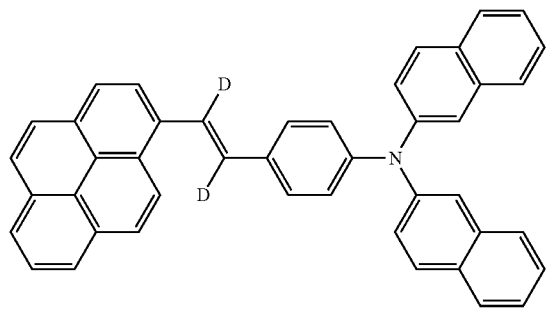
58
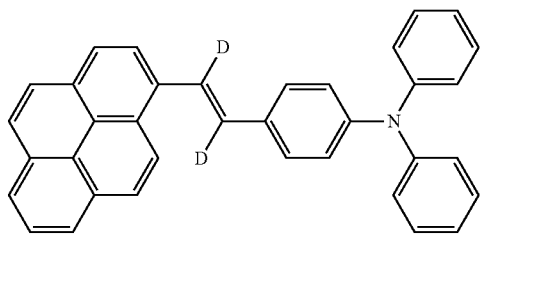

-continued
59
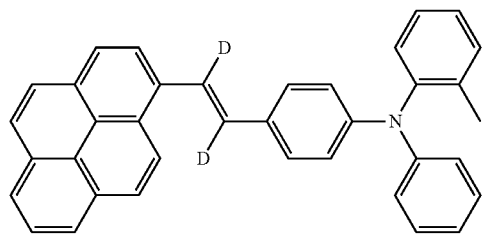
60
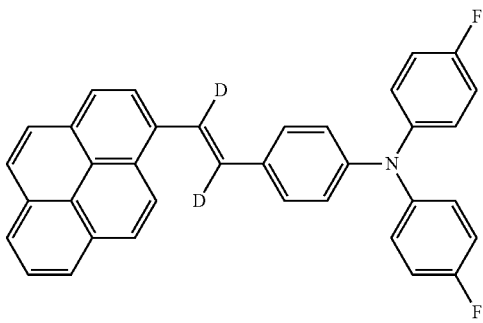
61
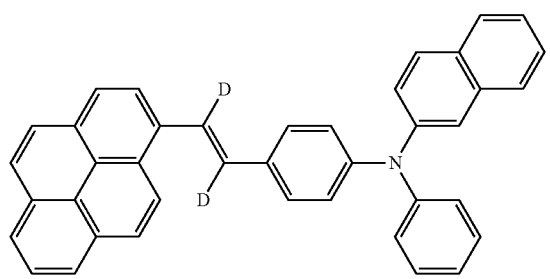
62
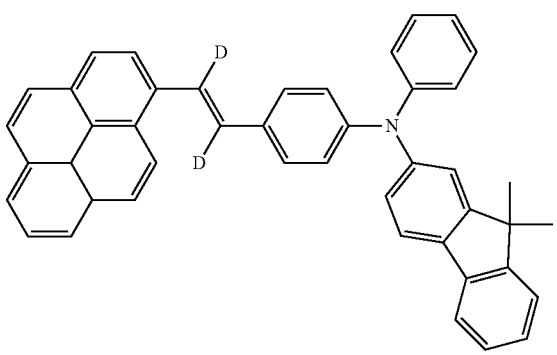
63
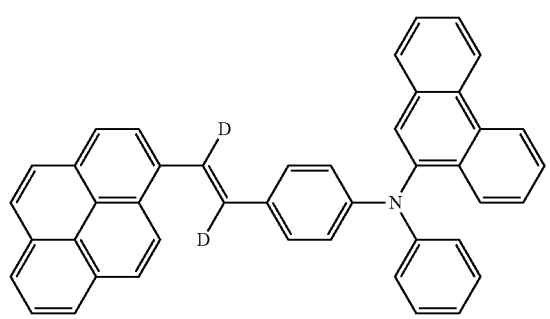
64
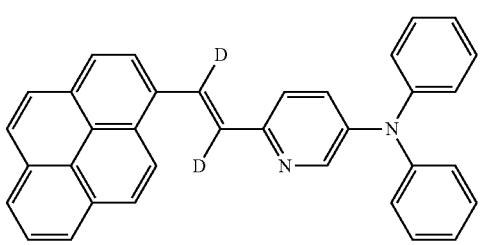
65
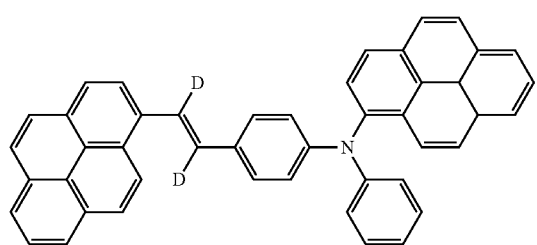
66
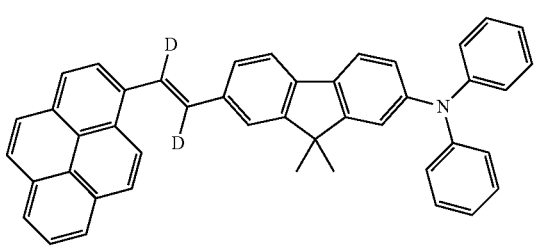
67
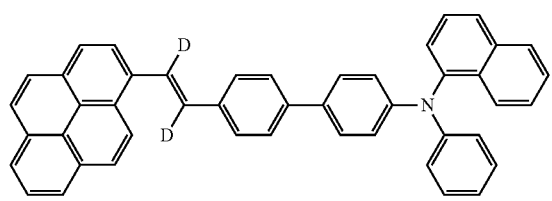
68
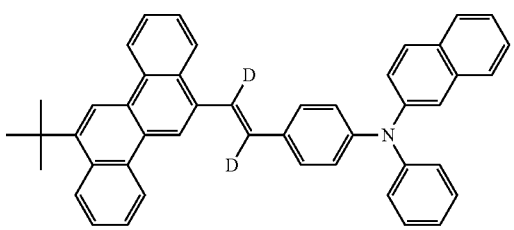

-continued
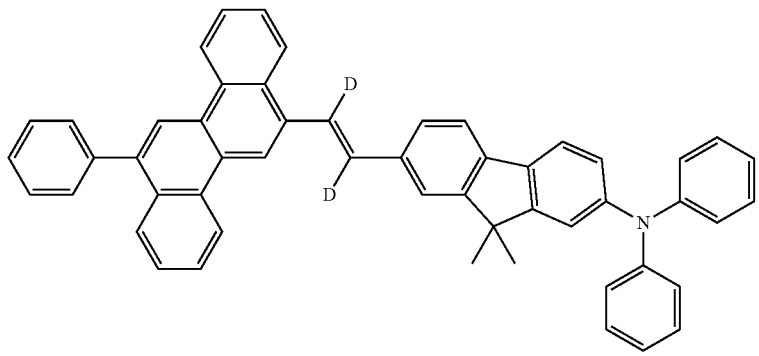
69
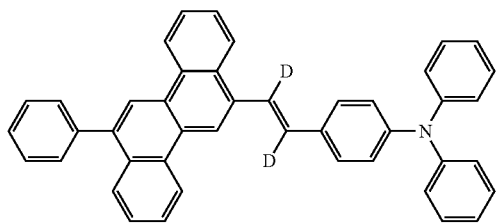
70
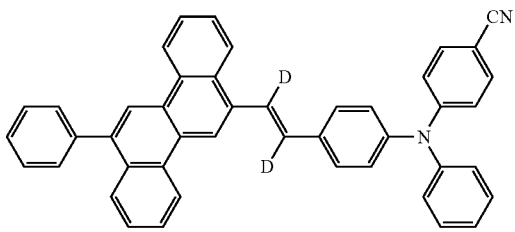
71
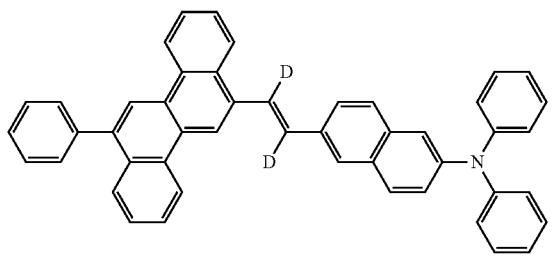
72
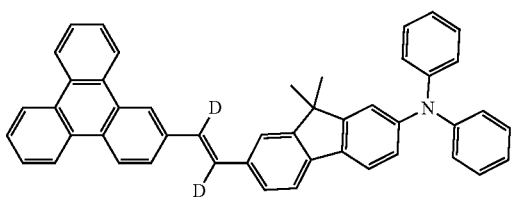
73
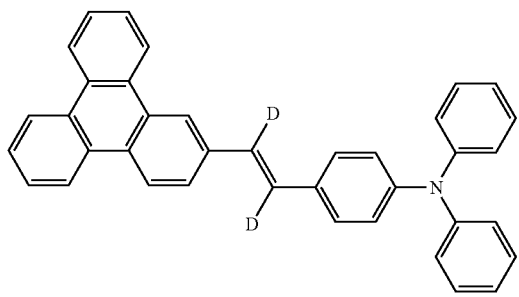
74
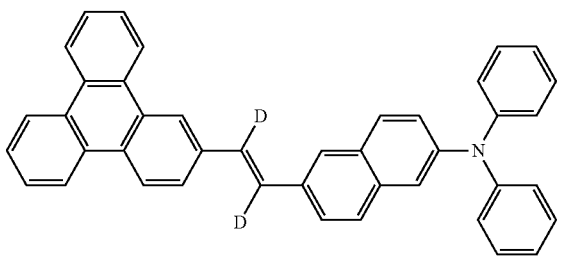
75
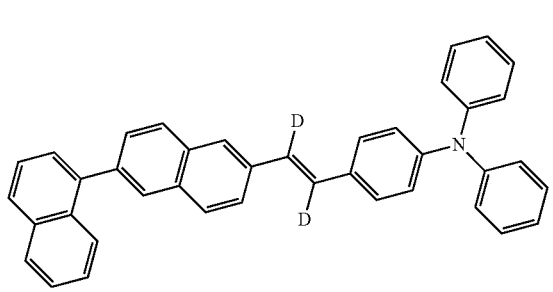
76
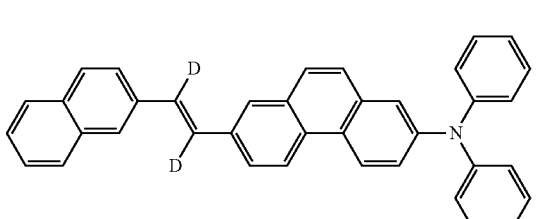
77

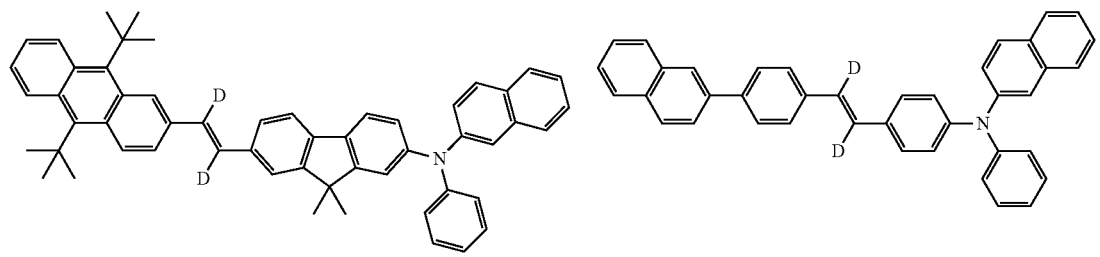
79
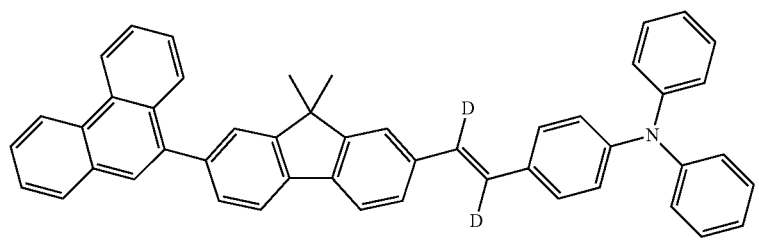
80
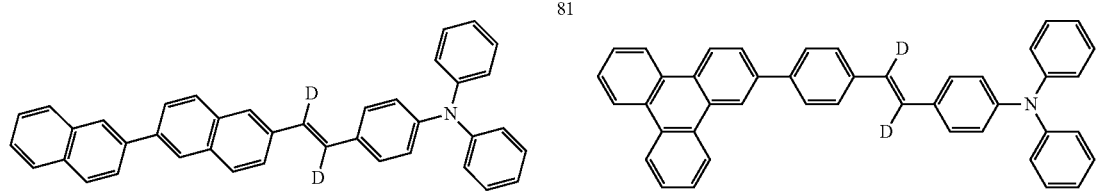
81
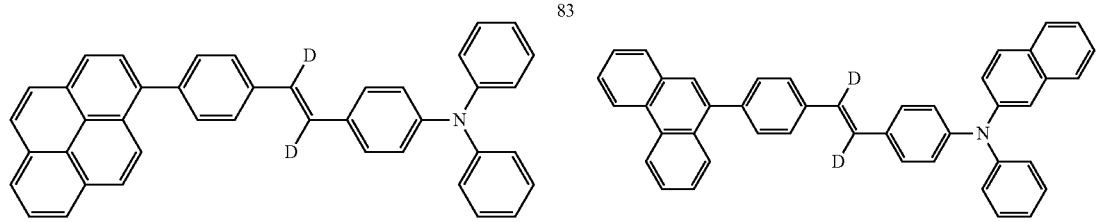
82
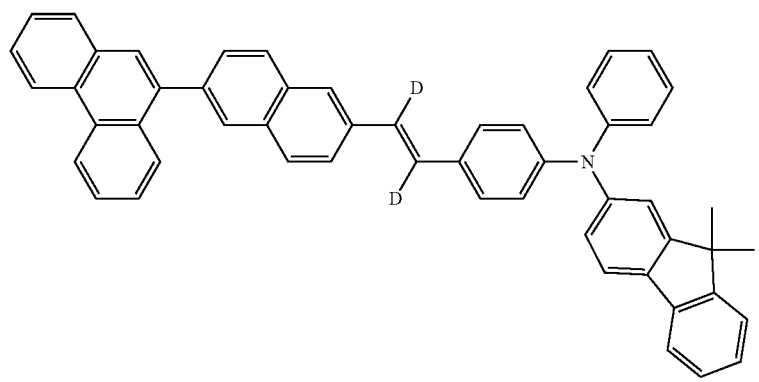
83
84
85
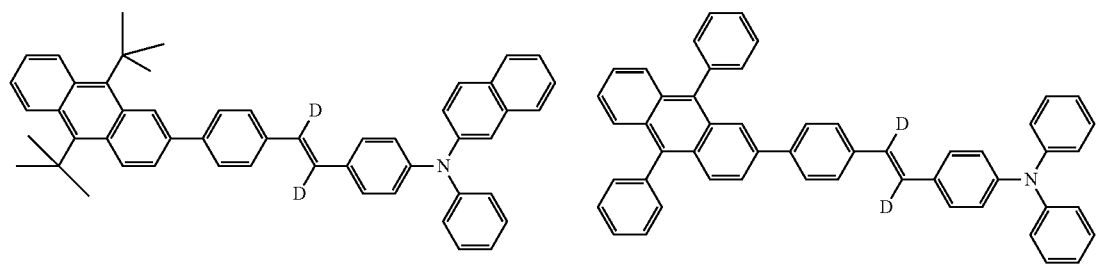
86
87

-continued
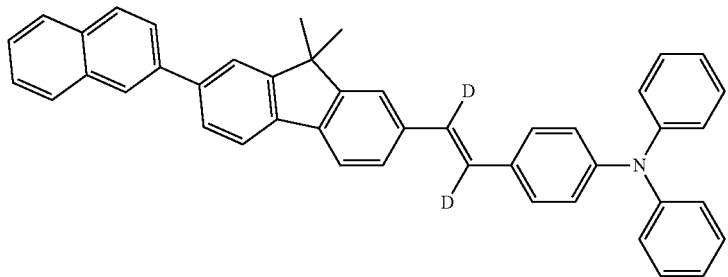
88
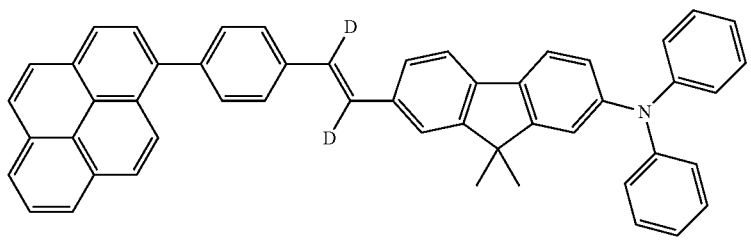
89
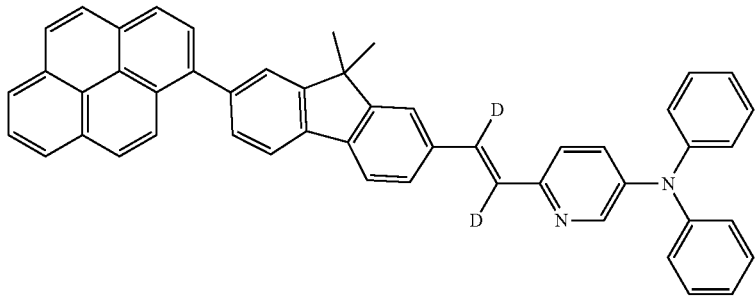
90
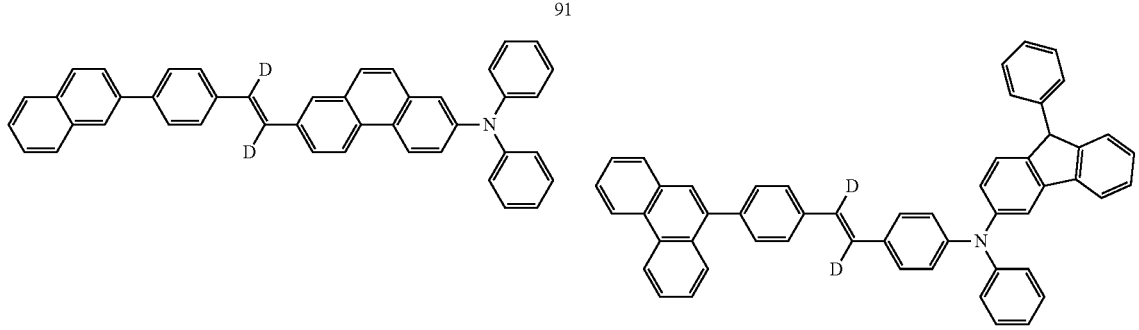
91    92
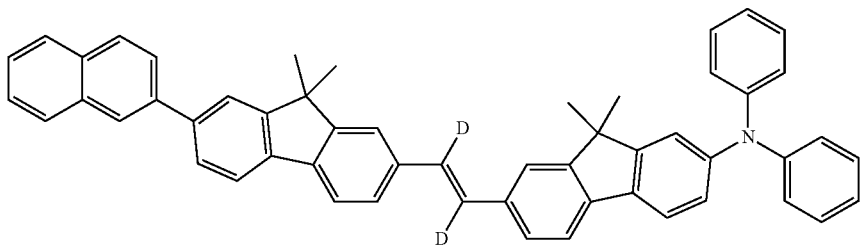
93

-continued
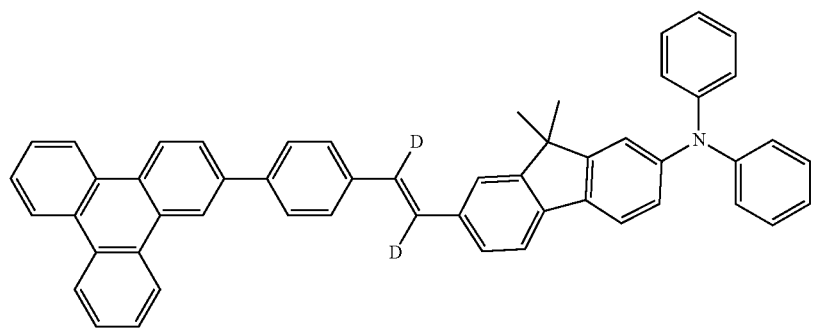
94
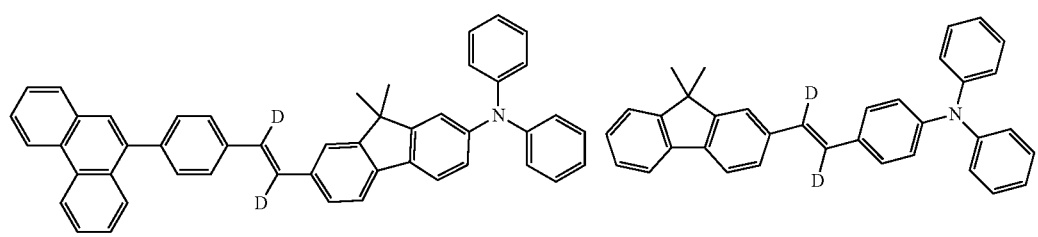
101
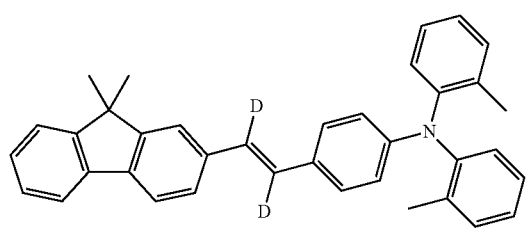
102
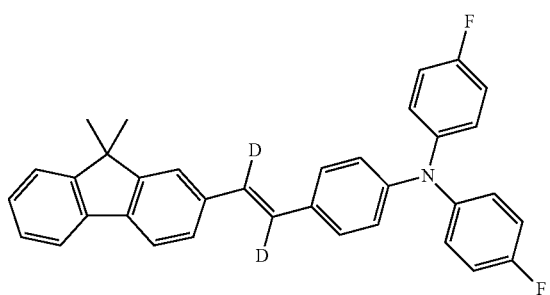
103
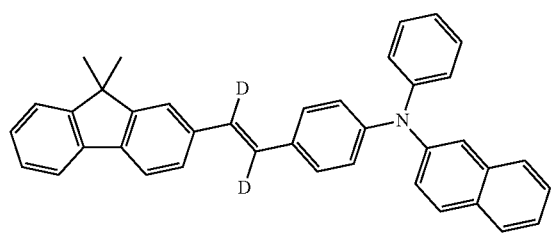
104
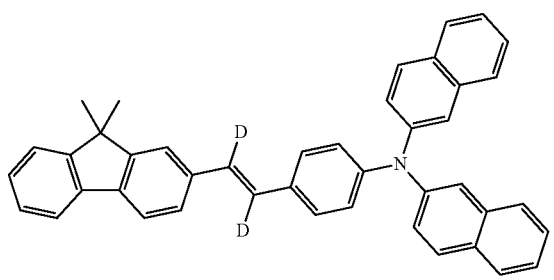
105
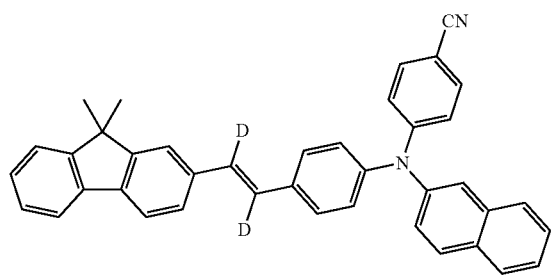
106
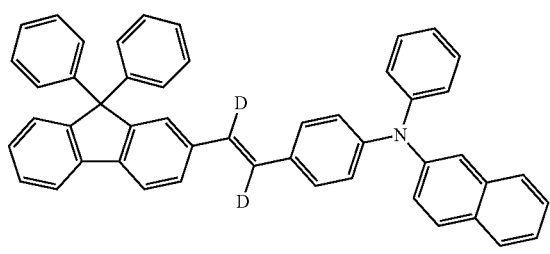
107

-continued
108
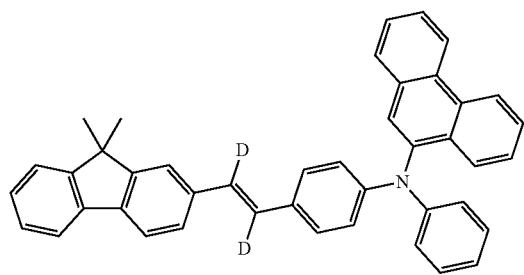
109
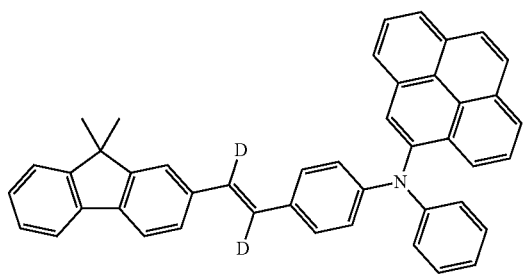
110
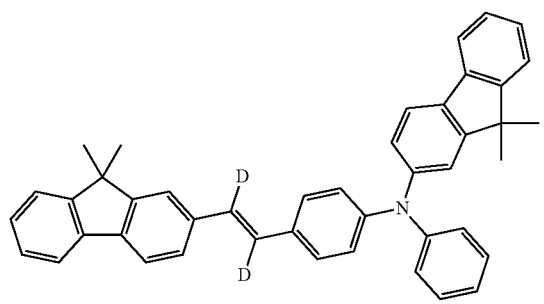
111
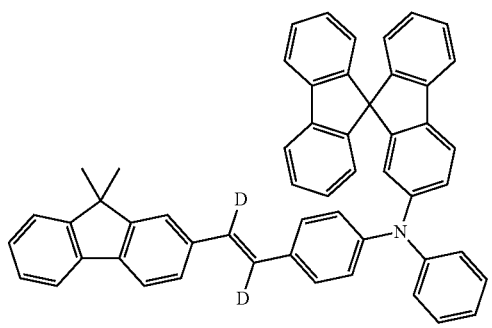
112
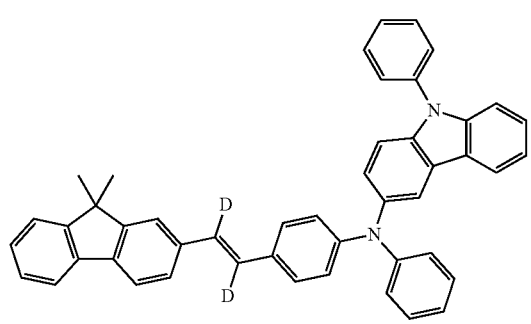
113
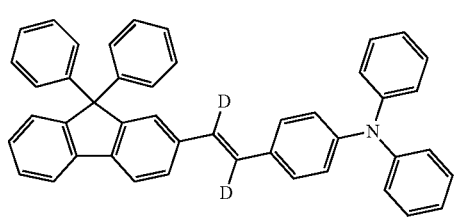
114
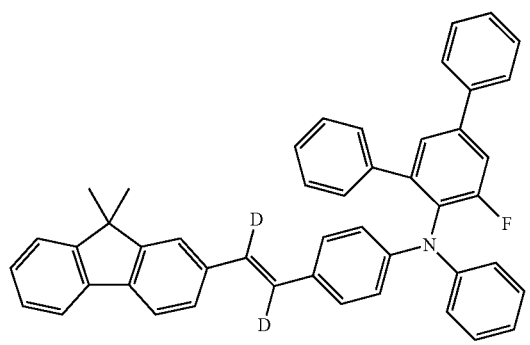
115
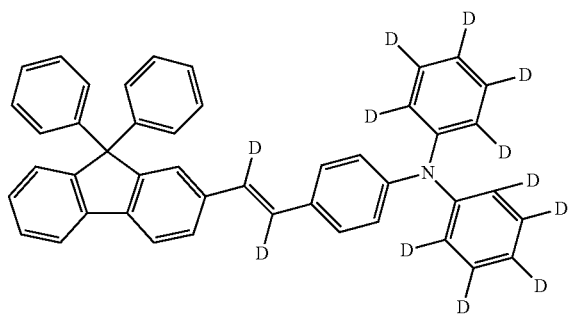

-continued
116
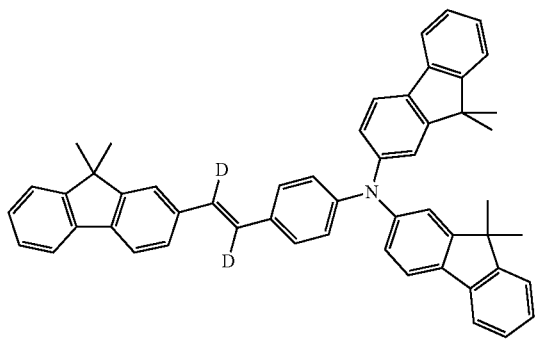
117
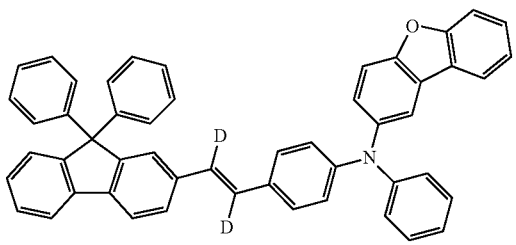
118
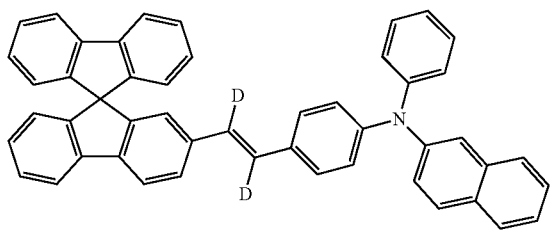
119
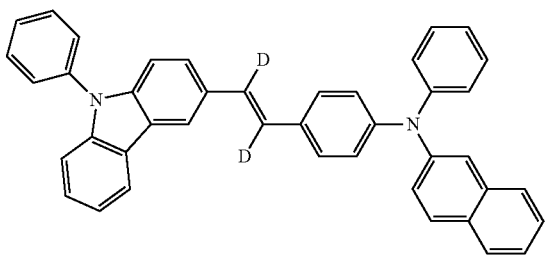
120
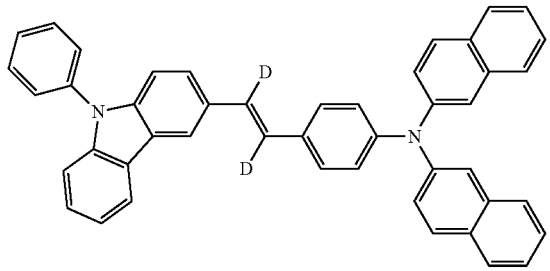
121
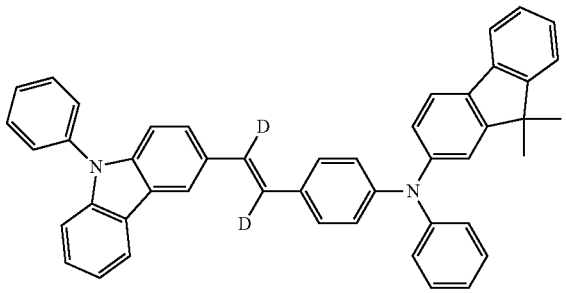
122
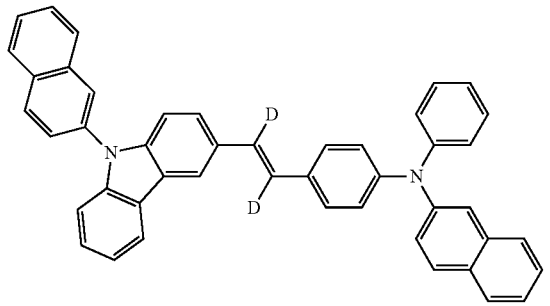
123
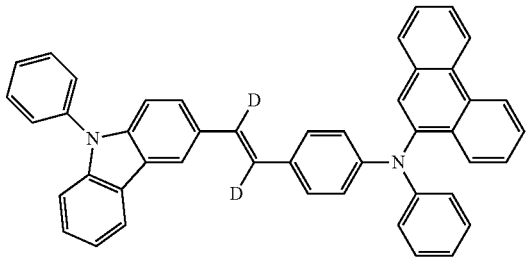
124
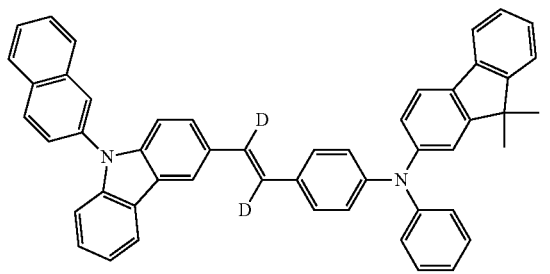
125
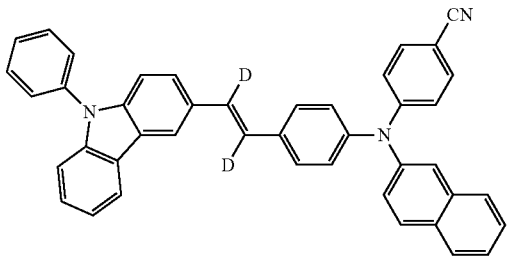

-continued
126
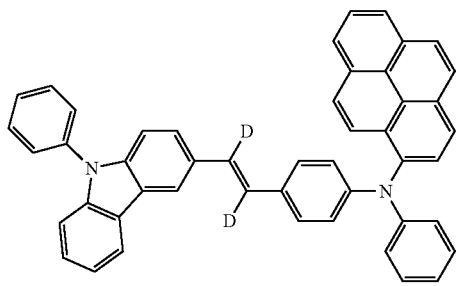
127
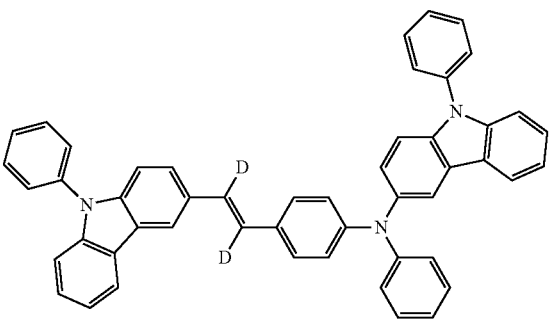
128
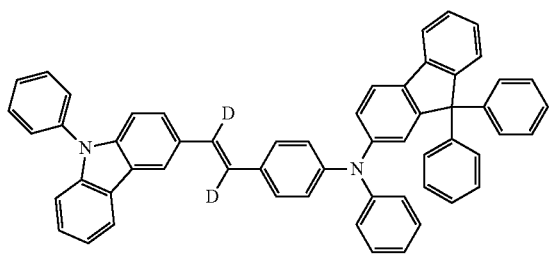
129
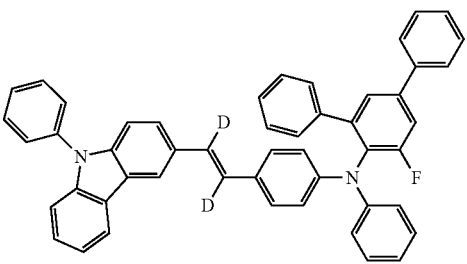
130
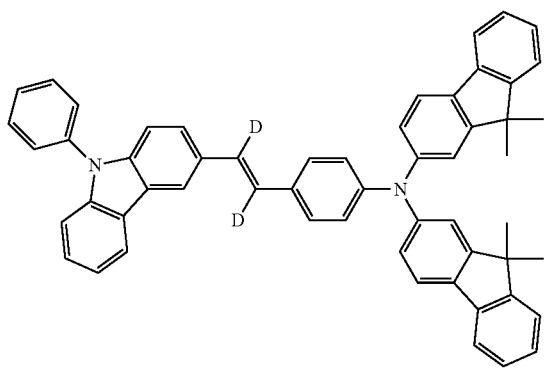
131
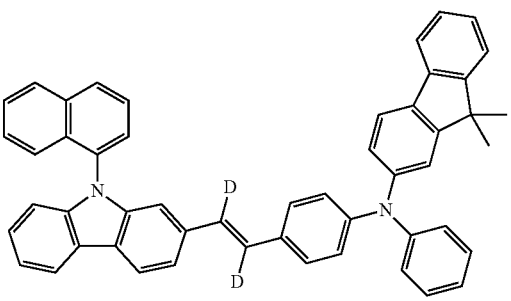
132
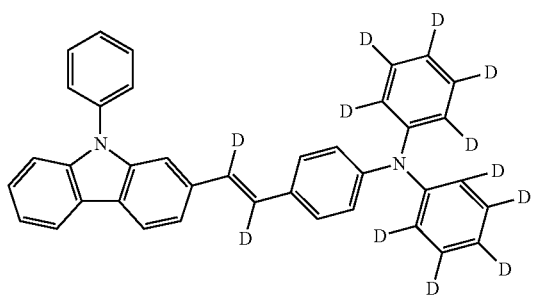
133
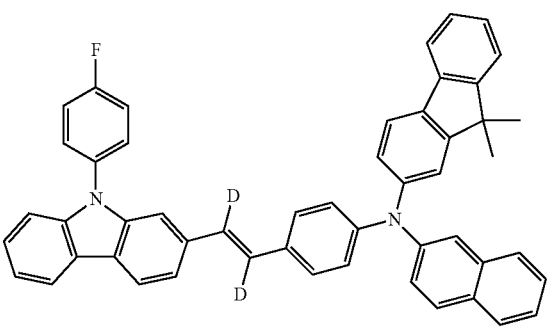
134
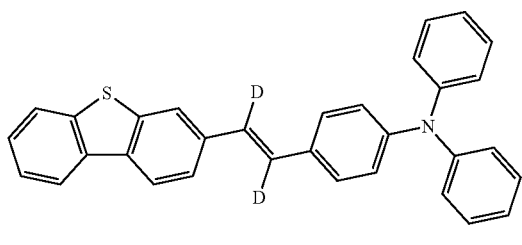
135
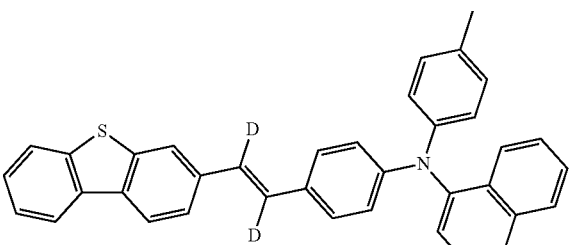

-continued
136
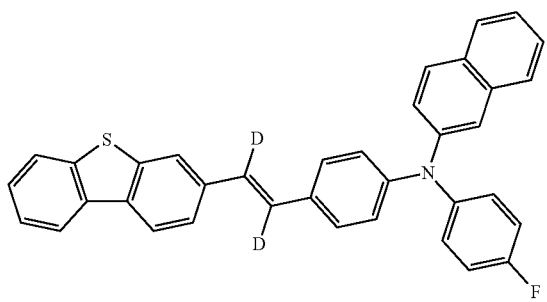
137
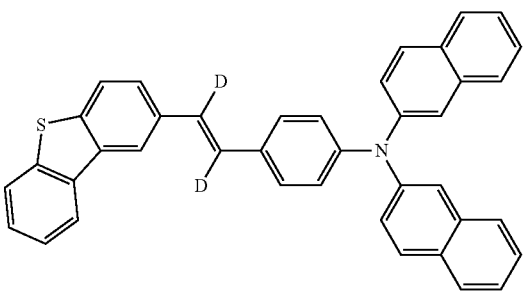
138
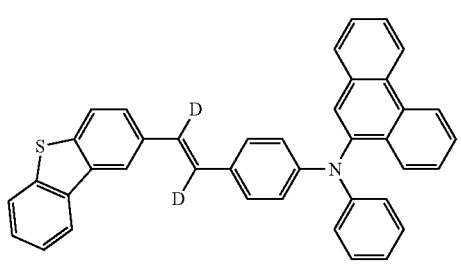
139
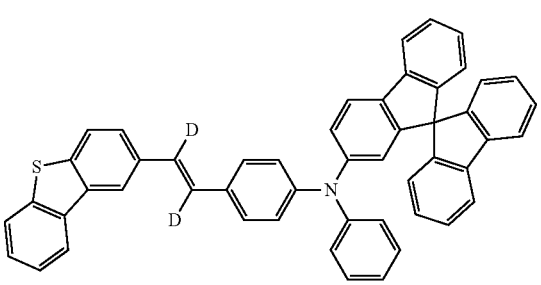
140
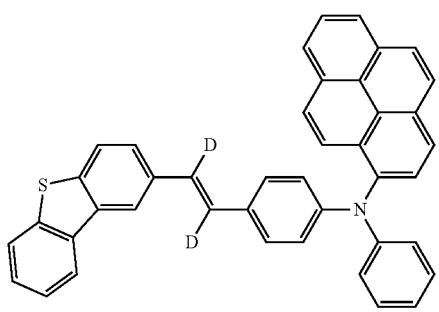
141
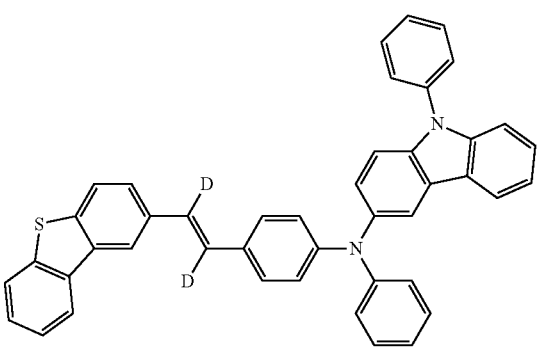
142
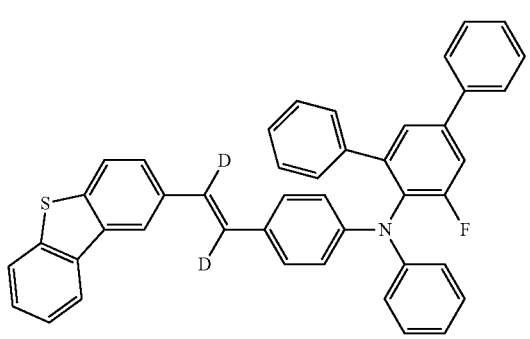
143
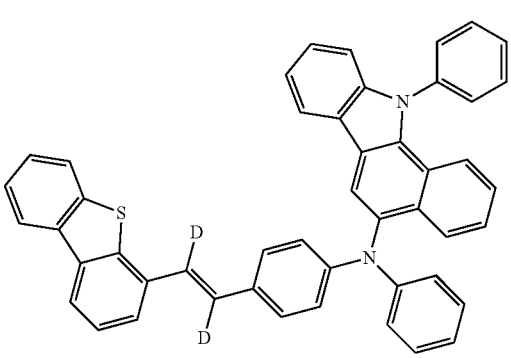
144
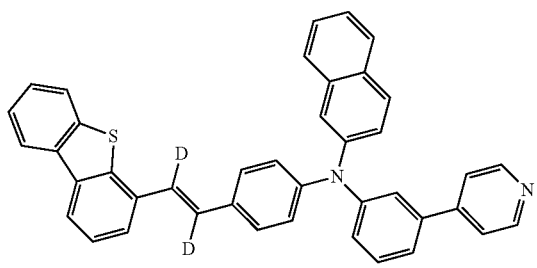
145
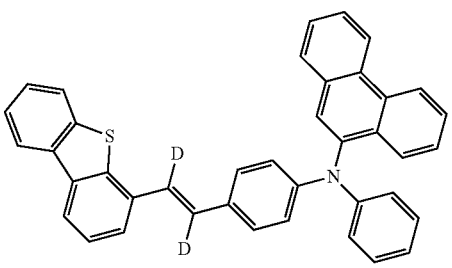

-continued
146
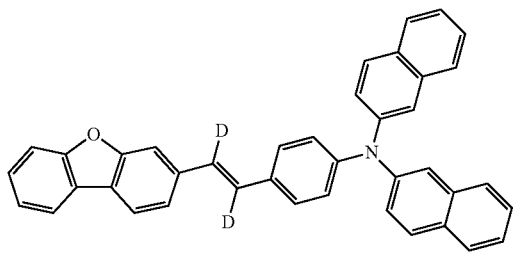
147
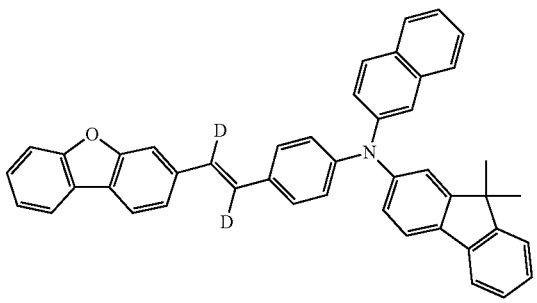
148
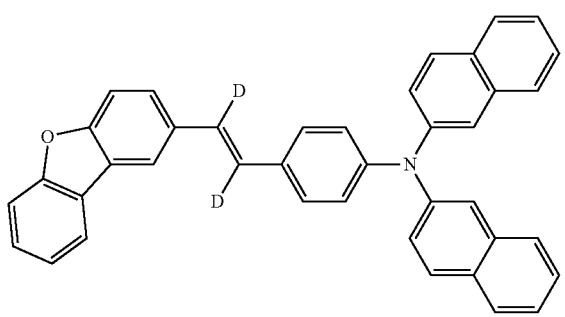
149
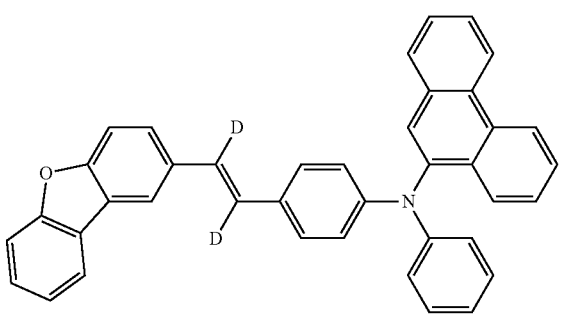
150
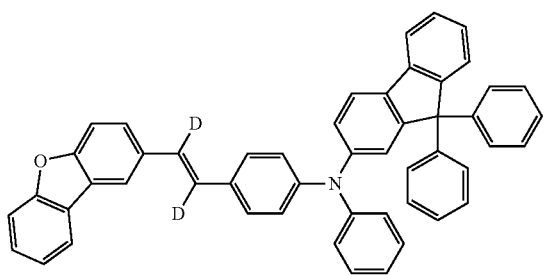
151
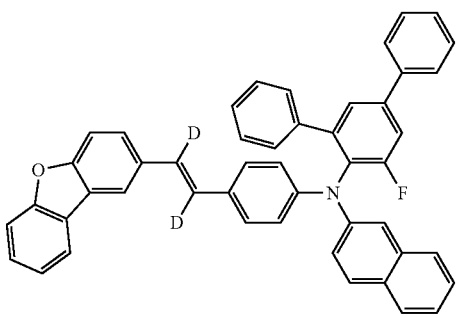
152
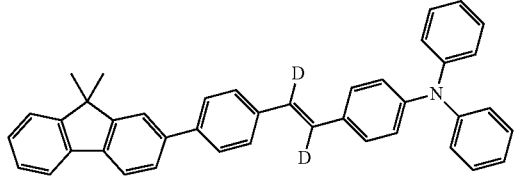
153
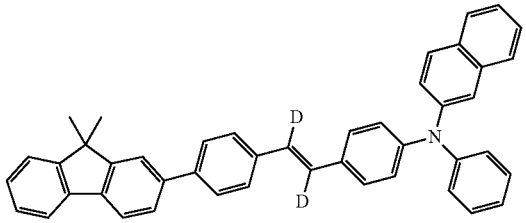
154
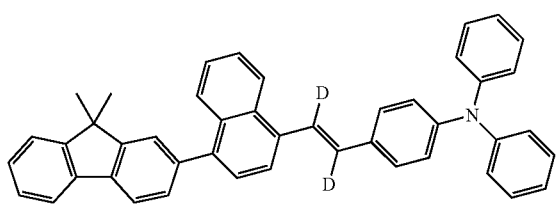
155
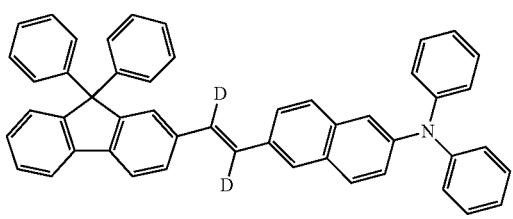

156
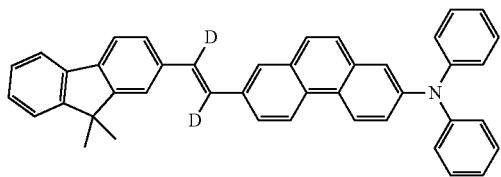
157
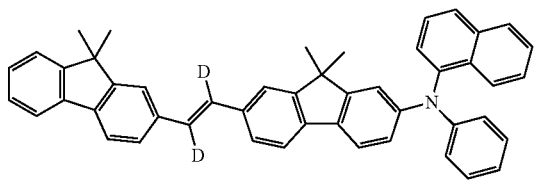
158
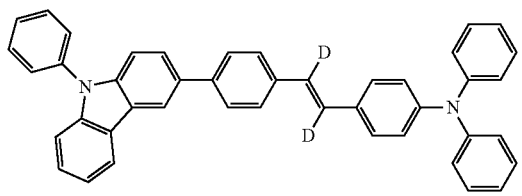
159
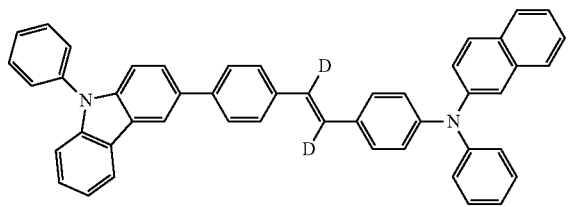
160
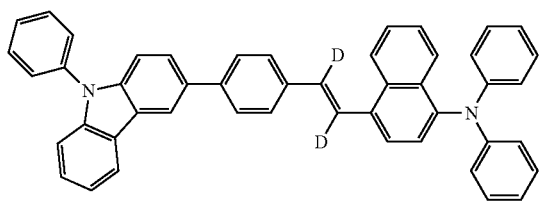
161
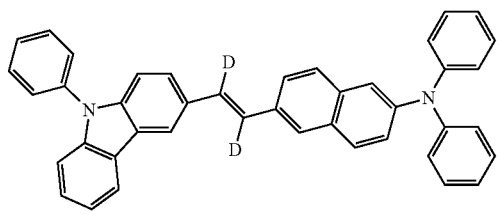
162
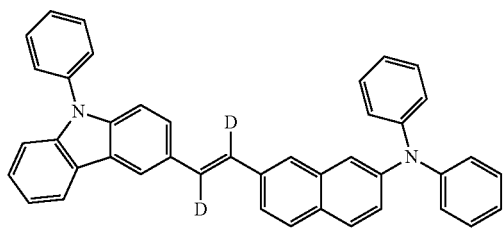
163
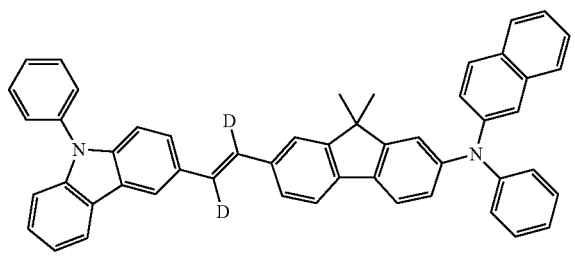
164
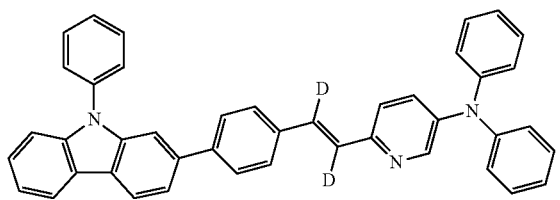
165
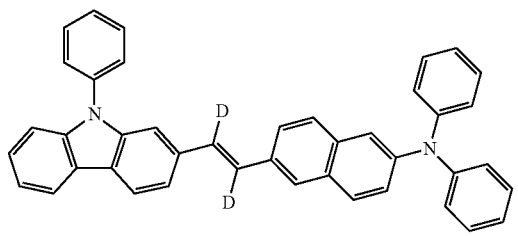
166
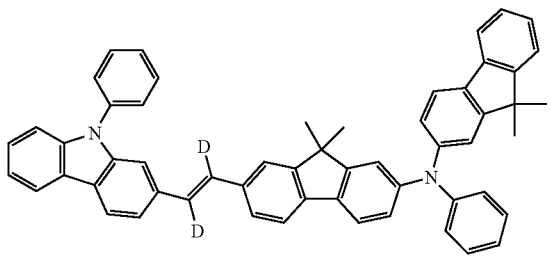
167
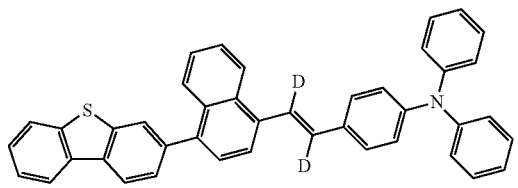

-continued
168
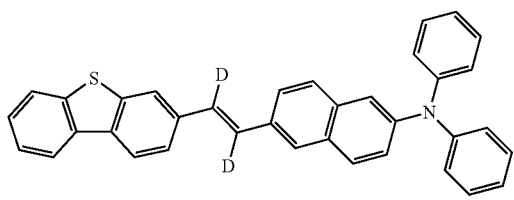
169
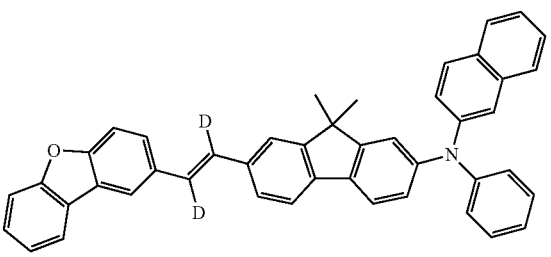
170
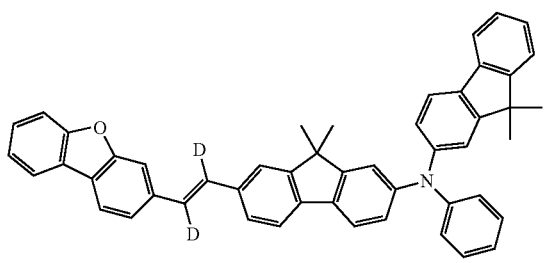
171
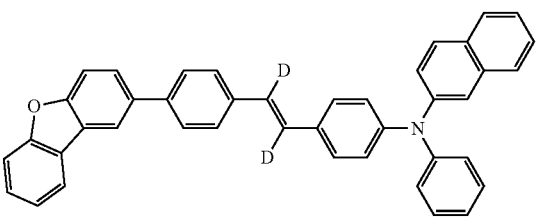
172
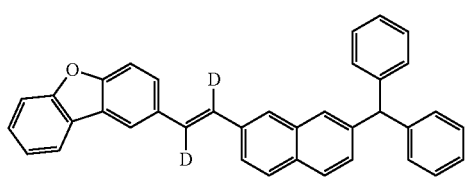
173
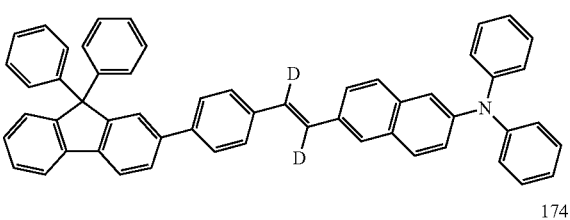
174
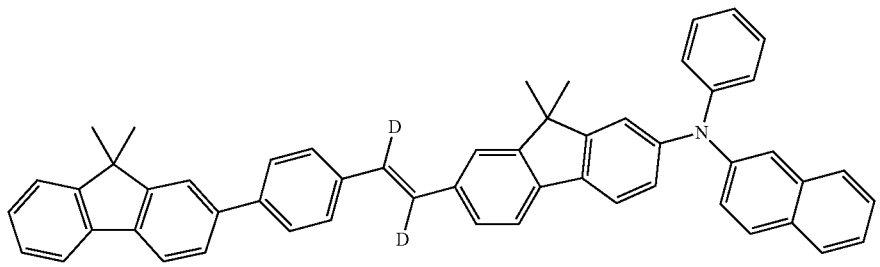
175
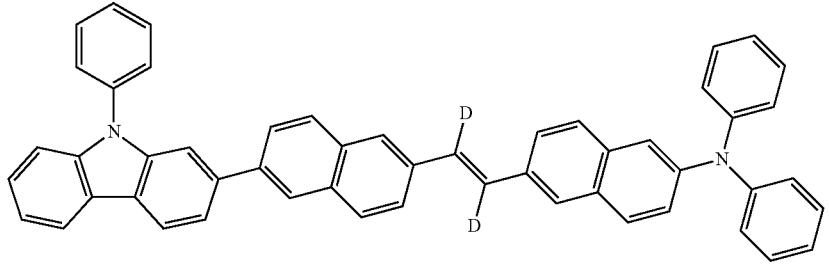
176
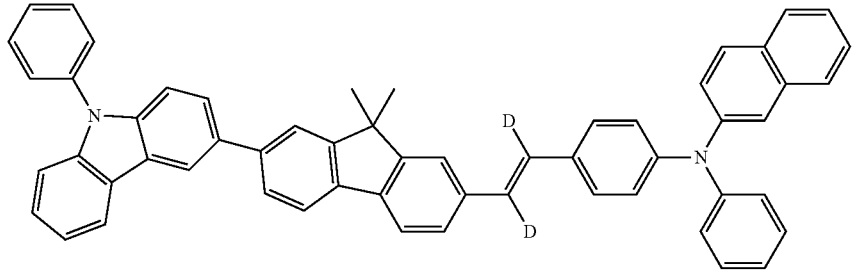

-continued
177
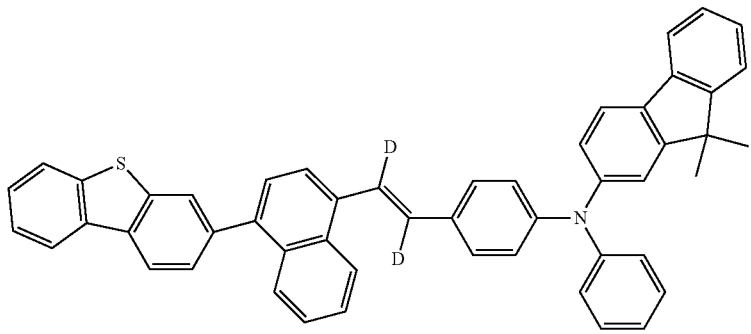
178
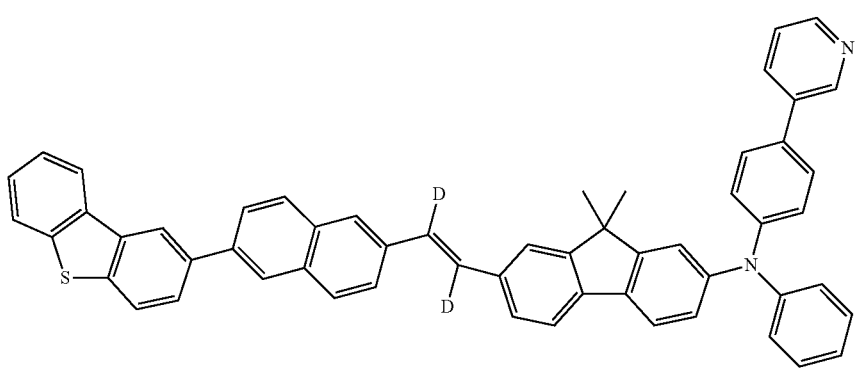
179
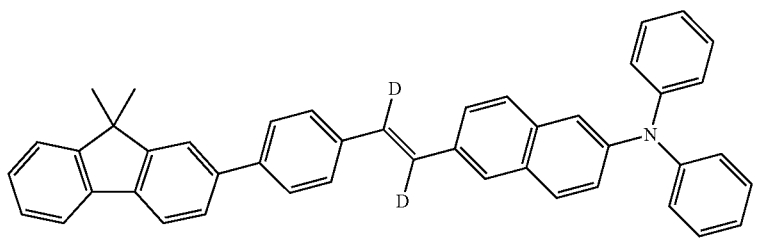
180
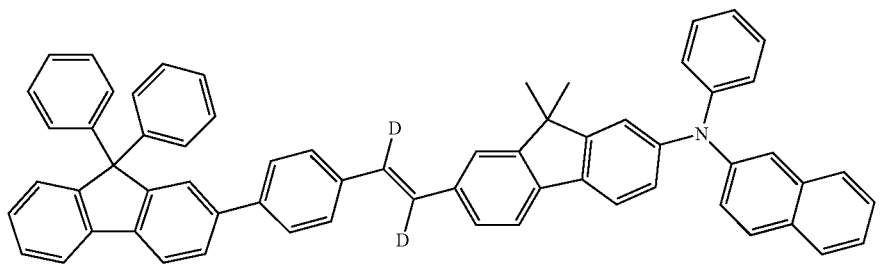
181
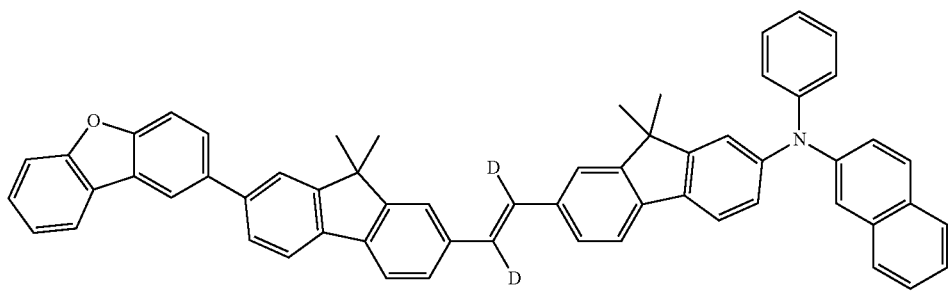

-continued

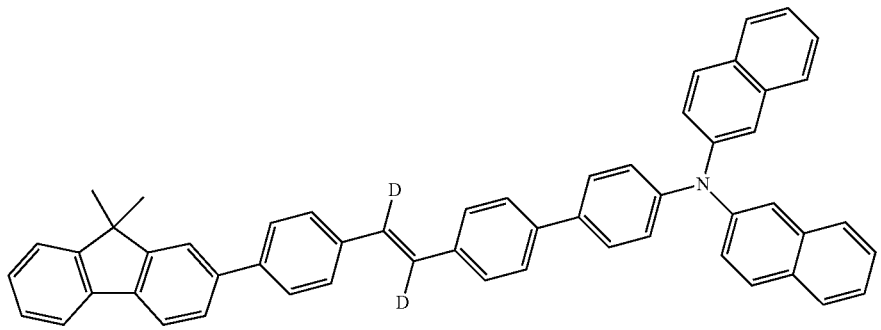

12. A composition, comprising:
a styryl-based compound represented by Formula 1:

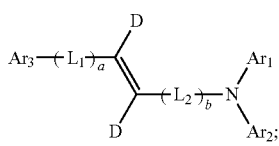

[Formula 1]

and
at least one of a styryl-based compound represented by Formula 1-1H-1, a styryl-based compound represented by Formula 1-1H-2, and a styryl-based compound represented by Formula 1-2H:

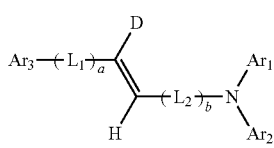

[Formula 1-1H-1]

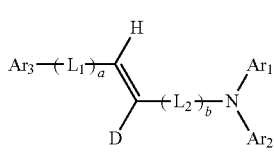

[Formula 1-1H-2]

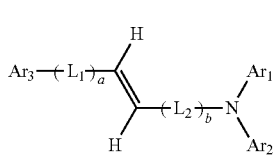

[Formula 1-2H]

wherein $Ar_3$ is a substituted or unsubstituted $C_8$-$C_{20}$ aryl group having two ore more rings fused with each other, or a substituted, or unsubstituted $C_2$-$C_{20}$ heteroaryl group having two or more rings fused with each other;
$Ar_1$ and $Ar_2$ are each independently a substituted or unsubstituted $C_5$-$C_{60}$ aryl group or a substituted or unsubstituted $C_2$-$C_{60}$ heteroaryl group;
$L_1$ and $L_2$ are each independently a substituted or unsubstituted $C_5$-$C_{60}$ arylene group or a substituted or unsubstituted $C_2$-$C_{60}$ heteroarylene group; and
a and b are each independently an integer of 0 to 5, wherein a deuterium substitution rate represented by Equation 1 below is 70% or more:

deuterium substitution rate(%)=$N_D/N_{D+H}$×100  (1)

wherein $N_D$ is the number of deuterium atoms bonded to carbon atoms of the styryl group in Formulae 1, 1-1H-1, and 1-1H-2 above; and $N_{D+H}$ is the total number of deuterium atoms and hydrogen atoms that are bonded to carbon atoms of the styryl group in Formulae 1, 1-1H-1, 1-1H-2, and 1-2H above.

13. An organic light-emitting diode (OLED) comprising:
a first electrode;
a second electrode facing the first electrode; and
an organic layer interposed between the first electrode and the second electrode, the organic layer comprising at least one of the styryl-based compound of claim 1 or a composition containing the styryl-based compound of claim 1.

14. The OLED of claim 13, wherein the organic layer comprises at least one selected from the group consisting of a hole injection layer, a hole transport layer, a functional layer having hole injection and transport abilities, a buffer layer, an electron blocking layer, an emission layer, a hole blocking layer, an electron transport layer, an electron injection layer, and a functional layer having electron injection and transport abilities.

15. The OLED of claim 14, wherein the organic layer comprises the emission layer, and the emission layer comprises the styryl-based compound or the composition containing the styryl-based compound.

16. The OLED of claim 15, wherein the emission layer further comprises at least one selected from the group consisting of an anthracene-based compound represented by Formula 400 below and an anthracene-based compound represented by Formula 401 below as a host:

Formula 400

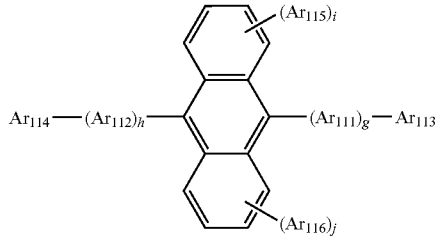

Formula 401

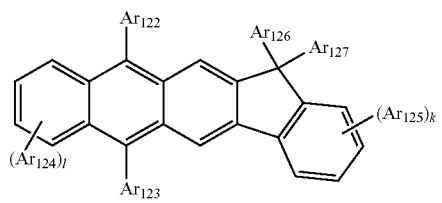

wherein $Ar_{111}$ and $Ar_{112}$ are each independently a substituted or unsubstituted $C_5$-$C_{60}$ arylene group;

$Ar_{113}$ through $Ar_{116}$ and $Ar_{122}$ through $Ar_{125}$ are each independently a substituted or unsubstituted $C_1$-$C_{10}$ alkyl group or a substituted or unsubstituted $C_5$-$C_{60}$ aryl group;

$Ar_{126}$ and $Ar_{127}$ are each independently a $C_1$-$C_{10}$ alkyl group; and g, h, i, j, k, and l are each independently an integer of 0 to 4.

17. The LED of claim 14, wherein the organic layer comprises at least one selected from the group consisting of a hole injection layer, a hole transport layer, and a functional layer having hole transport and injection abilities, and at least one selected from the hole injection layer, the hole transport layer, and the functional layer having hole transport and injection abilities comprises the styryl-based compound or the composition containing the styryl-based compound.

* * * * *